US012091662B2

(12) United States Patent
Kordasiewicz et al.

(10) Patent No.: US 12,091,662 B2
(45) Date of Patent: Sep. 17, 2024

(54) COMPOSITIONS FOR MODULATING TAU EXPRESSION

(71) Applicant: Biogen MA Inc., Cambridge, MA (US)

(72) Inventors: Holly Kordasiewicz, San Diego, CA (US); Eric E. Swayze, Encinitas, CA (US); Susan M. Freier, San Diego, CA (US); Huynh-Hoa Bui, San Diego, CA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 18/155,945

(22) Filed: Jan. 18, 2023

(65) Prior Publication Data

US 2023/0323351 A1   Oct. 12, 2023

Related U.S. Application Data

(62) Division of application No. 16/986,770, filed on Aug. 6, 2020, now Pat. No. 11,591,595, which is a division of application No. 15/593,173, filed on May 11, 2017, now Pat. No. 10,793,856, which is a division of application No. 14/906,047, filed as application No. PCT/US2014/047486 on Jul. 21, 2014, now Pat. No. 9,683,235.

(60) Provisional application No. 62/014,486, filed on Jun. 19, 2014, provisional application No. 61/885,371, filed on Oct. 1, 2013, provisional application No. 61/879,621, filed on Sep. 18, 2013, provisional application No. 61/856,551, filed on Jul. 19, 2013.

(51) Int. Cl.
*C12N 15/113* (2010.01)
*A61K 31/711* (2006.01)
*C07H 21/02* (2006.01)
*C12Q 1/68* (2018.01)

(52) U.S. Cl.
CPC .......... *C12N 15/113* (2013.01); *A61K 31/711* (2013.01); *C07H 21/02* (2013.01); *C12N 2310/11* (2013.01); *C12N 2310/315* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| | | | |
|---|---|---|---|
| 3,687,808 A | 8/1972 | Merigan et al. |
| 4,845,205 A | 7/1989 | Huynh Dinh et al. |
| 4,880,635 A | 11/1989 | Janoff et al. |
| 4,906,477 A | 3/1990 | Kurono et al. |
| 4,911,928 A | 3/1990 | Wallach |
| 4,917,951 A | 4/1990 | Wallach |
| 4,920,016 A | 4/1990 | Allen et al. |
| 4,921,757 A | 5/1990 | Wheatley et al. |
| 5,034,506 A | 7/1991 | Summerton et al. |
| 5,130,302 A | 7/1992 | Spielvogel et al. |
| 5,134,066 A | 7/1992 | Rogers et al. |
| 5,149,797 A | 9/1992 | Pederson et al. |
| 5,166,315 A | 11/1992 | Summerton et al. |
| 5,175,273 A | 12/1992 | Bischofberger et al. |
| 5,185,444 A | 2/1993 | Summerton et al. |
| 5,367,066 A | 11/1994 | Urdea et al. |
| 5,432,272 A | 7/1995 | Benner |
| 5,434,257 A | 7/1995 | Matteucci et al. |
| 5,457,187 A | 10/1995 | Gmelner et al. |
| 5,457,191 A | 10/1995 | Cook et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,587,470 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,698,685 A | 12/1997 | Summerton et al. |
| 5,750,692 A | 5/1998 | Cook et al. |
| 5,763,588 A | 6/1998 | Matteucci et al. |
| 5,801,154 A | 9/1998 | Baracchini et al. |
| 5,808,027 A | 9/1998 | Cook et al. |
| 5,811,534 A | 9/1998 | Cook et al. |
| 5,830,653 A | 11/1998 | Froehler et al. |
| 5,837,853 A | 11/1998 | Takashima et al. |
| 5,859,221 A | 1/1999 | Cook et al. |

(Continued)

FOREIGN PATENT DOCUMENTS

BR   PI0801674   2/2010
BR   PI0901526   1/2011

(Continued)

OTHER PUBLICATIONS

U.S. Appl. No. 60/130,377, filed Apr. 21, 1999, Pachuk et al.
U.S. Appl. No. 60/399,998, filed Jul. 31, 2002, Pachuk et al.
U.S. Appl. No. 60/419,532, filed Oct. 18, 2002, Pachuk et al.
Agrawal, S. et al., Proc. Natl. Acad. Sci. USA 87, 1401-1405 (1990).
Albaek et al., J. Org. Chem., 2006, 71, 7731-7740.
Allshire, 2002, Science 297, 1818-1819.
Altmann et al., Biochem. Soc. Trans., 1996, 24, 630-637.
Altmann et al., Chimia, 1996, 50, 168-176.
Altmann et al., Nucleosides Nucleotides, 1997, 16, 917-926.

(Continued)

*Primary Examiner* — Sean McGarry
(74) *Attorney, Agent, or Firm* — Choate, Hall & Stewart LLP; Stephanie L. Schonewald; Andrew N. Ming-Lum

(57) ABSTRACT

Disclosed herein are antisense compounds and methods for decreasing Tau mRNA and protein expression. Such methods, compounds, and compositions are useful to treat, prevent, or ameliorate Tau-associated diseases, disorders, and conditions.

15 Claims, No Drawings

Specification includes a Sequence Listing.

(56) References Cited

U.S. PATENT DOCUMENTS

| | | |
|---|---|---|
| 5,948,903 A | 9/1999 | Cook et al. |
| 6,005,087 A | 12/1999 | Cook et al. |
| 6,005,096 A | 12/1999 | Matteucci et al. |
| 6,166,199 A | 12/2000 | Cook et al. |
| 6,268,490 B1 | 7/2001 | Imanishi et al. |
| 6,525,191 B1 | 2/2003 | Ramasamy |
| 6,531,584 B1 | 3/2003 | Cook et al. |
| 6,582,908 B2 | 6/2003 | Fodor et al. |
| 6,617,162 B2 | 9/2003 | Dobie et al. |
| 6,670,461 B1 | 12/2003 | Wengel et al. |
| 6,673,661 B1 | 1/2004 | Liu et al. |
| 6,770,748 B2 | 8/2004 | Imanishi et al. |
| 6,794,499 B2 | 9/2004 | Wegel et al. |
| 7,034,133 B2 | 4/2006 | Wengel et al. |
| 7,053,207 B2 | 5/2006 | Wengel |
| 7,084,125 B2 | 8/2006 | Wengel |
| 7,217,805 B2 | 5/2007 | Imanishi et al. |
| 7,314,923 B2 | 1/2008 | Kaneko et al. |
| 7,399,845 B2 | 7/2008 | Seth et al. |
| 7,427,672 B2 | 9/2008 | Imanishi et al. |
| 7,547,684 B2 | 6/2009 | Seth et al. |
| 7,569,575 B2 | 8/2009 | Sorensen et al. |
| 7,569,686 B1 | 8/2009 | Bhat et al. |
| 7,572,582 B2 | 8/2009 | Wengel et al. |
| 7,666,854 B2 | 2/2010 | Seth et al. |
| 7,696,345 B2 | 4/2010 | Allerson et al. |
| 7,741,457 B2 | 6/2010 | Seth et al. |
| 7,745,391 B2 | 6/2010 | Mintz et al. |
| 7,750,131 B2 | 7/2010 | Woldike et al. |
| 7,858,747 B2 | 12/2010 | Woldike et al. |
| 7,875,733 B2 | 1/2011 | Bhat et al. |
| 7,939,677 B2 | 5/2011 | Bhat et al. |
| 8,022,193 B2 | 9/2011 | Swayze et al. |
| 8,030,467 B2 | 10/2011 | Seth et al. |
| 8,034,909 B2 | 10/2011 | Wengel et al. |
| 8,080,644 B2 | 12/2011 | Wengel et al. |
| 8,088,746 B2 | 1/2012 | Seth et al. |
| 8,088,904 B2 | 1/2012 | Swayze et al. |
| 8,124,745 B2 | 2/2012 | Allerson et al. |
| 8,153,365 B2 | 4/2012 | Wengel et al. |
| 8,178,503 B2 | 5/2012 | Rigoutsos et al. |
| 8,268,980 B2 | 9/2012 | Seth et al. |
| 8,278,283 B2 | 10/2012 | Seth et al. |
| 8,278,425 B2 | 10/2012 | Prakash et al. |
| 8,278,426 B2 | 10/2012 | Seth et al. |
| 8,329,890 B2 | 12/2012 | Davidson et al. |
| 8,440,803 B2 | 5/2013 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| RE44,779 E | 2/2014 | Imanishi et al. |
| 8,796,437 B2 | 8/2014 | Swayze et al. |
| 8,871,729 B2 | 10/2014 | Yague et al. |
| 9,005,906 B2 | 4/2015 | Swayze et al. |
| 9,012,421 B2 | 4/2015 | Migawa et al. |
| 9,084,813 B2 | 7/2015 | Roberson et al. |
| 9,198,982 B2 | 12/2015 | Roberson et al. |
| 9,644,207 B2 | 5/2017 | Rigo et al. |
| 9,683,235 B2 | 6/2017 | Freier |
| 10,273,474 B2 | 4/2019 | Miller et al. |
| 10,407,680 B2 | 9/2019 | Kordasiewicz |
| 10,793,856 B2 | 10/2020 | Kordasiewicz |
| 11,591,595 B2 | 2/2023 | Kordasiewicz et al. |
| 11,781,135 B2 | 10/2023 | Miller et al. |
| 2001/0053519 A1 | 12/2001 | Fodor et al. |
| 2002/0018995 A1 | 2/2002 | Ghetti et al. |
| 2002/0045575 A1 | 4/2002 | Skov |
| 2003/0158403 A1 | 8/2003 | Manoharan et al. |
| 2003/0175906 A1 | 9/2003 | Manoharan et al. |
| 2003/0219770 A1 | 11/2003 | Eshleman et al. |
| 2003/0228597 A1 | 12/2003 | Cowsert et al. |
| 2004/0054156 A1 | 3/2004 | Draper et al. |
| 2004/0110149 A1* | 6/2004 | Bennett .............. C12N 15/1137 536/23.5 |
| 2004/0171570 A1 | 9/2004 | Allerson et al. |
| 2004/0241651 A1 | 12/2004 | Olek et al. |
| 2005/0108783 A1 | 5/2005 | Koike et al. |
| 2005/0130923 A1 | 6/2005 | Bhat et al. |
| 2005/0153336 A1 | 7/2005 | Bennett et al. |
| 2005/0244851 A1 | 11/2005 | Blume et al. |
| 2005/0255487 A1 | 11/2005 | Khvorova et al. |
| 2006/0216722 A1 | 9/2006 | Betsholtz et al. |
| 2007/0031844 A1 | 2/2007 | Khvorova et al. |
| 2007/0054869 A1 | 3/2007 | Bennett et al. |
| 2007/0203333 A1 | 8/2007 | McSwiggen et al. |
| 2007/0287831 A1 | 12/2007 | Seth et al. |
| 2008/0003570 A1 | 1/2008 | Rogers et al. |
| 2008/0015162 A1 | 1/2008 | Bhanot et al. |
| 2008/0039618 A1 | 2/2008 | Allerson et al. |
| 2008/0249058 A1 | 10/2008 | Roberson et al. |
| 2008/0318210 A1 | 12/2008 | Bentwich |
| 2009/0012281 A1 | 1/2009 | Swayze et al. |
| 2009/0162365 A1 | 6/2009 | Feinstein |
| 2009/0076725 A1 | 7/2009 | Morrissey et al. |
| 2009/0176728 A1 | 7/2009 | Yague et al. |
| 2010/0261175 A1 | 10/2010 | Rasmussen et al. |
| 2011/0054005 A1 | 3/2011 | Naito et al. |
| 2011/0041191 A1 | 6/2011 | Huang et al. |
| 2011/0150897 A1 | 6/2011 | Meyer et al. |
| 2011/0244561 A1 | 10/2011 | Davidson et al. |
| 2011/0263687 A1 | 10/2011 | Mattick et al. |
| 2012/0005898 A1 | 1/2012 | Molema et al. |
| 2013/0046007 A1 | 2/2013 | Bennett |
| 2013/0078359 A1 | 3/2013 | Rajesh et al. |
| 2013/0123133 A1 | 5/2013 | Ward et al. |
| 2013/0130378 A1 | 5/2013 | Manoharan et al. |
| 2013/0203836 A1 | 8/2013 | Rajeev et al. |
| 2014/0155462 A1 | 6/2014 | Brown et al. |
| 2014/0315983 A1 | 10/2014 | Brown et al. |
| 2015/0057329 A1 | 2/2015 | Bhanot et al. |
| 2015/0191727 A1 | 7/2015 | Migawa et al. |
| 2015/0275205 A1 | 10/2015 | Miller et al. |
| 2016/0032285 A1 | 2/2016 | Rigo et al. |
| 2016/0145617 A1 | 5/2016 | Kordasiewicz et al. |
| 2017/0211064 A1 | 7/2017 | Rigo et al. |
| 2018/0051283 A1 | 2/2018 | Rigo et al. |
| 2018/0094261 A1 | 4/2018 | Kordasiewicz et al. |
| 2018/0119145 A1 | 5/2018 | Kordasiewicz et al. |
| 2019/0211332 A1 | 7/2019 | Kordasiewicz |
| 2020/0032257 A1 | 1/2020 | Miller et al. |
| 2020/0199589 A1 | 6/2020 | Kordasiewicz |
| 2021/0071176 A1 | 3/2021 | Kordasiewicz et al. |
| 2023/0323351 A1 | 10/2023 | Kordasiewicz et al. |

FOREIGN PATENT DOCUMENTS

| | | |
|---|---|---|
| CN | 1696294 | 11/2005 |
| CN | 101115846 A | 1/2008 |
| CN | 102625809 | 8/2012 |
| CN | 102753186 | 10/2012 |
| CN | 105264091 | 1/2016 |
| EP | 0616032 A2 | 9/1994 |
| EP | 0653169 | 5/1995 |
| EP | 1152009 | 11/2001 |
| EP | 2877579 A1 | 6/2015 |
| EP | 3058069 A1 | 8/2016 |
| GB | 2471149 | 12/2010 |
| IT | GE20130015 | 1/2015 |
| JP | H06329551 | 11/1994 |
| JP | 2000297097 | 10/2000 |
| JP | 2004187609 | 7/2004 |
| JP | 2008520191 | 6/2008 |
| JP | 2010525303 | 7/2010 |
| JP | 2011502514 | 1/2011 |
| JP | 2013107902 | 6/2013 |
| JP | 2016527154 | 9/2016 |
| RU | 2353385 C2 | 4/2009 |
| RU | 2376018 C2 | 12/2009 |
| RU | 2448974 C2 | 4/2012 |
| TW | 1657819 B | 5/2019 |
| WO | WO 1998039352 | 9/1998 |

(56) References Cited

FOREIGN PATENT DOCUMENTS

| | | |
|---|---|---|
| WO | WO 1999014226 | 3/1999 |
| WO | WO 1999021439 | 5/1999 |
| WO | WO 1999062548 | 12/1999 |
| WO | WO 2000063364 | 10/2000 |
| WO | WO 2001032703 | 5/2001 |
| WO | WO 2001072765 | 10/2001 |
| WO | WO 2002066672 | 8/2002 |
| WO | WO 2002081494 | 10/2002 |
| WO | WO 2003004602 | 1/2003 |
| WO | WO-2003/054143 A2 | 7/2003 |
| WO | WO 2004017072 | 2/2004 |
| WO | WO 2004035765 | 4/2004 |
| WO | WO 2004058940 | 7/2004 |
| WO | WO 2004011613 | 9/2004 |
| WO | WO 2004106356 | 12/2004 |
| WO | WO 2005017143 | 2/2005 |
| WO | WO 2005021570 | 3/2005 |
| WO | WO 2005040180 | 5/2005 |
| WO | WO 2006047673 | 5/2006 |
| WO | WO 2007027775 | 3/2007 |
| WO | WO-2007/092182 A2 | 8/2007 |
| WO | WO 2007107789 | 9/2007 |
| WO | WO 2007134181 | 11/2007 |
| WO | WO 2008101157 | 8/2008 |
| WO | WO 2008124066 | 10/2008 |
| WO | WO 2008131807 | 11/2008 |
| WO | WO 2008150729 | 12/2008 |
| WO | WO 2008154401 | 12/2008 |
| WO | WO 2009006478 | 1/2009 |
| WO | WO 2009061851 | 5/2009 |
| WO | WO 2009067647 | 5/2009 |
| WO | WO 2009100320 | 8/2009 |
| WO | WO 2010036698 | 4/2010 |
| WO | WO 2010048497 | 4/2010 |
| WO | WO 2010148249 | 12/2010 |
| WO | WO 2011005786 | 1/2011 |
| WO | WO 2011005793 | 1/2011 |
| WO | WO 2011022606 | 2/2011 |
| WO | WO 2011017521 | 5/2011 |
| WO | WO 2011079263 | 6/2011 |
| WO | WO 2011107993 | 9/2011 |
| WO | WO 2011131693 | 10/2011 |
| WO | WO 2011139702 | 11/2011 |
| WO | WO 2012005898 | 1/2012 |
| WO | WO 2012018881 | 2/2012 |
| WO | WO-2012/162179 A1 | 11/2012 |
| WO | WO 2012177639 | 12/2012 |
| WO | WO 2013078441 | 5/2013 |
| WO | WO 2013079716 | 6/2013 |
| WO | WO 2013148260 | 10/2013 |
| WO | WO 2013173647 | 11/2013 |
| WO | WO 2014012081 | 1/2014 |
| WO | WO 2014114937 | 7/2014 |
| WO | WO 2014153236 | 9/2014 |
| WO | WO 2014179620 | 11/2014 |
| WO | WO 2014200909 | 12/2014 |
| WO | WO 2015010135 | 1/2015 |
| WO | WO 2015072913 | 5/2015 |
| WO | WO 2015106128 | 7/2015 |
| WO | WO 2016019063 | 2/2016 |
| WO | WO 2016126995 | 8/2016 |
| WO | WO 2016127002 | 8/2016 |
| WO | WO 2016151523 | 9/2016 |
| WO | WO 2017015555 | 1/2017 |
| WO | WO 2017055102 | 4/2017 |
| WO | WO 2017109679 | 6/2017 |
| WO | WO 2013148283 | 10/2017 |
| WO | WO 2018064593 | 4/2018 |
| WO | WO 2019175260 | 9/2019 |
| WO | WO 2020007892 | 1/2020 |
| WO | WO 2020227618 | 11/2020 |
| WO | WO-2023/176503 A1 | 9/2023 |

OTHER PUBLICATIONS

Altschul et al., J. Mol. Biol., 1990, 215, 403-410.
Andorfer et al., "Hyperphosphorylation and aggregation of tau in mice expressing normal human tau isoforms" Journal of Neurochemistry (2003) 86: 582-590.
Australian Patent Examination Report for Application No. 2013202595 dated Jul. 4, 2014 (15 pages).
Australian Patent Examination Report for Application No. 2013202595, dated Mar. 17, 2016, 3 pages.
Australian Patent Examination Report for Application No. 2016202220, dated Jan. 12, 2017, 4 pages.
Badiola et al., "Tau phosphorylation and aggregation as a therapeutic target in tauopathies," CNS Neurol. Disord. Drug Targets, Dec. 2010, vol. 9, No. 6, pp. 727-740.
Baker et al., J. Biol. Chem., 1997, 272, 11944-12000.
Baker, C. et al., Nucleic Acids Res. 18, 3537-3543 (1990).
Bennett et al., "Pharmacological Properties of 2'-O-Methoxyethyl-Modified Oligonucleotides", Antisense Drug Technology: Principles, Strategies and Applications, 2nd Edition, 2007, pp. 273-303.
Bevins, R.A. and Besheer, J., J. Nature Protocols, 2006, 1: 1306-1311.
Bi et al., 'Tau-Targeted Immunization Impedes Progression fo Neurofibrillary Histopathology in Aged P30 IL Tau Transgenic Mice Plos One (2011) 6(12):e26860.
Boiziau et al., "Antisense 2-0-alkyl oligoribonucleotides are efficient inhibitors of reverse transcription", Nucleic Acids Research, 1995, 23(1):64-71.
Braasch et al., "Novel antisense and peptide nucleic acid strategies for controlling gene expression" Biochemistry (2002) 41(14):4503-4510.
Braasch et al., Chem. Biol., 2001, 8, 1-7.
Branch et al., "A good antisense molecule is hard to find," TIBS (1998) 23:45-50.
Buck et al., "Design strategies and performance of custom DNA sequencing primers", Biotechniques, 1999, 27(3):528-536.
Caceres et al., "Inhibition of neurite polarity by tau antisense oligonucleotides in primary cerebellar neurons" Nature (1990) 343:461-463.
Caceres et al., "The Effect of Tau antisense Oligonucleotides on Neurite Formation of Cultured Cerebellar Macroneurons" J. Neuroscience (1991) 11(6):1515-1523.
Canadian Patent Office Action for Application No. 2866392, dated Feb. 5, 2018, 6 pages.
Chernolovskaya et al., "Chemical modification of siRNA", Current Opinion in Molecular Therapeutics, 2010, 12(2):1-10.
Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.
ClinicalTrials.gov, "Safety, Tolerability, Pharmacokinetics, and Pharmacodynamics of Ionis-Maptrx in patients with mild Alzheimer's Disease", NCT03186989 online Jun. 14, 2017.
Craig et al., "Towards a small molecule inhibitor of tau exon 10 splicing: Identification of compounds that stabilise the 5'-splice site stem-loop" Alzheimer's & Dementia: The Journal of the Alzheimer's Association (2012) 8(4): P636.
Crooke et al., "Antisense Drug Technology", Second Edition, CRC Press, 2008, Chapters 1-28.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277(2):923-937.
Cummings et al., "Alzheimer's disease drug development pipeline: 2021," Alzheimer's & Dementia: Translational Research & Clinical Interventions, May 2021, 7(10):1-24.
Davies et al., "Hyperphosphorylation and aggregation of tau in mice expressing normal human tau isoforms", Journal of Neurochemistry, 2003, 86:582-590.

(56) References Cited

OTHER PUBLICATIONS

Dawson, "Tau Exon 10 Splicing Tauopathy", presentation given at CurePSP 2010 International Research Symposium, Nov. 18, 2010, San Diego, CA.
Dawson, "The Effects of the CBD-Associated Tau Gene HI Haplotype on Tau Expression," Abstract presented at CurePSP 2010 International Research Symposium, Nov. 18, 2010, San Diego, CA (retrieved online Jan. 13, 2016).
Dawson, H.N. et al., J. Neurosci. 27: 9155-9168, 2007.
Deacon, R. M., Nat. Protocol. 2006, 1:1117-9.
DeVos et al., "Antisense oligonucleotides: treating neurodegeneration at the level of RNA" Neurotherapeutics (2013) 10(3): 486-497.
DeVos et al., "Antisense Reduction of Human Tau in the CNS of P301S mice both Prevents and Reverses Hyperphosphorylated Tau Deposition" abstract presented at Keystone Symposium: Long Noncoding RNAs: Marching toward Mechanism, Feb. 27-Mar. 4, 2014, Santa Fe, NM, 39 pages.
DeVos et al., "Antisense Reduction of Tau in Adult Mice Protects against Seizures" J. Neuroscience (2013) 33(31): 12887-12897.
DeVos et al., "Antisense Reduction of the Human Tau Transgene in the CNS of P301S mice Robustly Decreases Tau Deposition" abstract presented at Keystone Symposia: New Frontiers in Neurodegenerative Disease Research, Feb. 3-8, 2013, Santa Fe, NM, 1 page.
DeVos et al., "Reducing Human Tau in the CNS of P301S mice Dramatically Reverses Tau Pathology" abstract presented at14th International Conference on Alzheimer's Drug Discovery, Sep. 9-10, 2013, Jersey City, NJ, 1 page.
DeVos et al., "Tau reduction prevents neuronal loss and reverses pathological tau deposition and seeding in mice with tauopathy", Science Translational Medicine, 2017, 9(374):1-14.
DeVos et al., "Using antisense oligonucleotides to knockdown endogenous brain tau in vivo" Alzheimer's & Dementia: The Journal of the Alzheimer's Association (2012) 8(4): P205.
DeVos et al., "Using antisense oligonucleotides to knockdown endogenous brain tau in vivo" poster presentation at AAIC 2012; Jul. 14-19, 2012, 1 page.
Donahue et al., "Stabilization of the Tau Exon 10 Stem Loop Alters Pre-mRNA Splicing" J. Biol. Chem. (2006) 281(33):23302-23306.
Duff et al., "Characterization of Pathology in Transgenic Mice Over Expression Human Genomic and cDNA Tau Transgenes", Neurobiology of Disease, 2000, 7:87-98.
Elayadi et al., Curr. Opinion Inves. Drugs, 2001, 2, 558-561.
Englisch et al., "Chemically Modified Oligonucleotides as Probes and Inhibitors" Angewandte Chemie, International Edition (1991) 30(6): 613-629.
European Patent Office Action for Application No. 13770075.3 dated Aug. 16, 2018, 8 pages.
European Patent Office Action for Application No. 13770075.3 dated Feb. 8, 2018, 5 pages.
Extended European Search Report for Application No. 13770075.3 dated Oct. 2, 2015, 8 pages.
Extended European Search Report for Application No. 14767904.7, dated Sep. 19, 2016, 10 pages.
Extended Examination Report for EP 14826839.4 dated Jul. 6, 2017, 11 pages.
Freier et al., Nucleic Acids Research, 1997, 25(22), 4429-4443.
Frieden et al., Nucleic Acids Research, 2003, 21, 6365-6372.
Frost, S. Digital Telerential Screen, 2012, 91-100.
Furdon, P. et al., Nucleic Acids Res. 17, 9193-9204 (1989).
Gagnon et al., "HD Therapeutics—CHDI Fifth Annual Conference," Presented at the CHDI Fifth Annual Therapeutics Conference in Palm Springs, CA, Feb. 8-11, 2010, IDrugs, Apr. 2010, 13(4):219-223.
Gautschi et al., J. Natl. Cancer Inst., 93:463-471, 2001.
GenBank Accession No. AK226139.1 (2007), 3 pages.
GenBank Accession No. NM_001123066.3 (2015), 6 pages.
GenBank Accession No. NM_001123067.3 (2015), 5 pages.
GenBank Accession No. NM_001203251.1 (2015), 5 pages.
GenBank Accession No. NM_001203252.1 (2015), 6 pages.
GenBank Accession No. NM_001285455.1, 2013, 4 pages.
GenBank Accession No. NM_005910.5 (2015), 6 pages.
GenBank Accession No. NM_016834.4 (2015), 4 pages.
GenBank Accession No. NM_016835.4 (2015), 19 pages.
GenBank Accession NT_010783.15 (2013), 5 pages.
GenBank Accession NT010783.14 (2008)., 7 pages.
GenkBank Accession No. NM_16841.4 (2015)., 3 pages.
Goedert et al., "Cloning and Sequencing of the cDNA Encoding a Core Protein of the Paired Helical Filament of Alzheimers Disease: Identification as the Microtubule-Associated Protein Tau" PNAS (1988) 85(11):4051-4055.
Goedert, M. et al., Neurosci. Lett. 1995, 167-9.
Gordon et al., "Antisense suppression of tau in cultured ray oligodendrocytes inhibits process formation", Journal of Neuroscience Research, May 2008, 86(12):2591-2601.
Gupta, N. et al., Can. J. Ophtalmol., 2008, 43:53-60.
Hall et al., 2002, Science, 297, 2232-2237.
Hatta et al., "Mechanisms of the inhibition of reverse transcription by unmodified and modified antisense oligonucleotides", 1993, 330(2):161-164.
Ho, W. L. et al., Molecular Vision, 2012, 18:2700-2710.
International Search Report and Written Opinion for Application No. PCT/US2013/31500 dated Jun. 5, 2013 (12 pages).
International Search Report and Written Opinion for Application No. PCT/US2014/047486, dated Feb. 9, 2015, 12 pages.
International Search Report and Written Opinion for Application No. PCT/US2015/042740, dated Dec. 15, 2015, 13 pages.
International Search Report and Written Opinion in International Application No. PCT/US2022/074014, mailed on Nov. 29, 2022, 16 pages.
International Search Report for application PCT/US2014/029752 dated Sep. 18, 2014, 10 pages.
International Search Report for Application PCT/US2017/054540 dated Jan. 18, 2018, 11 pages.
Japanese Patent Office Action for Application No. 2015503306, dated Jun. 12, 2018, 13 pages with English Translation.
Japanese Patent Office Action for Application No. 2015503306, dated Nov. 22, 2016, 5 pages with English Translation.
Jenuwein, 2002, Science, 297, 2215-2218.
Jiang et al., "Aberrant Splicing of tau Pre-mRNA Caused by Intronic Mutations Associated with the Inherited Dementia Frontotemporal Dementia with Parkinsonsism Linked to Chromosome 17" Mol. Cell Biol. (2000) 20(11):4036-4048.
Jones et al., "Targeting hyperphosphorylated tau with sodium selenate suppresses seizures in rodent models" Neurobiology of Disease (2012) 897-901.
Jones, L.J. et al., Analytical Biochemistry, 1998, 265, 368-374.
Kabanov et al., "A new class of antivirals: antisense oligonucleotides combined with a hydrophobic substituent effectively inhibit influenza vims reproduction and synthesis of vims-specific proteins in MDCK cells" FEBS Lett. (1990) 259:327-330.
Kalbfuss, B. et al., "Correction of Alternative Splicing of Tau in Frontotemporal Dementia and Parkinsonism Linked to Chromosome 17," Journal of Biological Chemistry, 2001, vol. 276, pp. 42986-42993.
Koshkin et al., Tetrahedron, 1998, 54, 3607-3630.
Kroschwitz, The Concise Encyclopedia of Polymer Science and Engineering, John Wiley & Sons, 1990, 858-859.
Kumar et al., "Design, synthesis, biophysical and primer extension studies of novel acyclic butyl nucleic acid (BuNA)," Org. Biomol. Chem, 2013, 11:5853-5865.
Kumar et al., Bioorg. Med. Chem. Lett., 1998, 8, 2219-2222.
Lane et al., "Discovery and early clinical development of Ionis-Maptrx, The first tau-lowering antisense oligonucelotide, in patients with mild AD", abstract presented at the Alzheimer's Association International Conference, Jul. 2017, London, England.
Letsinger et al., "Cholesteryl-conjugated oligonucleotides: Synthesis, properties, and activity as inhibitors of replication of human immunodeficiency vims in cell culture" PNAS (1989) 86:6553-6556.
Leumann, J. C., Bioorganic & Medicinal Chemistry, 2002, 10, 841-854.
Maher and Dolnick, Nuc. Acid. Res. 16:3341-3358, 1988.

(56) References Cited

OTHER PUBLICATIONS

Manoharan et al., "Chemical Modifications to Improve Uptake and Bioavailability of Antisense Oligonucleotides" Ann. N.Y. Acad. Sci. (1992) 660:306.
Manoharan et al., "Cholic Acid-Oligonucleotide Conjugates for Antisense Applications" Bioorg. Med. Chem. Lett. (1994) 4:1053-1060.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Lipidic Nucleic Acids", Tetrahedron Lett., 1995, 36(21):3651-3564.
Manoharan et al., "Oligonucleotide Conjugates: Alteration of the Pharmacokinetic Properties of Antisense Agents" Nucleosides & Nucleotides (1995) 14(3-5): 969-973.
Martin, P., Helv. Chim. Acta, 1995, 78, 486-504.
Mignon et al., "Design of the First-in-Human Study of IONIS-MAPTRx, a Tau-lowering Antisense Oligonucleotide, in Patients With Alzheimer Disease (S2.006)," Neurology, Apr. 2018, 7 pages.
Mishra et al., "Improved leishmanicidal effect of phosphorotioate antisense oligonucleotides by LDL-mediated delivery" Biochim. Biophys. Acta (1995) 1264:229-237.
Morita et al., Bioorganic Medicinal Chemistry, 2003, 11, 2211-2226.
New England Biolabs 1998/99 Catalog (cover page and pp. 121 and 284).
Nishina et al., "Chimeric antisense oligonucleotide conjugated to alpha-tocopherol", Molecular Therapy Nucleic Acids, 2015, 4:e220.
Nishina et al., "Efficient in vivo delivery of siRNA to the liver by conjugation of alpha-tocopherol", Molecular Therapy, 2008, 16(4):734-740.
Oberhauser et al., "Effective incoiporation of 2'-O-methyl-oligoribonucleotides into liposomes and enhanced cell association through modifications with thiocholesterol" Nucl. Acids Res. (1992) 20(3):533-538.
Oka et al., "An Oxazaphospholidine approach for the steroid controlled synthesis of oligonucleoside phosphorothioates", J. Am. Chem. Soc., 2003, 125:8307-8317.
Orum et al., Curr. Opinion Mol. Ther., 2001, 3, 239-243.
Pal-Bhadra et al., 2004, Science, 303, 669-672.
Peacey et al., "Targeting a pre-mRNA structure with bipartite antisense molecules modulates tau alternative splicing" Nucleic Acids Research (2012) 40(19):9836-9849.
Pizzi et al., "Antisense Strategy Unravels Tau Proteins as Molecular Risk Factors for Glutamate-Induced Neurodegeneration" Cellular and Molecular Neurobiology (1994) 14(5):569-578.
Prakash, "An overview of sugar-modified oligonucleotides for antisense therapeutics", Chemistry and Biodiversity, Sep. 2011, 8(9):1616-1641.
Reynolds et al., "Rational siRNA design for RNA interference" Nature Biotechnology (2004) 22(3):326-330.
Rodriguez-Martin, T. et al., Reprograming of tau alternative splicing by spliceosome-mediated RNA trans-splicing: Implications for taupathies, Proceedings of the National Academy of Sciences, 2005, Vo. 102, No. 43, pp. 15659-15664.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi and P. D. Cook Eds. ACS Symposium Series 580; Chapters 3 and 4, pp. 40-65.
Sanghvi et al., "Heterocyclic Base Modifications in Nucleic Acids and Their Applications in Antisense Oligonucleotides" Antisense Research and Applications (1993) pp. 273-288.
Sapir et al., "Tau's role in the developing brain: implications for intellectual disability" Human Molecular Genetics (2012) 21(8):1681-1692.
Sazani et al., "Therapeutic potential of antisense olignocleotides as modulators of alternative splicing", J. Clinical Invest, 2003, 112:481-486.
Schoch et al., "Antisense oligonucleotide-mediated tau splicing reduces behavioral deficits and tau pathology in a tauopathy model" abstract presented at Keystone Symposium: Alzheimer's Disease, Mar. 2-7, 2014, Keystone, CO.
Schoch et al., "Antisense oligonucleotide-mediated tau splicing reduces behavioral deficits and tau pathology in a tauopathy model" poster presented at Keystone Symposium: Alzheimer's Disease, Mar. 2-7, 2014, Keystone, CO.
Shea et al., "Synthesis, hybridization properties and antiviral activity of lipid-oligodeoxynucleotide conjugates" Nucl. Acids Res. (1990) 18(13):3777-3783.
Singh et al., Chem. Commun., 1998, 4, 455-456.
Singh et al., J. Org. Chem., 1998, 63, 10035-10039.
Smith and Waterman, Adv. Appl. Math., 1981, 2, 482-489.
Soeda et al., "New Insights Into Drug Discovery Targeting Tau Protein," Frontiers in Molecular Neuroscience, Dec. 2020, 13:1-24.
Southwell et al., "Antisense oligonucleotide therapeutics for inherited neurodegenerative diseases," Trends in Molecular Medicine, Nov. 2012, 18(11):634-643.
Spicakova et al., "Expression and silencing of the Microtubule-Associated Protein Tau in breast cancer cells", Molecular Cancer Therapeutics, Nov. 2010, 9(11):2970-2981.
Sproat, B. et al., Nucleic Acids Res. 17, 3373-3386 (1989).
Srivastava et al., J. Am. Chem. Soc., 2007, 129(26), 8362-8379.
Svinarchuk et al., "Inhibition of HIV proliferation in MT-4 cells by antisense oligonucleotide conjugated to lipophilic groups" Biochimie (1993) 75:49-54.
Usman et al., "Exploiting the chemical synthesis of RNA", Trends in Biochemical Sciences, Sep. 1992, 17(9):334-339.
Verdel et al., 2004, Science, 303, 672-676.
Vickers et al., "Efficient Reduction of Target RNAs by Small Interfering RNA and Rnase H-dependent Antisense Agents," J. Biol. Chem., 2003, 279(9):7108-7118.
Volpe et al., 2002, Science, 297, 1833-1837.
Wahlestedt et al., Proc. Natl. Acad. Sci. U.S.A., 2000, 97, 5633-5638.
Walder, R. and Walder, J., Proc. Natl. Acad. Sci. USA 85, 5011-5015 (1988).
Wan et al., "Synthesis, biophysical properties and biological activity of second generation antisense oligonucleotides containing chiral phosphorothioate linkages", Nucleic Acids Research, 2014, 42(22):13456-12468.
Wang et al., "A Novel Tau Transcript in Cultured Human Neuroblastoma Cells Expression Nuclear Tau" J. Cell Biol. (1993) 121(2):257-267.
Wolfe et al., "Tau Mutations in Neurodegenerative Diseases", J. Biol Chem, 2009, 284(10):3021-3025.
Wolfe M.S., "The Roll of Tau in Neurodegenerative Diseases and Its Potential as a Therapeutic Target" Scientifica (2012) 1-20.
Woolf et al., Proc. Natl. Acad. Sci. USA 89:7305-7309, 1992.
Yamada et al., Neurosci. 2011, 31: 13110-117.
Yoshiyama, Y. et al., Neuron 53: 337-351, 2007.
Zhang and Madden, Genome Res., 1997, 7, 649-656.
Zhou et al., "Fine Tuning of Electrostatics around the Intemucleotidic Phosphate through Incorporation of Modified 2',4'-Carbocyclic-LNAs and -ENAs Leads to Significant Modulation of Antisense Properties" J. Org. Chem. (2009) 74:118-134.
Pizzi et al., "Inhibition of Glutamate-induced Neurotoxicity by a Tau Antisense Oligonucleotide in Primary Culture of Rat Cerebellar Granule Cells," European Journal of Neuroscience, Jul. 31, 1995, 7(7):1603-1613.
U.S. Appl. No. 14/387,853, filed Sep. 25, 2014, U.S. Pat. No. 10,273,474, Miller.
U.S. Appl. No. 16/298,607, filed Mar. 11, 2019, Miller.
U.S. Appl. No. 18/366,521, filed Aug. 7, 2023, Miller.
U.S. Appl. No. 14/906,047, filed Jan. 19, 2016, U.S. Pat. No. 9,683,235, Kordasiewicz.
U.S. Appl. No. 15/593,173, filed May 11, 2017, U.S. Pat. No. 10,793,856, Kordasiewicz.
U.S. Appl. No. 16/986,770, filed Aug. 6, 2020, U.S. Pat. No. 11,591,595, Kordasiewicz.
U.S. Appl. No. 16/336,443, filed Mar. 25, 2019, Kordasiewicz.
U.S. Appl. No. 15/721,366, filed Sep. 29, 2017, U.S. Pat. No. 10,407,680, Kordasiewicz.

(56) References Cited

OTHER PUBLICATIONS

U.S. Appl. No. 16/527,574, filed Jul. 31, 2019, U.S. Pat. No. 11,053,498, Kordasiewicz.
U.S. Appl. No. 17/339,475, filed Jun. 4, 2021, Kordasiewicz.
U.S. Appl. No. 17/574,681, filed Jan. 13, 2022, Kordasiewicz.
U.S. Appl. No. 17/821,512, filed Aug. 23, 2022, Kordasiewicz.
Grünweller, A et al., Comparison of different antisense strategies in mammalian cells using locked nucleic acids, 2'-O-methyl RNA, phosphorothioates and small interfering RNA, Nucleic Acids Research, 31(12):3185-3193 (2003).
Miller, T. M. et al., A Phase I, Randomised, First-in-Human Study of an Antisense Oligonucleotide Directed Against SOD1 Delivered Intrathecally in SOD1-Familial ALS Patients, Lancet Nueurol., 12(5): 435-442 (2013).
Monia, et al., Selective Inhibition of Mutant Ha-ras mRNA Expression by Antisense Oligonucleotides*, The Journal of Biological Chemistry, 267(28): 19954-19962 (1992).
Wagner, R. W. et al., Potent and selective inhibition of gene expression by an antisense heptanucleotide, Nature Biotechnol., 14(7):840-844 (1996).

* cited by examiner

COMPOSITIONS FOR MODULATING TAU EXPRESSION

CROSS-REFERENCE TO RELATED APPLICATIONS

This application is a divisional of U.S. application Ser. No. 16/986,770, filed Aug. 6, 2020, (now U.S. Pat. No. 11,591,595), which is a divisional of U.S. application Ser. No. 15/593,173, filed May 11, 2017, (now U.S. Pat. No. 10,793,856), which is a divisional of U.S. application Ser. No. 14/906,047, filed Jan. 19, 2016, (now U.S. Pat. No. 9,683,235), which is a 371 of International Application No. PCT/US2014/047486, filed Jul. 21, 2014, which claims benefit of priority to U.S. Provisional Application Nos. 62/014,486, filed Jun. 19, 2014; 61/885,371, filed Oct. 1, 2013; 61/879,621, filed Sep. 18, 2013; and 61/856,551, filed Jul. 19, 2013, the contents of all of which are hereby incorporated by reference in their entireties.

SEQUENCE LISTING

The present application is being filed along with a Sequence Listing in electronic format. The Sequence Listing is provided as a file entitled 13751-0327004SEQ_ST26.xml created Jan. 17, 2023, which is 3,497 Kb in size. The information in the electronic format of the sequence listing is incorporated herein by reference in its entirety.

FIELD

Provided are compositions and methods for reducing expression of Tau mRNA and protein in an animal. Such methods are useful to treat, prevent, or ameliorate neurodegenerative diseases, including Tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome by inhibiting expression of Tau in an animal.

BACKGROUND

The primary function of Tau is to bind to and stabilize microtubules, which are important structural components of the cytoskeleton involved in mitosis, cytokinesis, and vesicular transport. Tau is found in multiple tissues, but is particularly abundant in axons of neurons. In humans, there are six isoforms of Tau that are generated by alternative splicing of exons 2, 3, and 10. Splicing of exons 2 and 3 at the N-terminus of the protein leads to inclusion of zero, one, or two 29 amino acid acidic domains and is termed 0N, 1N, or 2N Tau respectively. The influence of these domains on Tau function is not fully clear, though may play a role in interactions with the plasma membrane. Inclusion of exon 10 at the C-terminus leads to inclusion of the microtubule binding domain encoded by exon 10. Since there are 3 microtubule binding domains elsewhere in Tau, this Tau isoform (with exon 10 included) is termed 4R Tau, where 'R' refers to the number of repeats of microtubule binding domains. Tau without exon 10 is termed 3R Tau. Since more microtubule binding domains (4R compared with 3R) increases the binding to microtubules, 4R Tau presumably significantly increases microtubule binding and assembly. The ratio of 3R/4R Tau is developmentally regulated, with fetal tissues expressing exclusively 3R Tau and adult human tissues expressing approximately equal levels of 3R/4R Tau. Deviations from the normal ratio of 3R/4R Tau are characteristic of neurodegenerative FTD Tauopathies. It is not known how changing the 3R/4R Tau ratio at a later stage in the adult animal will affect Tau pathogenesis.

Serine-threonine directed phosphorylation regulates the microtubule binding ability of Tau. Hyperphosphorylation promotes detachment of Tau from microtubules. Other post translational modifications of Tau have been described; however the significance of these is unclear. Phosphorylation of Tau is also developmentally regulated with higher phosphorylation in fetal tissues and much lower phosphorylation in the adult. One characteristic of neurodegenerative disorders is aberrantly increased Tau phosphorylation.

The microtubule network is involved in many important processes within the cell including structural integrity needed for maintaining morphology of cells and operating transport machinery. Since binding of Tau to microtubules stabilizes microtubules, Tau is likely to be a key mediator of some of these processes and disruption of normal Tau in neurodegenerative diseases may disrupt some of these key cellular processes.

One of the early indicators that Tau may be important in neurodegenerative syndromes was the recognition that Tau is a key component of neurofibrillary inclusions in Alzheimer's disease. In fact, neurofibrillary inclusions are aggregates of hyperphosphorylated Tau protein. Along with amyloid beta containing plaques, neurofibrillary inclusions are a hallmark of Alzheimer's disease and correlate significantly with cognitive impairment. 95% of Tau accumulations in AD are found in neuronal processes and is termed neuritic dystrophy. The process(es) whereby this microtubule associated protein becomes disengaged from microtubules and forms accumulations of proteins and how this relates to neuronal toxicity is not well understood.

Neuronal Tau inclusions are a pathological characteristic of not only Alzheimer's disease, but also a subset of Frontotemporal dementia (FTD), PSP, and CBD. The link between Tau and neurodegeneration was solidified by the discovery that mutations in the Tau gene cause a subset of FTD. These genetic data have also highlighted the importance of the 3R:4R ratio of Tau. Many of the Tau mutations that cause FTD lead to a change in Tau splicing which leads to preferential inclusion of exon 10, and thus to increased 4R Tau. The overall Tau levels are normal. Whether the Tau isoform change or the amino acid change or both cause neurodegeneration remains unknown. Recent data suggest that PSP may also be associated with an increased 4R:3R Tau ratio.

To help understand the influence of Tau ratios on neurodegeneration, a mouse model based on one of the splicing Tau mutations (N279K) has been generated using a minigene that includes the Tau promoter and the flanking intronic sequences of exon 10. As in humans, these mice demonstrate increased levels of 4R Tau compared with transgenics expressing WT Tau and develop behavioral and motor abnormalities as well as accumulations of aggregated Tau in the brain and spinal cord.

The protein "Tau" has been associated with multiple diseases of the brain including Alzheimer's disease, frontotemporal dementia, progressive supranuclear palsy, corticobasal ganglionic degeneration, dementia pugilistica, parkinsonism linked to chromosome, Lytico-Bodig disease, tangle-predominant dementia, ganglioglioma, gangliocytoma, meningioangiomatosis, subacute sclerosing panencephalitis, lead encephalopathy, tuberous sclerosis, Hallervorden-Spatz disease, Pick's disease, argyrophilic grain disease, corticobasal degeneration or frontotemporal lobar degeneration and others. Tau-associated disorders such as AD are the most common cause of dementia in the elderly. AD affects an estimated 15 million people worldwide and 40% of the population above 85 years of age. AD is characterized by two pathological hallmarks: Tau neurofibrillary inclusions (NFT) and amyloid-β (Aβ) plaques.

There is currently a lack of acceptable options for treating such neurodegenerative diseases. It is therefore an object herein to provide methods for the treatment of such diseases.

SUMMARY

Provided herein are methods, compounds, and compositions for modulating expression of Tau mRNA and protein. In certain embodiments, compounds useful for modulating expression of Tau mRNA and protein are antisense compounds. In certain embodiments, the antisense compounds are antisense oligonucleotides.

In certain embodiments, modulation can occur in a cell or tissue. In certain embodiments, the cell or tissue is in an animal. In certain embodiments, the animal is a human. In certain embodiments, Tau mRNA levels are reduced. In certain embodiments, Tau protein levels are reduced. Such reduction can occur in a time-dependent manner or in a dose-dependent manner.

Also provided are methods, compounds, and compositions useful for preventing, treating, and ameliorating diseases, disorders, and conditions. In certain embodiments, such Tau related diseases, disorders, and conditions are neurodegenerative diseases. In certain embodiments, such neurodegenerative diseases, disorders, and conditions include Tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome Such diseases, disorders, and conditions can have one or more risk factors, causes, or outcomes in common. Certain risk factors and causes for development of neurodegenerative disorder include growing older, having a personal or family history, or genetic predisposition. Certain symptoms and outcomes associated with development of a neurodegenerative disorder include but are not limited to: presence of hyperphosphorylated Tau, presence of neurofibrillary inclusions, reduction of neurological function, reduced memory, reduced motor function, reduced motor coordination, and confusion.

In certain embodiments, methods of treatment include administering a Tau antisense compound to an individual in need thereof. In certain embodiments, methods of treatment include administering a Tau antisense oligonucleotide to an individual in need thereof.

The present disclosure provides the following non-limiting numbered embodiments:

Embodiment 1: A compound, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 20-2443 and SEQ ID NOs: 2478-2483.

Embodiment 2: A compound, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 2444-2477 and SEQ ID NOs: 2484-2565.

Embodiment 3: A compound, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 20-2565.

Embodiment 4: A compound, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135980 of SEQ ID NO: 1.

Embodiment 5: A compound, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135853-135872 of SEQ ID NO: 1.

Embodiment 6: A compound, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135929 of SEQ ID NO: 1.

Embodiment 7: A compound, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135914 of SEQ ID NO: 1.

Embodiment 8: The compound of embodiments 4-7, wherein the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1.

Embodiment 9: The compound of any preceding embodiment, consisting of a single-stranded modified oligonucleotide.

Embodiment 10: The compound of any preceding embodiment, wherein at least one internucleoside linkage is a modified internucleoside linkage.

Embodiment 11: The compound of embodiment 10, wherein at least one modified internucleoside linkage is a phosphorothioate internucleoside linkage.

Embodiment 12: The compound of embodiment 10, wherein each modified internucleoside linkage is a phosphorothioate internucleoside linkage.

Embodiment 13: The compound of any preceding embodiment, wherein at least one internucleoside linkage is a phosphodiester internucleoside linkage.

Embodiment 14: The compound of any preceding embodiment, wherein at least one internucleoside linkage is a phosphorothioate linkage and at least one internucleoside linkage is a phosphodiester linkage.

Embodiment 15: The compound of any preceding embodiment, wherein at least one nucleoside comprises a modified nucleobase.

Embodiment 16: The compound of embodiment 15, wherein the modified nucleobase is a 5-methylcytosine.

Embodiment 17: The compound of any preceding embodiment, wherein at least one nucleoside of the modified oligonucleotide comprises a modified sugar.

Embodiment 18: The compound of embodiment 17, wherein the at least one modified sugar is a bicyclic sugar.

Embodiment 19: The compound of embodiment 18, wherein the bicyclic sugar comprises a chemical link between the 2' and 4' position of the sugar 4'-CH2-N(R)—O-2' bridge wherein R is, independently, H, C1-C12 alkyl, or a protecting group.

Embodiment 20: The compound of embodiment 18, wherein the bicyclic sugar comprises a 4'-CH2-N(R)—O-2' bridge wherein R is, independently, H, C1-C12 alkyl, or a protecting group.

Embodiment 21: The compound of embodiment 17, wherein at least one modified sugar comprises a 2'-O-methoxyethyl group.

Embodiment 22: The compound of embodiment 17, wherein the modified sugar comprises a 2'-O(CH$_2$)$_2$—OCH$_3$ group.

Embodiment 23: The compound of any preceding embodiment, wherein the modified oligonucleotide comprises:
 a gap segment consisting of 10 linked deoxynucleosides;
 a 5' wing segment consisting of 5 linked nucleosides; and
 a 3' wing segment consisting of 5 linked nucleosides;
 wherein the gap segment is positioned between the 5' wing segment and the 3' wing segment and wherein each nucleoside of each wing segment comprises a modified sugar.

Embodiment 24: The compound of any preceding embodiment, wherein the modified oligonucleotide comprises:
 a gap segment consisting of 9 linked deoxynucleosides;
 a 5' wing segment consisting of 5 linked nucleosides; and
 a 3' wing segment consisting of 5 linked nucleosides;
 wherein the gap segment is positioned between the 5' wing segment and the 3' wing segment and wherein each nucleoside of each wing segment comprises a modified sugar.

Embodiment 25: The compound of any preceding embodiment, wherein the modified oligonucleotide comprises:
 a gap segment consisting of 7 linked deoxynucleosides;
 a 5' wing segment consisting of 5 linked nucleosides; and
 a 3' wing segment consisting of 6 linked nucleosides;
 wherein the gap segment is positioned between the 5' wing segment and the 3' wing segment and wherein each nucleoside of each wing segment comprises a modified sugar.

Embodiment 26: The compound of any preceding embodiment, wherein the modified oligonucleotide comprises:
 a gap segment consisting of 8 linked deoxynucleosides;
 a 5' wing segment consisting of 5 linked nucleosides; and
 a 3' wing segment consisting of 5 linked nucleosides;
 wherein the gap segment is positioned between the 5' wing segment and the 3' wing segment and wherein each nucleoside of each wing segment comprises a modified sugar.

Embodiment 27: The compound of any preceding embodiment, wherein the modified oligonucleotide comprises:
 a gap segment consisting of 8 linked deoxynucleosides;
 a 5' wing segment consisting of 4 linked nucleosides; and
 a 3' wing segment consisting of 6 linked nucleosides;
 wherein the gap segment is positioned between the 5' wing segment and the 3' wing segment and wherein each nucleoside of each wing segment comprises a modified sugar.

Embodiment 28: The compound of any preceding embodiment, wherein the modified oligonucleotide comprises:
 a gap segment consisting of 8 linked deoxynucleosides;
 a 5' wing segment consisting of 6 linked nucleosides; and
 a 3' wing segment consisting of 4 linked nucleosides;
 wherein the gap segment is positioned between the 5' wing segment and the 3' wing segment and wherein each nucleoside of each wing segment comprises a modified sugar.

Embodiment 29: The compound of any preceding embodiment, wherein the modified oligonucleotide consists of 20 linked nucleosides.

Embodiment 30: The compound of any preceding embodiment, wherein the modified oligonucleotide consists of 19 linked nucleosides.

Embodiment 31: The compound of any preceding embodiment, wherein the modified oligonucleotide consists of 18 linked nucleosides.

Embodiment 32: A composition comprising the compound of any preceding embodiment or salt thereof and at least one of a pharmaceutically acceptable carrier or diluent.

Embodiment 33: A method comprising administering to an animal the compound or composition of any preceding embodiment.

Embodiment 34: The method of embodiment 33, wherein the animal is a human.

Embodiment 35: The method of embodiment 33, wherein administering the compound prevents, treats, ameliorates, or slows progression of a tau associated disease, disorder or condition.

Embodiment 36: The method of embodiment 35, wherein the disease, disorder or condition is a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

Embodiment 37: Use of the compound or composition of any preceding embodiment for the manufacture of a medicament for treating a neurodegenerative disorder.

Embodiment 38: A compound consisting of ISIS 613099.
Embodiment 39: A compound consisting of ISIS 613361.
Embodiment 40: A compound consisting of ISIS 613370.
Embodiment 41: A compound consisting of ISIS 623782.
Embodiment 42: A compound consisting of ISIS 623996.

Embodiment 43: A composition comprising the compound of any of embodiments 38-42, or salt thereof, and at least one of a pharmaceutically acceptable carrier or diluent.

Embodiment 44: A method comprising administering to an animal the compound or composition of any of embodiments 38-43.

Embodiment 45: The method of embodiment 44, wherein the animal is a human.

Embodiment 46: The method of embodiment 44, wherein administering the compound prevents, treats, ameliorates, or slows progression of a tau associated disease, disorder or condition.

Embodiment 47: The method of embodiment 46, wherein the disease, disorder or condition is a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

Embodiment 48: Use of the compound or composition of any of embodiments 38-43 for the manufacture of a medicament for treating a neurodegenerative disorder.

DETAILED DESCRIPTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Additionally, as used herein, the use of "and" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this disclosure, including, but not limited to, patents, patent applications, published patent applications, articles, books, treatises, and GENBANK Accession Numbers and associated sequence information obtainable through databases such as National Center for Biotechnology Information (NCBI) and other data referred to throughout in the disclosure herein are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis.

Unless otherwise indicated, the following terms have the following meanings:

"2'-O-methoxyethyl" (also 2'-MOE and 2'-OCH$_2$CH$_2$—OCH$_3$ and MOE) refers to an O-methoxyethyl modification of the 2' position of a furanose ring. A 2'-O-methoxyethyl modified sugar is a modified sugar.

"2'-MOE nucleoside" (also 2'-O-methoxyethyl nucleoside) means a nucleoside comprising a 2'-MOE modified sugar moiety.

"2'-substituted nucleoside" means a nucleoside comprising a substituent at the 2'-position of the furanose ring other than H or OH. In certain embodiments, 2' substituted nucleosides include nucleosides with bicyclic sugar modifications.

"5-methylcytosine" means a cytosine modified with a methyl group attached to the 5 position. A 5-methylcytosine is a modified nucleobase.

"About" means within ±7% of a value. For example, if it is stated, "the compounds affected at least about 70% inhibition of Tau", it is implied that the Tau levels are inhibited within a range of 63% and 77%.

"Administered concomitantly" refers to the co-administration of two pharmaceutical agents in any manner in which the pharmacological effects of both are manifest in the patient at the same time. Concomitant administration does not require that both pharmaceutical agents be administered in a single pharmaceutical composition, in the same dosage form, or by the same route of administration. The effects of both pharmaceutical agents need not manifest themselves at the same time. The effects need only be overlapping for a period of time and need not be coextensive.

"Administering" means providing a pharmaceutical agent to an animal, and includes, but is not limited to administering by a medical professional and self-administering.

"Amelioration" refers to a lessening, slowing, stopping, or reversing of at least one indicator of the seventy of a condition or disease. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antibody" refers to a molecule characterized by reacting specifically with an antigen in some way, where the antibody and the antigen are each defined in terms of the other. Antibody may refer to a complete antibody molecule or any fragment or region thereof, such as the heavy chain, the light chain, Fab region, and Fc region.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding. Examples of antisense compounds include single-stranded and double-stranded compounds, such as, antisense oligonucleotides, siRNAs, shRNAs, ssRNAs, and occupancy-based compounds.

"Antisense inhibition" means reduction of target nucleic acid levels in the presence of an antisense compound complementary to a target nucleic acid compared to target nucleic acid levels or in the absence of the antisense compound.

"Antisense mechanisms" are all those mechanisms involving hybridization of a compound with a target nucleic acid, wherein the outcome or effect of the hybridization is either target degradation or target occupancy with concomitant stalling of the cellular machinery involving, for example, transcription or splicing.

"Antisense oligonucleotide" means a single-stranded oligonucleotide having a nucleobase sequence that permits hybridization to a corresponding segment of a target nucleic acid.

"Base complementarity" refers to the capacity for the precise base pairing of nucleobases of an antisense oligonucleotide with corresponding nucleobases in a target nucleic acid (i.e., hybridization), and is mediated by Watson-Crick, Hoogsteen or reversed Hoogsteen hydrogen binding between corresponding nucleobases.

"Bicyclic sugar" means a furanose ring modified by the bridging of two atoms. A bicyclic sugar is a modified sugar.

"Bicyclic nucleoside" (also BNA) means a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring.

"Cap structure" or "terminal cap moiety" means chemical modifications, which have been incorporated at either terminus of an antisense compound.

"cEt" or "constrained ethyl" means a bicyclic nucleoside having a sugar moiety comprising a bridge connecting the 4'-carbon and the 2'-carbon, wherein the bridge has the formula: 4'-CH(CH$_3$)—O-2'.

"Constrained ethyl nucleoside" (also cEt nucleoside) means a nucleoside comprising a bicyclic sugar moiety comprising a 4'-CH(CH$_3$)—O-2' bridge.

"Chemically distinct region" refers to a region of an antisense compound that is in some way chemically different than another region of the same antisense compound. For example, a region having 2'-O-methoxyethyl nucleosides is chemically distinct from a region having nucleosides without 2'-O-methoxyethyl modifications.

"Chimeric antisense compound" means an antisense compound that has at least two chemically distinct regions, each position having a plurality of subunits.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Comprise," "comprises," and "comprising" will be understood to imply the inclusion of a stated step or element or group of steps or elements but not the exclusion of any other step or element or group of steps or elements.

"Contiguous nucleobases" means nucleobases immediately adjacent to each other.

"Designing" or "designed to" refer to the process of designing an oligomeric compound that specifically hybridizes with a selected nucleic acid molecule.

"Diluent" means an ingredient in a composition that lacks pharmacological activity, but is pharmaceutically necessary or desirable. For example, in drugs that are injected, the diluent may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" in the context of modulating an activity or of treating or preventing a condition means the administration of that amount of pharmaceutical agent to a subject in need of such modulation, treatment, or prophylaxis, either in a single dose or as part of a series, that is effective for modulation of that effect, or for treatment or prophylaxis or improvement of that condition. The effective amount may vary among individuals depending on the health and physical condition of the individual to be treated, the taxonomic group of the individuals to be treated, the formulation of the composition, assessment of the individual's medical condition, and other relevant factors.

"Efficacy" means the ability to produce a desired effect.

"Expression" includes all the functions by which a gene's coded information is converted into structures present and operating in a cell. Such structures include, but are not limited to the products of transcription and translation.

"Fully complementary" or "100% complementary" means each nucleobase of a first nucleic acid has a complementary nucleobase in a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap" and the external regions may be referred to as the "wings."

"Gap-narrowed" means a chimeric antisense compound having a gap segment of 9 or fewer contiguous 2'-deoxyribonucleosides positioned between and immediately adjacent to 5' and 3' wing segments having from 1 to 6 nucleosides.

"Gap-widened" means a chimeric antisense compound having a gap segment of 12 or more contiguous 2'-deoxyribonucleosides positioned between and immediately adjacent to 5' and 3' wing segments having from 1 to 6 nucleosides.

"Hybridization" means the annealing of complementary nucleic acid molecules. In certain embodiments, complementary nucleic acid molecules include, but are not limited to, an antisense compound and a target nucleic acid. In certain embodiments, complementary nucleic acid molecules include, but are not limited to, an antisense oligonucleotide and a nucleic acid target.

"Identifying an animal having a Tau associated disease" means identifying an animal having been diagnosed with a Tau associated disease or predisposed to develop a Tau associated disease. Individuals predisposed to develop a Tau associated disease include those having one or more risk factors for developing a Tau associated disease, including, growing older, having a personal or family history, or genetic predisposition of one or more Tau associated diseases. Such identification may be accomplished by any method including evaluating an individual's medical history and standard clinical tests or assessments, such as genetic testing.

"Immediately adjacent" means there are no intervening elements between the immediately adjacent elements.

"Individual" means a human or non-human animal selected for treatment or therapy.

"Inhibiting Tau" means reducing the level or expression of a Tau mRNA and/or protein. In certain embodiments, Tau mRNA and/or protein levels are inhibited in the presence of an antisense compound targeting Tau, including an antisense oligonucleotide targeting Tau, as compared to expression of Tau mRNA and/or protein levels in the absence of a Tau antisense compound, such as an antisense oligonucleotide.

"Inhibiting the expression or activity" refers to a reduction or blockade of the expression or activity and does not necessarily indicate a total elimination of expression or activity.

"Internucleoside linkage" refers to the chemical bond between nucleosides.

"Linked nucleosides" means adjacent nucleosides linked together by an internucleoside linkage.

"Locked nucleic acid" or "LNA" or "LNA nucleosides" means nucleic acid monomers having a bridge connecting two carbon atoms between the 4' and 2'position of the nucleoside sugar unit, thereby forming a bicyclic sugar. Examples of such bicyclic sugar include, but are not limited to A) α-L-Methyleneoxy (4'-CH$_2$—O-2') LNA, (B) β-D-Methyleneoxy (4'-CH$_2$—O-2') LNA, (C) Ethyleneoxy (4'-(CH$_2$)$_2$—O-2') LNA, (D) Aminooxy (4'-CH$_2$—O—N(R)-2') LNA and (E) Oxyamino (4'-CH$_2$—N(R)—O-2') LNA, as depicted below.

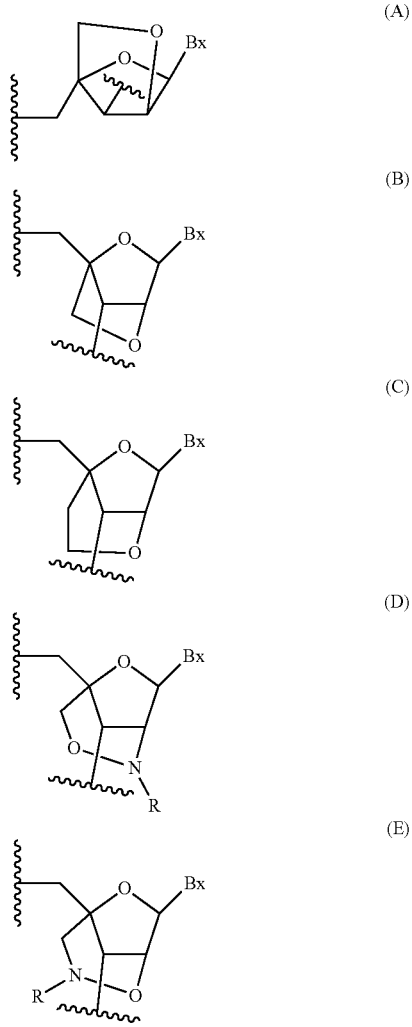

As used herein, LNA compounds include, but are not limited to, compounds having at least one bridge between the 4' and the 2' position of the sugar wherein each of the bridges independently comprises 1 or from 2 to 4 linked groups independently selected from —[C(R$_1$)(R$_2$)]$_n$—, —C(R$_1$)=C(R$_2$)—, —C(R$_1$)=N—, —C(=NR$_1$)—, —C(=O)—, —C(=S)—, —O—, —Si(R$_1$)$_2$—, —S(=O)$_x$—, and —N(R$_1$)—; wherein: x is 0, 1, or 2; n is 1, 2, 3, or 4; each R$_1$ and R$_2$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, a heterocycle radical, a substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

Examples of 4'-2' bridging groups encompassed within the definition of LNA include, but are not limited to one of formulae: —[C(R$_1$)(R$_2$)]$_n$—, —[C(R$_1$)(R$_2$)]$_n$—O—, —C(R$_1$R$_2$)—N(R$_1$)—O— or —C(R$_1$R$_2$)—O—N(R$_1$)—. Furthermore, other bridging groups encompassed with the definition of LNA are 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R$_1$)-2' and 4'-CH$_2$—N(R$_1$)—O-2'- bridges, wherein each R$_1$ and R$_2$ is, independently, H, a protecting group or C$_1$-C$_{12}$ alkyl.

Also included within the definition of LNA according to the invention are LNAs in which the 2'-hydroxyl group of the ribosyl sugar ring is connected to the 4' carbon atom of the sugar ring, thereby forming a methyleneoxy (4'-CH$_2$—O-2') bridge to form the bicyclic sugar moiety. The bridge can also be a methylene (—CH$_2$—) group connecting the 2' oxygen atom and the 4' carbon atom, for which the term methyleneoxy (4'-CH$_2$—O-2') LNA is used. Furthermore; in the case of the bicyclic sugar moiety having an ethylene bridging group in this position, the term ethyleneoxy (4'-CH$_2$CH$_2$—O-2') LNA is used. α-L-methyleneoxy (4'-CH$_2$—O-2'), an isomer of methyleneoxy (4'-CH$_2$—O-2') LNA is also encompassed within the definition of LNA, as used herein.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e., a phosphodiester internucleoside bond).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

A "modified nucleoside" means a nucleoside having, independently, a modified sugar moiety and/or modified nucleobase.

"Modified nucleotide" means a nucleotide having, independently, a modified sugar moiety, modified internucleoside linkage, and/or modified nucleobase.

"Modified oligonucleotide" means an oligonucleotide comprising at least one modified internucleoside linkage, modified sugar, and/or modified nucleobase.

"Modified sugar" means substitution and/or any change from a natural sugar moiety.

"Monomer" means a single unit of an oligomer. Monomers include, but are not limited to, nucleosides and nucleotides, whether naturally occurring or modified.

"Motif" means the pattern of unmodified and modified nucleosides in an antisense compound.

"Natural sugar moiety" means a sugar moiety found in DNA (2'-H) or RNA (2'-OH).

"Naturally occurring internucleoside linkage" means a 3' to 5' phosphodiester linkage.

"Non-complementary nucleobase" refers to a pair of nucleobases that do not form hydrogen bonds with one another or otherwise support hybridization.

"Nucleic acid" refers to molecules composed of monomeric nucleotides. A nucleic acid includes, but is not limited to, ribonucleic acids (RNA), deoxyribonucleic acids (DNA), single-stranded nucleic acids, double-stranded nucleic acids, small interfering ribonucleic acids (siRNA), and microRNAs (miRNA).

"Nucleobase" means a heterocyclic moiety capable of pairing with a base of another nucleic acid.

"Nucleobase complementarity" refers to a nucleobase that is capable of base pairing with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

"Nucleobase sequence" means the order of contiguous nucleobases independent of any sugar, linkage, and/or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo, or tricyclo sugar mimetics, e.g., non furanose sugar units. Nucleotide mimetic includes those structures used to replace the nucleoside and the linkage at one or more positions of an oligomeric compound such as for example peptide nucleic acids or morpholinos (morpholinos linked by —N(H)—C(=O)—O— or other non-phosphodiester linkage). Sugar surrogate overlaps with the slightly broader term nucleoside mimetic but is intended to indicate replacement of the sugar unit (furanose ring) only. The tetrahydropyranyl rings provided herein are illustrative of an example of a sugar surrogate wherein the furanose sugar group has been replaced with a tetrahydropyranyl ring system. "Mimetic" refers to groups that are substituted for a sugar, a nucleobase, and/or internucleoside linkage. Generally, a mimetic is used in place of the sugar or sugar-internucleoside linkage combination, and the nucleobase is maintained for hybridization to a selected target.

"Nucleotide" means a nucleoside having a phosphate group covalently linked to the sugar portion of the nucleoside.

"Off-target effect" refers to an unwanted or deleterious biological effect associated with modulation of RNA or protein expression of a gene other than the intended target nucleic acid.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection (e.g., bolus injection) or infusion. Parenteral administration includes subcutaneous administration, intravenous administration, intramuscular administration, intraarterial administration, intraperitoneal administration, or intracranial administration, e.g., intrathecal or intracerebroventricular administration.

"Peptide" means a molecule formed by linking at least two amino acids by amide bonds. Without limitation, as used herein, peptide refers to polypeptides and proteins.

"Pharmaceutical agent" means a substance that provides a therapeutic benefit when administered to an individual. For example, in certain embodiments, an antisense oligonucleotide targeted to Tau is a pharmaceutical agent.

"Pharmaceutical composition" means a mixture of substances suitable for administering to a subject. For example, a pharmaceutical composition may comprise an antisense oligonucleotide and a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e., linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" or "preventing" refers to delaying or forestalling the onset or development of a disease, disorder, or condition for a period of time from minutes to days, weeks to months, or indefinitely.

"Prodrug" means a therapeutic agent that is prepared in an inactive form that is converted to an active form (i.e., drug) within the body or cells thereof by the action of endogenous enzymes or other chemicals and/or conditions.

"Prophylactically effective amount" refers to an amount of a pharmaceutical agent that provides a prophylactic or preventative benefit to an animal.

"Region" is defined as a portion of the target nucleic acid having at least one identifiable structure, function, or characteristic.

"Ribonucleotide" means a nucleotide having a hydroxy at the 2' position of the sugar portion of the nucleotide. Ribonucleotides may be modified with any of a variety of substituents.

"Salts" mean a physiologically and pharmaceutically acceptable salts of antisense compounds, i.e., salts that retain the desired biological activity of the parent oligonucleotide and do not impart undesired toxicological effects thereto.

"Segments" are defined as smaller or sub-portions of regions within a target nucleic acid.

"Shortened" or "truncated" versions of antisense oligonucleotides taught herein have one, two or more nucleosides deleted.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies.

"Single-stranded oligonucleotide" means an oligonucleotide which is not hybridized to a complementary strand.

"Sites," as used herein, are defined as unique nucleobase positions within a target nucleic acid.

"Slows progression" means decrease in the development of the said disease.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e., under physiological conditions in the case of in vivo assays and therapeutic treatments.

"Stringent hybridization conditions" or "stringent conditions" refer to conditions under which an oligomeric compound will hybridize to its target sequence, but to a minimal number of other sequences.

"Subject" means a human or non-human animal selected for treatment or therapy.

"Target" refers to a protein, the modulation of which is desired.

"Target gene" refers to a gene encoding a target.

"Targeting" or "targeted" means the process of design and selection of an antisense compound that will specifically hybridize to a target nucleic acid and induce a desired effect.

"Target nucleic acid," "target RNA," and "target RNA transcript" and "nucleic acid target" all mean a nucleic acid capable of being targeted by antisense compounds.

"Target region" means a portion of a target nucleic acid to which one or more antisense compounds is targeted.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Tau" means mammalian microtubule-associated protein tau (MAPT), including human microtubule-associated protein tau (MAPT).

"Tau associated disease" means any disease associated with any Tau nucleic acid or expression product thereof. Such diseases may include a neurodegenerative disease. Such neurodegenerative diseases may include Tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

"Tau mRNA" means any messenger RNA expression product of a DNA sequence encoding Tau.

"Tau nucleic acid" means any nucleic acid encoding Tau. For example, in certain embodiments, a Tau nucleic acid includes a DNA sequence encoding Tau, an RNA sequence transcribed from DNA encoding Tau (including genomic DNA comprising introns and exons), and an mRNA sequence encoding Tau. "Tau mRNA" means an mRNA encoding a Tau protein.

"Tau protein" means the polypeptide expression product of a Tau nucleic acid.

"Therapeutically effective amount" means an amount of a pharmaceutical agent that provides a therapeutic benefit to an individual.

"Treat" or "treating" or "treatment" refers administering a composition to effect an alteration or improvement of the disease or condition.

"Unmodified nucleobases" mean the purine bases adenine (A) and guanine (G), and the pyrimidine bases thymine (T), cytosine (C) and uracil (U).

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

"Wing segment" means a plurality of nucleosides modified to impart to an oligonucleotide properties such as enhanced inhibitory activity, increased binding affinity for a target nucleic acid, or resistance to degradation by in vivo nucleases.

Certain Embodiments

Certain embodiments provide methods, compounds, and compositions for inhibiting Tau mRNA and protein expression. Certain embodiments provide methods, compounds, and composition for decreasing Tau mRNA and protein levels.

Certain embodiments provide antisense compounds targeted to a Tau nucleic acid. In certain embodiments, the Tau nucleic acid is the sequence set forth in GENBANK Accession No. GENBANK Accession No. NT_010783.15 truncated from nucleotides 9240000 to U.S. Pat. No. 9,381,000 (incorporated herein as SEQ ID NO: 1), GENBANK Accession No. NM_001123066.3 (incorporated herein as SEQ ID NO: 2), GENBANK Accession No. NM_016841.4, a variant mRNA sequence which skips exons 3, 4, 6, 8, 10, and 12 (incorporated herein as SEQ ID NO: 3), GENBANK Accession No. NT_010783.14 truncated from nucleotides 2624000 to U.S. Pat. No. 2,761,000 (incorporated herein as SEQ ID NO: 4), GENBANK Accession No. DR002467.1 (incorporated herein as SEQ ID NO: 5), GENBANK Accession No. NM_001203251.1 (incorporated herein as SEQ ID NO: 6), and GENBANK Accession No. NM_016835.4 (incorporated herein as SEQ ID NO: 7).

Certain embodiments provide methods for the treatment, prevention, or amelioration of diseases, disorders, and conditions associated with Tau in an individual in need thereof. Also contemplated are methods for the preparation of a medicament for the treatment, prevention, or amelioration of a disease, disorder, or condition associated with Tau. Tau associated diseases, disorders, and conditions include neurodegenerative diseases. In certain embodiments, tau associated diseases include Tauopathies, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 20-2443 and SEQ ID NOs: 2478-2483.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 2444-2477 and SEQ ID NOs: 2484-2565.

Certain embodiments provide compounds, comprising a modified oligonucleotide consisting of 12 to 30 linked nucleosides and having a nucleobase sequence comprising at least 8, at least 9, at least 10, at least 11, at least 12, at least 13, at least 14, at least 15, at least 16, at least 17, at least 18, at least 19, or at least 20 consecutive nucleobases of any of the nucleobase sequences of SEQ ID NOs: 20-2565.

Certain embodiments provide compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135980 of SEQ ID NO: 1.

Certain embodiments provide compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135853-135872 of SEQ ID NO: 1.

Certain embodiments provide compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135929 of SEQ ID NO: 1.

Certain embodiments provide compounds, comprising a modified oligonucleotide consisting of 12 to 30 linked nucleosides and comprising a nucleobase sequence comprising at least 8, at least 9, at least 10, at least 11, at least 12, at least 13, at least 14, at least 15, at least 16, at least 17, at least 18, at least 19, or at least 20 consecutive nucleobases complementary to an equal length portion of nucleobases 135783-135914 of SEQ ID NO: 1.

In certain embodiments the nucleobase sequence of the modified oligonucleotide is at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% complementary to SEQ ID NO: 1.

In certain embodiments, the compound is a single-stranded modified oligonucleotide.

In certain embodiments, at least one internucleoside linkage of the modified oligonucleotide is a modified internucleoside linkage.

In certain embodiments, at least one modified internucleoside linkage is a phosphorothioate internucleoside linkage.

In certain embodiments, each modified internucleoside linkage is a phosphorothioate internucleoside linkage.

In certain embodiments, at least one internucleoside linkage is a phosphodiester internucleoside linkage.

In certain embodiments, at least one internucleoside linkage is a phosphorothioate linkage and at least one internucleoside linkage is a phosphodiester linkage.

In certain embodiments, at least one nucleoside comprises a modified nucleobase.

In certain embodiments, the modified nucleobase is a 5-methylcytosine.

In certain embodiments, at least one nucleoside of the modified oligonucleotide comprises a modified sugar.

In certain embodiments, at least one modified sugar is a bicyclic sugar.

In certain embodiments, the bicyclic sugar comprises a chemical link between the 2' and 4' position of the sugar 4'-CH2-N(R)—O-2' bridge wherein R is, independently, H, C1-C12 alkyl, or a protecting group.

In certain embodiments, the bicyclic sugar comprises a 4'-CH2-N(R)—O-2' bridge wherein R is, independently, H, C1-C12 alkyl, or a protecting group.

In certain embodiments, at least one modified sugar comprises a 2'-O-methoxyethyl group.

In certain embodiments, the modified sugar comprises a 2'-O(CH$_2$)$_2$—OCH$_3$ group.

In certain embodiments, the modified oligonucleotide comprises:
a gap segment consisting of 10 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting of 9 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting of 7 linked deoxynucleosides;
a 5' wing segment consisting of 5 linked nucleosides; and
a 3' wing segment consisting of 6 linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting of 8 linked deoxynucleosides;
a 5' wing segment consisting of 5 linked nucleosides; and
a 3' wing segment consisting of 5 linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting of 8 linked deoxynucleosides;
a 5' wing segment consisting of 4 linked nucleosides; and
a 3' wing segment consisting of 6 linked nucleosides;
wherein the gap segment is positioned between the 5' wing segment and the 3' wing segment and wherein each nucleoside of each wing segment comprises a modified sugar.

In certain embodiments, the modified oligonucleotide comprises:
a gap segment consisting of 8 linked deoxynucleosides;
a 5' wing segment consisting of 6 linked nucleosides; and
a 3' wing segment consisting of 4 linked nucleosides;

wherein the gap segment is positioned between the 5' wing segment and the 3' wing segment and wherein each nucleoside of each wing segment comprises a modified sugar.

In certain embodiments, the modified oligonucleotide consists of 20 linked nucleosides.

In certain embodiments, the modified oligonucleotide consists of 19 linked nucleosides.

In certain embodiments, the modified oligonucleotide consists of 18 linked nucleosides.

Certain embodiments provide compositions comprising any compound described herein or salt thereof and at least one of a pharmaceutically acceptable carrier or diluent.

Certain embodiments provide methods comprising administering to an animal any compound or composition described herein.

In certain embodiments, the animal is a human.

In certain embodiments, administering the compound prevents, treats, ameliorates, or slows progression of a tau associated disease, disorder or condition.

In certain embodiments, the disease, disorder or condition is a Tauopathy, Alzheimer's Disease, Fronto-temporal Dementia (FTD), FTDP-17, Progressive Supranuclear Palsy (PSP), Chronic Traumatic Encephalopathy (CTE), Cortico-basal Ganglionic Degeneration (CBD), Epilepsy, or Dravet's Syndrome.

Certain embodiments provide use of any of the compounds or compositions of described herein for the manufacture of a medicament for treating a neurodegenerative disorder.

Certain embodiments provide compounds according to the following formula (Ia):

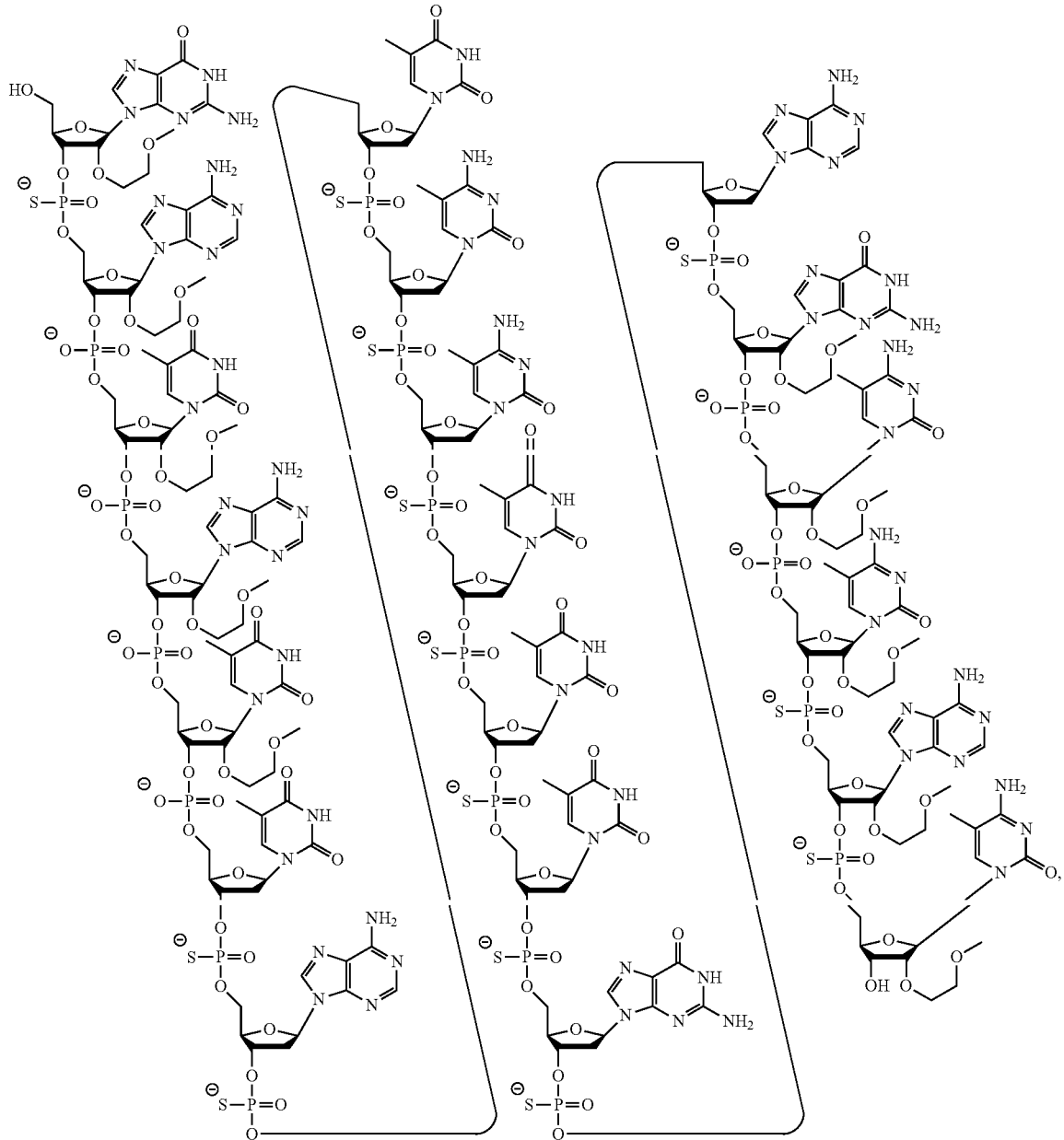

(Ia)

or a pharmaceutically acceptable salt thereof. In certain embodiments, provided are pharmaceutical compositions comprising the compound having the formula (Ia).

Certain embodiments provide compounds according to the following formula (IIa):

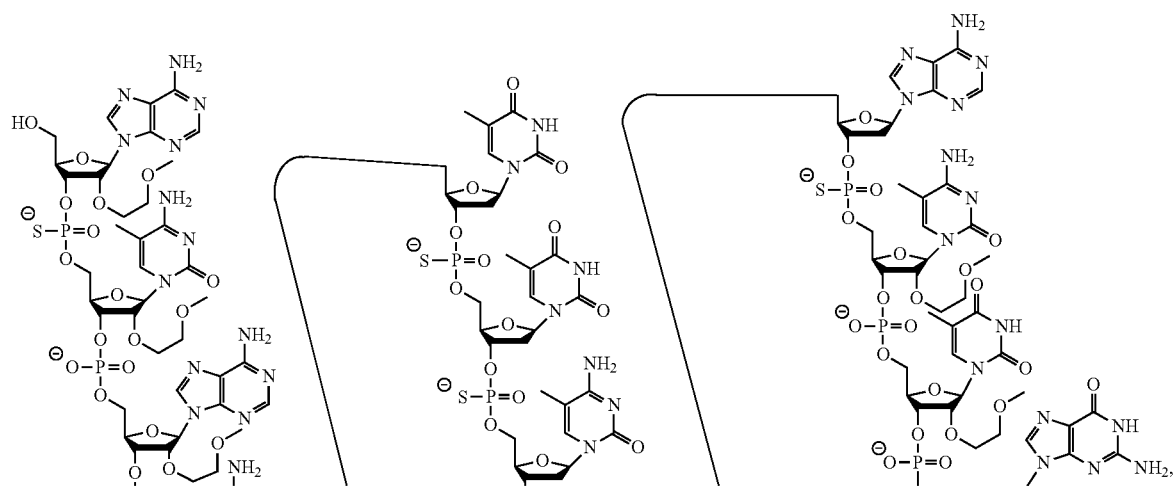

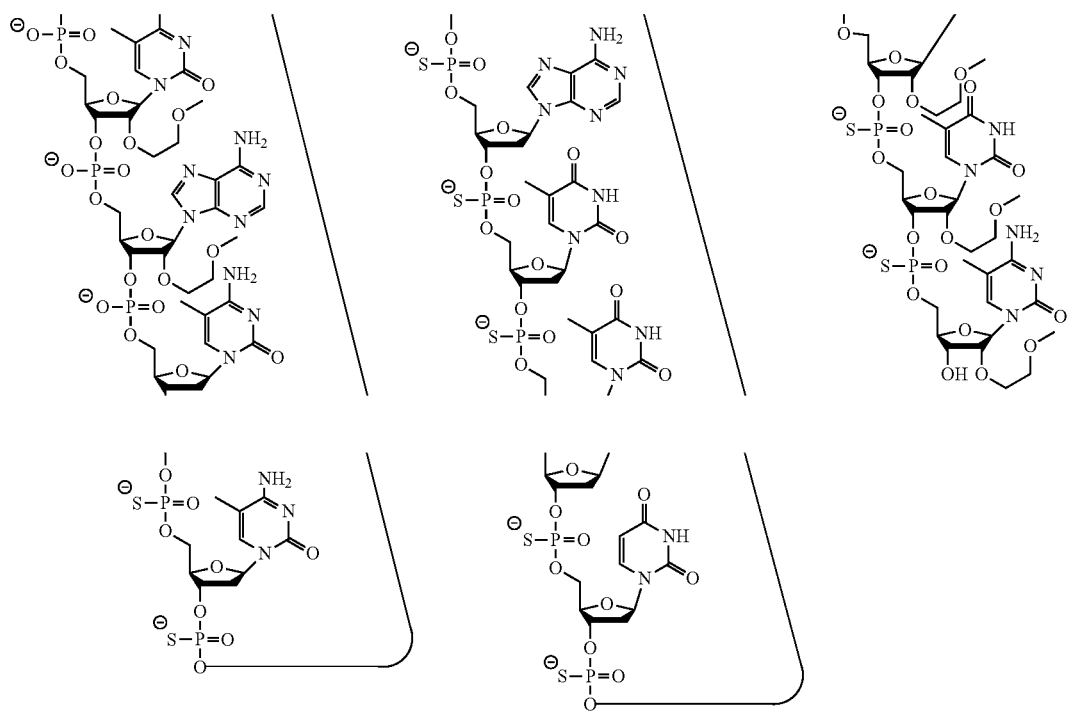

(IIa)

or a pharmaceutically acceptable salt thereof. In certain embodiments, provided are pharmaceutical compositions comprising the compound having the formula (IIa).

Certain embodiments provide compounds according to the following formula (IIIa):

(IIIa)
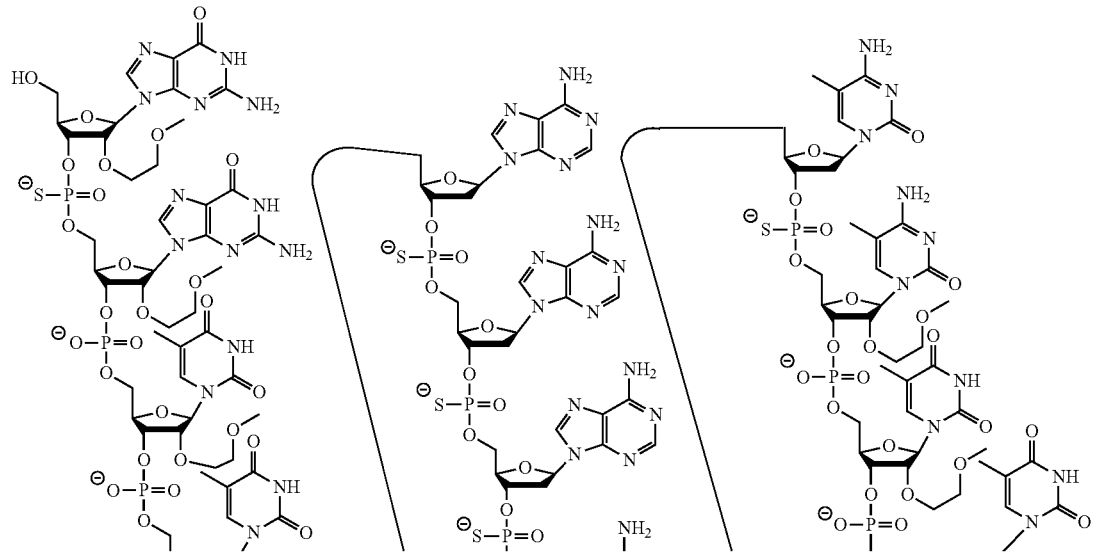
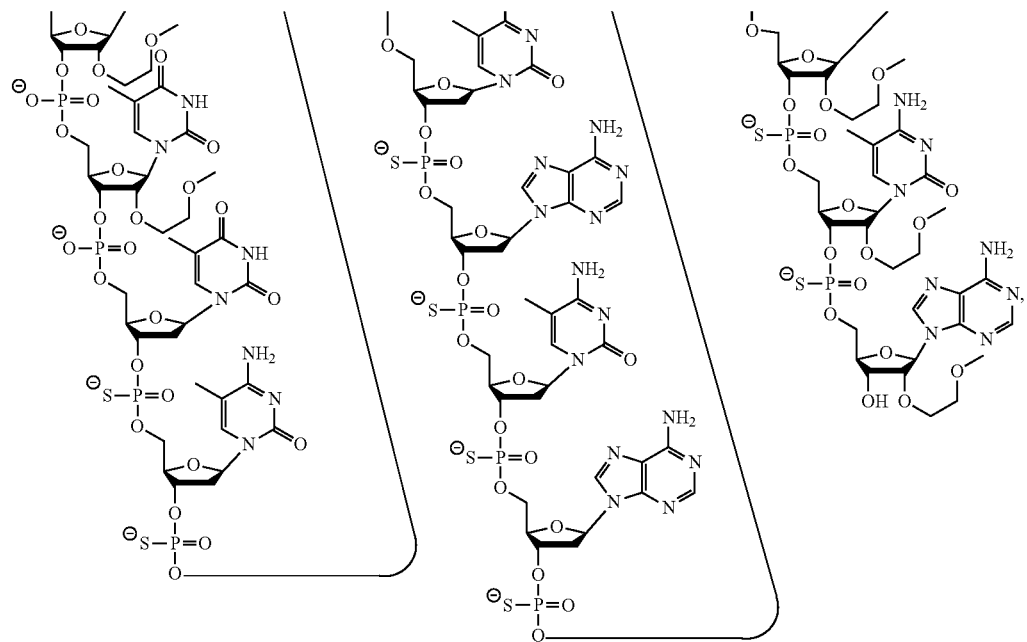
or a pharmaceutically acceptable salt thereof. In certain embodiments, provided are pharmaceutical compositions comprising the compound having the formula (IIIa).
Certain embodiments provide compounds according to the following formula (IVa):

(IVa)
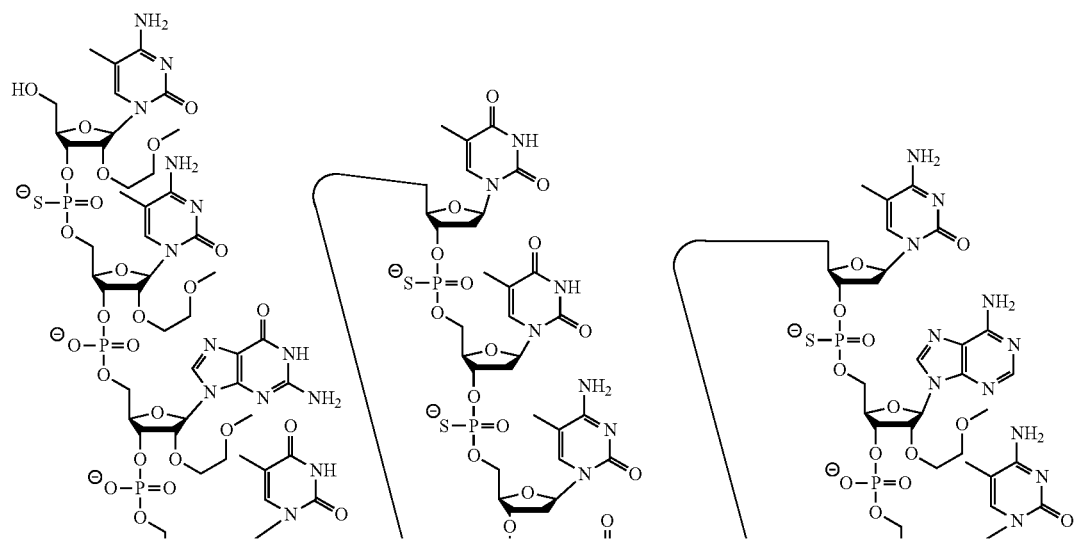
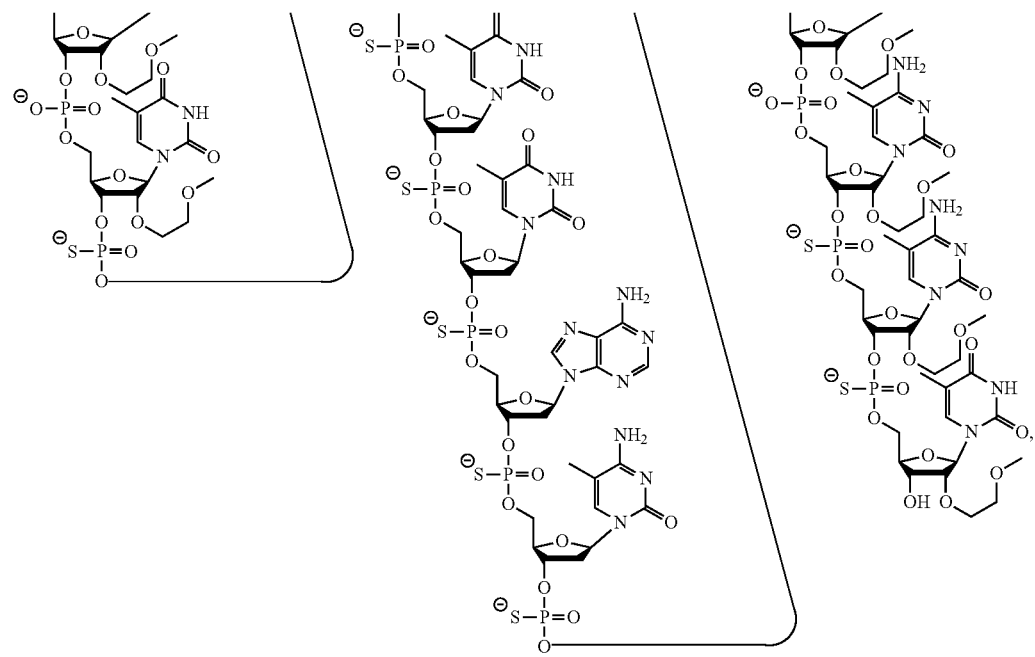
or a pharmaceutically acceptable salt thereof. In certain embodiments, provided are pharmaceutical compositions comprising the compound having the formula (IVa).
Certain embodiments provide compounds according to the following formula (Va):

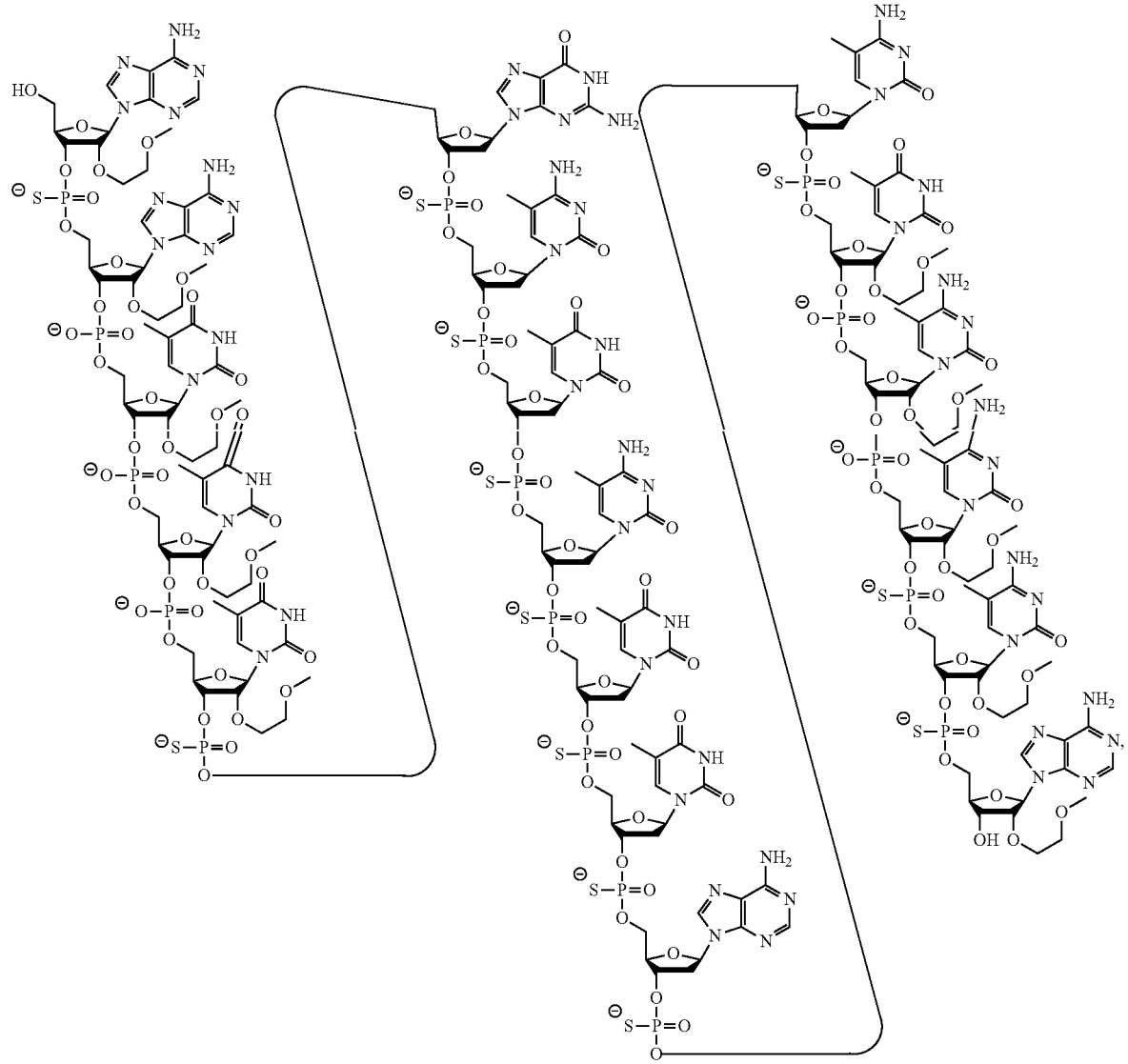

(Va)

or a pharmaceutically acceptable salt thereof. In certain embodiments, provided are pharmaceutical compositions comprising the compound having the formula (Va).

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a Tau nucleic acid is 12 to 30 subunits in length. In certain embodiments, an antisense compound targeted to Tau nucleic acid is 12 to 25 subunits in length. In certain embodiments, an antisense compound targeted to Tau nucleic acid is 12 to 22 subunits in length. In certain embodiments, an antisense compound targeted to Tau nucleic acid is 14 to 20 subunits in length. In certain embodiments, an antisense compound targeted to Tau nucleic acid is 15 to 25 subunits in length. In certain embodiments, an antisense compound targeted to Tau nucleic acid is 18 to 22 subunits in length. In certain embodiments, an antisense compound targeted to Tau nucleic acid is 19 to 21 subunits in length. In certain embodiments, the antisense compound is 8 to 80, 12 to 50, 13 to 30, 13 to 50, 14 to 30, 14 to 50, 15 to 30, 15 to 50, 16 to 30, 16 to 50, 17 to 30, 17 to 50, 18 to 30, 18 to 50, 19 to 30, 19 to 50, or 20 to 30 linked subunits in length.

In certain embodiments, an antisense compound targeted to a Tau nucleic acid is 12 subunits in length. In certain embodiments, an antisense compound targeted to a Tau nucleic acid is 13 subunits in length. In certain embodiments, an antisense compound targeted to a Tau nucleic acid is 14 subunits in length. In certain embodiments, an antisense compound targeted to a Tau nucleic acid is 15 subunits in length. In certain embodiments, an antisense compound targeted to a Tau nucleic acid is 16 subunits in length. In certain embodiments, an antisense compound targeted to a Tau nucleic acid is 17 subunits in length. In certain embodiments, an antisense compound targeted to a Tau nucleic acid is 18 subunits in length. In certain embodiments, an antisense compound targeted to a Tau nucleic acid is 19 subunits in length. In certain embodiments, an antisense compound targeted to a Tau nucleic acid is 20 subunits in length. In certain embodiments, an antisense compound targeted to a Tau nucleic acid is 21 subunits in length. In certain embodiments, an antisense compound targeted to a Tau nucleic acid is 22 subunits in length. In certain embodiments, an antisense compound targeted to a Tau nucleic acid is 23 subunits in length. In certain embodiments, an antisense compound targeted to a Tau nucleic acid is 24 subunits in length. In certain embodiments, an antisense compound targeted to a Tau nucleic acid is 25 subunits in length. In certain embodiments, an antisense compound targeted to a Tau nucleic acid is 26 subunits in length. In certain embodiments, an antisense compound targeted to a Tau nucleic acid is 27 subunits in length. In certain embodiments, an antisense compound targeted to a Tau nucleic acid is 28 subunits in length. In certain embodiments, an antisense compound targeted to a Tau nucleic acid is 29 subunits in length. In certain embodiments, an antisense compound targeted to a Tau nucleic acid is 30 subunits in length. In certain embodiments, the antisense compound targeted to a Tau nucleic acid is 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked subunits in length, or a range defined by any two of the above values. In certain embodiments the antisense compound is an antisense oligonucleotide, and the linked subunits are nucleosides.

In certain embodiments antisense oligonucleotides targeted to a Tau nucleic acid may be shortened or truncated. For example, a single subunit may be deleted from the 5' end (5' truncation), or alternatively from the 3' end (3' truncation). A shortened or truncated antisense compound targeted to a Tau nucleic acid may have two subunits deleted from the 5' end, or alternatively may have two subunits deleted from the 3' end, of the antisense compound. Alternatively, the deleted nucleosides may be dispersed throughout the antisense compound, for example, in an antisense compound having one nucleoside deleted from the 5' end and one nucleoside deleted from the 3' end.

When a single additional subunit is present in a lengthened antisense compound, the additional subunit may be located at the 5' or 3' end of the antisense compound. When two or more additional subunits are present, the added subunits may be adjacent to each other, for example, in an antisense compound having two subunits added to the 5' end (5' addition), or alternatively to the 3' end (3' addition), of the antisense compound. Alternatively, the added subunits may be dispersed throughout the antisense compound, for example, in an antisense compound having one subunit added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a Tau nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—CH$_3$, among others), and bicyclic sugar modified nucleosides (such bicyclic sugar modified nucleosides may include those having a 4'-(CH$_2$)n-O-2' bridge, where n=1 or n=2 and 4'-CH$_2$—O—CH$_2$-2'). In certain embodiments, wings may include several modified sugar moieties, including, for example 2'-MOE. In certain embodiments, wings may include several modified and unmodified sugar moieties. In certain embodiments, wings may include various combinations of 2'-MOE nucleosides and 2'-deoxynucleosides.

Each distinct region may comprise uniform sugar moieties, variant, or alternating sugar moieties. The wing-gap-wing motif is frequently described as "X-Y-Z", where "X" represents the length of the 5' wing, "Y" represents the length of the gap, and "Z" represents the length of the 3' wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5' wing and the 3' wing. Thus, no intervening nucleotides exist between the 5' wing and gap, or the gap and the 3' wing. Any of the antisense compounds described herein can have a gapmer motif. In certain embodiments, "X" and "Z" are the same; in other embodiments they are different.

In certain embodiments, gapmers provided herein include, for example 20-mers having a motif of 5-10-5.

In certain embodiments, gapmers provided herein include, for example 19-mers having a motif of 5-9-5.

In certain embodiments, gapmers provided herein include, for example 18-mers having a motif of 5-8-5.

In certain embodiments, gapmers provided herein include, for example 18-mers having a motif of 4-8-6.

In certain embodiments, gapmers provided herein include, for example 18-mers having a motif of 6-8-4.

In certain embodiments, gapmers provided herein include, for example 18-mers having a motif of 5-7-6.

Target Nucleic Acids, Target Regions and Nucleotide Sequences

Nucleotide sequences that encode Tau include, without limitation, the following: GENBANK Accession No. NT_010783.15 truncated from nucleotides 9240000 to U.S. Pat. No. 9,381,000 (incorporated herein as SEQ ID NO: 1), GENBANK Accession No. NM_001123066.3 (incorporated herein as SEQ ID NO: 2), GENBANK Accession No. NM_016841.4, a variant mRNA sequence which skips exons 3, 4, 6, 8, 10, and 12 (incorporated herein as SEQ ID NO: 3), GENBANK Accession No. NT_010783.14 truncated from nucleotides 2624000 to U.S. Pat. No. 2,761,000 (incorporated herein as SEQ ID NO: 4), GENBANK Accession No. DR002467.1 (incorporated herein as SEQ ID NO: 5), GENBANK Accession No. NM_001203251.1 (incorporated herein as SEQ ID NO: 6), and GENBANK Accession No. NM_016835.4 (incorporated herein as SEQ ID NO: 7).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for Tau can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in Tau mRNA levels are indicative of inhibition of Tau expression. Reductions in levels of a Tau protein are also indicative of inhibition of target mRNA expression. Reduction of percent of cells staining positive for hyperphosphorylated Tau are indicative of inhibition of Tau expression. Further, phenotypic changes are indicative of inhibition of Tau expression. Improvement in neurological function is indicative of inhibition of Tau expression. Improved memory and motor function are indicative of inhibition of Tau expression. Reduction of neurofibrillary inclusions is indicative of inhibition of Tau expression.

Hybridization

In some embodiments, hybridization occurs between an antisense compound disclosed herein and a Tau nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a Tau nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a Tau nucleic acid).

Non-complementary nucleobases between an antisense compound and a Tau nucleic acid may be tolerated provided that the antisense compound remains able to specifically hybridize to a target nucleic acid. Moreover, an antisense compound may hybridize over one or more segments of a Tau nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a Tau nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e., 100% complementary) to a target nucleic acid, or specified portion thereof. For example, an antisense compound may be fully complementary to a Tau nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e., linked) or non-contiguous. In one embodiment, a non-complementary nucleobase is located in the wing segment of a gapmer antisense oligonucleotide.

In certain embodiments, antisense compounds that are, or are up to 11, 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a Tau nucleic acid, or specified portion thereof.

In certain embodiments, antisense compounds that are, or are up to 11, 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a Tau nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 9 nucleobase portion of a target segment. In certain embodiments, the antisense compounds are complementary to at least a 10 nucleobase portion of a target segment. In certain embodiments, the antisense compounds, are complementary to at least an 11 nucleobase portion of a target segment. In certain embodiments, the antisense compounds, are complementary to at least a 12 nucleobase portion of a target segment. In certain embodiments, the antisense compounds, are complementary to at least a 13 nucleobase portion of a target segment. In certain embodiments, the antisense compounds, are complementary to at least a 14 nucleobase portion of a target segment. In certain embodiments, the antisense compounds, are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

In certain embodiments, a portion of the antisense compound is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

In certain embodiments, a portion of the antisense oligonucleotide is compared to an equal length portion of the target nucleic acid. In certain embodiments, an 8, 9, 10, 11, 12, 13, 14, 15, 16, 17, 18, 19, 20, 21, 22, 23, 24, or 25 nucleobase portion is compared to an equal length portion of the target nucleic acid.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a Tau nucleic acid comprise one or more modified internucleoside linkages. In certain embodiments, the modified internucleoside linkages are interspersed throughout the antisense compound. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise chemically modified ribofuranose ring moieties. Examples of chemically modified ribofuranose rings include without limitation, addition of substituent groups (including 5' and 2' substituent groups, bridging of non-geminal ring atoms to form bicyclic nucleic acids (BNA), replacement of the ribosyl ring oxygen atom with S, N(R), or $C(R_1)(R_2)$ (R, $R_1$ and $R_2$ are each independently H, $C_1$-$C_{12}$ alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-$OCH_3$, 2'-$OCH_2CH_3$, 2'-$OCH_2CH_2F$ and 2'-$O(CH_2)_2OCH_3$ substituent groups. The substituent at the 2' position can also be selected from allyl, amino, azido, thio, O-allyl, O—$C_1$-$C_{10}$ alkyl, $OCF_3$, $OCH_2F$, $O(CH_2)_2SCH_3$, $O(CH_2)_2$—O—$N(R_m)(R_n)$, O—$CH_2$—C(=O)—$N(R_m)(R_n)$, and O—$CH_2$—C(=O)—$N(R_j)$—$(CH_2)_2$—$N(R_m)(R_n)$, where each $R_j$, $R_m$ and $R_n$ is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include without limitation nucleosides comprising a bridge between the 4' and the 2' ribosyl ring atoms. In certain embodiments, antisense compounds provided herein include one or more bicyclic nucleosides comprising a 4' to 2' bridge. Examples of such 4' to 2' bridged bicyclic nucleosides, include but are not limited to one of the formulae: 4'-(CH$_2$)—O-2' (LNA); 4'-(CH$_2$)—S-2'; 4'-(CH$_2$)$_2$—O-2' (ENA); 4'-CH(CH$_3$)—O-2' and 4'-CH (CH$_2$OCH$_3$)—O-2' (and analogs thereof see U.S. Pat. No. 7,399,845, issued on Jul. 15, 2008); 4'-C(CH$_3$)(CH$_3$)—O-2' (and analogs thereof see published International Application WO/2009/006478, published Jan. 8, 2009); 4'-CH$_2$—N (OCH$_3$)-2' (and analogs thereof see published International Application WO/2008/150729, published Dec. 11, 2008); 4'-CH$_2$—O—N(CH$_3$)-2' (see published U.S. Patent Application US2004-0171570, published Sep. 2, 2004); 4'-CH$_2$—N(R)—O-2', wherein R is H, C$_1$-C$_{12}$ alkyl, or a protecting group (see U.S. Pat. No. 7,427,672, issued on Sep. 23, 2008); 4'-CH$_2$—C(H)(CH$_3$)-2' (see Chattopadhyaya et al., *J. Org. Chem.*, 2009, 74, 118-134); and 4'-CH$_2$—C—(=CH$_2$)-2' (and analogs thereof see published International Application WO 2008/154401, published on Dec. 8, 2008).

Further reports related to bicyclic nucleosides can also be found in published literature (see for example: Singh et al., *Chem. Commun.*, 1998, 4, 455-456; Koshkin et al., *Tetrahedron*, 1998, 54, 3607-3630; Wahlestedt et al., *Proc. Natl. Acad. Sci. U.S.A.*, 2000, 97, 5633-5638; Kumar et al., *Bioorg. Med. Chem. Lett.*, 1998, 8, 2219-2222; Singh et al., *J. Org. Chem.*, 1998, 63, 10035-10039; Srivastava et al., *J Am. Chem. Soc.*, 2007, 129(26) 8362-8379; Elayadi et al., *Curr. Opinion Invest. Drugs*, 2001, 2, 558-561; Braasch et al., *Chem. Biol.*, 2001, 8, 1-7; and Orum et al., *Curr. Opinion Mol. Ther.*, 2001, 3, 239-243; U.S. Pat. Nos. 6,268,490; 6,525,191; 6,670,461; 6,770,748; 6,794,499; 7,034,133; 7,053,207; 7,399,845; 7,547,684; and 7,696,345; U.S. Patent Publication No. US2008-0039618; US2009-0012281; U.S. Patent Ser. Nos. 60/989,574; 61/026,995; 61/026,998; 61/056,564; 61/086,231; 61/097,787; and 61/099,844; Published PCT International applications WO 1994/014226; WO 2004/106356; WO 2005/021570; WO 2007/134181; WO 2008/150729; WO 2008/154401; and WO 2009/006478. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —[C(R$_a$)(R$_b$)]$_n$—, —C(R$_a$) =C(R$_b$)—, —C(R$_a$)=N—, —C(=O)—, —C(=NR$_a$)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl or a protecting group.

In certain embodiments, the bridge of a bicyclic sugar moiety is —[C(R$_a$)(R$_b$)]$_n$—, —[C(R$_a$)(R$_b$)]$_n$O—, —C(R$_a$R$_b$)—N(R)—O— or —C(R$_a$R$_b$)—O—N(R)—. In certain embodiments, the bridge is 4'-CH$_2$-2', 4'-(CH$_2$)$_2$-2', 4'-(CH$_2$)$_3$-2', 4'-CH$_2$—O-2', 4'-(CH$_2$)$_2$—O-2', 4'-CH$_2$—O—N(R)-2' and 4'-CH$_2$—N(R)—O-2'- wherein each R is, independently, H, a protecting group or C$_1$-C$_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-CH$_2$—O-2') BNA's have been incorporated into antisense oligonucleotides that showed antisense activity (Frieden et al., *Nucleic Acids Research*, 2003, 21, 6365-6372).

In certain embodiments, bicyclic nucleosides include, but are not limited to, (A) α-L-methyleneoxy (4'-CH$_2$—O-2') BNA, (B) β-D-methyleneoxy (4'-CH$_2$—O-2') BNA, (C) ethyleneoxy (4'-(CH$_2$)$_2$—O-2') BNA, (D) aminooxy (4'-CH$_2$—O—N(R)-2') BNA, (E) oxyamino (4'-CH$_2$—N(R)—O-2') BNA, and (F) methyl(methyleneoxy) (4'-CH(CH$_3$)—O-2') BNA, (G) methylene-thio (4'-CH$_2$—S-2') BNA, (H) methylene-amino (4'-CH$_2$—N(R)-2') BNA, (I) methyl carbocyclic (4'-CH$_2$—CH(CH$_3$)-2') BNA, and (J) propylene carbocyclic (4'-(CH$_2$)$_3$-2') BNA as depicted below.

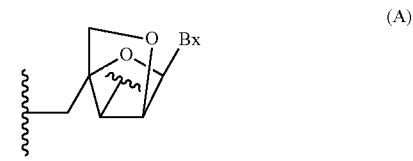

(A)

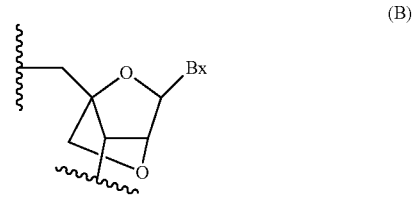

(B)

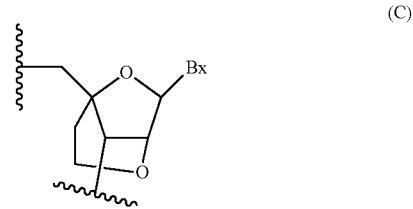

(C)

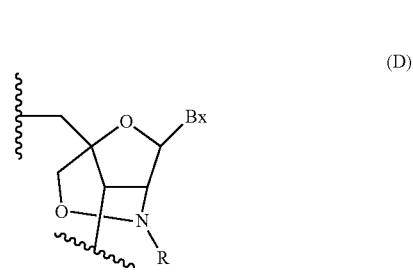

(D)

-continued (E)
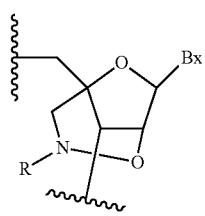

(F)
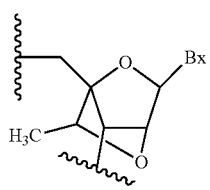

(G)
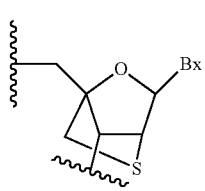

(H)
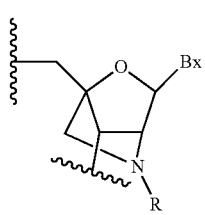

(I)
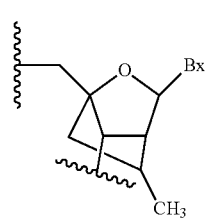

(J)
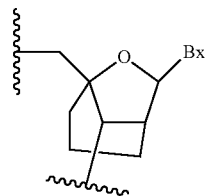

wherein Bx is the base moiety and R is independently H, a protecting group or $C_1$-$C_{12}$ alkyl.

In certain embodiments, bicyclic nucleosides are provided having Formula I:

I
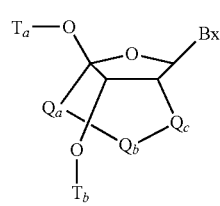

wherein:
Bx is a heterocyclic base moiety;
-$Q_a$-$Q_b$-$Q_c$- is —$CH_2$—N($R_c$)—$CH_2$—, —C(=O)—N($R_c$)—$CH_2$—, —$CH_2$—O—N($R_c$)—, —$CH_2$—N($R_c$)—O— or —N($R_c$)—O—$CH_2$;
$R_c$ is $C_1$-$C_{12}$ alkyl or an amino protecting group; and
$T_a$ and $T_b$ are each, independently H, a hydroxyl protecting group, a conjugate group, a reactive phosphorus group, a phosphorus moiety or a covalent attachment to a support medium.

In certain embodiments, bicyclic nucleosides are provided having Formula II:

II
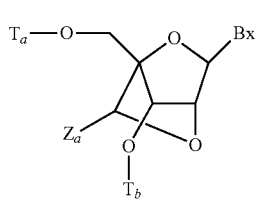

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, OC(=X)$J_c$, and $NJ_eC(=X)NJ_cJ_d$, wherein each $J_c$, $J_d$ and $J_e$ is, independently, H, $C_1$-$C_6$ alkyl, or substituted $C_1$-$C_6$ alkyl and X is O or $NJ_c$.

In certain embodiments, bicyclic nucleosides are provided having Formula III:

III
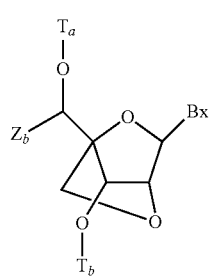

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl or substituted acyl (C(=O)—).

In certain embodiments, bicyclic nucleosides are provided having Formula IV:

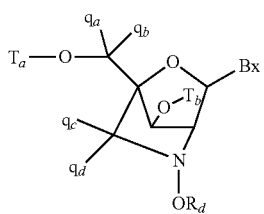

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl;
each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl or substituted $C_1$-$C_6$ aminoalkyl;

In certain embodiments, bicyclic nucleosides are provided having Formula V:

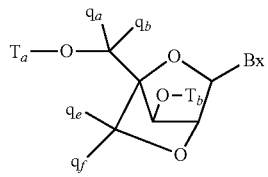

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, O—$C(=O)NJ_jJ_k$, $N(H)C(=NH)NJ_jJ_k$, $N(H)C(=O)NJ_jJ_k$ or $N(H)C(=S)NJ_jJ_k$;
or $q_e$ and $q_f$ together are $=C(q_g)(q_h)$;
$q_g$ and $q_h$ are each, independently, H, halogen, $C_1$-$C_{12}$ alkyl or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine and uracil, along with their oligomerization, and nucleic acid recognition properties have been described (Koshkin et al., *Tetrahedron*, 1998, 54, 3607-3630). BNAs and preparation thereof are also described in WO 98/39352 and WO 99/14226.

Analogs of methyleneoxy (4'-$CH_2$—O-2') BNA and 2'-thio-BNAs, have also been prepared (Kumar et al., *Bioorg. Med. Chem. Lett.*, 1998, 8, 2219-2222). Preparation of locked nucleoside analogs comprising oligodeoxyribo-nucleotide duplexes as substrates for nucleic acid polymerases has also been described (Wengel et al., WO 99/14226). Furthermore, synthesis of 2'-amino-BNA, a novel conformationally restricted high-affinity oligonucleotide analog has been described in the art (Singh et al., *J. Org. Chem.*, 1998, 63, 10035-10039). In addition, 2'-amino- and 2'-methylamino-BNA's have been prepared and the thermal stability of their duplexes with complementary RNA and DNA strands has been previously reported.

In certain embodiments, bicyclic nucleosides are provided having Formula VI:

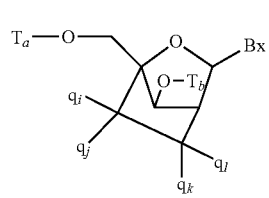

wherein:
Bx is a heterocyclic base moiety;
$T_a$ and $T_b$ are each, independently H, a hydroxyl protecting group, a conjugate group, a reactive phosphorus group, a phosphorus moiety or a covalent attachment to a support medium;
each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, O—$C(=O)NJ_jJ_k$, $N(H)C(=NH)NJ_jJ_k$, $N(H)C(=O)NJ_jJ_k$ or $N(H)C(=S)NJ_jJ_k$; and
$q_i$ and $q_j$ or $q_l$ and $q_k$ together are $=C(q_g)(q_h)$, wherein $q_g$ and $q_h$ are each, independently, H, halogen, $C_1$-$C_{12}$ alkyl or substituted $C_1$-$C_{12}$ alkyl.

One carbocyclic bicyclic nucleoside having a 4'-$(CH_2)_3$-2' bridge and the alkenyl analog bridge 4'-CH=CH—$CH_2$-2' have been described (Freier et al., *Nucleic Acids Research*, 1997, 25(22), 4429-4443 and Albaek et al., *J. Org. Chem.*, 2006, 71, 7731-7740). The synthesis and preparation of carbocyclic bicyclic nucleosides along with their oligomerization and biochemical studies have also been described (Srivastava et al., *J. Am. Chem. Soc.*, 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting two carbon atoms of the furanose ring connects the 2' carbon atom and the 4' carbon atom of the sugar ring.

As used herein, "monocyclic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: O[(CH$_2$)$_n$O]$_m$CH$_3$, O(CH$_2$)$_n$NH$_2$, O(CH$_2$)$_n$CH$_3$, O(CH$_2$)$_n$F, O(CH$_2$), ONH$_2$, OCH$_2$C(=O)N(H)CH$_3$, and O(CH$_2$), ON[(CH$_2$)$_n$CH$_3$]$_2$, where n and m are from 1 to about 10. Other 2'-substituent groups can also be selected from: C$_1$-C$_{12}$ alkyl, substituted alkyl, alkenyl, alkynyl, alkaryl, aralkyl, O-alkaryl or O-aralkyl, SH, SCH$_3$, OCN, Cl, Br, CN, F, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving pharmacokinetic properties, or a group for improving the pharmacodynamic properties of an antisense compound, and other substituents having similar properties. In certain embodiments, modified nucleosides comprise a 2'-MOE side chain (Baker et al., *J. Biol. Chem.,* 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (Martin, *Helv. Chim. Acta,* 1995, 78, 486-504; Altmann et al., *Chimia,* 1996, 50, 168-176; Altmann et al., *Biochem. Soc. Trans.,* 1996, 24, 630-637; and Altmann et al., *Nucleosides Nucleotides,* 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, *Bioorg. Med. Chem.,* 2002, 10, 841-854), fluoro HNA (F-HNA) or those compounds having Formula VII:

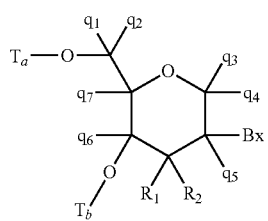

VII wherein independently for each of said at least one tetrahydropyran nucleoside analog of Formula VII:
Bx is a heterocyclic base moiety;
T$_a$ and T$_b$ are each, independently, an internucleoside linking group linking the tetrahydropyran nucleoside analog to the antisense compound or one of T$_a$ and T$_b$ is an internucleoside linking group linking the tetrahydropyran nucleoside analog to the antisense compound and the other of T$_a$ and T$_b$ is H, a hydroxyl protecting group, a linked conjugate group or a 5' or 3'-terminal group;
q$_1$, q$_2$, q$_3$, q$_4$, q$_5$, q$_6$ and q$_7$ are each independently, H, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl or substituted C$_2$-C$_6$ alkynyl; and each of R$_1$ and R$_2$ is selected from hydrogen, hydroxyl, halogen, substituted or unsubstituted alkoxy, NJ$_1$J$_2$, SJ$_1$, N$_3$, OC(=X)J$_1$, OC(=X)NJ$_1$J$_2$, NJ$_3$C(=X)NJ$_1$J$_2$ and CN, wherein X is O, S or NJ$_1$ and each J$_1$, J$_2$ and J$_3$ is, independently, H or C$_1$-C$_6$ alkyl.

In certain embodiments, the modified THP nucleosides of Formula VII are provided wherein q$_1$, q$_2$, q$_3$, q$_4$, q$_5$, q$_6$ and q$_7$ are each H. In certain embodiments, at least one of q$_1$, q$_2$, q$_3$, q$_4$, q$_5$, q$_6$ and q$_7$ is other than H. In certain embodiments, at least one of q$_1$, q$_2$, q$_3$, q$_4$, q$_5$, q$_6$ and q$_7$ is methyl. In certain embodiments, THP nucleosides of Formula VII are provided wherein one of R$_1$ and R$_2$ is fluoro. In certain embodiments, R$_1$ is fluoro and R$_2$ is H; R$_1$ is methoxy and R$_2$ is H, and R$_1$ is H and R$_2$ is methoxyethoxy.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring; and nucleosides with non-bridging 2'substituents, such as allyl, amino, azido, thio, O-allyl, O—C$_1$-C$_{10}$ alkyl, —OCF$_3$, O—(CH$_2$)$_2$—O—CH$_3$, 2'-O(CH$_2$)$_2$SCH$_3$, O—(CH$_2$)$_2$—O—N(R$_m$)(R$_n$), or O—CH$_2$—C(=O)—N(R$_m$)(R$_n$), where each R$_m$ and R$_n$ is, independently, H or substituted or unsubstituted C$_1$-C$_{10}$ alkyl. 2'-modified nucleosides may further comprise other modifications, for example at other positions of the sugar and/or at the nucleobase.

As used herein, "2'-F" refers to a nucleoside comprising a sugar comprising a fluoro group at the 2' position.

As used herein, "2'-OMe" or "2'-OCH$_3$" or "2'-O-methyl" each refers to a nucleoside comprising a sugar comprising an —OCH$_3$ group at the 2' position of the sugar ring.

As used herein, "MOE" or "2'-MOE" or "2'-OCH$_2$CH$_2$OCH$_3$" or "2'-O-methoxyethyl" each refers to a nucleoside comprising a sugar comprising a —OCH$_2$CH$_2$OCH$_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see for example review article: Leumann, *Bioorg. Med. Chem.,* 2002, 10, 841-854).

Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds comprise one or more nucleosides having modified sugar moieties. In certain embodiments, the modified sugar moiety is 2'-MOE. In certain embodiments, the 2'-MOE modified nucleosides are arranged in a gapmer motif. In certain embodiments, the modified sugar moiety is a bicyclic nucleoside having a (4'-CH(CH$_3$)—O-2') bridging group. In certain embodiments, the (4'-CH(CH$_3$)—O-2') modified nucleosides are arranged throughout the wings of a gapmer motif.

Compositions and Methods for Formulating Pharmaceutical Compositions

Antisense oligonucleotides may be admixed with pharmaceutically acceptable active or inert substances for the preparation of pharmaceutical compositions or formulations. Compositions and methods for the formulation of pharmaceutical compositions are dependent upon a number of criteria, including, but not limited to, route of administration, extent of disease, or dose to be administered.

An antisense compound targeted to a Tau nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a Tau nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of Tau nucleic acids can be tested in vitro in a variety of cell types. Cell types used for such analyses are available from commerical vendors (e.g. American Type Culture Collection, Manassas, VA; Zen-Bio, Inc., Research Triangle Park, NC; Clonetics Corporation, Walkersville, MD) and are cultured according to the vendor's instructions using commercially available reagents (e.g. Invitrogen Life Technologies, Carlsbad, CA). Illustrative cell types include, but are not limited to, HepG2 cells, Hep3B cells, and primary hepatocytes.

In Vitro Testing of Antisense Oligonucleotides

Described herein are methods for treatment of cells with antisense oligonucleotides, which can be modified appropriately for treatment with other antisense compounds.

Cells may be treated with antisense oligonucleotides when the cells reach approximately 60-80% confluency in culture.

One reagent commonly used to introduce antisense oligonucleotides into cultured cells includes the cationic lipid transfection reagent LIPOFECTIN (Invitrogen, Carlsbad, CA). Antisense oligonucleotides may be mixed with LIPOFECTIN in OPTI-MEM 1 (Invitrogen, Carlsbad, CA) to achieve the desired final concentration of antisense oligonucleotide and a LIPOFECTIN concentration that may range from 2 to 12 ug/mL per 100 nM antisense oligonucleotide.

Another reagent used to introduce antisense oligonucleotides into cultured cells includes LIPOFECTAMINE (Invitrogen, Carlsbad, CA). Antisense oligonucleotide is mixed with LIPOFECTAMINE in OPTI-MEM 1 reduced serum medium (Invitrogen, Carlsbad, CA) to achieve the desired concentration of antisense oligonucleotide and a LIPOFECTAMINE concentration that may range from 2 to 12 ug/mL per 100 nM antisense oligonucleotide.

Another technique used to introduce antisense oligonucleotides into cultured cells includes electroporation.

Cells are treated with antisense oligonucleotides by routine methods. Cells may be harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL Reagent (Invitrogen, Carlsbad, CA) according to the manufacturer's recommended protocols.

Analysis of Inhibition of Target Levels or Expression

Inhibition of levels or expression of a Tau nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM 7600, 7700, or 7900 Sequence Detection System, available from PE-Applied Biosystems, Foster City, CA and used according to manufacturer's instructions.

Quantitative Real-Time PCR Analysis of Target RNA Levels

Quantitation of target RNA levels may be accomplished by quantitative real-time PCR using the ABI PRISM 7600, 7700, or 7900 Sequence Detection System (PE-Applied Biosystems, Foster City, CA) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents may be obtained from Invitrogen (Carlsbad, CA). RT real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN (Invitrogen, Inc. Carlsbad, CA). Cyclophilin A expression is quantified by real time PCR, by being run simultaneously with the target, multiplexing, or separately. Total RNA is quantified using RIBOGREEN RNA quantification reagent (Invitrogen, Inc. Eugene, OR). Methods of RNA quantification by RIBOGREEN are taught in Jones, L. J., et al, (Analytical Biochemistry, 1998, 265, 368-374). A CYTOFLUOR 4000 instrument (PE Applied Biosystems) is used to measure RIBOGREEN fluorescence.

Probes and primers are designed to hybridize to a Tau nucleic acid. Methods for designing real-time PCR probes and primers are well known in the art, and may include the use of software such as PRIMER EXPRESS Software (Applied Biosystems, Foster City, CA).

Analysis of Protein Levels

Antisense inhibition of Tau nucleic acids can be assessed by measuring Tau protein levels. Protein levels of Tau can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, MI), or can be prepared via conventional monoclonal or polyclonal antibody generation methods well known in the art.

In Vivo Testing of Antisense Compounds

Antisense compounds, for example, antisense oligonucleotides, are tested in animals to assess their ability to inhibit expression of Tau and produce phenotypic changes, such as, improved cognition and motor function. In certain embodiments, cognition is measured by novel object recognition and nestlet building activity. In certain embodiments, motor function is measured by walking initiation analysis, rotarod, grip strength, pole climb, open field performance, balance beam, hindpaw footprint testing in the animal. In certain embodiments, antisense compounds, for example, antisense oligonucleotides, are tested in animals to assess their ability to reduce hyperphosphorylated tau and neurofibrillary tangles. In certain embodiments, antisense compounds, for example, antisense oligonucleotides, are tested to assess their ability to prevent, and/or reduce severity of, seizures in a pentylenetetrazol (PTZ) induced seizure model.

Testing may be performed in normal animals, or in experimental disease models. For administration to animals, antisense oligonucleotides are formulated in a pharmaceutically acceptable diluent, such as phosphate-buffered saline. Administration includes parenteral routes of administration, such as intraperitoneal, intravenous, and subcutaneous. Calculation of antisense oligonucleotide dosage and dosing frequency is within the abilities of those skilled in the art, and depends upon factors such as route of administration and animal body weight. Following a period of treatment with antisense oligonucleotides, RNA is isolated from CNS tissue or CSF and changes in Tau nucleic acid expression are measured.

Certain Indications

In certain embodiments, provided herein are methods, compounds, and compositions of treating an individual comprising administering one or more pharmaceutical compositions described herein. In certain embodiments, the individual has a neurodegenerative disease. In certain embodiments, the individual is at risk for developing a neurodegenerative disease, including, but not limited to, a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome. In certain embodiments, the individual has been identified as having a Tau associated disease. In certain embodiments, provided herein are methods for prophylactically reducing Tau expression in an individual. Certain embodiments include treating an individual in need thereof by administering to an individual a therapeutically effective amount of an antisense compound targeted to a Tau nucleic acid.

In one embodiment, administration of a therapeutically effective amount of an antisense compound targeted to a Tau nucleic acid is accompanied by monitoring of Tau levels in an individual, to determine an individual's response to administration of the antisense compound. An individual's response to administration of the antisense compound may be used by a physician to determine the amount and duration of therapeutic intervention.

In certain embodiments, administration of an antisense compound targeted to a Tau nucleic acid results in reduction of Tau expression by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values. In certain embodiments, administration of an antisense compound targeted to a Tau nucleic acid results in improved motor function in an animal. In certain embodiments, administration of a Tau antisense compound improves motor function by at least 15, 20, 25, 30, 35, 40, 45, 50, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%, or a range defined by any two of these values.

In certain embodiments, pharmaceutical compositions comprising an antisense compound targeted to Tau are used for the preparation of a medicament for treating a patient suffering or susceptible to a neurodegenerative disease including a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, and Dravet's Syndrome.

Certain Hotspot Regions

1. Nucleobases 135783-135980 of SEQ ID NO: 1

In certain embodiments, antisense oligonucleotides are designed to target nucleobases 135783-135980 of SEQ ID NO: 1 (GENBANK Accession No. GENBANK Accession No. NT_010783.15 truncated from nucleotides 9240000 to 9381000). In certain embodiments, nucleobases 135783-135980 are a hotspot region. In certain embodiments, nucleobases 135783-135980 are targeted by antisense oligonucleotides. In certain embodiments, the antisense oligonucleotides are 18, 19, or 20 nucleobases in length. In certain embodiments, the antisense oligonucleotides are gapmers. In certain embodiments, the gapmers are 5-10-5 MOE gapmers, 5-9-5 MOE gapmers, 5-7-6 MOE gapmers, and 5-8-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 135783-135980 are targeted by the following ISIS numbers: 424879, 424880, 548937, 613114-613120, 622096-622150, 623988-623996, 664511-664542, and 664661-664819.

In certain embodiments, nucleobases 135783-135980 are targeted by the following SEQ ID NOs: 56, 57, 248, 462-467, 1668-1698, 2025-2048, 2301-2309, 2331-2443, and 2478-2483.

In certain embodiments, antisense oligonucleotides targeting nucleobases 135783-135980 achieve at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, or at least 93% reduction of Tau mRNA and/or protein levels in vitro and/or in vivo.

2. Nucleobases 135853-135872 of SEQ ID NO: 1

In certain embodiments, antisense oligonucleotides are designed to target nucleobases 135853-135872 of SEQ ID NO: 1 (GENBANK Accession No. GENBANK Accession No. NT_010783.15 truncated from nucleotides 9240000 to 9381000). In certain embodiments, nucleobases 135853-135872 are a hotspot region. In certain embodiments, nucleobases 135853-135872 are targeted by antisense oligonucleotides. In certain embodiments, the antisense oligonucleotides are 18, 19, or 20 nucleobases in length. In certain embodiments, the antisense oligonucleotides are gapmers. In certain embodiments, the gapmers are 5-10-5 MOE gapmers, 5-9-5 MOE gapmers, 5-7-6 MOE gapmers, or 5-8-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 135853-135872 are targeted by the following ISIS numbers: 424879, 424880, 613117, 613118, 622114-622125, 623993-623996, 664522-664542, 664676-664713, 664729-664766, and 664783-664819.

In certain embodiments, nucleobases 135853-135872 are targeted by the following SEQ ID NOs: 56, 57, 248, 464-465, 1668-1673, 2039-2048, 2306-2309, 2345-2443, and 2478-2483.

In certain embodiments, antisense oligonucleotides targeting nucleobases 135853-135872 achieve at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, or at least 87% reduction of Tau mRNA and/or protein levels in vitro and/or in vivo.

3. Nucleobases 135783-135929 of SEO ID NO: 1

In certain embodiments, antisense oligonucleotides are designed to target nucleobases 135783-135929 of SEQ ID NO: 1 (GENBANK Accession No. GENBANK Accession No. NT_010783.15 truncated from nucleotides 9240000 to 9381000). In certain embodiments, nucleobases 135783-135929 are a hotspot region. In certain embodiments, nucleobases 135783-135929 are targeted by antisense oligonucleotides. In certain embodiments, the antisense oligonucleotides are 18, 19, or 20 nucleobases in length. In certain embodiments, the antisense oligonucleotides are gapmers. In certain embodiments, the gapmers are 5-10-5 MOE gapmers, 5-9-5 MOE gapmers, 5-7-6 MOE gapmers, or 5-8-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 135783-135929 are targeted by the following ISIS numbers: 424879, 424880, 548937, 613114-613119, 622096-622138, 623988-623996, 664511-664542, and 664661-664819.

In certain embodiments, nucleobases 135783-135929 are targeted by the following SEQ ID NOs: 56, 57, 248, 462-466, 1668-1686, 2025-2048, 2301-2309, 2331-2443, and 2478-2483.

In certain embodiments, antisense oligonucleotides targeting nucleobases 135783-135929 achieve at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, or at least 93% reduction of Tau mRNA and/or protein levels in vitro and/or in vivo.

4. Nucleobases 135783-135914 of SEQ ID NO: 1

In certain embodiments, antisense oligonucleotides are designed to target nucleobases 135783-135914 of SEQ ID NO: 1 (GENBANK Accession No. GENBANK Accession No. NT_010783.15 truncated from nucleotides 9240000 to 9381000). In certain embodiments, nucleobases 135783-135914 are a hotspot region. In certain embodiments, nucleobases 135783-135914 are targeted by antisense oligonucleotides. In certain embodiments, the antisense oligonucleotides are 18, 19, or 20 nucleobases in length. In certain embodiments, the antisense oligonucleotides are gapmers. In certain embodiments, the gapmers are 5-10-5 MOE gapmers, 5-9-5 MOE gapmers, 5-7-6 MOE gapmers, or 5-8-5 MOE gapmers. In certain embodiments, the nucleosides of the antisense oligonucleotides are linked by phosphorothioate internucleoside linkages. In certain embodiments, the nucleosides of the antisense oligonucleotides are linked by phosphodiester internucleoside linkages. In certain embodiments, the nucleosides of the antisense oligonucleotides are linked by phosphorothioate and phosphodiester internucleotide linkages (e.g., the antisense oligonucleotides have "mixed backbones").

In certain embodiments, nucleobases 135783-135914 are targeted by the following ISIS numbers: 424879, 424880, 548937, 613114-613119, 622096-622133, 623988-623996, 664511-664542, 664661-664819.

In certain embodiments, nucleobases 135783-135914 are targeted by the following SEQ ID NOs: 56, 57, 248, 462-466, 1668-1681, 2025-2048, 2301-2309, 2331-2443, and 2478-2483.

In certain embodiments, nucleobases 135783-135914 are targeted by the following ISIS numbers: 424879, 424880, 548937, 613114-613119, 622096-622133, and 623988-623996.

In certain embodiments, nucleobases 135783-135914 are targeted by the following SEQ ID NOs: 56, 57, 248, 462-466, 1668-1681, 2025-2048, and 2301-2309.

In certain embodiments, antisense oligonucleotides targeting nucleobases 135783-135914 achieve at least 12%, at least 13%, at least 14%, at least 15%, at least 16%, at least 17%, at least 18%, at least 19%, 20%, at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, or at least 93% reduction of Tau mRNA and/or protein levels in vitro and/or in vivo.

EXAMPLES

Non-Limiting Disclosure and Incorporation by Reference

While certain compounds, compositions, and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Inhibition of Human Tau in HepG2 Cells by MOE Gapmers

Antisense oligonucleotides were designed targeting a tau nucleic acid and were tested for their effects on tau mRNA in vitro. Cultured HepG2 cells were transfected using Lipofectin reagent with 100 nM antisense oligonucleotide. After a treatment period of approximately 24 hours, RNA was isolated from the cells and tau mRNA levels were measured by quantitative real-time PCR. Human primer probe set RTS3104 (forward sequence AAGATTGGGTCCCTGGACAAT, designated herein as SEQ ID NO: 10; reverse sequence AGCTTGTGGGTTTCAATCTTTTTATT, designated herein as SEQ ID NO: 11; probe sequence CACCCACGTCCCTGGCGGA, designated herein as SEQ ID NO: 12) was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-10-5 MOE gapmers. The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 1 below is targeted to either the human tau genomic sequence, designated herein as SEQ ID NO: 1 (GENBANK Accession No. NT_010783.15 truncated from nucleotides 9240000 to 9381000) or to the human tau mRNA sequence, designated herein as SEQ ID NO: 2 (GENBANK Accession No. NM_001123066.3). 'n/a' indicates that the oligonucleotide does not target the gene sequence with 100% complementarity. The sequences listed in Table 2 do not target either SEQ ID NO: 1 or 2 with 100% complementarity, but instead target SEQ ID NO: 3 (GENBANK Accession No. NM_016841.4, a variant mRNA sequence which skips exons 3, 4, 6, 8, 10, and 12) or SEQ ID NO: 4 (GENBANK Accession No. NT_010783.14 truncated from nucleotides 2624000 to 2761000).

TABLE 1

Inhibition of Tau mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 424863 | n/a | n/a | TTGTAGACTATTTGCACACT | 59 | 2240 | 2259 | 20 |
| 433519 | 28769 | 28788 | CACAGGCAGATGCGAACCCT | 57 | n/a | n/a | 21 |
| 433520 | 47181 | 47200 | TGGTGGAGACAAGACATTCT | 57 | n/a | n/a | 22 |
| 433521 | 71387 | 71406 | CCATCCCCTAATAGTTAGCA | 29 | n/a | n/a | 23 |
| 433522 | 72861 | 72880 | CATGAGGCTTGGGATCTGAA | 49 | n/a | n/a | 24 |
| 433474 | 73879 | 73898 | GTGATCTTCCATCACTTCGA | 61 | 345 | 364 | 25 |
| 433523 | 73980 | 73999 | GTCCACTAACCTTTCAGGCC | 63 | n/a | n/a | 26 |
| 433518 | 83423 | 83442 | AGCATCAGAGGTTTCAGAGC | 46 | 501 | 520 | 27 |
| 424852 | 83437 | 83456 | GTTGGAGTGCTCTTAGCATC | 58 | 515 | 534 | 28 |
| 433513 | 85934 | 85953 | GGCAGCCTGCTTGCCGGGAG | 68 | 573 | 592 | 29 |
| 433524 | 87927 | 87946 | GAGGATTTCCTTGGAGAGAG | 53 | n/a | n/a | 30 |
| 433525 | 89950 | 89969 | GTTCACTGACCTTGGGTCAC | 38 | n/a | n/a | 31 |
| 433526 | 91248 | 91267 | ATGATTTCTAGAGGTCATGC | 61 | n/a | n/a | 32 |
| 433514 | 95121 | 95140 | AGAGGAAATCCACAGGGAGG | 43 | 1120 | 1139 | 33 |
| 433515 | 95372 | 95391 | TTCAGAGGGCTCTGGAAGGT | 58 | 1371 | 1390 | 34 |
| 433527 | 95790 | 95809 | ACACCATGAGGGCACCCGTC | 65 | n/a | n/a | 35 |
| 433528 | 98549 | 98568 | ACCATGCGAGCTGATAAAAT | 46 | n/a | n/a | 36 |
| 433516 | 101406 | 101425 | AAGGTTTTAGCAGAGGAACG | 50 | 1514 | 1533 | 37 |
| 433517 | 101507 | 101526 | AGGAAGGTGGCTCTGGGCAC | 73 | 1615 | 1634 | 38 |
| 433476 | 103087 | 103106 | CCAGAGCTGGGTGGTGTCTT | 60 | n/a | n/a | 39 |
| 433477 | 108040 | 108059 | GGTGGAGTACGGACCACTGC | 71 | 2006 | 2025 | 40 |
| 433478 | 108054 | 108073 | AAGACGGCGACTTGGGTGGA | 65 | 2020 | 2039 | 41 |
| 424857 | 108148 | 108167 | TGGTGCTTCAGGTTCTCAGT | 54 | 2114 | 2133 | 42 |
| 433529 | 121819 | 121838 | TTATCTGCACCTTTGGTAGC | 29 | n/a | n/a | 43 |
| 424859 | 121828 | 121847 | TCTTATTAATTATCTGCACC | 50 | 2149 | 2168 | 44 |
| 424860 | 121838 | 121857 | AGATCCAGCTTCTTATTAAT | 36 | 2159 | 2178 | 45 |
| 424861 | 121846 | 121865 | CGTTGCTAAGATCCAGCTTC | 48 | 2167 | 2186 | 46 |
| 424862 | 121865 | 121884 | GAGCCACACTTGGACTGGAC | 79 | 2186 | 2205 | 47 |
| 433530 | 122497 | 122516 | GGTGGCGCAGGCTAAGCATA | 52 | n/a | n/a | 48 |
| 424864 | 125798 | 125817 | GAGCCACACTTGGAGGTCAC | 63 | 2279 | 2298 | 49 |
| 433531 | 125834 | 125853 | ACAGGGCTACCTGGTTTATG | 53 | n/a | n/a | 50 |
| 424866 | 130141 | 130160 | ATTTTACTTCCACCTGGCCA | 70 | 2329 | 2348 | 51 |
| 433479 | 130188 | 130207 | GGACCCAATCTTCGACTGGA | 70 | 2376 | 2395 | 52 |
| 424926 | 135467 | 135486 | GTGGGTTTCAATCTGCAAGA | 39 | n/a | n/a | 53 |

TABLE 1-continued

Inhibition of Tau mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 424869 | 135475 | 135494 | GTCAGCTTGTGGGTTTCAAT | 74 | 2438 | 2457 | 54 |
| 433480 | 135673 | 135692 | GATCACAAACCCTGCTTGGC | 60 | 2636 | 2655 | 55 |
| 424879 | 135848 | 135867 | TGATTTTGAAGTCCCGAGCC | 64 | 2811 | 2830 | 56 |
| 424880 | 135853 | 135872 | ATCACTGATTTTGAAGTCCC | 54 | 2816 | 2835 | 57 |
| 433481 | 136033 | 136052 | CAGAAGCAGCTTTCAGAGCC | 38 | 2996 | 3015 | 58 |
| 433482 | 136118 | 136137 | AAATCCTTTGTTGCTGCCAC | 37 | 3081 | 3100 | 59 |
| 424882 | 136425 | 136444 | CCCACAGGCTGCCCTGCAGA | 57 | 3388 | 3407 | 60 |
| 433483 | 136491 | 136510 | GGAGGTCATCCACGAAGTGC | 67 | 3454 | 3473 | 61 |
| 433484 | 136577 | 136596 | GGAAGCCCCTCAACTCAGGC | 28 | 3540 | 3559 | 62 |
| 433485 | 136655 | 136674 | GGTCTGCAAAGTGGCCAAAA | 49 | 3618 | 3637 | 63 |
| 424883 | 136675 | 136694 | TGGTTAGCCCTAAAGTCCCA | 54 | 3638 | 3657 | 64 |
| 433486 | 136686 | 136705 | ACAAAGAGAACTGGTTAGCC | 39 | 3649 | 3668 | 65 |
| 424884 | 136703 | 136722 | AAGAGGCACAAGTCCTTACA | 40 | 3666 | 3685 | 66 |
| 433487 | 136748 | 136767 | CAGAGATGCCAGTGGCCCAG | 70 | 3711 | 3730 | 67 |
| 433488 | 137083 | 137102 | GGAACCGAATCAGATCATGA | 54 | 4046 | 4065 | 68 |
| 433489 | 137387 | 137406 | TGGAGGGCTGATACTATGCA | 45 | 4350 | 4369 | 69 |
| 433490 | 137430 | 137449 | AAAAGAACCATTTCCAAGGG | 41 | 4393 | 4412 | 70 |
| 433491 | 137540 | 137559 | ATCCAACTACAACTCAACAG | 17 | 4503 | 4522 | 71 |
| 424894 | 137579 | 137598 | ATCATAGTCACTCTGGTGAA | 56 | 4542 | 4561 | 72 |
| 433492 | 137694 | 137713 | GCCACACGAGTCCCAGTGTG | 45 | 4657 | 4676 | 73 |
| 433493 | 137731 | 137750 | AAAACTTGGGAGGCCCCAGC | 50 | 4694 | 4713 | 74 |
| 433494 | 138173 | 138192 | GATCCAGGACAGGCAATTCA | 58 | 5136 | 5155 | 75 |
| 433495 | 138205 | 138224 | TCCTCAGGCAGGCAGCTTGG | 49 | 5168 | 5187 | 76 |
| 433496 | 138303 | 138322 | TTCTCATGGCAGCAGATGGA | 51 | 5266 | 5285 | 77 |
| 433497 | 138338 | 138357 | TTAGGCAGCAATGTTTTGCA | 18 | 5301 | 5320 | 78 |
| 433498 | 138503 | 138522 | AGAGTTCTGGGCCCAGAGAC | 73 | 5466 | 5485 | 79 |
| 433499 | 138675 | 138694 | AGGAAGAGGAACCGAGGTGC | 59 | 5638 | 5657 | 80 |
| 433500 | 138774 | 138793 | TCTTAGGCTGGCCCCAAGAG | 36 | 5737 | 5756 | 81 |
| 433501 | 138812 | 138831 | TCAATTTATCTGCCAGCACT | 28 | 5775 | 5794 | 82 |
| 433502 | 138845 | 138864 | TCCTCATTTAAGATCACAAG | 36 | 5808 | 5827 | 83 |
| 433503 | 138983 | 139002 | ATGGAACTATTGATAAAGTG | 47 | 5946 | 5965 | 84 |
| 433504 | 139003 | 139022 | CACCACTGAAGTCAATTTAA | 23 | 5966 | 5985 | 85 |
| 433505 | 139112 | 139131 | AGTTTAAGTGCTGCACCCCA | 52 | 6075 | 6094 | 86 |
| 433506 | 139137 | 139156 | GAAATCATGAAAAGGGTTAC | 25 | 6100 | 6119 | 87 |
| 433507 | 139154 | 139173 | CTCTAGCAAATGTGGTTGAA | 42 | 6117 | 6136 | 88 |
| 433508 | 139229 | 139248 | AGCCAGCTGCCTGGGAAAGC | 70 | 6192 | 6211 | 89 |

TABLE 1-continued

Inhibition of Tau mRNA by 5-10-5 MOE gapmers targeting SEQ ID NOs: 1 and 2

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 433509 | 139359 | 139378 | TAGAGGGAAGGATGCCAAGG | 56 | 6322 | 6341 | 90 |
| 433510 | 139406 | 139425 | GTGTGTCTGGAGCCAGTGTG | 49 | 6369 | 6388 | 91 |
| 424910 | 139675 | 139694 | GAAATCATGGGACTTGCAAG | 52 | 6638 | 6657 | 92 |
| 433512 | 139729 | 139748 | AAAGCTAAGCTAAGATGATT | 31 | 6692 | 6711 | 93 |
| 424913 | 139797 | 139816 | TTACAGCAACAGTCAGTGTA | 42 | 6760 | 6779 | 94 |

TABLE 2

Inhibition of Tau mRNA by 5-10-5 MOE gapmers targeting SEQ ID NOs: 3 and 4

| ISIS NO | Target SEQ ID NO | Target Start Site | Sequence | % inhibition | SEQ ID NO |
|---|---|---|---|---|---|
| 424917 | 3 | 968 | TTGTAGACTATTTGCACCTT | 51 | 95 |
| 433475 | 3 | 443 | TCTTCAGCTTTCAGGCCAGC | 68 | 96 |
| 433511 | 4 | 135519 | AGAAGTTTTATGAAGCCGCA | 13 | 97 |

Example 2: Dose-Dependent Antisense Inhibition of Human Tau in HepG2 Cells by 5-10-5 MOE Gapmers Gapmers from studies described above exhibiting significant in vitro inhibition of Tau mRNA were selected and tested at various doses in HepG2 cells. Cells were plated at a density of 10,000 cells per well and transfected using Lipofectin reagent with 12.5 nM, 25.0 nM, 50.0 nM, 100.0 nM, or 200.0 nM concentrations of antisense oligonucleotide, as specified in the Table below. After a treatment period of approximately 16 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells. Tau mRNA levels were significantly reduced in a dose-dependent manner in antisense oligonucleotide treated cells.

TABLE 3

| ISIS No | 12.5 nM | 25.0 nM | 50.0 nM | 100.0 nM | 200.0 nM |
|---|---|---|---|---|---|
| 424862 | 17 | 24 | 41 | 64 | 84 |
| 424866 | 14 | 25 | 47 | 63 | 84 |
| 433498 | 27 | 42 | 61 | 79 | 82 |
| 433508 | 25 | 31 | 53 | 66 | 83 |
| 433517 | 25 | 34 | 57 | 72 | 78 |
| 433487 | 18 | 30 | 38 | 60 | 76 |
| 433477 | 23 | 31 | 51 | 71 | 80 |
| 433475 | 18 | 33 | 57 | 71 | 85 |
| 433513 | 24 | 30 | 50 | 71 | 77 |
| 433483 | 23 | 28 | 41 | 58 | 74 |
| 433527 | 19 | 32 | 46 | 60 | 77 |

Example 3: Antisense Inhibition of Human Tau in SH-SY5Y Cells by 5-10-5 MOE Gapmers Additional antisense oligonucleotides were designed targeting a Tau nucleic acid and were tested for their effects on Tau mRNA in vitro. The antisense oligonucleotides were tested in a series of experiments that had similar culture conditions. The results for each experiment are presented in separate tables shown below. Cultured SH-SY5Y cells were transfected using electroporation with 7,000 nM antisense oligonucleotide. After a treatment period of approximately 24 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of Tau, relative to untreated control cells.

The newly designed chimeric antisense oligonucleotides in the Tables below were designed as 5-10-5 MOE gapmers.

The gapmers are 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to either the human Tau genomic sequence, designated herein as SEQ ID NO: 1 (GENBANK Accession No. NT_010783.15 truncated from nucleotides 9240000 to 9381000) or to the human Tau mRNA sequence, designated herein as SEQ ID NO: 2 (GENBANK Accession No. NM_001123066.3). 'n/a' indicates that the antisense oligonucleotide does not target that particular gene sequence with 100% complementarity.

TABLE 4

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548786 | 73867 | 73886 | CACTTCGAACTCCTGGCGGG | 73 | 333 | 352 | 98 |
| 548787 | 73869 | 73888 | ATCACTTCGAACTCCTGGCG | 64 | 335 | 354 | 99 |
| 548788 | 73871 | 73890 | CCATCACTTCGAACTCCTGG | 78 | 337 | 356 | 100 |
| 548789 | 73873 | 73892 | TTCCATCACTTCGAACTCCT | 49 | 339 | 358 | 101 |
| 548790 | 73875 | 73894 | TCTTCCATCACTTCGAACTC | 33 | 341 | 360 | 102 |
| 548791 | 73877 | 73896 | GATCTTCCATCACTTCGAAC | 54 | 343 | 362 | 103 |
| 433474 | 73879 | 73898 | GTGATCTTCCATCACTTCGA | 86 | 345 | 364 | 25 |
| 548792 | 73906 | 73925 | CCTGTCCCCCAACCCGTACG | 38 | 372 | 391 | 104 |
| 548793 | 73908 | 73927 | TTCCTGTCCCCCAACCCGTA | 58 | 374 | 393 | 105 |
| 548794 | 73910 | 73929 | CTTTCCTGTCCCCCAACCCG | 55 | 376 | 395 | 106 |
| 548795 | 73912 | 73931 | ATCTTTCCTGTCCCCCAACC | 14 | 378 | 397 | 107 |
| 548796 | 73914 | 73933 | TGATCTTTCCTGTCCCCCAA | 59 | 380 | 399 | 108 |
| 548797 | 73916 | 73935 | CCTGATCTTTCCTGTCCCCC | 67 | 382 | 401 | 109 |
| 548798 | 73918 | 73937 | CCCCTGATCTTTCCTGTCCC | 67 | 384 | 403 | 110 |
| 548799 | 73920 | 73939 | CCCCCCTGATCTTTCCTGTC | 33 | 386 | 405 | 111 |
| 548800 | 73922 | 73941 | AGCCCCCCTGATCTTTCCTG | 45 | 388 | 407 | 112 |
| 548801 | 73924 | 73943 | GTAGCCCCCCTGATCTTTCC | 62 | 390 | 409 | 113 |
| 548802 | 73926 | 73945 | GTGTAGCCCCCCTGATCTTT | 42 | 392 | 411 | 114 |
| 548803 | 73928 | 73947 | TGGTGTAGCCCCCCTGATCT | 58 | 394 | 413 | 115 |
| 548804 | 73930 | 73949 | CATGGTGTAGCCCCCCTGAT | 62 | 396 | 415 | 116 |
| 548805 | 73932 | 73951 | TGCATGGTGTAGCCCCCCTG | 82 | 398 | 417 | 117 |
| 548806 | 73934 | 73953 | GGTGCATGGTGTAGCCCCCC | 79 | 400 | 419 | 118 |
| 548807 | 73936 | 73955 | TTGGTGCATGGTGTAGCCCC | 58 | 402 | 421 | 119 |
| 548808 | 73938 | 73957 | TCTTGGTGCATGGTGTAGCC | 60 | 404 | 423 | 120 |
| 548809 | 73940 | 73959 | GGTCTTGGTGCATGGTGTAG | 67 | 406 | 425 | 121 |
| 548810 | 73945 | 73964 | CTCTTGGTCTTGGTGCATGG | 61 | 411 | 430 | 122 |
| 548811 | 73958 | 73977 | CGTCCGTGTCACCCTCTTGG | 73 | 424 | 443 | 123 |
| 548812 | 98559 | 98578 | GCTTTACTGACCATGCGAG | 68 | 1449 | 1468 | 124 |
| 548813 | 98561 | 98580 | TTGCTTTTACTGACCATGCG | 64 | 1451 | 1470 | 125 |
| 548814 | 98563 | 98582 | CTTTGCTTTTACTGACCATG | 40 | 1453 | 1472 | 126 |
| 548815 | 98565 | 98584 | GTCTTTGCTTTTACTGACCA | 60 | 1455 | 1474 | 127 |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548816 | 98567 | 98586 | CCGTCTTTGCTTTTACTGAC | 50 | 1457 | 1476 | 128 |
| 548817 | 98569 | 98588 | TCCCGTCTTTGCTTTTACTG | 46 | 1459 | 1478 | 129 |
| 548818 | 98571 | 98590 | AGTCCCGTCTTTGCTTTTAC | 41 | 1461 | 1480 | 130 |
| 548819 | 98573 | 98592 | CCAGTCCCGTCTTTGCTTTT | 37 | 1463 | 1482 | 131 |
| 548820 | 98577 | 98596 | GCTTCCAGTCCCGTCTTTGC | 43 | 1467 | 1486 | 132 |
| 548821 | 98579 | 98598 | TCGCTTCCAGTCCCGTCTTT | 35 | 1469 | 1488 | 133 |
| 548822 | 98581 | 98600 | CATCGCTTCCAGTCCCGTCT | 73 | 1471 | 1490 | 134 |
| 548823 | 98583 | 98602 | GTCATCGCTTCCAGTCCCGT | 63 | 1473 | 1492 | 135 |
| 548824 | 98585 | 98604 | TTGTCATCGCTTCCAGTCCC | 50 | 1475 | 1494 | 136 |
| 548825 | 98587 | 98606 | TTTTGTCATCGCTTCCAGTC | 46 | 1477 | 1496 | 137 |
| 548826 | 103023 | 103042 | GGCCCTTCTGGCCTGGAGGG | 64 | 1747 | 1766 | 138 |
| 548827 | 103025 | 103044 | CTGGCCCTTCTGGCCTGGAG | 29 | 1749 | 1768 | 139 |
| 548828 | 103027 | 103046 | GCCTGGCCCTTCTGGCCTGG | 40 | 1751 | 1770 | 140 |
| 548829 | 103029 | 103048 | TGGCCTGGCCCTTCTGGCCT | 12 | 1753 | 1772 | 141 |
| 548830 | 103031 | 103050 | GTTGGCCTGGCCCTTCTGGC | 53 | 1755 | 1774 | 142 |
| 548831 | 103052 | 103071 | TTTTGCTGGAATCCTGGTGG | 20 | 1776 | 1795 | 143 |
| 548832 | 103054 | 103073 | GTTTTTGCTGGAATCCTGGT | 29 | 1778 | 1797 | 144 |
| 548833 | 103056 | 103075 | GGGTTTTTGCTGGAATCCTG | 51 | 1780 | 1799 | 145 |
| 548834 | 103075 | 103094 | GGTGTCTTTGGAGCGGGCGG | 44 | 1799 | 1818 | 146 |
| 548835 | 103077 | 103096 | GTGGTGTCTTTGGAGCGGGC | 30 | 1801 | 1820 | 147 |
| 548836 | 103079 | 103098 | GGGTGGTGTCTTTGGAGCGG | 38 | 1803 | 1822 | 148 |
| 548837 | 103081 | 103100 | CTGGGTGGTGTCTTTGGAGC | 29 | 1805 | 1824 | 149 |
| 548838 | 103083 | 103102 | AGCTGGGTGGTGTCTTTGGA | 37 | 1807 | 1826 | 150 |
| 548839 | 103085 | 103104 | AGAGCTGGGTGGTGTCTTTG | 0 | 1809 | 1828 | 151 |
| 548840 | 107921 | 107940 | ATCCCCTGATTTTGGAGGTT | 27 | 1887 | 1906 | 152 |
| 548841 | 107923 | 107942 | CGATCCCCTGATTTTGGAGG | 65 | 1889 | 1908 | 153 |
| 548842 | 107925 | 107944 | TGCGATCCCCTGATTTTGGA | 53 | 1891 | 1910 | 154 |
| 548843 | 107927 | 107946 | GCTGCGATCCCCTGATTTTG | 23 | 1893 | 1912 | 155 |
| 548844 | 107929 | 107948 | CCGCTGCGATCCCCTGATTT | 32 | 1895 | 1914 | 156 |
| 548845 | 107931 | 107950 | AGCCGCTGCGATCCCCTGAT | 51 | 1897 | 1916 | 157 |
| 548846 | 107933 | 107952 | GTAGCCGCTGCGATCCCCTG | 14 | 1899 | 1918 | 158 |
| 548847 | 107968 | 107987 | CGGCTGCCGGGAGTGCCTGG | 33 | 1934 | 1953 | 159 |
| 548848 | 107970 | 107989 | AGCGGCTGCCGGGAGTGCCT | 52 | 1936 | 1955 | 160 |
| 548849 | 107972 | 107991 | GGAGCGGCTGCCGGGAGTGC | 44 | 1938 | 1957 | 161 |
| 548850 | 108047 | 108066 | CGACTTGGGTGGAGTACGGA | 10 | 2013 | 2032 | 162 |
| 548851 | 108049 | 108068 | GGCGACTTGGGTGGAGTACG | 29 | 2015 | 2034 | 163 |
| 548852 | 108051 | 108070 | ACGGCGACTTGGGTGGAGTA | 39 | 2017 | 2036 | 164 |

TABLE 4-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548853 | 108053 | 108072 | AGACGGCGACTTGGGTGGAG | 6 | 2019 | 2038 | 165 |
| 548854 | 108055 | 108074 | GAAGACGGCGACTTGGGTGG | 0 | 2021 | 2040 | 166 |
| 548855 | 108057 | 108076 | CGGAAGACGGCGACTTGGGT | 40 | 2023 | 2042 | 167 |
| 548856 | 108059 | 108078 | GGCGGAAGACGGCGACTTGG | 38 | 2025 | 2044 | 168 |
| 548857 | 108061 | 108080 | TTGGCGGAAGACGGCGACTT | 41 | 2027 | 2046 | 169 |
| 548858 | 108063 | 108082 | TCTTGGCGGAAGACGGCGAC | 35 | 2029 | 2048 | 170 |
| 548859 | 108065 | 108084 | GCTCTTGGCGGAAGACGGCG | 54 | 2031 | 2050 | 171 |
| 548860 | 108067 | 108086 | CGGCTCTTGGCGGAAGACGG | 58 | 2033 | 2052 | 172 |
| 548861 | 108069 | 108088 | GGCGGCTCTTGGCGGAAGAC | 55 | 2035 | 2054 | 173 |
| 433498 | 138503 | 138522 | AGAGTTCTGGGCCCAGAGAC | 53 | 5466 | 5485 | 79 |

TABLE 5

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548885 | n/a | n/a | GGGAGATTCTTTCAGGCCAG | 0 | 444 | 463 | 174 |
| 548893 | n/a | n/a | GAGCTTTGAGTTGAGGGACC | 0 | 1432 | 1451 | 175 |
| 548894 | n/a | n/a | GACCATGCGAGCTTTGAGTT | 13 | 1440 | 1459 | 176 |
| 548895 | n/a | n/a | TACTGACCATGCGAGCTTTG | 33 | 1444 | 1463 | 177 |
| 548881 | 6183 | 6202 | ATAGTCGACAGAGGCGAGGA | 43 | 283 | 302 | 178 |
| 548882 | 73840 | 73859 | CATCCTGGTTCAAAGTTCAC | 30 | 306 | 325 | 179 |
| 548883 | 73846 | 73865 | CTCAGCCATCCTGGTTCAAA | 39 | 312 | 331 | 180 |
| 548884 | 73847 | 73866 | GCTCAGCCATCCTGGTTCAA | 53 | 313 | 332 | 181 |
| 548886 | 83401 | 83420 | GGTTCCTCAGATCCGTCCTC | 53 | 479 | 498 | 182 |
| 548887 | 83438 | 83457 | TGTTGGAGTGCTCTTAGCAT | 33 | 516 | 535 | 183 |
| 548888 | 85939 | 85958 | TGCGCGGCAGCCTGCTTGCC | 32 | 578 | 597 | 184 |
| 548889 | 94699 | 94718 | ACCACCTTACCACTTTCAGG | 35 | 698 | 717 | 185 |
| 548890 | 94775 | 94794 | GGGAGCCCCAGGCATGCCGG | 45 | 774 | 793 | 186 |
| 548891 | 95125 | 95144 | TTGGAGAGGAAATCCACAGG | 13 | 1124 | 1143 | 187 |
| 548892 | 95131 | 95150 | GAAACTTTGGAGAGGAAATC | 0 | 1130 | 1149 | 188 |
| 548896 | 98557 | 98576 | TTTTACTGACCATGCGAGCT | 40 | 1447 | 1466 | 189 |
| 548897 | 101425 | 101444 | AAGGCAAGGCCTATTTTTCA | 34 | 1533 | 1552 | 190 |
| 548898 | 101469 | 101488 | TGGATCAGAGGGTCTGAGCT | 40 | 1577 | 1596 | 191 |
| 548899 | 101501 | 101520 | GTGGCTCTGGGCACACAGCA | 63 | 1609 | 1628 | 192 |
| 548900 | 108037 | 108056 | GGAGTACGGACCACTGCCAC | 37 | 2003 | 2022 | 193 |
| 433477 | 108040 | 108059 | GGTGGAGTACGGACCACTGC | 21 | 2006 | 2025 | 40 |

TABLE 5-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548862 | 108071 | 108090 | CAGGCGGCTCTTGGCGGAAG | 24 | 2037 | 2056 | 194 |
| 548863 | 108073 | 108092 | TGCAGGCGGCTCTTGGCGGA | 34 | 2039 | 2058 | 195 |
| 548864 | 108075 | 108094 | TCTGCAGGCGGCTCTTGGCG | 40 | 2041 | 2060 | 196 |
| 548865 | 108129 | 108148 | TGGAGCCGATCTTGGACTTG | 23 | 2095 | 2114 | 197 |
| 548866 | 108131 | 108150 | AGTGGAGCCGATCTTGGACT | 4 | 2097 | 2116 | 198 |
| 548901 | 108134 | 108153 | CTCAGTGGAGCCGATCTTGG | 28 | 2100 | 2119 | 199 |
| 548902 | 108136 | 108155 | TTCTCAGTGGAGCCGATCTT | 9 | 2102 | 2121 | 200 |
| 548903 | 108155 | 108174 | TCCCGGCTGGTGCTTCAGGT | 33 | 2121 | 2140 | 201 |
| 548904 | 121675 | 121694 | TTTCGGACTTGGCAGAGGCA | 50 | n/a | n/a | 202 |
| 548905 | 121728 | 121747 | GAGTGACATGCGCCACCCTG | 65 | n/a | n/a | 203 |
| 548906 | 121736 | 121755 | CTTTCGATGAGTGACATGCG | 19 | n/a | n/a | 204 |
| 548907 | 121794 | 121813 | AAAAGGATGAGTGACACGCC | 58 | n/a | n/a | 205 |
| 548908 | 121916 | 121935 | GTGAAGGTACTCACACTGCC | 34 | n/a | n/a | 206 |
| 548909 | 121917 | 121936 | TGTGAAGGTACTCACACTGC | 21 | n/a | n/a | 207 |
| 548910 | 121992 | 122011 | CTATGCAGTGTCTCGCAAGT | 39 | n/a | n/a | 208 |
| 548911 | 122001 | 122020 | GGATTTATTCTATGCAGTGT | 38 | n/a | n/a | 209 |
| 548912 | 122002 | 122021 | AGGATTTATTCTATGCAGTG | 37 | n/a | n/a | 210 |
| 548913 | 122015 | 122034 | TGAGAGCCCAAGAAGGATTT | 15 | n/a | n/a | 211 |
| 548914 | 122022 | 122041 | CAGATCCTGAGAGCCCAAGA | 33 | n/a | n/a | 212 |
| 548915 | 122025 | 122044 | AGCCAGATCCTGAGAGCCCA | 55 | n/a | n/a | 213 |
| 548916 | 122137 | 122156 | GGACCCAGAAATGCTGGGAC | 18 | n/a | n/a | 214 |
| 548917 | 125555 | 125574 | AAATGTGTTGTCGAAATTCT | 0 | n/a | n/a | 215 |
| 548918 | 125568 | 125587 | AGTCAGGGTGGAAAAATGTG | 0 | n/a | n/a | 216 |
| 548919 | 125578 | 125597 | AGCACATCCTAGTCAGGGTG | 39 | n/a | n/a | 217 |
| 548920 | 125587 | 125606 | GCCATGAGGAGCACATCCTA | 45 | n/a | n/a | 218 |
| 548921 | 125600 | 125619 | GTGGTTCCCAGCTGCCATGA | 38 | n/a | n/a | 219 |
| 548922 | 125603 | 125622 | ACAGTGGTTCCCAGCTGCCA | 38 | n/a | n/a | 220 |
| 548923 | 125619 | 125638 | CCCAGGCCCTTATTGGACAG | 19 | n/a | n/a | 221 |
| 548867 | 125778 | 125797 | CTTGCTCAGGTCAACTGGTT | 45 | 2259 | 2278 | 222 |
| 548925 | 125812 | 125831 | GGATGTTGCCTAATGAGCCA | 35 | 2293 | 2312 | 223 |
| 548926 | 130194 | 130213 | GTCCAGGGACCCAATCTTCG | 87 | 2382 | 2401 | 224 |
| 548927 | 130196 | 130215 | TTGTCCAGGGACCCAATCTT | 48 | 2384 | 2403 | 225 |
| 548928 | 135478 | 135497 | AAGGTCAGCTTGTGGGTTTC | 52 | 2441 | 2460 | 226 |
| 548868 | 135518 | 135537 | CTCCGCCCCGTGGTCTGTCT | 37 | 2481 | 2500 | 227 |
| 548869 | 135520 | 135539 | ATCTCCGCCCCGTGGTCTGT | 25 | 2483 | 2502 | 228 |
| 548870 | 135522 | 135541 | CGATCTCCGCCCCGTGGTCT | 48 | 2485 | 2504 | 229 |
| 548871 | 135524 | 135543 | CACGATCTCCGCCCCGTGGT | 38 | 2487 | 2506 | 230 |

TABLE 5-continued

| ISIS NO | SEQ ID NO: 1 Start Site | SEQ ID NO: 1 Stop Site | Sequence | % inhibition | SEQ ID NO: 2 Start Site | SEQ ID NO: 2 Stop Site | SEQ ID NO |
|---|---|---|---|---|---|---|---|
| 548872 | 135526 | 135545 | TACACGATCTCCGCCCCGTG | 33 | 2489 | 2508 | 231 |
| 548873 | 135528 | 135547 | TGTACACGATCTCCGCCCCG | 22 | 2491 | 2510 | 232 |
| 548874 | 135530 | 135549 | CTTGTACACGATCTCCGCCC | 38 | 2493 | 2512 | 233 |
| 548875 | 135532 | 135551 | GACTTGTACACGATCTCCGC | 13 | 2495 | 2514 | 234 |
| 548876 | 135534 | 135553 | GCGACTTGTACACGATCTCC | 40 | 2497 | 2516 | 235 |
| 548877 | 135536 | 135555 | TGGCGACTTGTACACGATCT | 33 | 2499 | 2518 | 236 |
| 548878 | 135538 | 135557 | ACTGGCGACTTGTACACGAT | 25 | 2501 | 2520 | 237 |
| 548879 | 135540 | 135559 | CCACTGGCGACTTGTACACG | 19 | 2503 | 2522 | 238 |
| 548929 | 135546 | 135565 | CAGACACCACTGGCGACTTG | 33 | 2509 | 2528 | 239 |
| 548930 | 135593 | 135612 | GCTGCCGGTGGAGGAGACAT | 29 | 2556 | 2575 | 240 |
| 548931 | 135594 | 135613 | TGCTGCCGGTGGAGGAGACA | 19 | 2557 | 2576 | 241 |
| 548932 | 135600 | 135619 | TGTCGATGCTGCCGGTGGAG | 20 | 2563 | 2582 | 242 |
| 548933 | 135601 | 135620 | ATGTCGATGCTGCCGGTGGA | 20 | 2564 | 2583 | 243 |
| 548934 | 135610 | 135629 | GAGTCTACCATGTCGATGCT | 23 | 2573 | 2592 | 244 |
| 548880 | 135654 | 135673 | CCAGGGAGGCAGACACCTCG | 28 | 2617 | 2636 | 245 |
| 548935 | 135662 | 135681 | CTGCTTGGCCAGGGAGGCAG | 14 | 2625 | 2644 | 246 |
| 548936 | 135674 | 135693 | TGATCACAAACCCTGCTTGG | 25 | 2637 | 2656 | 247 |
| 548937 | 135786 | 135805 | CCGAACTGCGAGGAGCAGCT | 66 | 2749 | 2768 | 248 |
| 433498 | 138503 | 138522 | AGAGTTCTGGGCCCAGAGAC | 34 | 5466 | 5485 | 79 |

Example 4: Dose-Dependent Antisense Inhibition of Human Tau in SH-SY5Y Cells by 5-10-5 MOE Gapmers Gapmers from studies described above exhibiting significant in vitro inhibition of Tau mRNA were selected and tested at various doses in SH-SY-5Y cells. Cells were plated at a density of 20,000 cells per well and transfected using electroporation with 1.25 µM, 2.50 µM, 5.00 µM, 10.00 µM, and 20.00 µM concentrations of antisense oligonucleotide, as specified in the Table below. After a treatment period of approximately 16 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of Tau, relative to untreated control cells. Tau mRNA levels were significantly reduced in a dose-dependent manner in antisense oligonucleotide treated cells.

TABLE 6

| ISIS No | 1.25 µM | 2.50 µM | 5.00 µM | 10.00 µM | 20.00 µM |
|---|---|---|---|---|---|
| 433474 | 29 | 54 | 74 | 83 | 88 |
| 433477 | 0 | 0 | 11 | 33 | 59 |
| 433498 | 0 | 10 | 30 | 53 | 71 |
| 548786 | 9 | 29 | 51 | 66 | 82 |
| 548787 | 19 | 27 | 61 | 85 | 87 |
| 548788 | 31 | 31 | 54 | 72 | 94 |
| 548805 | 19 | 48 | 62 | 81 | 96 |
| 548806 | 25 | 50 | 75 | 80 | 95 |
| 548811 | 21 | 42 | 60 | 74 | 94 |
| 548812 | 47 | 39 | 64 | 77 | 91 |
| 548822 | 0 | 32 | 52 | 62 | 91 |
| 548899 | 19 | 50 | 69 | 87 | 93 |
| 548905 | 11 | 32 | 57 | 80 | 95 |
| 548907 | 14 | 28 | 44 | 80 | 91 |
| 548937 | 24 | 43 | 66 | 82 | 91 |

Example 5: Antisense Inhibition of Human Tau in SH-SY5Y Cells by 5-10-5 MOE Gapmers Additional antisense oligonucleotides were designed targeting a Tau nucleic acid and were tested for their effects on Tau mRNA in vitro. Cultured SH-SY5Y cells were plated at a density of 20,000 cells per well and were transfected using electroporation with 6,000 nM antisense oligonucleotide. After a treatment period of approximately 24 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are phosphorothioate linkages. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to the human tau genomic sequence, designated herein as SEQ ID NO: 1 (GENBANK Accession No. NT_010783.15 truncated from nucleotides 9240000 to 9381000).

TABLE 7

| ISIS NO | SEQ ID NO: 1 Start Site | SEQ ID NO: 1 Stop Site | Sequence | % inhibition | SEQ ID NO |
|---|---|---|---|---|---|
| 433474 | 73879 | 73898 | GTGATCTTCCATCACTTCGA | 63 | 25 |
| 559166 | 26760 26944 | 26779 26963 | TGCTTACACACCACACAC | 0 | 249 |
| 559167 | 26761 26945 | 26780 26964 | ATGCTTACACACCACACA | 4 | 250 |
| 559168 | 26762 26946 | 26781 26965 | CATGCTTACACACCACACAC | 0 | 251 |
| 559169 | 81022 81125 | 81041 81144 | TACAGATATATGATTGGATG | 0 | 252 |
| 559170 | 81023 81126 | 81042 81145 | GTACAGATATATGATTGGAT | 0 | 253 |
| 559171 | 81024 81127 | 81043 81146 | TGTACAGATATATGATTGGA | 0 | 254 |
| 559172 | 81025 81128 | 81044 81147 | ATGTACAGATATATGATTGG | 0 | 255 |
| 559173 | 81026 81129 | 81045 81148 | TATGTACAGATATATGATTG | 0 | 256 |
| 559174 | 81027 81130 | 81046 81149 | TTATGTACAGATATATGATT | 0 | 257 |
| 559175 | 81028 81131 | 81047 81150 | ATTATGTACAGATATATGAT | 0 | 258 |
| 559176 | 81029 81132 | 81048 81151 | GATTATGTACAGATATATGA | 0 | 259 |
| 559177 | 81030 81133 | 81049 81152 | GGATTATGTACAGATATATG | 0 | 260 |
| 559178 | 81031 81134 | 81050 81153 | TGGATTATGTACAGATATAT | 0 | 261 |
| 559179 | 81032 81135 | 81051 81154 | ATGGATTATGTACAGATATA | 0 | 262 |
| 559180 | 81033 81136 | 81052 81155 | AATGGATTATGTACAGATAT | 0 | 263 |
| 559181 | 81034 81137 | 81053 81156 | GAATGGATTATGTACAGATA | 0 | 264 |
| 559182 | 81035 81138 | 81054 81157 | AGAATGGATTATGTACAGAT | 0 | 265 |
| 559183 | 81036 81139 | 81055 81158 | AAGAATGGATTATGTACAGA | 0 | 266 |
| 559184 | 81037 81140 | 81056 81159 | GAAGAATGGATTATGTACAG | 0 | 267 |
| 559185 | 81038 81141 | 81057 81160 | GGAAGAATGGATTATGTACA | 0 | 268 |

TABLE 7-continued

| ISIS NO | SEQ ID NO: 1 Start Site | SEQ ID NO: 1 Stop Site | Sequence | % inhibition | SEQ ID NO |
|---|---|---|---|---|---|
| 559186 | 81039 81142 | 81058 81161 | GGGAAGAATGGATTATGTAC | 0 | 269 |
| 559187 | 81040 81143 | 81059 81162 | AGGGAAGAATGGATTATGTA | 0 | 270 |
| 559188 | 81041 81144 | 81060 81163 | GAGGGAAGAATGGATTATGT | 0 | 271 |
| 559189 | 81042 81145 | 81061 81164 | CGAGGGAAGAATGGATTATG | 0 | 272 |
| 559190 | 81043 81146 | 81062 81165 | CCGAGGGAAGAATGGATTAT | 33 | 273 |
| 559191 | 81044 81147 | 81063 81166 | ACCGAGGGAAGAATGGATTA | 12 | 274 |
| 559192 | 81045 81148 | 81064 81167 | AACCGAGGGAAGAATGGATT | 1 | 275 |
| 559193 | 81046 81149 | 81065 81168 | GAACCGAGGGAAGAATGGAT | 0 | 276 |
| 559194 | 81047 81150 | 81066 81169 | TGAACCGAGGGAAGAATGGA | 0 | 277 |
| 559195 | 81048 81151 | 81067 81170 | ATGAACCGAGGGAAGAATGG | 0 | 278 |
| 559196 | 81049 81152 | 81068 81171 | GATGAACCGAGGGAAGAATG | 0 | 279 |
| 559197 | 81050 81153 | 81069 81172 | GGATGAACCGAGGGAAGAAT | 0 | 280 |
| 559198 | 81051 81154 | 81070 81173 | TGGATGAACCGAGGGAAGAA | 0 | 281 |
| 559199 | 81052 81155 | 81071 81174 | ATGGATGAACCGAGGGAAGA | 0 | 282 |
| 559200 | 81053 81156 | 81072 81175 | GATGGATGAACCGAGGGAAG | 0 | 283 |
| 559201 | 81054 81157 | 81073 81176 | GGATGGATGAACCGAGGGAA | 1 | 284 |
| 559202 | 81055 81158 | 81074 81177 | TGGATGGATGAACCGAGGGA | 0 | 285 |
| 559203 | 81056 81159 | 81075 81178 | ATGGATGGATGAACCGAGGG | 0 | 286 |
| 559204 | 81057 81160 | 81076 81179 | GATGGATGGATGAACCGAGG | 0 | 287 |
| 559205 | 81058 81161 | 81077 81180 | GGATGGATGGATGAACCGAG | 0 | 288 |
| 559206 | 81096 81199 | 81115 81218 | AAGGATGAAGGAAGGGATGG | 0 | 289 |
| 559207 | 81097 81200 | 81116 81219 | GAAGGATGAAGGAAGGGATG | 0 | 290 |
| 559208 | 81098 81201 | 81117 81220 | GGAAGGATGAAGGAAGGGAT | 0 | 291 |
| 559209 | 81100 81203 | 81119 81222 | TAGGAAGGATGAAGGAAGGG | 0 | 292 |
| 559210 | 81101 81204 | 81120 81223 | ATAGGAAGGATGAAGGAAGG | 0 | 293 |

TABLE 7-continued

| ISIS NO | SEQ ID NO: 1 Start Site | SEQ ID NO: 1 Stop Site | Sequence | % inhibition | SEQ ID NO |
|---|---|---|---|---|---|
| 559211 | 81102 81205 | 81121 81224 | GATAGGAAGGATGAAGGAAG | 0 | 294 |
| 559212 | 81103 81206 | 81122 81225 | TGATAGGAAGGATGAAGGAA | 0 | 295 |
| 559213 | 81104 81207 | 81123 81226 | ATGATAGGAAGGATGAAGGA | 0 | 296 |
| 559214 | 81105 81208 | 81124 81227 | GATGATAGGAAGGATGAAGG | 0 | 297 |
| 559215 | 81106 81209 | 81125 81228 | GGATGATAGGAAGGATGAAG | 0 | 298 |
| 559216 | 81107 81210 | 81126 81229 | TGGATGATAGGAAGGATGAA | 0 | 299 |
| 559217 | 81108 81211 | 81127 81230 | ATGGATGATAGGAAGGATGA | 0 | 300 |
| 559218 | 81109 81212 | 81128 81231 | GATGGATGATAGGAAGGATG | 0 | 301 |
| 559219 | 81110 81213 | 81129 81232 | GGATGGATGATAGGAAGGAT | 0 | 302 |
| 559220 | 81111 81214 | 81130 81233 | TGGATGGATGATAGGAAGGA | 0 | 303 |
| 559221 | 81112 81215 | 81131 81234 | TTGGATGGATGATAGGAAGG | 0 | 304 |
| 559222 | 81113 81216 | 81132 81235 | ATTGGATGGATGATAGGAAG | 0 | 305 |
| 559223 | 81114 81217 | 81133 81236 | GATTGGATGGATGATAGGAA | 0 | 306 |
| 559224 | 81115 81218 | 81134 81237 | TGATTGGATGGATGATAGGA | 0 | 307 |
| 559225 | 81116 81219 | 81135 81238 | ATGATTGGATGGATGATAGG | 0 | 308 |
| 559226 | 81117 81220 | 81136 81239 | TATGATTGGATGGATGATAG | 0 | 309 |
| 559227 | 80890 81472 | 80909 81491 | AGATATGGGTGGATGGATGG | 0 | 310 |
| 559228 | 80891 81473 | 80910 81492 | AAGATATGGGTGGATGGATG | 0 | 311 |
| 559229 | 80892 81474 | 80911 81493 | GAAGATATGGGTGGATGGAT | 0 | 312 |
| 559230 | 98881 98918 | 98900 98937 | ACACACCTTCATTTACTGTC | 79 | 313 |
| 559231 | 98882 98919 | 98901 98938 | AACACACCTTCATTTACTGT | 56 | 314 |
| 559232 | 98883 98920 | 98902 98939 | AAACACACCTTCATTTACTG | 59 | 315 |
| 559233 | 98884 98921 | 98903 98940 | CAAACACACCTTCATTTACT | 51 | 316 |
| 559234 | 98885 98922 | 98904 98941 | TCAAACACACCTTCATTTAC | 25 | 317 |
| 559235 | 98887 98924 | 98906 98943 | TTTCAAACACACCTTCATTT | 25 | 318 |

TABLE 7-continued

| ISIS NO | SEQ ID NO: 1 Start Site | SEQ ID NO: 1 Stop Site | Sequence | % inhibition | SEQ ID NO |
|---|---|---|---|---|---|
| 559236 | 98888 98925 | 98907 98944 | TTTTCAAACACACCTTCATT | 14 | 319 |
| 559237 | 98889 98926 | 98908 98945 | GTTTTCAAACACACCTTCAT | 42 | 320 |
| 559238 | 98890 98927 | 98909 98946 | GGTTTTCAAACACACCTTCA | 79 | 321 |
| 559239 | 98891 98928 | 98910 98947 | TGGTTTTCAAACACACCTTC | 87 | 322 |
| 559240 | 111795 111819 | 111814 111838 | GAAAACAGAGAAAAGCACAA | 12 | 323 |
| 559241 | 119594 119905 | 119613 119924 | AGAAGTGATATCATATCCTA | 63 | 324 |
| 559242 | 119595 119906 | 119614 119925 | AAGAAGTGATATCATATCCT | 74 | 325 |

Example 6: Dose-Dependent Antisense Inhibition of Human Tau in SH-SY5Y Cells by 5-10-5 MOE Gapmers Gapmers from studies described above exhibiting significant in vitro inhibition of Tau mRNA were selected and tested at various doses in SH-SY-5Y cells. Cells were plated at a density of 20,000 cells per well and transfected using electroporation with 0.625 µM, 1.25 µM, 2.500 µM, 5.00 µM, 10.00 µM, and 20.00 µM concentrations of antisense oligonucleotide, as specified in the Table below. After a treatment period of approximately 16 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of Tau, relative to untreated control cells. Tau mRNA levels were significantly reduced in a dose-dependent manner in antisense oligonucleotide treated cells.

TABLE 8

| ISIS No | 0.625 µM | 1.25 µM | 2.50 µM | 5.00 µM | 10.00 µM | 20.00 µM |
|---|---|---|---|---|---|---|
| 433474 | 17 | 39 | 53 | 73 | 81 | 88 |
| 559230 | 30 | 50 | 67 | 81 | 92 | 94 |
| 559231 | 0 | 16 | 26 | 44 | 63 | 83 |
| 559232 | 10 | 12 | 23 | 30 | 62 | 79 |
| 559233 | 5 | 10 | 21 | 38 | 62 | 81 |
| 559237 | 0 | 16 | 27 | 31 | 58 | 88 |
| 559238 | 25 | 18 | 72 | 77 | 86 | 86 |
| 559239 | 26 | 47 | 64 | 80 | 88 | 93 |
| 559241 | 0 | 18 | 34 | 61 | 74 | 95 |
| 559242 | 13 | 20 | 23 | 47 | 71 | 83 |

Example 7: Antisense Inhibition of Human Tau in SH-SY5Y Cells by MOE Gapmers with Phosphorothioate and Phosphodiester Internucleoside Linkages Antisense oligonucleotides were designed targeting a tau nucleic acid and were tested for their effects on tau mRNA in vitro. The antisense oligonucleotides were tested in a series of experiments that had similar culture conditions. The results for each experiment are presented in separate tables shown below. Cultured SH-SY5Y cells were transfected using electroporation with 8,000 nM antisense oligonucleotide. After a treatment period of approximately 24 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-10-5 MOE gapmers. The gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are either phosphorothioate linkages or phosphodiester linkages. All cytosine residues throughout each gapmer are 5-methylcytosines. The 'Chemistry' column describes the internucleoside linkages of each oligonucleotide. 's' indicates phosphorothioate linkage and 'o' indicates phosphodiester linkage. "Start site" indicates the 5'-most nucleoside to which the gapmer is targeted in the human gene sequence. "Stop site" indicates the 3'-most nucleoside to which the gapmer is targeted in the human gene sequence.

Each gapmer listed in the Tables below is targeted to either the human Tau genomic sequence, designated herein as SEQ ID NO: 1 (GENBANK Accession No. NT_010783.15 truncated from nucleotides 9240000 to 9381000), human Tau mRNA sequences, designated herein as SEQ ID NO: 2 (GENBANK Accession No. NM_001123066.3) or SEQ ID NO: 3 (GENBANK Accession No. NM_016841.4). Several oligonucleotides, presented in Tables 10, 12, and 16, target variant mRNA sequences, designated herein as SEQ ID NO: 5 (GENBANK Accession No. DR002467.1), SEQ ID NO: 6 (GENBANK Accession No. NM_001203251.1) or SEQ ID NO: 7 (GEN- BANK Accession No. NM_016835.4). The oligonucleotides are presented in the various tables according to the main gene sequence that they target with 100% complementarity. 'n/a' indicates that the antisense oligonucleotide does not target that particular gene sequence with 100% complementarity.

TABLE 9

Inhibition of Tau mRNA by 5-10-5 MOE gapmers with phosphorothioate and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 433475 | n/a | n/a | TCTTCAGCTTTCAGGCCAGC | 41 | 443 | 462 | sssssssssssssssssss | 96 |
| 613242 | n/a | n/a | CTTCAGCTTTCAGGCCAGCG | 54 | 442 | 461 | soooosssssssssssooss | 326 |
| 613243 | n/a | n/a | TCTTCAGCTTTCAGGCCAGC | 43 | 443 | 462 | soooosssssssssssooss | 96 |
| 613244 | n/a | n/a | CCATGCGAGCTTGGGTCACG | 64 | 511 | 530 | soooosssssssssssooss | 327 |
| 613245 | n/a | n/a | CAGCCCCTTGGCTTTTTTG | 30 | 565 | 584 | soooosssssssssssooss | 328 |
| 613247 | n/a | n/a | TTGCACCTTCCCGCCTCCCG | 53 | 957 | 976 | soooosssssssssssooss | 329 |
| 613240 | 5897 | 5916 | TGCCGCTCGGCCGTCCGGCG | 9 | n/a | n/a | soooosssssssssssooss | 330 |
| 613249 | 6292 | 6311 | GCCCGGCGCACGAAGCCCCA | 80 | n/a | n/a | soooosssssssssssooss | 331 |
| 613250 | 7099 | 7118 | AGAAAGAAATCCGCCCCGAG | 45 | n/a | n/a | soooosssssssssssooss | 332 |
| 613251 | 11709 | 11728 | ATAATGGAATACTTATTGCA | 54 | n/a | n/a | soooosssssssssssooss | 333 |
| 613252 | 11819 | 11838 | GCAGGAGCATGGCACCTGGA | 79 | n/a | n/a | soooosssssssssssooss | 334 |
| 613253 | 12081 | 12100 | ACTCGCTGACATGGTGTTTG | 87 | n/a | n/a | soooosssssssssssooss | 335 |
| 613254 | 13386 | 13405 | GATGACTCCACAATGTAAAC | 75 | n/a | n/a | soooosssssssssssooss | 336 |
| 613255 | 16760 | 16779 | CCTATAGGATTATCCAGGAA | 88 | n/a | n/a | soooosssssssssssooss | 337 |
| 613256 | 16987 | 17006 | CATTTCTCATCAGCCATCGA | 81 | n/a | n/a | soooosssssssssssooss | 338 |
| 613257 | 17428 | 17447 | ACCAAAGACTTCAGATCAGC | 88 | n/a | n/a | soooosssssssssssooss | 339 |
| 613412 | 73879 | 73898 | GTGATCTTCCATCACTTCGA | 82 | 345 | 364 | soooosssssssssssooss | 25 |
| 613246 | 103087 | 103106 | CCAGAGCTGGGTGGTGTCTT | 51 | 686 | 705 | soooosssssssssssooss | 39 |
| 613181 | 138046 | 138065 | AGCTTCTGGGAGCTGCAGAT | 80 | 3737 | 3756 | soooosssssssssssooss | 340 |
| 613182 | 138083 | 138102 | AGAGGAACCCAGTCTGAGGG | 49 | 3774 | 3793 | soooosssssssssssooss | 341 |
| 613183 | 138116 | 138135 | AGGCTGCGCTGCCCCTCCAG | 68 | 3807 | 3826 | soooosssssssssssooss | 342 |
| 613184 | 138149 | 138168 | AATCCCTGCTGTGGTCGCAG | 63 | 3840 | 3859 | soooosssssssssssooss | 343 |
| 613185 | 138182 | 138201 | TCTAGAGCAGATCCAGGACA | 53 | 3873 | 3892 | soooosssssssssssooss | 344 |
| 613186 | 138215 | 138234 | AAGTCATCCTTCCTCAGGCA | 63 | 3906 | 3925 | soooosssssssssssooss | 345 |
| 613187 | 138248 | 138267 | CAAGGCTTTGGGAACAGTGT | 78 | 3939 | 3958 | soooosssssssssssooss | 346 |
| 613188 | 138250 | 138269 | GTCAAGGCTTTGGGAACAGT | 84 | 3941 | 3960 | soooosssssssssssooss | 347 |
| 613189 | 138281 | 138300 | TTGTGCAAGGTCAGCGGGCT | 75 | 3972 | 3991 | soooosssssssssssooss | 348 |
| 613190 | 138314 | 138333 | CGGCTTCCCTTTTCTCATGG | 75 | 4005 | 4024 | soooosssssssssssooss | 349 |
| 613191 | 138347 | 138366 | TGAGTTTCTTTAGGCAGCAA | 82 | 4038 | 4057 | soooosssssssssssooss | 350 |
| 613192 | 138380 | 138399 | AACCAGAAGTGGCAGAATTG | 47 | 4071 | 4090 | soooosssssssssssooss | 351 |
| 613193 | 138413 | 138432 | CAAGTCCCTCAGGGTTGCCT | 78 | 4104 | 4123 | soooosssssssssssooss | 352 |
| 613194 | 138454 | 138473 | CGAAGCTGCCAGCCCCAGGG | 70 | 4145 | 4164 | soooosssssssssssooss | 353 |

TABLE 9-continued

Inhibition of Tau mRNA by 5-10-5 MOE gapmers with
phosphorothioate and phosphodiester internucleoside
linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613195 | 138487 | 138506 | AGACTTCCTTTCAGGTAAAG | 77 | 4178 | 4197 | soooosssssssssssooss | 354 |
| 613196 | 138503 | 138522 | AGAGTTCTGGGCCCAGAGAC | 58 | 4194 | 4213 | soooosssssssssssooss | 79 |
| 613197 | 138520 | 138539 | AGGGAGGCTCTTGGTGGAGA | 35 | 4211 | 4230 | soooosssssssssssooss | 355 |
| 613198 | 138553 | 138572 | ACTTAGGAGAATTGCTGGGA | 75 | 4244 | 4263 | soooosssssssssssooss | 356 |
| 613199 | 138586 | 138605 | CCCACATTTCCTTCTCCTTC | 72 | 4277 | 4296 | soooosssssssssssooss | 357 |
| 613200 | 138636 | 138655 | ACTGTTGGCAGTAATGAGGG | 71 | 4327 | 4346 | soooosssssssssssooss | 358 |
| 613201 | 138674 | 138693 | GGAAGAGGAACCGAGGTGCG | 61 | 4365 | 4384 | soooosssssssssssooss | 359 |
| 613202 | 138707 | 138726 | CATGGTGCTGAAGAGCAGGG | 71 | 4398 | 4417 | soooosssssssssssooss | 360 |
| 613203 | 138740 | 138759 | GGGAGATCCCAGAGCCTTCC | 53 | 4431 | 4450 | soooosssssssssssooss | 361 |
| 613204 | 138773 | 138792 | CTTAGGCTGGCCCCAAGAGC | 64 | 4464 | 4483 | soooosssssssssssooss | 362 |
| 613205 | 138806 | 138825 | TATCTGCCAGCACTGATCAC | 56 | 4497 | 4516 | soooosssssssssssooss | 363 |
| 613206 | 138839 | 138858 | TTTAAGATCACAAGCCAGCG | 62 | 4530 | 4549 | soooosssssssssssooss | 364 |
| 613207 | 138872 | 138891 | GAGGAGTGCCCAGCCCTGGG | 54 | 4563 | 4582 | soooosssssssssssooss | 365 |
| 613208 | 138905 | 138924 | CTGGCTCTGCAGGTGGGAGA | 44 | 4596 | 4615 | soooosssssssssssooss | 366 |
| 613209 | 138938 | 138957 | TACAGTATATCCTATCTAGC | 57 | 4629 | 4648 | soooosssssssssssooss | 367 |
| 613210 | 138971 | 138990 | ATAAAGTGAGTCAGCAGCTT | 71 | 4662 | 4681 | soooosssssssssssooss | 368 |
| 613211 | 139004 | 139023 | TCACCACTGAAGTCAATTTA | 72 | 4695 | 4714 | soooosssssssssssooss | 369 |
| 613212 | 139037 | 139056 | AGCACAACAAGCAATAGCAA | 80 | 4728 | 4747 | soooosssssssssssooss | 370 |
| 613213 | 139070 | 139089 | ACTATCTTACACATTCCTCC | 48 | 4761 | 4780 | soooosssssssssssooss | 371 |
| 613214 | 139103 | 139122 | GCTGCACCCCAAGATCTCCC | 79 | 4794 | 4813 | soooosssssssssssooss | 372 |
| 613215 | 139136 | 139155 | AAATCATGAAAAGGGTTACG | 61 | 4827 | 4846 | soooosssssssssssooss | 373 |
| 613216 | 139169 | 139188 | GTGGCTGCTCCCTCCCTCTA | 60 | 4860 | 4879 | soooosssssssssssooss | 374 |
| 613217 | 139188 | 139207 | CCCAAGGGCCTCTAACTCCG | 64 | 4879 | 4898 | soooosssssssssssooss | 375 |
| 613218 | 139202 | 139221 | TGGAAAAGAGAAACCCCAAG | 56 | 4893 | 4912 | soooosssssssssssooss | 376 |
| 613219 | 139229 | 139248 | AGCCAGCTGCCTGGGAAAGC | 63 | 4920 | 4939 | soooosssssssssssooss | 89 |
| 613220 | 139235 | 139254 | TGAACTAGCCAGCTGCCTGG | 46 | 4926 | 4945 | soooosssssssssssooss | 377 |
| 613221 | 139268 | 139287 | TATTCCTACGCCTGCACCTG | 54 | 4959 | 4978 | soooosssssssssssooss | 378 |
| 613222 | 139301 | 139320 | AGAGGGCAGCAGGCCAAAGC | 48 | 4992 | 5011 | soooosssssssssssooss | 379 |
| 613223 | 139337 | 139356 | TTAGGGAGGCATGATTGTGG | 55 | 5028 | 5047 | soooosssssssssssooss | 380 |
| 613224 | 139368 | 139387 | CCAACGGCTTAGAGGGAAGG | 61 | 5059 | 5078 | soooosssssssssssooss | 381 |
| 613225 | 139370 | 139389 | TGCCAACGGCTTAGAGGGAA | 65 | 5061 | 5080 | soooosssssssssssooss | 382 |
| 613226 | 139403 | 139422 | TGTCTGGAGCCAGTGTGAGA | 56 | 5094 | 5113 | soooosssssssssssooss | 383 |
| 613227 | 139436 | 139455 | CGAGTGATCTCAGCTCCAAA | 79 | 5127 | 5146 | soooosssssssssssooss | 384 |
| 613228 | 139502 | 139521 | TGATCACCTCTGCCCTCGCC | 72 | 5193 | 5212 | soooosssssssssssooss | 385 |

TABLE 9-continued

Inhibition of Tau mRNA by 5-10-5 MOE gapmers with
phosphorothioate and phosphodiester internucleoside
linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613229 | 139535 | 139554 | TGAAGCTGCAGGTCTGTAGA | 57 | 5226 | 5245 | soooosssssssssssooss | 386 |
| 613230 | 139568 | 139587 | CTTTTCAAAGCTGAAGAGAA | 57 | 5259 | 5278 | soooosssssssssssooss | 387 |
| 613231 | 139601 | 139620 | AGGTGAGGCTCTAGGCCAGT | 76 | 5292 | 5311 | soooosssssssssssooss | 388 |
| 613232 | 139636 | 139655 | CAACATGGCAAACTCATGGG | 76 | 5327 | 5346 | soooosssssssssssooss | 389 |
| 613233 | 139669 | 139688 | ATGGGACTTGCAAGTGCCAG | 83 | 5360 | 5379 | soooosssssssssssooss | 390 |
| 613234 | 139702 | 139721 | CCTCCCCCCACCCTCAGAAT | 15 | 5393 | 5412 | soooosssssssssssooss | 391 |
| 613235 | 139735 | 139754 | AGACAGAAAGCTAAGCTAAG | 50 | 5426 | 5445 | soooosssssssssssooss | 392 |
| 613236 | 139768 | 139787 | TTAAAACACACAATACACTA | 46 | 5459 | 5478 | soooosssssssssssooss | 393 |
| 613237 | 139801 | 139820 | ACTTTTACAGCAACAGTCAG | 54 | 5492 | 5511 | soooosssssssssssooss | 394 |
| 613238 | 139834 | 139853 | TTTAATCAGAGTAATAACTT | 12 | 5525 | 5544 | soooosssssssssssooss | 395 |

TABLE 10

Inhibition of Tau mRNA by 5-10-5 MOE gapmers
with phosphorothioate and phosphodiester
internucleoside linkages targeting SEQ ID
NOs: 5 and 6

| ISIS NO | Target SEQ ID NO | Target Start Site | Sequence | % inhibition | Linkage chemistry | SEQ ID NO |
|---|---|---|---|---|---|---|
| 613239 | 5 | 3 | TGCCCTTCGCGGTCCCTTCG | 2 | soooosssssssssssooss | 396 |
| 613241 | 5 | 424 | CTGTCCCCCAAACCCG | 56 | soooosssssssssssoos | 397 |
| 613248 | 6 | 524 | GCTTCCGCTGTTGGAGTGCTTACG | 62 | soooosssssssssssooss | 398 |

TABLE 11

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 433475 | n/a | n/a | TCTTCAGCTTTCAGGCCAGC | 17 | 443 | 462 | sssssssssssssssssss | 96 |
| 613027 | 5901 | 5920 | GCCCTGCCGCTCGGCCGTCC | 29 | 1 | 20 | soooosssssssssssooss | 399 |
| 613028 | 5934 | 5953 | TTCTCCTCCGGCCACTAGTG | 22 | 34 | 53 | soooosssssssssssooss | 400 |
| 613029 | 5987 | 6006 | GAACGCGAGCCTCCCCAGGG | 1 | 87 | 106 | soooosssssssssssooss | 401 |
| 613030 | 6020 | 6039 | GAGGCCGGCGGGCGGCGCAG | 2 | 120 | 139 | soooosssssssssssooss | 402 |
| 613031 | 6053 | 6072 | GAGGGCGCGCGCCGGCGAAG | 0 | 153 | 172 | soooosssssssssssooss | 403 |
| 613032 | 6086 | 6105 | TTGGTGCCGGAGCTGGTGGG | 54 | 186 | 205 | soooosssssssssssooss | 404 |

TABLE 11-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613033 | 6119 | 6138 | GGCAGAAGGTGGGCGGTGGC | 74 | 219 | 238 | sooooossssssssssooss | 405 |
| 613034 | 6185 | 6204 | TGATAGTCGACAGAGGCGAG | 71 | 285 | 304 | sooooossssssssssooss | 406 |
| 613035 | 73867 | 73886 | CACTTCGAACTCCTGGCGGG | 67 | 333 | 352 | sooooossssssssssooss | 98 |
| 613036 | 73869 | 73888 | ATCACTTCGAACTCCTGGCG | 72 | 335 | 354 | sooooossssssssssooss | 99 |
| 613037 | 73871 | 73890 | CCATCACTTCGAACTCCTGG | 69 | 337 | 356 | sooooossssssssssooss | 100 |
| 613412 | 73879 | 73898 | GTGATCTTCCATCACTTCGA | 72 | 345 | 364 | sooooossssssssssooss | 25 |
| 613038 | 73906 | 73925 | CCTGTCCCCAACCCGTACG | 44 | 372 | 391 | sooooossssssssssooss | 104 |
| 613039 | 73932 | 73951 | TGCATGGTGTAGCCCCCCTG | 80 | 398 | 417 | sooooossssssssssooss | 117 |
| 613040 | 73934 | 73953 | GGTGCATGGTGTAGCCCCCC | 73 | 400 | 419 | sooooossssssssssooss | 118 |
| 613041 | 73939 | 73958 | GTCTTGGTGCATGGTGTAGC | 77 | 405 | 424 | sooooossssssssssooss | 407 |
| 613042 | 73958 | 73977 | CGTCCGTGTCACCCTCTTGG | 79 | 424 | 443 | sooooossssssssssooss | 123 |
| 613044 | 83397 | 83416 | CCTCAGATCCGTCCTCAGTG | 67 | n/a | n/a | sooooossssssssssooss | 408 |
| 613045 | 83430 | 83449 | TGCTCTTAGCATCAGAGGTT | 89 | n/a | n/a | sooooossssssssssooss | 409 |
| 613046 | 85902 | 85921 | CTAAGGGTGCTGTCACATCT | 69 | n/a | n/a | sooooossssssssssooss | 410 |
| 613047 | 85934 | 85953 | GGCAGCCTGCTTGCCGGGAG | 51 | n/a | n/a | sooooossssssssssooss | 29 |
| 613048 | 85935 | 85954 | CGGCAGCCTGCTTGCCGGGA | 51 | n/a | n/a | sooooossssssssssooss | 411 |
| 613049 | 85968 | 85987 | TGGTTCCTTCTGGGATCTCC | 76 | n/a | n/a | sooooossssssssssooss | 412 |
| 613051 | 94719 | 94738 | CTCGGAGGAAGCCTTCCTGG | 53 | n/a | n/a | sooooossssssssssooss | 413 |
| 613052 | 94752 | 94771 | TGAGCTGGTGGCTCAGACCT | 41 | n/a | n/a | sooooossssssssssooss | 414 |
| 613053 | 94825 | 94844 | CCTGTCCCCGAAGGTTGGCG | 61 | n/a | n/a | sooooossssssssssooss | 415 |
| 613054 | 94875 | 94894 | GGTGCTTGAGCAGCTCAGGG | 70 | n/a | n/a | sooooossssssssssooss | 416 |
| 613055 | 94908 | 94927 | GCGGCCCCTCCTGGTGCAGG | 47 | n/a | n/a | sooooossssssssssooss | 417 |
| 613056 | 94941 | 94960 | CCGGCCTCTCTTTGCCCCCT | 31 | n/a | n/a | sooooossssssssssooss | 418 |
| 613057 | 94974 | 94993 | CGTCGCGGTCTTCATCCACC | 42 | n/a | n/a | sooooossssssssssooss | 419 |
| 613058 | 95038 | 95057 | GGCCGCCCATCTTGGGCTGG | 0 | n/a | n/a | sooooossssssssssooss | 420 |
| 613059 | 95071 | 95090 | ATGCTGGTGGCTTCTCTGGC | 53 | n/a | n/a | sooooossssssssssooss | 421 |
| 613060 | 95098 | 95117 | ATGGCACCCTCCGCTGGGAA | 39 | n/a | n/a | sooooossssssssssooss | 422 |
| 613061 | 95121 | 95140 | AGAGGAAATCCACAGGGAGG | 30 | n/a | n/a | sooooossssssssssooss | 33 |
| 613062 | 95154 | 95173 | GCTCTGAGGCTGGGATCTCT | 70 | n/a | n/a | sooooossssssssssooss | 423 |
| 613063 | 95187 | 95206 | GCCCTTTGGCCCGCCCTACA | 67 | n/a | n/a | sooooossssssssssooss | 424 |
| 613064 | 95235 | 95254 | CGTTGGGTGTGATTTCCACG | 61 | n/a | n/a | sooooossssssssssooss | 425 |
| 613065 | 95268 | 95287 | AATGCTCCTCCGAGTGCGCC | 85 | n/a | n/a | sooooossssssssssooss | 426 |
| 613066 | 95313 | 95332 | CCTCTGGCCCCTCTCCAGGG | 43 | n/a | n/a | sooooossssssssssooss | 427 |
| 613067 | 95346 | 95365 | CTTTTGTGTCCTCTCCCAAA | 42 | n/a | n/a | sooooossssssssssooss | 428 |
| 613068 | 95379 | 95398 | GCTGCTTTTCAGAGGGCTCT | 51 | n/a | n/a | sooooossssssssssooss | 429 |

TABLE 11-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613069 | 95412 | 95431 | GGCTGACGGGCTTCCCCCGC | 61 | n/a | n/a | sooooosssssssssssooss | 430 |
| 613070 | 95429 | 95448 | TTTGAGTTGAGGGACCCGGC | 33 | n/a | n/a | sooooosssssssssssooss | 431 |
| 613073 | 98559 | 98578 | GCTTTTACTGACCATGCGAG | 79 | 522 | 541 | sooooosssssssssssooss | 124 |
| 613074 | 98581 | 98600 | CATCGCTTCCAGTCCCGTCT | 78 | 544 | 563 | sooooosssssssssssooss | 134 |
| 613075 | 98587 | 98606 | TTTTGTCATCGCTTCCAGTC | 35 | 550 | 569 | sooooosssssssssssooss | 137 |
| 613076 | 101406 | 101425 | AAGGTTTTAGCAGAGGAACG | 63 | n/a | n/a | sooooosssssssssssooss | 37 |
| 613077 | 101457 | 101476 | TCTGAGCTACCAGGAGTGGG | 65 | n/a | n/a | sooooosssssssssssooss | 432 |
| 613078 | 101491 | 101510 | GCACACAGCAGGGCTGGAGG | 68 | n/a | n/a | sooooosssssssssssooss | 433 |
| 613079 | 101501 | 101520 | GTGGCTCTGGGCACACAGCA | 77 | n/a | n/a | sooooosssssssssssooss | 192 |
| 613080 | 101507 | 101526 | AGGAAGGTGGCTCTGGGCAC | 69 | n/a | n/a | sooooosssssssssssooss | 38 |
| 613081 | 101537 | 101556 | GGGAAGTGACAGAAGAGACG | 46 | n/a | n/a | sooooosssssssssssooss | 434 |
| 613082 | 101570 | 101589 | GTTTCATCTCCTTTGCTCCA | 57 | n/a | n/a | sooooosssssssssssooss | 435 |
| 613083 | 102995 | 103014 | CCGCGGTGTGGCGATCTTCG | 9 | 594 | 613 | sooooosssssssssssooss | 436 |
| 613084 | 103028 | 103047 | GGCCTGGCCCTTCTGGCCTG | 14 | 627 | 646 | sooooosssssssssssooss | 437 |
| 613085 | 103075 | 103094 | GGTGTCTTTGGAGCGGGCGG | 37 | 674 | 693 | sooooosssssssssssooss | 146 |
| 613086 | 105445 | 105464 | CTTCTCTGGACTTGCTTAGT | 45 | n/a | n/a | sooooosssssssssssooss | 438 |
| 613087 | 105475 | 105494 | CTCTCAGATCTGGGCCCTGC | 41 | n/a | n/a | sooooosssssssssssooss | 439 |
| 613088 | 105478 | 105497 | CCTCTCTCAGATCTGGGCCC | 49 | n/a | n/a | sooooosssssssssssooss | 440 |
| 613089 | 107932 | 107951 | TAGCCGCTGCGATCCCCTGA | 19 | 719 | 738 | sooooosssssssssssooss | 441 |
| 613090 | 107968 | 107987 | CGGCTGCCGGGAGTGCCTGG | 31 | 755 | 774 | sooooosssssssssssooss | 159 |
| 613091 | 108021 | 108040 | CCACCTTCTTGGGCTCCCGG | 17 | 808 | 827 | sooooosssssssssssooss | 442 |
| 613092 | 108040 | 108059 | GGTGGAGTACGGACCACTGC | 20 | 827 | 846 | sooooosssssssssssooss | 40 |
| 613093 | 108054 | 108073 | AAGACGGCGACTTGGGTGGA | 0 | 841 | 860 | sooooosssssssssssooss | 41 |
| 613094 | 108101 | 108120 | CAGGTCTGGCATGGGCACGG | 67 | 888 | 907 | sooooosssssssssssooss | 443 |
| 613095 | 108134 | 108153 | CTCAGTGGAGCCGATCTTGG | 31 | 921 | 940 | sooooosssssssssssooss | 199 |
| 613096 | 108167 | 108186 | CACCTTCCCGCCTCCCGGCT | 47 | 954 | 973 | sooooosssssssssssooss | 444 |
| 613097 | 121845 | 121864 | GTTGCTAAGATCCAGCTTCT | 49 | n/a | n/a | sooooosssssssssssooss | 445 |
| 613098 | 121865 | 121884 | GAGCCACACTTGGACTGGAC | 85 | n/a | n/a | sooooosssssssssssooss | 47 |
| 613099 | 121878 | 121897 | GATATTATCCTTTGAGCCAC | 88 | n/a | n/a | sooooosssssssssssooss | 446 |
| 613101 | 125784 | 125803 | GGTCACCTTGCTCAGGTCAA | 68 | 993 | 1012 | sooooosssssssssssooss | 447 |
| 613102 | 125817 | 125836 | ATGATGGATGTTGCCTAATG | 14 | 1026 | 1045 | sooooosssssssssssooss | 448 |
| 613103 | 130141 | 130160 | ATTTTACTTCCACCTGGCCA | 22 | 1057 | 1076 | sooooosssssssssssooss | 51 |

TABLE 12

Inhibition of Tau mRNA by 5-10-5 MOE gapmers with phosphorothioate and phosphodiester internucleoside linkages targeting SEQ ID NOs: 6 and 7

| ISIS NO | Target SEQ ID NO | Target Start Site | Sequence | % inhibition | Linkage chemistry | SEQ ID NO |
|---|---|---|---|---|---|---|
| 613043 | 6 | 442 | GAGATTCTTTCAGGCCAGCG | 17 | soooosssssssssssoos s | 449 |
| 613050 | 7 | 685 | TTTCAGGCTCTTGGGTCACG | 0 | soooosssssssssssoos s | 450 |
| 613071 | 7 | 1430 | GCTTTGAGTTGAGGGACCCG | 23 | soooosssssssssssoos s | 451 |
| 613072 | 7 | 1444 | TACTGACCATGCGAGCTTTG | 73 | soooosssssssssssoos s | 177 |
| 613100 | 7 | 2178 | TATTTGCACACTGCCGCCTC | 13 | soooosssssssssssoos s | 452 |

TABLE 13

Inhibition of Tau mRNA by 5-10-5 MOE gapmers with phosphorothioate and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 433475 | n/a | n/a | TCTTCAGCTTTCAGGCCAGC | 23 | 443 | 462 | sssssssssssssssssss | 96 |
| 613412 | 73879 | 73898 | GTGATCTTCCATCACTTCGA | 76 | 345 | 364 | soooossssssssssooss | 25 |
| 613104 | 130143 | 130162 | AGATTTTACTTCCACCTGGC | 59 | 1059 | 1078 | soooossssssssssooss | 453 |
| 613105 | 130176 | 130195 | CGACTGGACTCTGTCCTTGA | 47 | 1092 | 1111 | soooossssssssssooss | 454 |
| 613106 | 130225 | 130244 | TATTTCCTCCGCCAGGGACG | 90 | 1141 | 1160 | soooossssssssssooss | 455 |
| 613107 | 135483 | 135502 | CGCGGAAGGTCAGCTTGTGG | 43 | 1174 | 1193 | soooossssssssssooss | 456 |
| 613108 | 135516 | 135535 | CCGCCCCGTGGTCTGTCTTG | 44 | 1207 | 1226 | soooossssssssssooss | 457 |
| 613109 | 135549 | 135568 | CCCCAGACACCACTGGCGAC | 36 | 1240 | 1259 | soooossssssssssooss | 458 |
| 613110 | 135590 | 135609 | GCCGGTGGAGGAGACATTGC | 51 | 1281 | 1300 | soooossssssssssooss | 459 |
| 613111 | 135654 | 135673 | CCAGGGAGGCAGACACCTCG | 61 | 1345 | 1364 | soooossssssssssooss | 245 |
| 613112 | 135697 | 135716 | AATTATTGACCGCCCCAGGG | 33 | 1388 | 1407 | soooossssssssssooss | 460 |
| 613113 | 135730 | 135749 | TTTTTCCACACTCTCTCATT | 41 | 1421 | 1440 | soooossssssssssooss | 461 |
| 613114 | 135783 | 135802 | AACTGCGAGGAGCAGCTGGG | 51 | 1474 | 1493 | soooossssssssssooss | 462 |
| 613115 | 135786 | 135805 | CCGAACTGCGAGGAGCAGCT | 78 | 1477 | 1496 | soooossssssssssooss | 248 |
| 613116 | 135816 | 135835 | CAAAAGCAGGTTAAGTGATT | 28 | 1507 | 1526 | soooossssssssssooss | 463 |
| 613117 | 135849 | 135868 | CTGATTTTGAAGTCCCGAGC | 69 | 1540 | 1559 | soooossssssssssooss | 464 |
| 613118 | 135869 | 135888 | ATTTGCTCTTACTCCCATCA | 80 | 1560 | 1579 | soooossssssssssooss | 465 |
| 613119 | 135882 | 135901 | TTGGAAAGATGAAATTTGCT | 52 | 1573 | 1592 | soooossssssssssooss | 466 |
| 613120 | 135948 | 135967 | TGTTGGATGTGGCCATGTTT | 63 | 1639 | 1658 | soooossssssssssooss | 467 |
| 613121 | 136049 | 136068 | GTCCCTTGAAATCCCCCAGA | 45 | 1740 | 1759 | soooossssssssssooss | 468 |
| 613122 | 136082 | 136101 | CCACAACAGGGCCAGAGGTG | 55 | 1773 | 1792 | soooossssssssssooss | 469 |
| 613123 | 136115 | 136134 | TCCTTTGTTGCTGCCACTGC | 59 | 1806 | 1825 | soooossssssssssooss | 470 |
| 613124 | 136148 | 136167 | GCCTGTGGCTCCACGAACAC | 72 | 1839 | 1858 | soooossssssssssooss | 471 |

TABLE 13-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613125 | 136181 | 136200 | CCCCGTCACACTCACACAAG | 43 | 1872 | 1891 | soooosssssssssssooss | 472 |
| 613126 | 136214 | 136233 | GGCCTCCCCGTGGCCTCCC | 37 | 1905 | 1924 | soooosssssssssssooss | 473 |
| 613127 | 136247 | 136266 | TGCTTCCTCTCCCCTCTGCC | 41 | 1938 | 1957 | soooosssssssssssooss | 474 |
| 613128 | 136295 | 136314 | GATGTCTACTCTCCAGCACG | 32 | 1986 | 2005 | soooosssssssssssooss | 475 |
| 613129 | 136328 | 136347 | ATAGGCCTTGGCTCTCCCAG | 73 | 2019 | 2038 | soooosssssssssssooss | 476 |
| 613130 | 136361 | 136380 | AGGACAGGCGGCCGCTCAGA | 46 | 2052 | 2071 | soooosssssssssssooss | 477 |
| 613131 | 136394 | 136413 | TGACCCACAGCAGGCCCCCA | 14 | 2085 | 2104 | soooosssssssssssooss | 478 |
| 613132 | 136427 | 136446 | CTCCCACAGGCTGCCCTGCA | 46 | 2118 | 2137 | soooosssssssssssooss | 479 |
| 613133 | 136460 | 136479 | CAGCTTGCCTTCTCTTTTTA | 58 | 2151 | 2170 | soooosssssssssssooss | 480 |
| 613134 | 136491 | 136510 | GGAGGTCATCCACGAAGTGC | 45 | 2182 | 2201 | soooosssssssssssooss | 61 |
| 613135 | 136493 | 136512 | AAGGAGGTCATCCACGAAGT | 41 | 2184 | 2203 | soooosssssssssssooss | 481 |
| 613136 | 136515 | 136534 | GACATCAAGGTCAGTCTTTT | 80 | 2206 | 2225 | soooosssssssssssooss | 482 |
| 613137 | 136541 | 136560 | AGGGAGGAAGAGGCCAGCGC | 60 | 2232 | 2251 | soooosssssssssssooss | 483 |
| 613138 | 136574 | 136593 | AGCCCCTCAACTCAGGCCCC | 53 | 2265 | 2284 | soooosssssssssssooss | 484 |
| 613139 | 136607 | 136626 | TCAATAAAACAGGGTTTCTG | 38 | 2298 | 2317 | soooosssssssssssooss | 485 |
| 613140 | 136640 | 136659 | CAAAATCATGGCAGCAGTTC | 26 | 2331 | 2350 | soooosssssssssssooss | 486 |
| 613141 | 136673 | 136692 | GTTAGCCCTAAAGTCCCAGG | 76 | 2364 | 2383 | soooosssssssssssooss | 487 |
| 613142 | 136706 | 136725 | CCCAAGAGGCACAAGTCCTT | 57 | 2397 | 2416 | soooosssssssssssooss | 488 |
| 613143 | 136739 | 136758 | CAGTGGCCCAGGCTTGGAAA | 63 | 2430 | 2449 | soooosssssssssssooss | 489 |
| 613144 | 136748 | 136767 | CAGAGATGCCAGTGGCCCAG | 43 | 2439 | 2458 | soooosssssssssssooss | 67 |
| 613145 | 136772 | 136791 | TGCCTCCCAGACCCCCACAC | 23 | 2463 | 2482 | soooosssssssssssooss | 490 |
| 613146 | 136805 | 136824 | AGTGGCCGTGGGAAGGACAG | 17 | 2496 | 2515 | soooosssssssssssooss | 491 |
| 613147 | 136838 | 136857 | ACAACAGCACAGCGGCGCAG | 61 | 2529 | 2548 | soooosssssssssssooss | 492 |
| 613148 | 136845 | 136864 | ACGGCAGACAACAGCACAGC | 59 | 2536 | 2555 | soooosssssssssssooss | 493 |
| 613149 | 136899 | 136918 | GAATTCGGGACATTGTGACG | 42 | 2590 | 2609 | soooosssssssssssooss | 494 |
| 613150 | 136933 | 136952 | CAGGGTCATTACTGAGAAGG | 39 | 2624 | 2643 | soooosssssssssssooss | 495 |
| 613151 | 136966 | 136985 | CTCAGTATGGAGTAGGTACC | 52 | 2657 | 2676 | soooosssssssssssooss | 496 |
| 613152 | 136999 | 137018 | TGTGCCTGGACTTTGCCTTC | 61 | 2690 | 2709 | soooosssssssssssooss | 497 |
| 613153 | 137032 | 137051 | GGAACTGAGAGTGAGAGGCT | 62 | 2723 | 2742 | soooosssssssssssooss | 498 |
| 613154 | 137077 | 137096 | GAATCAGATCATGAGATTCG | 30 | 2768 | 2787 | soooosssssssssssooss | 499 |
| 613155 | 137110 | 137129 | CACATCTGTGACGGGAGGAG | 26 | 2801 | 2820 | soooosssssssssssooss | 500 |
| 613156 | 137143 | 137162 | CACCTAGGGTCACAGCTGAG | 33 | 2834 | 2853 | soooosssssssssssooss | 501 |
| 613157 | 137176 | 137195 | GAAAGGGCTCTCTCCATGTC | 54 | 2867 | 2886 | soooosssssssssssooss | 502 |
| 613158 | 137214 | 137233 | GTGGGCTCAGCACAGGAAGG | 23 | 2905 | 2924 | soooosssssssssssooss | 503 |
| 613159 | 137229 | 137248 | ACCCAGCCTGCTGCTGTGGG | 36 | 2920 | 2939 | soooosssssssssssooss | 504 |

TABLE 13-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613160 | 137247 | 137266 | ACCACTGACAACCAAGACAC | 22 | 2938 | 2957 | soooosssssssssssooss | 505 |
| 613161 | 137280 | 137299 | GCCCTGGGTGCCTTGCCCTT | 53 | 2971 | 2990 | soooosssssssssssooss | 506 |
| 613162 | 137322 | 137341 | ACAAGCTAGGGTGCAAGTGG | 47 | 3013 | 3032 | soooosssssssssssooss | 507 |
| 613163 | 137364 | 137383 | GGAGCTGAGCAGCGGGCTGG | 45 | 3055 | 3074 | soooosssssssssssooss | 508 |
| 613164 | 137401 | 137420 | CCCTTTGTCGGGTGTGGAGG | 8 | 3092 | 3111 | soooosssssssssssooss | 509 |
| 613165 | 137453 | 137472 | TGGCTTCCAGCTGGGACTGG | 65 | 3144 | 3163 | soooosssssssssssooss | 510 |
| 613166 | 137486 | 137505 | ATATGTTCAGCTGCTCCAGC | 58 | 3177 | 3196 | soooosssssssssssooss | 511 |
| 613167 | 137529 | 137548 | ACTCAACAGGGTGCAGATGG | 54 | 3220 | 3239 | soooosssssssssssooss | 512 |
| 613168 | 137562 | 137581 | GAATCCAAGCATAAACAGAC | 55 | 3253 | 3272 | soooosssssssssssooss | 513 |
| 613169 | 137595 | 137614 | TTTTTTTCTTTTCACTATCA | 34 | 3286 | 3305 | soooosssssssssssooss | 514 |
| 613170 | 137629 | 137648 | AGCATTTCAAGATACATGCG | 59 | 3320 | 3339 | soooosssssssssssooss | 515 |
| 613171 | 137692 | 137711 | CACACGAGTCCCAGTGTGGG | 11 | 3383 | 3402 | soooosssssssssssooss | 516 |
| 613172 | 137761 | 137780 | TTGGGTCCCAGGTGCTGAGG | 40 | 3452 | 3471 | soooosssssssssssooss | 517 |
| 613173 | 137794 | 137813 | ACGGCCTCCTTAGCTGCTAG | 73 | 3485 | 3504 | soooosssssssssssooss | 518 |
| 613174 | 137827 | 137846 | TAATCCTGTGCTTCAGGCCT | 32 | 3518 | 3537 | soooosssssssssssooss | 519 |
| 613175 | 137881 | 137900 | TGACACAGGGAGCCCCAAGG | 40 | 3572 | 3591 | soooosssssssssssooss | 520 |
| 613176 | 137914 | 137933 | AGCCAGACCAGCCACAAGAC | 16 | 3605 | 3624 | soooosssssssssssooss | 521 |
| 613177 | 137947 | 137966 | GCTATGACCAGAGAGAACCA | 29 | 3638 | 3657 | soooosssssssssssooss | 522 |
| 613178 | 137967 | 137986 | GGACTGCCATGAGACTTCGG | 26 | 3658 | 3677 | soooosssssssssssooss | 523 |
| 613179 | 137980 | 137999 | TAAGCCTCCTTTGGGACTGC | 64 | 3671 | 3690 | soooosssssssssssooss | 524 |
| 613180 | 138013 | 138032 | AGTGGCTTCCTTTTTCTTGT | 69 | 3704 | 3723 | soooosssssssssssooss | 525 |

TABLE 14

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 433475 | n/a | n/a | TCTTCAGCTTTCAGGCCAGC | 23 | 433 | 452 | ssssssssssssssssssss | 96 |
| 613258 | 18371 | 18390 | GGCAATGCCTGGAAGAAACT | 75 | n/a | n/a | soooosssssssssssooss | 526 |
| 613259 | 18411 | 18430 | CGCTGGTGAGAGTGTGACTG | 69 | n/a | n/a | soooosssssssssssooss | 527 |
| 613260 | 18449 | 18468 | ATCCGAGGGTGAGATGATAA | 75 | n/a | n/a | soooosssssssssssooss | 528 |
| 613261 | 19611 | 19630 | AATAATTTCTCCAGGCTCAT | 62 | n/a | n/a | soooosssssssssssooss | 529 |
| 613262 | 20955 | 20974 | GCTGACTTCGATTTGTTATT | 84 | n/a | n/a | soooosssssssssssooss | 530 |

TABLE 14-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613263 | 22139 | 22158 | TATCATATGGCACAAATTCT | 32 | n/a | n/a | sooooossssssssssooss | 531 |
| 613264 | 23662 | 23681 | CTACCTGGGACCACACCTTA | 61 | n/a | n/a | sooooossssssssssooss | 532 |
| 613265 | 25046 | 25065 | GGGTGGAGAGCCTGATGGTC | 47 | n/a | n/a | sooooossssssssssooss | 533 |
| 613266 | 25418 | 25437 | CTGTGAGCATCATGAAAGCC | 56 | n/a | n/a | sooooossssssssssooss | 534 |
| 613267 | 25606 | 25625 | TTTTATTATGAGGGAGATCA | 48 | n/a | n/a | sooooossssssssssooss | 535 |
| 613268 | 26186 | 26205 | AATAGTAGAGAAATGGAAAT | 39 | n/a | n/a | sooooossssssssssooss | 536 |
| 613269 | 26690 | 26709 | TAACATGACAGGGTTAGGCC | 67 | n/a | n/a | sooooossssssssssooss | 537 |
| 613270 | 26917 | 26936 | GCCCACACACATGCTCATGC | 57 | n/a | n/a | sooooossssssssssooss | 538 |
| 613271 | 27160 | 27179 | TGTGTTCAGTTACATGCCTT | 82 | n/a | n/a | sooooossssssssssooss | 539 |
| 613272 | 27569 | 27588 | GACCACCATGGTGGGCTGAC | 39 | n/a | n/a | sooooossssssssssooss | 540 |
| 613273 | 28227 | 28246 | GGCACCTCTCTGCAGACTTT | 85 | n/a | n/a | sooooossssssssssooss | 541 |
| 613274 | 30102 | 30121 | TGCTTCACACACCACAATGG | 60 | n/a | n/a | sooooossssssssssooss | 542 |
| 613275 | 31769 | 31788 | AACATTGCCGAGCACCAGCC | 63 | n/a | n/a | sooooossssssssssooss | 543 |
| 613276 | 31832 | 31851 | GACTCAGGAACATGTTAGCT | 70 | n/a | n/a | sooooossssssssssooss | 544 |
| 613277 | 32045 | 32064 | CACGGCTCAGCAGAGGAGAC | 23 | n/a | n/a | sooooossssssssssooss | 545 |
| 613278 | 32324 | 32343 | GCTGCTATCCTTCCTGGGCC | 57 | n/a | n/a | sooooossssssssssooss | 546 |
| 613279 | 32760 | 32779 | GGAAATGAAAGCTTCCCACG | 61 | n/a | n/a | sooooossssssssssooss | 547 |
| 613280 | 33359 | 33378 | AACAGTCAGAATACCCCCAA | 72 | n/a | n/a | sooooossssssssssooss | 548 |
| 613281 | 34056 | 34075 | TATAGGTAGAATATAAAACT | 17 | n/a | n/a | sooooossssssssssooss | 549 |
| 613282 | 35266 | 35285 | TATGAACAAAACTGCAGGAC | 45 | n/a | n/a | sooooossssssssssooss | 550 |
| 613283 | 35839 | 35858 | AGCCTCCAGAGTGACAGGTG | 63 | n/a | n/a | sooooossssssssssooss | 551 |
| 613284 | 36223 | 36242 | CCATAAGCCACTCCTGGTTG | 0 | n/a | n/a | sooooossssssssssooss | 552 |
| 613285 | 36410 | 36429 | CAGCTTGGAAGATACAGGAG | 63 | n/a | n/a | sooooossssssssssooss | 553 |
| 613286 | 38647 | 38666 | CAAACTTAAGAAAAGTTGCA | 67 | n/a | n/a | sooooossssssssssooss | 554 |
| 613287 | 39104 | 39123 | TGCTGGCAAAGAAGACAGGA | 69 | n/a | n/a | sooooossssssssssooss | 555 |
| 613288 | 40506 | 40525 | CCACTGATGGCCGGGTGCAG | 27 | n/a | n/a | sooooossssssssssooss | 556 |
| 613289 | 42727 | 42746 | TGGGTGTCAAATGGCTGGCT | 55 | n/a | n/a | sooooossssssssssooss | 557 |
| 613290 | 42955 | 42974 | TAGAAAGCTATTTAATAAAT | 0 | n/a | n/a | sooooossssssssssooss | 558 |
| 613291 | 43109 | 43128 | AGCCGTACATCAATGGTACA | 71 | n/a | n/a | sooooossssssssssooss | 559 |
| 613292 | 46627 | 46646 | GGCCCTACCATGGTCGATTT | 57 | n/a | n/a | sooooossssssssssooss | 560 |
| 613293 | 47399 | 47418 | ATCAGTGCCAGAGACAGAGG | 5 | n/a | n/a | sooooossssssssssooss | 561 |
| 613294 | 48115 | 48134 | TATTATTAACGAACAAAAAA | 0 | n/a | n/a | sooooossssssssssooss | 562 |
| 613295 | 48223 | 48242 | AGAGCAATACTTTGTGCTTA | 51 | n/a | n/a | sooooossssssssssooss | 563 |
| 613296 | 48608 | 48627 | AGACTCCTCAAATGTGCGCC | 53 | n/a | n/a | sooooossssssssssooss | 564 |
| 613297 | 49204 | 49223 | GAATGACGGCCGCCTCCTCT | 39 | n/a | n/a | sooooossssssssssooss | 565 |

TABLE 14-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
| --- | --- | --- | --- | --- | --- | --- | --- | --- |
| 613298 | 49696 | 49715 | TATGGAGGGCTTCTGGCCTC | 18 | n/a | n/a | soooosssssssssssooss | 566 |
| 613299 | 51161 | 51180 | GAGAAAGAGCGAGTAATTAG | 44 | n/a | n/a | soooosssssssssssooss | 567 |
| 613300 | 52250 | 52269 | TAGCTAGAAACTGTGTCCCT | 41 | n/a | n/a | soooosssssssssssooss | 568 |
| 613301 | 53908 | 53927 | CTGTGAGATCATCCCCTGGT | 51 | n/a | n/a | soooosssssssssssooss | 569 |
| 613302 | 54457 | 54476 | CAGCGCAGTGCAGGGAGTCA | 41 | n/a | n/a | soooosssssssssssooss | 570 |
| 613303 | 55975 | 55994 | GGGTACACAGAGAGGCCACT | 53 | n/a | n/a | soooosssssssssssooss | 571 |
| 613304 | 56155 | 56174 | GAACGATGCACTGCCTTGGC | 54 | n/a | n/a | soooosssssssssssooss | 572 |
| 613305 | 57402 | 57421 | CACCATATTACACCAGTTGT | 60 | n/a | n/a | soooosssssssssssooss | 573 |
| 613306 | 57696 | 57715 | CTGAAATGAATCCCCTGAAC | 0 | n/a | n/a | soooosssssssssssooss | 574 |
| 613307 | 57733 | 57752 | GTGTCCACGAATGCCCCTGG | 40 | n/a | n/a | soooosssssssssssooss | 575 |
| 613308 | 58392 | 58411 | ACGGATGGTTGCTGCTGATG | 47 | n/a | n/a | soooosssssssssssooss | 576 |
| 613309 | 61917 | 61936 | GTCCCTTTTGCTCCCAAAGA | 18 | n/a | n/a | soooosssssssssssooss | 577 |
| 613310 | 62489 | 62508 | CAGTCTTTTAATAAGTGAAA | 50 | n/a | n/a | soooosssssssssssooss | 578 |
| 613311 | 63219 | 63238 | TTAGCTAAATTGAGGCCCGG | 31 | n/a | n/a | soooosssssssssssooss | 579 |
| 613312 | 63257 | 63276 | GGAAAGGTATTGCCTCCTGA | 42 | n/a | n/a | soooosssssssssssooss | 580 |
| 613313 | 63627 | 63646 | GGTGACTACGCAGCCTGGAC | 57 | n/a | n/a | soooosssssssssssooss | 581 |
| 613314 | 64559 | 64578 | TTCAGGGCAATCCTTGAGGT | 41 | n/a | n/a | soooosssssssssssooss | 582 |
| 613315 | 64872 | 64891 | TGCTAATGCTTTGGGACCTA | 44 | n/a | n/a | soooosssssssssssooss | 583 |
| 613316 | 66922 | 66941 | TGGGTAGAGAGCAACTGTTC | 32 | n/a | n/a | soooosssssssssssooss | 584 |
| 613317 | 67104 | 67123 | ACACCCCTTCTCTGCACATC | 25 | n/a | n/a | soooosssssssssssooss | 585 |
| 613318 | 68893 | 68912 | CTGCTAGAGTTCGCCAACAG | 59 | n/a | n/a | soooosssssssssssooss | 586 |
| 613319 | 69457 | 69476 | TCTTATTCTCTAGGTGGGCT | 70 | n/a | n/a | soooosssssssssssooss | 587 |
| 613320 | 70922 | 70941 | CAGTGCAAGTGGGTATGAAG | 30 | n/a | n/a | soooosssssssssssooss | 588 |
| 613321 | 70928 | 70947 | CAGATGCAGTGCAAGTGGGT | 44 | n/a | n/a | soooosssssssssssooss | 589 |
| 613322 | 71310 | 71329 | GAAAAACTTTGTCCATAATT | 41 | n/a | n/a | soooosssssssssssooss | 590 |
| 613323 | 71665 | 71684 | TAATGAATGTATAACAGAAA | 0 | n/a | n/a | soooosssssssssssooss | 591 |
| 613324 | 71702 | 71721 | AAAAGGCAGATACTTTGTGG | 56 | n/a | n/a | soooosssssssssssooss | 592 |
| 613325 | 72456 | 72475 | CAGAGGTGTGAAAGTAAAAG | 0 | n/a | n/a | soooosssssssssssooss | 593 |
| 613326 | 72566 | 72585 | CAGCTAAAGCTTTGTGAACA | 31 | n/a | n/a | soooosssssssssssooss | 594 |
| 613327 | 72612 | 72631 | TGCAGCCCAGGTGAGCCAGC | 49 | n/a | n/a | soooosssssssssssooss | 595 |
| 613328 | 73748 | 73767 | GCCTCTCCTCCCAGTTCATG | 12 | n/a | n/a | soooosssssssssssooss | 596 |
| 613329 | 75140 | 75159 | GTTTTCTTATTTTAGCATT | 87 | n/a | n/a | soooosssssssssssooss | 597 |
| 613330 | 76340 | 76359 | GGAGGGACGAGAAACAGCAG | 0 | n/a | n/a | soooosssssssssssooss | 598 |
| 613331 | 79041 | 79060 | AGCTTCCAGCATGAACATAG | 77 | n/a | n/a | soooosssssssssssooss | 599 |
| 613332 | 79971 | 79990 | GAGCCCTGATATGATAGAGG | 57 | n/a | n/a | soooosssssssssssooss | 600 |

TABLE 14-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613333 | 80360 | 80379 | TGTACCATGCCTGGCAGATG | 78 | n/a | n/a | soooosssssssssssooss | 601 |
| 613334 | 81325 | 81344 | GTTAGATGTATGTATGATGG | 0 | n/a | n/a | soooosssssssssssooss | 602 |
| 613412 | 73879 | 73898 | GTGATCTTCCATCACTTCGA | 80 | 345 | 364 | soooosssssssssssooss | 25 |

TABLE 15

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 433475 | n/a | n/a | TCTTCAGCTTTCAGGCCAGC | 31 | 443 | 462 | ssssssssssssssssssss | 96 |
| 613335 | 82136 | 82155 | GCCTCCTCCTAGAGCTCCTG | 81 | n/a | n/a | soooosssssssssssooss | 603 |
| 613336 | 83231 | 83250 | CGGCCTCGCAACAAACCCAC | 55 | n/a | n/a | soooosssssssssssooss | 604 |
| 613337 | 83820 | 83839 | TCCACTGACCTGCCCCTTCC | 66 | n/a | n/a | soooosssssssssssooss | 605 |
| 613338 | 84269 | 84288 | TTTGCAACTTGTTCCTGCTT | 84 | n/a | n/a | soooosssssssssssooss | 606 |
| 613339 | 85073 | 85092 | TCTTGGGTGCAGGCGGAGCA | 53 | n/a | n/a | soooosssssssssssooss | 607 |
| 613340 | 86117 | 86136 | ACCCAAGATTCCCAGGAGCC | 77 | n/a | n/a | soooosssssssssssooss | 608 |
| 613341 | 86191 | 86210 | AGGCCCTAAATGCTCTGAGA | 75 | n/a | n/a | soooosssssssssssooss | 609 |
| 613342 | 86251 | 86270 | AGAAGTCTCTGGAACTGACG | 70 | n/a | n/a | soooosssssssssssooss | 610 |
| 613343 | 86714 | 86733 | TCACCAAACCAATGGCTGGC | 67 | n/a | n/a | soooosssssssssssooss | 611 |
| 613344 | 86774 | 86793 | GGTGAAATCCTGGCTAGGCC | 89 | n/a | n/a | soooosssssssssssooss | 612 |
| 613345 | 88487 | 88506 | TGCAGATTCGGCCTGAGTTT | 72 | n/a | n/a | soooosssssssssssooss | 613 |
| 613346 | 89131 | 89150 | CCAAACAAGAAAGACTGAGA | 55 | n/a | n/a | soooosssssssssssooss | 614 |
| 613347 | 89994 | 90013 | CCATGTCCCTCCCCCCAACC | 12 | n/a | n/a | soooosssssssssssooss | 615 |
| 613348 | 90126 | 90145 | ATTAGAAAAAAACCACTAGG | 37 | n/a | n/a | soooosssssssssssooss | 616 |
| 613349 | 92246 | 92265 | AGCTTACTAGAGTGCTCTTG | 81 | n/a | n/a | soooosssssssssssooss | 617 |
| 613350 | 92915 | 92934 | ATTTTTTTCTGGTTCATTCA | 71 | n/a | n/a | soooosssssssssssooss | 618 |
| 613351 | 94316 | 94335 | CGCTTAAGAGAGGGAGCATC | 72 | n/a | n/a | soooosssssssssssooss | 619 |
| 613352 | 94673 | 94692 | GTGGAGATACGCAGTGGTGG | 68 | n/a | n/a | soooosssssssssssooss | 620 |
| 613353 | 95790 | 95809 | ACACCATGAGGGCACCCGTC | 82 | n/a | n/a | soooosssssssssssooss | 35 |
| 613354 | 95918 | 95937 | CCCAAACCTGGCTCTGTCAC | 65 | n/a | n/a | soooosssssssssssooss | 621 |
| 613355 | 97224 | 97243 | ATCAACCAGCACCATCCACG | 65 | n/a | n/a | soooosssssssssssooss | 622 |
| 613356 | 97314 | 97333 | GGGTCTGTAAGCCTAAAGTG | 53 | n/a | n/a | soooosssssssssssooss | 623 |
| 613357 | 97315 | 97334 | TGGGTCTGTAAGCCTAAAGT | 56 | n/a | n/a | soooosssssssssssooss | 624 |
| 613358 | 97368 | 97387 | TATACTATGTGGCAGAATCA | 48 | n/a | n/a | soooosssssssssssooss | 625 |

TABLE 15-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613359 | 97478 | 97497 | CACATTCCCTCTACCCCATG | 57 | n/a | n/a | sooooosssssssssssooss | 626 |
| 613360 | 97507 | 97526 | TCATAGATTTTCTTCTTTGG | 75 | n/a | n/a | sooooosssssssssssooss | 627 |
| 613361 | 98881 | 98900 | ACACACCTTCATTTACTGTC | 95 | n/a | n/a | sooooosssssssssssooss | 313 |
|  | 98918 | 98937 |  |  | n/a | n/a | sooooosssssssssssooss |  |
| 613362 | 98882 | 98901 | AACACACCTTCATTTACTGT | 83 | n/a | n/a | sooooosssssssssssooss | 314 |
|  | 98919 | 98938 |  |  | n/a | n/a | sooooosssssssssssooss |  |
| 613363 | 98883 | 98902 | AAACACACCTTCATTTACTG | 79 | n/a | n/a | sooooosssssssssssooss | 315 |
|  | 98920 | 98939 |  |  | n/a | n/a | sooooosssssssssssooss |  |
| 613364 | 98884 | 98903 | CAAACACACCTTCATTTACT | 63 | n/a | n/a | sooooosssssssssssooss | 316 |
|  | 98921 | 98940 |  |  | n/a | n/a | sooooosssssssssssooss |  |
| 613365 | 98885 | 98904 | TCAAACACACCTTCATTTAC | 59 | n/a | n/a | sooooosssssssssssooss | 317 |
|  | 98922 | 98941 |  |  | n/a | n/a | sooooosssssssssssooss |  |
| 613366 | 98886 | 98905 | TTCAAACACACCTTCATTTA | 67 | n/a | n/a | sooooosssssssssssooss | 628 |
|  | 98923 | 98942 |  |  | n/a | n/a | sooooosssssssssssooss |  |
| 613367 | 98887 | 98906 | TTTCAAACACACCTTCATTT | 72 | n/a | n/a | sooooosssssssssssooss | 318 |
|  | 98924 | 98943 |  |  | n/a | n/a | sooooosssssssssssooss |  |
| 613368 | 98888 | 98907 | TTTTCAAACACACCTTCATT | 59 | n/a | n/a | sooooosssssssssssooss | 319 |
|  | 98925 | 98944 |  |  | n/a | n/a | sooooosssssssssssooss |  |
| 613369 | 98889 | 98908 | GTTTTCAAACACACCTTCAT | 90 | n/a | n/a | sooooosssssssssssooss | 320 |
|  | 98926 | 98945 |  |  | n/a | n/a | sooooosssssssssssooss |  |
| 613370 | 98890 | 98909 | GGTTTTCAAACACACCTTCA | 96 | n/a | n/a | sooooosssssssssssooss | 321 |
|  | 98927 | 98946 |  |  | n/a | n/a | sooooosssssssssssooss |  |
| 613371 | 98891 | 98910 | TGGTTTTCAAACACACCTTC | 95 | n/a | n/a | sooooosssssssssssooss | 322 |
|  | 98928 | 98947 |  |  | n/a | n/a | sooooosssssssssssooss |  |
| 613372 | 99560 | 99579 | CCCCAGCTGGCCGAGGCCCA | 81 | n/a | n/a | sooooosssssssssssooss | 629 |
| 613373 | 99816 | 99835 | GAGAAGGGTCCTGTCCCAGA | 76 | n/a | n/a | sooooosssssssssssooss | 630 |
| 613374 | 100743 | 100762 | AGTAAGTTGATGGAGATCAT | 83 | n/a | n/a | sooooosssssssssssooss | 631 |
| 613375 | 102894 | 102913 | CACCAGCCCCACTCCGCCAC | 61 | n/a | n/a | sooooosssssssssssooss | 632 |
| 613376 | 103875 | 103894 | TGCTCTGTCTCCAGAGACAT | 70 | n/a | n/a | sooooosssssssssssooss | 633 |
| 613377 | 104615 | 104634 | ATCCAAGATCCAGGCCAGGC | 63 | n/a | n/a | sooooosssssssssssooss | 634 |
| 613378 | 105870 | 105889 | AGAGACCCAGGGTGACCAGT | 76 | n/a | n/a | sooooosssssssssssooss | 635 |
| 613379 | 106909 | 106928 | CAAATTTCTCGATCCCCTTC | 18 | n/a | n/a | sooooosssssssssssooss | 636 |
| 613380 | 108411 | 108430 | CCTGAGGAGGGCACTCACAG | 61 | n/a | n/a | sooooosssssssssssooss | 637 |
| 613381 | 108891 | 108910 | GTGGCTACCCACGGCCACAG | 1 | n/a | n/a | sooooosssssssssssooss | 638 |
| 613382 | 108939 | 108958 | CTACCGGAGCACACACAGA | 65 | n/a | n/a | sooooosssssssssssooss | 639 |
| 613383 | 109303 | 109322 | CCCTAAGCCATGGTGGGTTT | 72 | n/a | n/a | sooooosssssssssssooss | 640 |
| 613384 | 109995 | 110014 | CCCTTGTCCCCACAGCCACA | 72 | n/a | n/a | sooooosssssssssssooss | 641 |

TABLE 15-continued

Inhibition of Tau mRNA by 5-10-5 MOE gapmers with phosphorothioate
and phosphodiester internucleoside linkages targeting SEQ ID NOs: 1 and 3

| ISIS NO | SEQ ID NO: 1 Start Site | SEQ ID NO: 1 Stop Site | Sequence | % inhibition | SEQ ID NO: 3 Start Site | SEQ ID NO: 3 Stop Site | Linkage chemistry | SEQ ID NO |
|---|---|---|---|---|---|---|---|---|
| 613385 | 110198 | 110217 | GGGTCACCTGTGAGTTATTT | 62 | n/a | n/a | soooossssssssssooss | 642 |
| 613386 | 113567 | 113586 | AGCTGCCTCCAGTTGTTTAT | 85 | n/a | n/a | soooossssssssssooss | 643 |
| 613387 | 114056 | 114075 | ACTTTAGCTCCATCTTCTCA | 49 | n/a | n/a | soooossssssssssooss | 644 |
| 613388 | 114755 | 114774 | CTATAATGGTCAGTGGTGTA | 67 | n/a | n/a | soooossssssssssooss | 645 |
| 613389 | 115899 | 115918 | TGAAGGAGAGGCTGTGGTGA | 41 | n/a | n/a | soooossssssssssooss | 646 |
| 613390 | 117387 | 117406 | TGTGACAACAAAGTTGTCCT | 46 | n/a | n/a | soooossssssssssooss | 647 |
| 613391 | 117654 | 117673 | CCCTGCAATCAACACAGGAG | 65 | n/a | n/a | soooossssssssssooss | 648 |
| 613392 | 119050 | 119069 | TCTAACATGCACATATTTAC | 60 | n/a | n/a | soooossssssssssooss | 649 |
| 613393 | 119190 | 119209 | AGCACTGGGTGTTTACAACA | 84 | n/a | n/a | soooossssssssssooss | 650 |
| 613394 | 119594 119905 | 119613 119924 | AGAAGTGATATCATATCCTA | 85 | n/a n/a | n/a n/a | soooossssssssssooss soooossssssssssooss | 324 |
| 613395 | 119595 119906 | 119614 119925 | AAGAAGTGATATCATATCCT | 68 | n/a n/a | n/a n/a | soooossssssssssooss soooossssssssssooss | 325 |
| 613396 | 120782 | 120801 | ACCCGGTGACCTTTCCTCTC | 67 | n/a | n/a | soooossssssssssooss | 651 |
| 613397 | 121728 | 121747 | GAGTGACATGCGCCACCCTG | 87 | n/a | n/a | soooossssssssssooss | 203 |
| 613398 | 121794 | 121813 | AAAAGGATGAGTGACACGCC | 66 | n/a | n/a | soooossssssssssooss | 205 |
| 613399 | 121940 | 121959 | GCCACAGCACGGCGCATGGG | 89 | n/a | n/a | soooossssssssssooss | 652 |
| 613400 | 124954 | 124973 | GCACCGCTCCCTCTGGGAAT | 49 | n/a | n/a | soooossssssssssooss | 653 |
| 613401 | 125298 | 125317 | AAATCTTGCTGGAAAGGCAG | 64 | n/a | n/a | soooossssssssssooss | 654 |
| 613402 | 125428 | 125447 | GACCCAGACATTTGCTCAGC | 86 | n/a | n/a | soooossssssssssooss | 655 |
| 613403 | 125982 | 126001 | GGGCTCCCGCAAGTTTCACA | 71 | n/a | n/a | soooossssssssssooss | 656 |
| 613404 | 127460 | 127479 | GAGAGGCCCTGTGGACAGCT | 75 | n/a | n/a | soooossssssssssooss | 657 |
| 613405 | 130381 | 130400 | CCCACTGGATGCTGCTGAGG | 34 | n/a | n/a | soooossssssssssooss | 658 |
| 613406 | 131662 | 131681 | GTGCCTAGTAACCCATTTAG | 54 | n/a | n/a | soooossssssssssooss | 659 |
| 613407 | 131796 | 131815 | CACCCACAGCAAGACCTAGA | 49 | n/a | n/a | soooossssssssssooss | 660 |
| 613408 | 133056 | 133075 | ACACAGAGAAGCTTCCAGAG | 70 | n/a | n/a | soooossssssssssooss | 661 |
| 613409 | 133304 | 133323 | AGCTATCACATGGACGAGTT | 67 | n/a | n/a | soooossssssssssooss | 662 |
| 613410 | 133548 | 133567 | CATTTAATACAGGCTTTGAT | 38 | n/a | n/a | soooossssssssssooss | 663 |
| 613411 | 134599 | 134618 | AGCCACTGATGCCCAGACAT | 69 | n/a | n/a | soooossssssssssooss | 664 |
| 613412 | 73879 | 73898 | GTGATCTTCCATCACTTCGA | 82 | 345 | 364 | soooossssssssssooss | 25 |

TABLE 16

Inhibition of Tau mRNA by 5-10-5 MOE gapmers with phosphorothioate and phosphodiester internucleoside linkages targeting SEQ ID NOs: 5 and 6

| ISIS NO | Target SEQ ID NO | Target Start Site | Sequence | % inhibition | Linkage chemistry | SEQ ID NO |
|---|---|---|---|---|---|---|
| 613239 | 5 | 3 | TGCCCTTCGCGGTCCCTTCG | 11 | soooosssssssssssooss | 396 |
| 613241 | 5 | 424 | CTGTCCCCCAAACCCGTACG | 48 | soooosssssssssssooss | 397 |
| 613248 | 6 | 524 | GCTTCCGCTGTTGGAGTGCT | 59 | soooosssssssssssooss | 398 |

Example 8: Dose-Dependent Antisense Inhibition of Human Tau in SH-SY5Y Cells by 5-10-5 MOE Gapmers with Phosphorothioate and Phosphodiester Internucleoside Linkages Gapmers from studies described above exhibiting significant in vitro inhibition of tau mRNA were selected and tested at various doses in SH-SY-5Y cells. Cells were plated at a density of 20,000 cells per well and transfected using electroporation with 1.25 µM, 2.500 µM, 5.00 µM, 10.00 µM, and 20.00 µM concentrations of antisense oligonucleotide, as specified in the Table below. After a treatment period of approximately 16 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of Tau, relative to untreated control cells. Tau mRNA levels were significantly reduced in a dose-dependent manner in antisense oligonucleotide treated cells.

TABLE 17

| ISIS No | 1.25 µM | 2.50 µM | 5.00 µM | 10.00 µM | 20.00 µM |
|---|---|---|---|---|---|
| 613118 | 46 | 47 | 73 | 92 | 93 |
| 613136 | 36 | 70 | 83 | 88 | 92 |
| 613115 | 32 | 49 | 82 | 86 | 94 |
| 613329 | 73 | 80 | 92 | 94 | 92 |
| 613273 | 46 | 24 | 48 | 60 | 85 |
| 613262 | 31 | 72 | 76 | 87 | 94 |
| 613271 | 44 | 66 | 84 | 89 | 94 |
| 613370 | 92 | 92 | 95 | 98 | 98 |
| 613361 | 88 | 86 | 89 | 94 | 96 |
| 613371 | 80 | 88 | 91 | 95 | 97 |
| 613369 | 58 | 85 | 89 | 95 | 96 |
| 613399 | 61 | 77 | 90 | 94 | 96 |
| 613344 | 80 | 79 | 93 | 95 | 95 |
| 613397 | 64 | 74 | 79 | 93 | 95 |
| 613412 | 45 | 66 | 70 | 81 | 96 |

TABLE 18

| ISIS No | 1.25 µM | 2.50 µM | 5.00 µM | 10.00 µM | 20.00 µM |
|---|---|---|---|---|---|
| 613255 | 54 | 61 | 80 | 91 | 90 |
| 613065 | 22 | 61 | 62 | 83 | 89 |

TABLE 18-continued

| ISIS No | 1.25 µM | 2.50 µM | 5.00 µM | 10.00 µM | 20.00 µM |
|---|---|---|---|---|---|
| 613257 | 45 | 69 | 82 | 86 | 91 |
| 613098 | 70 | 57 | 83 | 92 | 98 |
| 613253 | 44 | 67 | 74 | 86 | 91 |
| 613039 | 21 | 77 | 85 | 90 | 95 |
| 613188 | 0 | 35 | 72 | 86 | 87 |
| 613042 | 33 | 45 | 73 | 90 | 94 |
| 613233 | 21 | 54 | 69 | 75 | 89 |
| 613073 | 59 | 67 | 83 | 92 | 97 |
| 613187 | 8 | 54 | 74 | 61 | 84 |
| 613402 | 10 | 58 | 62 | 81 | 87 |
| 613045 | 57 | 72 | 92 | 96 | 95 |
| 613412 | 20 | 52 | 67 | 84 | 90 |
| 613099 | 71 | 66 | 89 | 91 | 95 |

Example 9: Antisense Inhibition of Human Tau in SH-SY5Y Cells by 5-10-5 MOE, 5-8-5 MOE, 4-8-6 MOE, or 6-8-4 MOE Gapmers Antisense oligonucleotides were designed targeting a tau nucleic acid and were tested for their effects on Tau mRNA in vitro. The antisense oligonucleotides were tested in a series of experiments that had similar culture conditions. ISIS 613412 was also included in the assays. The results for each experiment are presented in separate tables shown below. Cultured SH-SY5Y cells at a density of 20,000 cells per well were transfected using electroporation with 8,000 nM antisense oligonucleotide. After a treatment period of approximately 24 hours, RNA was isolated from the cells and Tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-8-5 MOE, 4-8-6 MOE, or 6-8-4 MOE gapmers. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 4-8-6 MOE gapmers are 18 nucleosides in length, wherein the central gap segment comprises of eight 2'-deoxynucleosides and is flanked by wing segments on the 5' direction and the 3' direction comprising four and six nucleosides respectively. The 6-8-4 MOE gapmers are 18 nucleosides in length, wherein the central gap segment comprises of eight 2'-deoxynucleosides and is flanked by wing segments on the 5' direction and the 3' direction comprising six and four nucleosides respectively. Each nucleoside in the 5' wing segment and each nucleoside in the 3' wing segment has a 2'-MOE modification. The internucleoside linkage motif throughout for each gapmer in the tables below, except for ISIS 613412, is 5'-sooosssssssssssooss-3', wherein each "s" represents a phosphorothioate internucleoside linkage and wherein each "o" represents a phosphodiester internucleoside linkage. The internucleoside linkage motif for ISIS 613412 is 5'-soooosssssssssssooss-3', wherein each "s" represents a phosphorothioate internucleoside linkage and wherein each "o" represents a phosphodiester internucleoside linkage. All cytosine residues throughout each gapmer are 5-methylcytosines. "Start site" indicates the 5'-most nucleoside to which the gapmer is targeted in the human gene sequence.

"Stop site" indicates the 3'-most nucleoside to which the gapmer is targeted human gene sequence. Each gapmer listed in the Tables below is targeted to either SEQ ID NO: 1 (GENBANK Accession No. NT_010783.15 truncated from nucleotides 9240000 to 9381000), SEQ ID NO: 4 (GENBANK Accession No. NT_010783.14 truncated from nucleotides 2624000 to 2761000), SEQ ID NO: 5 (GENBANK Accession No. DR002467.1), or SEQ ID NO: 6 (GENBANK Accession No. NM_001203251.1). 'n/a' indicates that the antisense oligonucleotide does not target that particular gene sequence with 100% complementarity.

TABLE 19

Inhibition of tau mRNA by 5-10-5 MOE and 5-8-5 MOE gapmers targeting SEQ ID NO: 1 and SEQ ID NO: 4

| ISIS NO | SEQ ID NO: 1 Start Site | SEQ ID NO: 1 Stop Site | Sequence | % inhibition | SEQ ID NO: 4 Start Site | SEQ ID NO: 4 Stop Site | Motif | SEQ ID NO |
|---|---|---|---|---|---|---|---|---|
| 613412 | 73879 | 73898 | GTGATCTTCCATCACTTCGA | 83 | 69842 | 69861 | 5-10-5 | 25 |
| 620887 | 98891 98928 | 98908 98945 | GTTTTCAAACACACCTTC | 89 | 94855 94892 | 94872 94909 | 5-8-5 | 665 |
| 621197 | n/a | n/a | TCGCCAACAGACATGTGA | 39 | 64850 | 64867 | 5-8-5 | 666 |
| 621196 | 67898 | 67915 | TGAAGGAGCCTGGGAAGT | 15 | 63891 | 63908 | 5-8-5 | 667 |
| 621198 | 69079 | 69096 | AGCAGAGATGTGGCTGGG | 50 | 65044 | 65061 | 5-8-5 | 668 |
| 621199 | 69622 | 69639 | GTGAGGTTGAAAAGTTTC | 34 | 65587 | 65604 | 5-8-5 | 669 |
| 621200 | 69802 | 69819 | TGGTTTCTGATGGTTTTT | 43 | 65767 | 65784 | 5-8-5 | 670 |
| 621201 | 70023 | 70040 | GTTGGAACTCCTGGGATC | 27 | 65988 | 66005 | 5-8-5 | 671 |
| 621202 | 70259 | 70276 | TCAGCATTTTTCTCCTCT | 47 | 66224 | 66241 | 5-8-5 | 672 |
| 621203 | 70531 | 70548 | CTGGAATGGTACGATCTC | 52 | 66496 | 66513 | 5-8-5 | 673 |
| 621204 | 70750 | 70767 | CCACTCTGGTGCAGGACG | 29 | 66715 | 66732 | 5-8-5 | 674 |
| 621205 | 70930 | 70947 | CAGATGCAGTGCAAGTGG | 43 | 66895 | 66912 | 5-8-5 | 675 |
| 621206 | 71110 | 71127 | GGGTTTCACCAGACCTCA | 29 | 67075 | 67092 | 5-8-5 | 676 |
| 621207 | 71306 | 71323 | CTTTGTCCATAATTTTTT | 34 | 67271 | 67288 | 5-8-5 | 677 |
| 621208 | 71487 | 71504 | TATAGCATGAGCATTTGT | 42 | 67452 | 67469 | 5-8-5 | 678 |
| 621209 | 71667 | 71684 | TAATGAATGTATAACAGA | 2 | 67632 | 67649 | 5-8-5 | 679 |
| 621210 | 71850 | 71867 | TCCTCCTGGCTGCCCTGT | 33 | 67815 | 67832 | 5-8-5 | 680 |
| 621211 | 72030 | 72047 | CATCCTGCCATACCAGAC | 32 | 67995 | 68012 | 5-8-5 | 681 |
| 621212 | 72224 | 72241 | TATCCGCCTCTCAAAGTG | 0 | 68189 | 68206 | 5-8-5 | 682 |
| 621213 | 72410 | 72427 | CACATTTGCATATTTTCA | 65 | 68373 | 68390 | 5-8-5 | 683 |
| 621214 | 72590 | 72607 | TCGGGTTGCCCCATTCAA | 27 | 68553 | 68570 | 5-8-5 | 684 |
| 621215 | 72770 | 72787 | AACCACCATTTACTCACA | 35 | 68733 | 68750 | 5-8-5 | 685 |
| 621216 | 72950 | 72967 | ACCGGCACCCACCAGGTC | 22 | 68913 | 68930 | 5-8-5 | 686 |
| 621217 | 73130 | 73147 | AGGGACAGCATCAGCAGA | 22 | 69093 | 69110 | 5-8-5 | 687 |
| 621218 | 73437 | 73454 | AGGCATGTGGCAGGTGCC | 12 | 69400 | 69417 | 5-8-5 | 688 |
| 621219 | 73617 | 73634 | ACCAACACCGCAGCAGTT | 35 | 69580 | 69597 | 5-8-5 | 689 |
| 621220 | 73797 | 73814 | GTTCTGAGGAGTGTTGGG | 0 | 69760 | 69777 | 5-8-5 | 690 |
| 621221 | 73978 | 73995 | ACTAACCTTTCAGGCCAG | 33 | 69941 | 69958 | 5-8-5 | 691 |
| 621222 | 74273 | 74290 | TAAATTATTTTAGAGACG | 0 | 70236 | 70253 | 5-8-5 | 692 |
| 621223 | 74467 | 74484 | CAAGGTAAATTTCTTTCT | 69 | 70430 | 70447 | 5-8-5 | 693 |
| 621224 | 74647 | 74664 | TCAGGCCTGATCTAAGTA | 14 | 70610 | 70627 | 5-8-5 | 694 |

TABLE 19-continued

Inhibition of tau mRNA by 5-10-5 MOE and 5-8-5 MOE gapmers targeting SEQ ID NO: 1 and SEQ ID NO: 4

| ISIS NO | SEQ ID NO: 1 Start Site | SEQ ID NO: 1 Stop Site | Sequence | % inhibition | SEQ ID NO: 4 Start Site | SEQ ID NO: 4 Stop Site | Motif | SEQ ID NO |
|---|---|---|---|---|---|---|---|---|
| 621225 | 74827 | 74844 | TCCCCAACCATGTGGTCT | 40 | 70790 | 70807 | 5-8-5 | 695 |
| 621226 | 75007 | 75024 | TGCCAGCCACACCCATGG | 52 | 70970 | 70987 | 5-8-5 | 696 |
| 621227 | 75187 | 75204 | AACTCCACGGCTTCCATG | 50 | 71150 | 71167 | 5-8-5 | 697 |
| 621228 | 75371 | 75388 | AGATAGAAATCTGAAACG | 34 | 71334 | 71351 | 5-8-5 | 698 |
| 621229 | 75551 | 75568 | GCTGGGCCGAGCTGCATT | 66 | 71514 | 71531 | 5-8-5 | 699 |
| 621230 | 75891 | 75908 | GGATTCAAAGGAGAAAAC | 35 | 71854 | 71871 | 5-8-5 | 700 |
| 621231 | 76192 | 76209 | ATTATTATTTGACATGGG | 75 | 72155 | 72172 | 5-8-5 | 701 |
| 621232 | 76373 | 76390 | AGGGTAGGCAGTGTTGTG | 4 | 72336 | 72353 | 5-8-5 | 702 |
| 621233 | 76553 | 76570 | CTCTCTTTGTCAGGAAAA | 58 | 72516 | 72533 | 5-8-5 | 703 |
| 621234 | 76942 | 76959 | CCTTTTTTTTAGGACGG | 0 | 72905 | 72922 | 5-8-5 | 704 |
| 621235 | 77222 | 77239 | GAGTTGACTGGGCACGGT | 33 | 73185 | 73202 | 5-8-5 | 705 |
| 621236 | 77414 | 77431 | TCATCTGTGAAGCGGACG | 81 | 73377 | 73394 | 5-8-5 | 706 |
| 621237 | 77594 | 77611 | GGCACAATCCATATGAGG | 56 | 73557 | 73574 | 5-8-5 | 707 |
| 621238 | 77781 | 77798 | GTTATTTTGGAACAGTTT | 87 | 73744 | 73761 | 5-8-5 | 708 |
| 621239 | 78117 | 78134 | CTGGACTTTATTTCATTT | 77 | 74080 | 74097 | 5-8-5 | 709 |
| 621240 | 78319 | 78336 | CAGTATATATAGTGCATA | 76 | 74282 | 74299 | 5-8-5 | 710 |
| 621241 | 78499 | 78516 | CAAAACAGCTCCTTGTAA | 14 | 74462 | 74479 | 5-8-5 | 711 |
| 621242 | 78679 | 78696 | ACTTTCATCTACTTTTCA | 32 | 74642 | 74659 | 5-8-5 | 712 |
| 621243 | 78859 | 78876 | CCAATCTGTCCCCAGCTT | 42 | 74822 | 74839 | 5-8-5 | 713 |
| 621244 | 79039 | 79056 | TCCAGCATGAACATAGCT | 65 | 75002 | 75019 | 5-8-5 | 714 |
| 621245 | 79219 | 79236 | TAGAGTCAGTTTCAGGAT | 75 | 75182 | 75199 | 5-8-5 | 715 |
| 621246 | 79399 | 79416 | GGTGGTATCACCAACAGC | 35 | 75362 | 75379 | 5-8-5 | 716 |
| 621247 | 79589 | 79606 | TTAAGGAATGGCTCTGGG | 42 | 75552 | 75569 | 5-8-5 | 717 |
| 621248 | 79769 | 79786 | GAACATGAGACATCTTGA | 8 | 75732 | 75749 | 5-8-5 | 718 |
| 621249 | 79949 | 79966 | AGCTGTGCCCAGTTAAAA | 53 | 75912 | 75929 | 5-8-5 | 719 |
| 621250 | 80129 | 80146 | TCTGGTCATATGAGGAAA | 55 | 76092 | 76109 | 5-8-5 | 720 |
| 621251 | 80309 | 80326 | AGTCATTATCATGTCACC | 89 | 76272 | 76289 | 5-8-5 | 721 |
| 621252 | 80489 | 80506 | GCTGAGCGAATTACCTAA | 75 | 76452 | 76469 | 5-8-5 | 722 |
| 621253 | 80669 | 80686 | CCTCTGTATGACAGAAAT | 48 | 76632 | 76649 | 5-8-5 | 723 |
| 621254 | 80849 | 80866 | GGTAACATGTAAAGCTTC | 79 | 76812 | 76829 | 5-8-5 | 724 |
| 621255 | 81033 81136 | 81050 81153 | TGGATTATGTACAGATAT | 28 | 76996 77099 | 77013 77116 | 5-8-5 | 725 |
| 621256 | 81110 81213 | 81127 81230 | ATGGATGATAGGAAGGAT | 20 | 77073 77176 | 77090 77193 | 5-8-5 | 726 |
| 621257 | 81393 | 81410 | GATGGAGGAAGGAATGAT | 5 | 77356 | 77373 | 5-8-5 | 727 |
| 621258 | 81629 | 81646 | CTGGATGGTTACATGGAT | 31 | 77592 | 77609 | 5-8-5 | 728 |

TABLE 19-continued

Inhibition of tau mRNA by 5-10-5 MOE and 5-8-5 MOE
gapmers targeting SEQ ID NO: 1 and SEQ ID NO: 4

| ISIS NO | SEQ ID NO: 1 Start Site | SEQ ID NO: 1 Stop Site | Sequence | % inhibition | SEQ ID NO: 4 Start Site | SEQ ID NO: 4 Stop Site | Motif | SEQ ID NO |
|---|---|---|---|---|---|---|---|---|
| 621259 | 81812 | 81829 | ATAATTGATGTATAATTA | 0 | 77775 | 77792 | 5-8-5 | 729 |
| 621260 | 81992 | 82009 | GTTCTGCCCCACCTGGGC | 56 | 77955 | 77972 | 5-8-5 | 730 |
| 621261 | 82198 | 82215 | GCCTCTCAGGGCCTCCGT | 76 | 78161 | 78178 | 5-8-5 | 731 |
| 621262 | 82378 | 82395 | GAAGGATGGCCACACAGA | 39 | 78341 | 78358 | 5-8-5 | 732 |
| 621263 | 82558 | 82575 | ATGGGCTTATCAATGCAT | 85 | 78521 | 78538 | 5-8-5 | 733 |
| 621264 | 82738 | 82755 | GAGGCCCAAATGATCACA | 56 | 78701 | 78718 | 5-8-5 | 734 |
| 621265 | 82918 | 82935 | GCTCAGGGCAGACACGGT | 66 | 78881 | 78898 | 5-8-5 | 735 |
| 621266 | 83098 | 83115 | CTTAACCAGCTAGTGGTG | 38 | 79061 | 79078 | 5-8-5 | 736 |
| 621267 | 83278 | 83295 | GTCCTGTGGAGCTGAAAA | 54 | 79241 | 79258 | 5-8-5 | 737 |
| 621268 | 83486 | 83503 | GGCTGGAGGCATGGAGGG | 7 | 79449 | 79466 | 5-8-5 | 738 |
| 621269 | 83666 | 83683 | TGCCTCCAGAGCACACAC | 55 | 79629 | 79646 | 5-8-5 | 739 |
| 621270 | 83846 | 83863 | AGGATACTAAACCAAGAT | 24 | 79809 | 79826 | 5-8-5 | 740 |
| 621271 | 84026 | 84043 | CACAGATGGGAAGCAAGA | 20 | 79989 | 80006 | 5-8-5 | 741 |
| 621272 | 84206 | 84223 | CATGAGGCAACAATCCAA | 70 | 80169 | 80186 | 5-8-5 | 742 |

TABLE 20

Inhibition of tau mRNA by 5-10-5 MOE and
5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 613412 | 73879 | 73898 | GTGATCTTCCATCACTTCGA | 80 | 5-10-5 | 25 |
| 620887 | 98891 98928 | 98908 98945 | GTTTTCAAACACACCTTC | 92 | 5-8-5 | 665 |
| 621273 | 84386 | 84403 | GCCGTAAGACCCAGCTCT | 58 | 5-8-5 | 743 |
| 621274 | 84566 | 84583 | GAAGAAGTACTGAGAAAG | 14 | 5-8-5 | 744 |
| 621275 | 84746 | 84763 | TAAGAACCTCAGCGGCAA | 56 | 5-8-5 | 745 |
| 621276 | 84926 | 84943 | TGAGGGAGCACTGAGAGT | 21 | 5-8-5 | 746 |
| 621277 | 85106 | 85123 | AGTTCAATGAAGGACATT | 69 | 5-8-5 | 747 |
| 621278 | 85287 | 85304 | ACTGTTGGATGGGTCCAC | 70 | 5-8-5 | 748 |
| 621279 | 85467 | 85484 | TTGGTCCATTTTGATTGG | 0 | 5-8-5 | 749 |
| 621280 | 85647 | 85664 | CGGCAGCCCTGTGTAAAC | 48 | 5-8-5 | 750 |
| 621281 | 85828 | 85845 | CCTTTGCTTCTTGCGCAG | 66 | 5-8-5 | 751 |
| 621282 | 86014 | 86031 | AGGGCCTTGACTGCCTGG | 15 | 5-8-5 | 752 |
| 621283 | 86194 | 86211 | AAGGCCCTAAATGCTCTG | 57 | 5-8-5 | 753 |

TABLE 20-continued

Inhibition of tau mRNA by 5-10-5 MOE and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621284 | 86384 | 86401 | CGCTCAGGTGATCTTGGG | 76 | 5-8-5 | 754 |
| 621285 | 86564 | 86581 | CTGATTGATTCCCCATCA | 64 | 5-8-5 | 755 |
| 621286 | 86746 | 86763 | TTCTTGTTGGGCAACTGG | 59 | 5-8-5 | 756 |
| 621287 | 86928 | 86945 | GAAATGCACTCAGAAGGG | 52 | 5-8-5 | 757 |
| 621288 | 87108 | 87125 | CCTCAGTGAAATAACTGT | 55 | 5-8-5 | 758 |
| 621289 | 87288 | 87305 | TGGCTGCAACTTTGAATG | 0 | 5-8-5 | 759 |
| 621290 | 87470 | 87487 | CTGGAGATGGCAGGCTGG | 39 | 5-8-5 | 760 |
| 621291 | 87653 | 87670 | CCCGTGGGCCCCATGTGG | 1 | 5-8-5 | 761 |
| 621292 | 87834 | 87851 | ATTGAGGACACCTGGTGT | 6 | 5-8-5 | 762 |
| 621293 | 88014 | 88031 | AAGGTCTGCATTGTCAGT | 61 | 5-8-5 | 763 |
| 621294 | 88194 | 88211 | CTGCTGGCCTCTCTGTAC | 56 | 5-8-5 | 764 |
| 621295 | 88374 | 88391 | TCGGACACGGTCACTGCC | 60 | 5-8-5 | 765 |
| 621296 | 88554 | 88571 | GTGCCTTGTCATGTGACA | 79 | 5-8-5 | 766 |
| 621297 | 88734 | 88751 | GGAAGCCATGTGGTAGCC | 50 | 5-8-5 | 767 |
| 621298 | 88918 | 88935 | CAGAGGCCACTGCCTCTG | 0 | 5-8-5 | 768 |
| 621299 | 89098 | 89115 | TTAATAGTACCAAAATCA | 25 | 5-8-5 | 769 |
| 621300 | 89278 | 89295 | TACATTTCCTTCCTCCCA | 10 | 5-8-5 | 770 |
| 621301 | 89470 | 89487 | CGGAGTCAGGCAGATGGG | 43 | 5-8-5 | 771 |
| 621302 | 89650 | 89667 | GCTATGACCTAGTAGGAA | 84 | 5-8-5 | 772 |
| 621303 | 89830 | 89847 | ATTGTTTACTAGAAACCA | 39 | 5-8-5 | 773 |
| 621304 | 90010 | 90027 | GGGCAGAGCCCACCCCAT | 40 | 5-8-5 | 774 |
| 621305 | 90190 | 90207 | AGGCTGGACAAGGCTAGC | 63 | 5-8-5 | 775 |
| 621306 | 90531 | 90548 | CATATTTGAGTTTCTTTT | 62 | 5-8-5 | 776 |
| 621307 | 90711 | 90728 | AATGATTACACAAAGCTG | 61 | 5-8-5 | 777 |
| 621308 | 90891 | 90908 | GAACAGTGTCTTTCCAGC | 73 | 5-8-5 | 778 |
| 621309 | 91071 | 91088 | ATGTGCCTTTCTGTGCCA | 89 | 5-8-5 | 779 |
| 621310 | 91251 | 91268 | AATGATTTCTAGAGGTCA | 54 | 5-8-5 | 780 |
| 621311 | 91431 | 91448 | CCATGATTCCAGGCTGCT | 80 | 5-8-5 | 781 |
| 621312 | 91816 | 91833 | CAGCCAGGCTAGTCTTGC | 80 | 5-8-5 | 782 |
| 621313 | 92037 | 92054 | AGGAGAATGTTCTTTTTT | 53 | 5-8-5 | 783 |
| 621314 | 92219 | 92236 | TTACTGTACTCTGATATA | 41 | 5-8-5 | 784 |
| 621315 | 92399 | 92416 | CCTTATGGGAGCCCTTTG | 54 | 5-8-5 | 785 |
| 621316 | 92579 | 92596 | CAGAGCGCAGCAGCACCT | 64 | 5-8-5 | 786 |
| 621317 | 92759 | 92776 | CTCACCAGCTCTGCTTTA | 53 | 5-8-5 | 787 |
| 621318 | 92939 | 92956 | CAGCTGATCAAGGGCACA | 84 | 5-8-5 | 788 |
| 621319 | 93123 | 93140 | AGACCTGCCATAAGACTC | 39 | 5-8-5 | 789 |

TABLE 20-continued

Inhibition of tau mRNA by 5-10-5 MOE and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621320 | 93380 | 93397 | CTGACTAAAATGTTATTT | 34 | 5-8-5 | 790 |
| 621321 | 93570 | 93587 | ACAGGCATGAGTTTTTTT | 61 | 5-8-5 | 791 |
| 621322 | 93840 | 93857 | CCCCTTTTTTTGGTTTG | 2 | 5-8-5 | 792 |
| 621323 | 94020 | 94037 | TCTGGAGCCGCCCTGGGC | 36 | 5-8-5 | 793 |
| 621324 | 94200 | 94217 | ATGACAGCTCTCCTGGTC | 38 | 5-8-5 | 794 |
| 621325 | 94380 | 94397 | ACTCTCAACTCCTCTGGT | 49 | 5-8-5 | 795 |
| 621326 | 94576 | 94593 | TCCTGTTGGAGGAGGCGC | 7 | 5-8-5 | 796 |
| 621327 | 95433 | 95450 | CCTTTGAGTTGAGGGACC | 60 | 5-8-5 | 797 |
| 621328 | 95613 | 95630 | GCCTGAGCACGGGAGGAG | 41 | 5-8-5 | 798 |
| 621329 | 95793 | 95810 | GACACCATGAGGGCACCC | 69 | 5-8-5 | 799 |
| 621330 | 95986 | 96003 | AGCACCTCCTGGGAGGCG | 18 | 5-8-5 | 800 |
| 621331 | 96166 | 96183 | GGTGGCATGTGGACCAGG | 50 | 5-8-5 | 801 |
| 621332 | 96346 | 96363 | TGTGGCTCTGAGGTCTCC | 72 | 5-8-5 | 802 |
| 621333 | 96526 | 96543 | GCCTCTGTCTTAACTTTT | 50 | 5-8-5 | 803 |
| 621334 | 96778 | 96795 | TTAGGGTACAGTGGTGTG | 18 | 5-8-5 | 804 |
| 621335 | 96958 | 96975 | CCTCTAGTAGGCCAGTAT | 62 | 5-8-5 | 805 |
| 621336 | 97141 | 97158 | AATCAAGTAAGTTTGGGA | 57 | 5-8-5 | 806 |
| 621337 | 97321 | 97338 | CAACTGGGTCTGTAAGCC | 47 | 5-8-5 | 807 |
| 621338 | 97506 | 97523 | TAGATTTTCTTCTTTGGT | 45 | 5-8-5 | 808 |
| 621339 | 97686 | 97703 | GGGCACGAATTCTCACTG | 53 | 5-8-5 | 809 |
| 621340 | 97866 | 97883 | TCCAGAATAGGAGAGGCT | 9 | 5-8-5 | 810 |
| 621341 | 98046 | 98063 | ACACTGCAGCCAGGCTTG | 63 | 5-8-5 | 811 |
| 621342 | 98226 | 98243 | TGCAGTCTCCCTAACCCA | 59 | 5-8-5 | 812 |
| 621343 | 98406 | 98423 | CTCTTTTCCCTTGAATCT | 33 | 5-8-5 | 813 |
| 621344 | 98607 | 98624 | GTCAGCTTACCTTGGCTT | 44 | 5-8-5 | 814 |
| 621345 | 98802 | 98819 | CAACTGCTCTTCCCTGGG | 68 | 5-8-5 | 815 |
| 621346 | 98982 | 98999 | TCTGGGTGCAGTTTATGC | 80 | 5-8-5 | 816 |
| 621347 | 99162 | 99179 | AGAATTTATGCTGGAAAT | 38 | 5-8-5 | 817 |
| 621348 | 99342 | 99359 | GGCCAGCTCTCCAAATCC | 56 | 5-8-5 | 818 |
| 621349 | 99522 | 99539 | CCCTAGACTCTGGGCAAC | 66 | 5-8-5 | 819 |

TABLE 21

Inhibition of Tau mRNA by 5-10-5 MOE and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 613412 | 73879 | 73898 | GTGATCTTCCATCACTTCGA | 91 | 5-10-5 | 25 |
| 620887 | 98891 | 98908 | GTTTTCAAACACACCTTC | 96 | 5-8-5 | 665 |
|  | 98928 | 98945 |  |  |  |  |
| 620965 | 20187 | 20204 | TCTAAGTAATTCGATATG | 27 | 5-8-5 | 820 |
| 620966 | 20375 | 20392 | AAACAGAAACTAGGGTGG | 63 | 5-8-5 | 821 |
| 620967 | 20571 | 20588 | TCCCGCTGGGATCCATGG | 40 | 5-8-5 | 822 |
| 620968 | 20751 | 20768 | TGTTGCCATTGGGCAGCC | 0 | 5-8-5 | 823 |
| 620969 | 20931 | 20948 | GACCTTCTAATTAGTCCA | 58 | 5-8-5 | 824 |
| 620970 | 21291 | 21308 | GCGATTCTCTCCTGTCTC | 53 | 5-8-5 | 825 |
| 620971 | 21567 | 21584 | ACTCAGATTTATTATTTT | 87 | 5-8-5 | 826 |
| 620972 | 21747 | 21764 | AAAGTACTATCCACTTGT | 77 | 5-8-5 | 827 |
| 620973 | 21927 | 21944 | CAAATCCTGGGTTCGAAT | 39 | 5-8-5 | 828 |
| 620974 | 22107 | 22124 | AGGTCTCTGCCCATGAAA | 59 | 5-8-5 | 829 |
| 620975 | 22287 | 22304 | AGATTTCTCCCTTCACCC | 46 | 5-8-5 | 830 |
| 620976 | 22467 | 22484 | TTAACATGATGGTGGTTT | 86 | 5-8-5 | 831 |
| 620977 | 22652 | 22669 | CATTGTGGAAATTAAACA | 50 | 5-8-5 | 832 |
| 620978 | 22837 | 22854 | TGTAGTCAATATTGAACT | 86 | 5-8-5 | 833 |
| 620979 | 23269 | 23286 | TTTTGAGAGCAGGTCTCG | 61 | 5-8-5 | 834 |
| 620980 | 23449 | 23466 | ATGGCAAACAGTACATGT | 80 | 5-8-5 | 835 |
| 620981 | 23631 | 23648 | AGGATTTAAGTGATTTTC | 66 | 5-8-5 | 836 |
| 620982 | 23826 | 23843 | TACAAAGACCCCTTTTCC | 51 | 5-8-5 | 837 |
| 620983 | 24016 | 24033 | AGCTGCCAGCAGTCCTTG | 81 | 5-8-5 | 838 |
| 620984 | 24196 | 24213 | CTGCTGTAGGAAATGACC | 77 | 5-8-5 | 839 |
| 620985 | 24377 | 24394 | AGCTCCAACCAGCTTTCT | 58 | 5-8-5 | 840 |
| 620986 | 24557 | 24574 | GTCCTGATTAACAGCTAA | 69 | 5-8-5 | 841 |
| 620987 | 24744 | 24761 | GTCTGTCTGCTGCCATCC | 81 | 5-8-5 | 842 |
| 620988 | 24924 | 24941 | GTAACTGATATGGTAACA | 85 | 5-8-5 | 843 |
| 620989 | 25286 | 25303 | AGCCCTCTTTGTACAGGA | 75 | 5-8-5 | 844 |
| 620990 | 25466 | 25483 | CTGTTCCAGTTGATCCAG | 53 | 5-8-5 | 845 |
| 620991 | 25668 | 25685 | GCAGTCTTTTTAAATTAA | 80 | 5-8-5 | 846 |
| 620992 | 25848 | 25865 | CCTCTGCTCACATAGAAA | 64 | 5-8-5 | 847 |
| 620993 | 26028 | 26045 | AGTACCTGCCTTGTTCCT | 52 | 5-8-5 | 848 |
| 620994 | 26208 | 26225 | AAGCATGGTAATACAAAA | 78 | 5-8-5 | 849 |
| 620995 | 26404 | 26421 | TTGATTAAAAAAAATAGC | 4 | 5-8-5 | 850 |
| 620996 | 26584 | 26601 | TTCATCCTTTCCAAGTGT | 58 | 5-8-5 | 851 |
| 620997 | 26764 | 26781 | CATGCTTACACACCACAC | 23 | 5-8-5 | 852 |
|  | 26948 | 26965 |  |  |  |  |

TABLE 21-continued

Inhibition of Tau mRNA by 5-10-5 MOE and
5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 620998 | 26762 26946 | 26779 26963 | TGCTTACACACCACACAC | 38 | 5-8-5 | 853 |
| 620999 | 27140 | 27157 | ATATGCTGAACACACACA | 75 | 5-8-5 | 854 |
| 621000 | 27320 | 27337 | CCACCGAGGTCTCATTGG | 52 | 5-8-5 | 855 |
| 621001 | 27500 | 27517 | GGGAGACCTCCCTTTCAA | 0 | 5-8-5 | 856 |
| 621002 | 27680 | 27697 | TCTCTGGGTGTAGAGACG | 54 | 5-8-5 | 857 |
| 621003 | 27861 | 27878 | GCAGGCTCGGGCTCCACG | 61 | 5-8-5 | 858 |
| 621004 | 28041 | 28058 | CCTTGTCAGATGGTTGAT | 55 | 5-8-5 | 859 |
| 621005 | 28221 | 28238 | TCTGCAGACTTTTCTCAA | 22 | 5-8-5 | 860 |
| 621006 | 28426 | 28443 | CTGGAGGGAGGTGATGTG | 7 | 5-8-5 | 861 |
| 621007 | 28616 | 28633 | GAAAGCTGCTGCTGAGGG | 63 | 5-8-5 | 862 |
| 621008 | 28981 | 28998 | GGGCAAAGATAATTCGAA | 61 | 5-8-5 | 863 |
| 621009 | 29165 | 29182 | CCTCACCCTGGGCAAGAA | 68 | 5-8-5 | 864 |
| 621010 | 29409 | 29426 | TTGCTGCTCGGGAGGCCG | 14 | 5-8-5 | 865 |
| 621011 | 29589 | 29606 | AAATGAAAGATGCTGGCT | 23 | 5-8-5 | 866 |
| 621012 | 29953 | 29970 | CAGAGAGGTCCAGCTACT | 58 | 5-8-5 | 867 |
| 621013 | 30133 | 30150 | AGCTCACTACAGCAGGCA | 93 | 5-8-5 | 868 |
| 621014 | 30607 | 30624 | TATTTCTTGCAATTCTTT | 78 | 5-8-5 | 869 |
| 621015 | 30787 | 30804 | GGAGGACTGTCTCTAGAG | 59 | 5-8-5 | 870 |
| 621016 | 30967 | 30984 | TCCGGCCTGGCGAACTGA | 40 | 5-8-5 | 871 |
| 621017 | 31278 | 31295 | CCTGCAAAGCTAATTTTA | 18 | 5-8-5 | 872 |
| 621018 | 31458 | 31475 | GAGCCCCTTTAAGCCTT | 65 | 5-8-5 | 873 |
| 621019 | 31654 | 31671 | GTACAAAGACTGTGTACG | 47 | 5-8-5 | 874 |
| 621020 | 31834 | 31851 | GACTCAGGAACATGTTAG | 81 | 5-8-5 | 875 |
| 621021 | 32023 | 32040 | TGAGGCAGCAATGCTGGG | 34 | 5-8-5 | 876 |
| 621022 | 32203 | 32220 | CACTGGGAGGTGTATAGA | 0 | 5-8-5 | 877 |
| 621023 | 32383 | 32400 | GCGAGGTGGGTGAAGGTT | 25 | 5-8-5 | 878 |
| 621024 | 32563 | 32580 | AAAAACTTTGGCAGTCAG | 80 | 5-8-5 | 879 |
| 621025 | 32743 | 32760 | GGTCTGCCCTGCACCAGG | 59 | 5-8-5 | 880 |
| 621026 | 32923 | 32940 | CTGAGCTCTCCGAGCTGC | 61 | 5-8-5 | 881 |
| 621027 | 33103 | 33120 | GTGAGGTGGTATCATTGG | 51 | 5-8-5 | 882 |
| 621028 | 33283 | 33300 | CTAGCTTGAATTCCTCCA | 81 | 5-8-5 | 883 |
| 621029 | 33463 | 33480 | AATCTGTGACTCAAGAAC | 47 | 5-8-5 | 884 |
| 621030 | 33708 | 33725 | GGGCCGTCTCTATTAAAA | 56 | 5-8-5 | 885 |
| 621031 | 33888 | 33905 | GGTATAATTTGTTTGGAC | 85 | 5-8-5 | 886 |
| 621032 | 34068 | 34085 | CTTTATTGCATATAGGTA | 86 | 5-8-5 | 887 |

TABLE 21-continued

Inhibition of Tau mRNA by 5-10-5 MOE and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621033 | 34248 | 34265 | ATCCAGTCCCAACATTGG | 30 | 5-8-5 | 888 |
| 621034 | 34428 | 34445 | CGGTCTCTCTGACTTGCC | 78 | 5-8-5 | 889 |
| 621035 | 34620 | 34637 | GAGGGCATTCCTCAAAGG | 10 | 5-8-5 | 890 |
| 621036 | 34800 | 34817 | AGTTCTCTGATTCTCAAA | 63 | 5-8-5 | 891 |
| 621037 | 34980 | 34997 | CCCCCAGTGCCCACAAGT | 48 | 5-8-5 | 892 |
| 621038 | 35160 | 35177 | CTAAAAGCTAAAGTGGGT | 49 | 5-8-5 | 893 |
| 621039 | 35340 | 35357 | AGGACCTGGCAGAGCTGC | 73 | 5-8-5 | 894 |
| 621040 | 35520 | 35537 | AAATCGAACACTTACATA | 20 | 5-8-5 | 895 |
| 621041 | 35721 | 35738 | TTGCCATCTTGGACAGGG | 89 | 5-8-5 | 896 |

TABLE 22

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 613412 | 73879 | 73898 | GTGATCTTCCATCACTTCGA | 85 | 5-10-5 | 25 |
| 620887 | 98891 98928 | 98908 98945 | GTTTTCAAACACACCTTC | 93 | 5-8-5 | 665 |
| 620888 | 98881 98918 | 98898 98935 | ACACCTTCATTTACTGTC | 95 | 5-8-5 | 897 |
| 620889 | 98890 98927 | 98907 98944 | TTTTCAAACACACCTTCA | 74 | 5-8-5 | 898 |
| 620890 | 98892 98929 | 98909 98946 | GGTTTTCAAACACACCTT | 96 | 5-8-5 | 899 |
| 620891 | 98893 98930 | 98910 98947 | TGGTTTTCAAACACACCT | 96 | 5-8-5 | 900 |
| 620892 | 6191 | 6208 | TACCTGATAGTCGACAGA | 53 | 5-8-5 | 901 |
| 620893 | 6371 | 6388 | GTCCCTTTCCAGGCCGCC | 70 | 5-8-5 | 902 |
| 620894 | 6551 | 6568 | CGCCCATTGCGGCAAAAG | 73 | 5-8-5 | 903 |
| 620895 | 6736 | 6753 | CACTGCTCGGGAGGTGCA | 62 | 5-8-5 | 904 |
| 620896 | 6938 | 6955 | TGTTCTCAGGCACGGCGC | 74 | 5-8-5 | 905 |
| 620897 | 7121 | 7138 | GCCCTGCGCTCCGAGCGC | 44 | 5-8-5 | 906 |
| 620898 | 7301 | 7318 | AAAAAAGATGGCACCTCG | 30 | 5-8-5 | 907 |
| 620899 | 7481 | 7498 | ACAAAGCAAAGAGCCCCC | 59 | 5-8-5 | 908 |
| 620900 | 7687 | 7704 | TCACGCCCGTTCCATGCG | 43 | 5-8-5 | 909 |
| 620901 | 7867 | 7884 | CCGGATGGGTAGCCAGCG | 47 | 5-8-5 | 910 |
| 620902 | 8047 | 8064 | CCCTCTCCGGACACCTGT | 69 | 5-8-5 | 911 |

TABLE 22-continued

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 620903 | 8227 | 8244 | AAATACACCCAGGGCCGC | 51 | 5-8-5 | 912 |
| 620904 | 8408 | 8425 | GATAGAATTAACCAGAAA | 33 | 5-8-5 | 913 |
| 620905 | 8588 | 8605 | AGCCTCGCAGTACCCAGG | 39 | 5-8-5 | 914 |
| 620906 | 8775 | 8792 | TCGCGAGATGGCAATACG | 55 | 5-8-5 | 915 |
| 620907 | 8956 | 8973 | TTCCTCCATTAACAGCGC | 49 | 5-8-5 | 916 |
| 620908 | 9157 | 9174 | CCCGCCTGCTGGGAATGG | 65 | 5-8-5 | 917 |
| 620909 | 9337 | 9354 | AGAACTCAAATTGGTCCT | 67 | 5-8-5 | 918 |
| 620910 | 9517 | 9534 | TATAAGCAGCTTATACAG | 34 | 5-8-5 | 919 |
| 620911 | 9697 | 9714 | CCAAGCCAGGTTATTGCT | 70 | 5-8-5 | 920 |
| 620912 | 9877 | 9894 | TCTAACAATTTATGGGCA | 81 | 5-8-5 | 921 |
| 620913 | 10057 | 10074 | AACAAATGGACTGTAACA | 59 | 5-8-5 | 922 |
| 620914 | 10240 | 10257 | TTCAAGGAGGGAGTAAGG | 12 | 5-8-5 | 923 |
| 620915 | 10420 | 10437 | AGGAAAGTGGTGGTGGAG | 22 | 5-8-5 | 924 |
| 620916 | 10600 | 10617 | TGCAGCCCAGCTGGTGAG | 35 | 5-8-5 | 925 |
| 620917 | 10781 | 10798 | TCCTTGTAGGATGTTTAA | 30 | 5-8-5 | 926 |
| 620918 | 10961 | 10978 | ACCTGCTACATAGCGGAA | 87 | 5-8-5 | 927 |
| 620919 | 11141 | 11158 | TTATAGATCATATCTGGG | 82 | 5-8-5 | 928 |
| 620920 | 11321 | 11338 | AAACAGAGCACCAATGTA | 36 | 5-8-5 | 929 |
| 620921 | 11501 | 11518 | ACCTCAGAGACTTGACCT | 54 | 5-8-5 | 930 |
| 620922 | 11681 | 11698 | CCCAGGAAGTGAGAAAAG | 20 | 5-8-5 | 931 |
| 620923 | 11864 | 11881 | CAGTTGGGAGCCATCTGG | 51 | 5-8-5 | 932 |
| 620924 | 12044 | 12061 | ATTGGGCTCAGCATGGAG | 30 | 5-8-5 | 933 |
| 620925 | 12224 | 12241 | TCCTTAACCATTAGGCCA | 70 | 5-8-5 | 934 |
| 620926 | 12404 | 12421 | TGGCCCTAGTGAGTACCG | 75 | 5-8-5 | 935 |
| 620927 | 12597 | 12614 | GCCCAGTTTGGTGCAGGG | 79 | 5-8-5 | 936 |
| 620928 | 12777 | 12794 | GGCGGGAAGGCAGGTCAG | 51 | 5-8-5 | 937 |
| 620929 | 12957 | 12974 | CAGTTTACCAATGTCAGC | 77 | 5-8-5 | 938 |
| 620930 | 13137 | 13154 | ATATATTGTTACTTAGTC | 83 | 5-8-5 | 939 |
| 620931 | 13317 | 13334 | CATAGGCAAAACAGACAA | 68 | 5-8-5 | 940 |
| 620932 | 13504 | 13521 | TAGTTGAATGTTTTGGAA | 73 | 5-8-5 | 941 |
| 620933 | 13702 | 13719 | ACGGCGGAGGCTGAGGCG | 10 | 5-8-5 | 942 |
| 620934 | 13882 | 13899 | AGGTGCAAGCTGGCCGGG | 44 | 5-8-5 | 943 |
| 620935 | 14062 | 14079 | TGATACCCTGTAAGAATA | 82 | 5-8-5 | 944 |
| 620936 | 14243 | 14260 | AATATAGCAAAGGGAATT | 54 | 5-8-5 | 945 |
| 620937 | 14423 | 14440 | TAGAGATAATTATGTCCC | 73 | 5-8-5 | 946 |

TABLE 22-continued

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 620938 | 14609 | 14626 | GCAATTACAGAGCCAGGG | 76 | 5-8-5 | 947 |
| 620939 | 14789 | 14806 | GCAGAACTGGATCCGATC | 69 | 5-8-5 | 948 |
| 620940 | 15035 | 15052 | CAAAGCCAGGATGGTCTC | 92 | 5-8-5 | 949 |
| 620941 | 15246 | 15263 | CCAAAGAGATTCCTTTTT | 79 | 5-8-5 | 950 |
| 620942 | 15924 | 15941 | GGCCTCATTTATATATAT | 20 | 5-8-5 | 951 |
| 620943 | 16156 | 16173 | TATGGGACAATCATAGCT | 56 | 5-8-5 | 952 |
| 620944 | 16336 | 16353 | AATTCTGATACATTGTCA | 81 | 5-8-5 | 953 |
| 620945 | 16516 | 16533 | GATGACTCTTCCAAATGG | 70 | 5-8-5 | 954 |
| 620946 | 16696 | 16713 | TCACTTCATTATTCAAGC | 84 | 5-8-5 | 955 |
| 620947 | 16876 | 16893 | GTGCAGCCGCCACTGGCC | 86 | 5-8-5 | 956 |
| 620948 | 17085 | 17102 | CGATAAGATCTTTTTAAA | 25 | 5-8-5 | 957 |
| 620949 | 17266 | 17283 | GACAGTATAATCTCCATT | 69 | 5-8-5 | 958 |
| 620950 | 17446 | 17463 | AGGCTAAAGTCAGCCCAC | 29 | 5-8-5 | 959 |
| 620951 | 17639 | 17656 | CTTGCACCCTGGTTTGGG | 40 | 5-8-5 | 960 |
| 620952 | 17819 | 17836 | TCCCTGTCTGGTTAGGAA | 80 | 5-8-5 | 961 |
| 620953 | 17999 | 18016 | ACGCGCCTGCCCCGTGCC | 50 | 5-8-5 | 962 |
| 620954 | 18179 | 18196 | CTCAAACCTGGCCACGCT | 64 | 5-8-5 | 963 |
| 620955 | 18359 | 18376 | GAAACTGGCGGGTCTGTT | 64 | 5-8-5 | 964 |
| 620956 | 18539 | 18556 | GGGAGGAATTTGGCAATG | 37 | 5-8-5 | 965 |
| 620957 | 18719 | 18736 | AAAGAGCACGGCATCTAT | 76 | 5-8-5 | 966 |
| 620958 | 18905 | 18922 | AAACTGTGAGGCACTGGG | 87 | 5-8-5 | 967 |
| 620959 | 19088 | 19105 | CATTTGACATTGGCCTGT | 72 | 5-8-5 | 968 |
| 620960 | 19283 | 19300 | ATTATTATCAGCATCTTC | 77 | 5-8-5 | 969 |
| 620961 | 19467 | 19484 | TTGCAGAGGCAGGAAGGC | 67 | 5-8-5 | 970 |
| 620962 | 19647 | 19664 | AGCAGCCTGGTTTAGAGG | 31 | 5-8-5 | 971 |
| 620963 | 19827 | 19844 | TCCACATCTTCCAGCCTC | 74 | 5-8-5 | 972 |
| 620964 | 20007 | 20024 | ATACAGACTCAGTCTCCT | 79 | 5-8-5 | 973 |

TABLE 23

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 613412 | 73879 | 73898 | GTGATCTTCCATCACTTCGA | 78 | 5-10-5 | 25 |
| 620887 | 98891 98928 | 98908 98945 | GTTTTCAAACACACCTTC | 93 | 5-8-5 | 665 |

TABLE 23-continued

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621042 | 35901 | 35918 | AGTCGACCGCACTCCTGC | 42 | 5-8-5 | 974 |
| 621043 | 36106 | 36123 | GCCCTGAGGGTCCACAGG | 20 | 5-8-5 | 975 |
| 621044 | 36286 | 36303 | AGGGCAGTGTCCTACCTC | 50 | 5-8-5 | 976 |
| 621045 | 36466 | 36483 | GTCCTCCCTTCCCCACAA | 29 | 5-8-5 | 977 |
| 621046 | 36653 | 36670 | CTGAATTCCTATCATGCG | 51 | 5-8-5 | 978 |
| 621047 | 36833 | 36850 | GAGAAAGAAGAGTGTGGT | 23 | 5-8-5 | 979 |
| 621048 | 37024 | 37041 | CTTAGGACAGATTCCTAG | 29 | 5-8-5 | 980 |
| 621049 | 37204 | 37221 | GTCAGAAGTGTTTTCCCA | 80 | 5-8-5 | 981 |
| 621050 | 37413 | 37430 | TCCAATTTTAAACTTAAA | 28 | 5-8-5 | 982 |
| 621051 | 37750 | 37767 | CTACTGTTTAAAAAGGCT | 66 | 5-8-5 | 983 |
| 621052 | 38013 | 38030 | GTAAACACCATCTCTAAA | 19 | 5-8-5 | 984 |
| 621053 | 38193 | 38210 | CTCTGATACTATTATAAG | 31 | 5-8-5 | 985 |
| 621054 | 38374 | 38391 | CTGAGCTATTTGAGAATT | 21 | 5-8-5 | 986 |
| 621055 | 38557 | 38574 | TCTGCATATATAATTATA | 57 | 5-8-5 | 987 |
| 621056 | 38737 | 38754 | CACATTGTTTAGATTTTC | 79 | 5-8-5 | 988 |
| 621057 | 38922 | 38939 | TTAGCACACCTGAAACGC | 51 | 5-8-5 | 989 |
| 621058 | 39102 | 39119 | GGCAAAGAAGACAGGAGA | 68 | 5-8-5 | 990 |
| 621059 | 39541 | 39558 | TGCTGAGGATGCTTTTTT | 72 | 5-8-5 | 991 |
| 621060 | 39721 | 39738 | GCTGGAAGATGAGGTGGT | 47 | 5-8-5 | 992 |
| 621061 | 39901 | 39918 | TGGGTGTTGGAGAAAACT | 24 | 5-8-5 | 993 |
| 621062 | 40100 | 40117 | GCTTTAAAAGCTCCTCAG | 65 | 5-8-5 | 994 |
| 621063 | 40347 | 40364 | CGAGCACTTGTAGTTCCA | 35 | 5-8-5 | 995 |
| 621064 | 40528 | 40545 | GCAGTGCTTTAAAAATAT | 22 | 5-8-5 | 996 |
| 621065 | 40709 | 40726 | GAAATTTCATGAAATATG | 37 | 5-8-5 | 997 |
| 621066 | 40889 | 40906 | TTACTTGCAATTGAAAGA | 6 | 5-8-5 | 998 |
| 621067 | 41069 | 41086 | GGAAAGACTACTCAGAGC | 57 | 5-8-5 | 999 |
| 621068 | 41249 | 41266 | GATGAAAGAGAATAACAA | 20 | 5-8-5 | 1000 |
| 621069 | 41429 | 41446 | ACCCATTATCTGCTCCCC | 66 | 5-8-5 | 1001 |
| 621070 | 41611 | 41628 | TTTTCAGTAACAACATAA | 51 | 5-8-5 | 1002 |
| 621071 | 41944 | 41961 | CCTTTAGCTTTCCTTTTC | 47 | 5-8-5 | 1003 |
| 621072 | 42124 | 42141 | CAAATTCTGTTTCTGTAA | 47 | 5-8-5 | 1004 |
| 621073 | 42304 | 42321 | GCAAAATAAGTGAACTG | 38 | 5-8-5 | 1005 |
| 621074 | 42492 | 42509 | TTGCAGTGACTTCTTGGG | 71 | 5-8-5 | 1006 |
| 621075 | 42672 | 42689 | AAACCCCTTCAACATCAG | 45 | 5-8-5 | 1007 |
| 621076 | 42853 | 42870 | ACAAGAGAAACATTTTAC | 53 | 5-8-5 | 1008 |
| 621077 | 43033 | 43050 | CACTTAGTAACCAAGCAA | 53 | 5-8-5 | 1009 |

TABLE 23-continued

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621078 | 43213 | 43230 | CATAGATGATATATTTTG | 78 | 5-8-5 | 1010 |
| 621079 | 43393 | 43410 | AAATCTTGAACTCCTGAA | 58 | 5-8-5 | 1011 |
| 621080 | 43620 | 43637 | GGAGTTTTTGTGTTTCTT | 77 | 5-8-5 | 1012 |
| 621081 | 43804 | 43821 | AAATTCTTAATGGTTCAG | 75 | 5-8-5 | 1013 |
| 621082 | 44051 | 44068 | AGATAGATCTCGGCTCAC | 81 | 5-8-5 | 1014 |
| 621083 | 44231 | 44248 | AACCTTTAATAAACTTTT | 43 | 5-8-5 | 1015 |
| 621084 | 44617 | 44634 | GTCCAAGAGGTTTTTTTT | 41 | 5-8-5 | 1016 |
| 621085 | 44809 | 44826 | GCAGTCACTGCATTCCAG | 27 | 5-8-5 | 1017 |
| 621086 | 45050 | 45067 | CAAAAACAGGGCTAGGCA | 21 | 5-8-5 | 1018 |
| 621087 | 45230 | 45247 | TTCCCTGAACAAATGGCA | 59 | 5-8-5 | 1019 |
| 621088 | 45412 | 45429 | CTCAAATGTAACATTTTA | 84 | 5-8-5 | 1020 |
| 621089 | 45592 | 45609 | TACACCTGGCCCATGACC | 41 | 5-8-5 | 1021 |
| 621090 | 45772 | 45789 | AAGTTCTGGCTCAAGCAA | 21 | 5-8-5 | 1022 |
| 621091 | 45955 | 45972 | ACAACTCTCTGGAAAAAA | 30 | 5-8-5 | 1023 |
| 621092 | 46135 | 46152 | AGTCCACGCCTGCATCTG | 63 | 5-8-5 | 1024 |
| 621093 | 46315 | 46332 | CAAGGCAACAGAGAGGCA | 42 | 5-8-5 | 1025 |
| 621094 | 46495 | 46512 | AACATGCATATAATTACC | 40 | 5-8-5 | 1026 |
| 621095 | 46675 | 46692 | TTGGAGGGACAATTCTCA | 46 | 5-8-5 | 1027 |
| 621096 | 46855 | 46872 | CGAAGAGGCCAGGACTGC | 34 | 5-8-5 | 1028 |
| 621097 | 47036 | 47053 | TTTGGCTCTGGTGATGGT | 45 | 5-8-5 | 1029 |
| 621098 | 47216 | 47233 | ACCAGGCAAAGGGACACC | 68 | 5-8-5 | 1030 |
| 621099 | 47396 | 47413 | TGCCAGAGACAGAGGTTG | 68 | 5-8-5 | 1031 |
| 621100 | 47576 | 47593 | CACACGCATGGCTTCATG | 55 | 5-8-5 | 1032 |
| 621101 | 47756 | 47773 | GAGGAAGGCATGAACTAA | 60 | 5-8-5 | 1033 |
| 621102 | 47936 | 47953 | TCCCATGCCCACGCATGT | 26 | 5-8-5 | 1034 |
| 621103 | 48116 | 48133 | ATTATTAACGAACAAAAA | 2 | 5-8-5 | 1035 |
| 621104 | 48302 | 48319 | ATGTCCAGATGTGGATCG | 52 | 5-8-5 | 1036 |
| 621105 | 48482 | 48499 | ATCAGACAGAAGAGCCAT | 55 | 5-8-5 | 1037 |
| 621106 | 48678 | 48695 | GCACAGTGCAACAGTGGG | 78 | 5-8-5 | 1038 |
| 621107 | 49171 | 49188 | GGCTTTCCCTTCCCTTCT | 33 | 5-8-5 | 1039 |
| 621108 | 49361 | 49378 | AGCTGGGAAAGTGGCAGG | 23 | 5-8-5 | 1040 |
| 621109 | 49561 | 49578 | ATGACAACTTGATTTGGG | 65 | 5-8-5 | 1041 |
| 621110 | 49741 | 49758 | GACCGCAACCTTGCCAAA | 43 | 5-8-5 | 1042 |
| 621111 | 50111 | 50128 | CTTTCAGAGACAGGCTCG | 41 | 5-8-5 | 1043 |
| 621112 | 50298 | 50315 | GGGCTCACCCCTGTAGTT | 9 | 5-8-5 | 1044 |

TABLE 23-continued

Inhibition of Tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621113 | 50766 | 50783 | CTCTTAAGGCCGAGTGCA | 39 | 5-8-5 | 1045 |
| 621114 | 50970 | 50987 | TGCTAGGCAAAAAACAA | 35 | 5-8-5 | 1046 |
| 621115 | 51150 | 51167 | TAATTAGAAACCTCCTCG | 10 | 5-8-5 | 1047 |
| 621116 | 51330 | 51347 | CAGGTCATATATGAAATC | 33 | 5-8-5 | 1048 |
| 621117 | 51521 | 51538 | TGTGCTTCCGAAAGTAGT | 63 | 5-8-5 | 1049 |
| 621118 | 51702 | 51719 | GCATCAAATCCATGCATT | 38 | 5-8-5 | 1050 |

TABLE 24

Inhibition of tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 613412 | 73879 | 73898 | GTGATCTTCCATCACTTCGA | 71 | 5-10-5 | 25 |
| 620887 | 98891 98928 | 98908 98945 | GTTTTCAAACACACCTTC | 84 | 5-8-5 | 665 |
| 621119 | 51894 | 51911 | ACTCTGAAGCACAGACAG | 21 | 5-8-5 | 1051 |
| 621120 | 52081 | 52098 | CTTACCTGGGCTGGATGG | 5 | 5-8-5 | 1052 |
| 621121 | 52261 | 52278 | TTCTGTCTATAGCTAGAA | 32 | 5-8-5 | 1053 |
| 621122 | 52441 | 52458 | AGATGGCTTCCTATTGTT | 32 | 5-8-5 | 1054 |
| 621123 | 52621 | 52638 | TGGTTTGGTCAGGCCTCA | 51 | 5-8-5 | 1055 |
| 621124 | 52803 | 52820 | ATTGTAACTCAAAGTGGG | 50 | 5-8-5 | 1056 |
| 621125 | 53004 | 53021 | AAACTCTACACCCCTGGG | 17 | 5-8-5 | 1057 |
| 621126 | 53264 | 53281 | CATACCAGGAAGGAAGGA | 17 | 5-8-5 | 1058 |
| 621127 | 53444 | 53461 | TGGACATATCAGAATTTG | 64 | 5-8-5 | 1059 |
| 621128 | 53624 | 53641 | CCCTTATTAGTGTCTACA | 68 | 5-8-5 | 1060 |
| 621129 | 53805 | 53822 | ACACTCTAGAGAGGTCCA | 68 | 5-8-5 | 1061 |
| 621130 | 53985 | 54002 | GACAGTACCCACGACACG | 32 | 5-8-5 | 1062 |
| 621131 | 54165 | 54182 | CCCCATTCTGGATCCTGG | 40 | 5-8-5 | 1063 |
| 621132 | 54348 | 54365 | ATTGTCTGTAAAATGTGG | 57 | 5-8-5 | 1064 |
| 621133 | 54528 | 54545 | ATTCTGTCTGACAGAGAC | 40 | 5-8-5 | 1065 |
| 621134 | 54711 | 54728 | CGATGGTGCACATCTATA | 45 | 5-8-5 | 1066 |
| 621135 | 54891 | 54908 | CAGTGTCCGCTGAACACA | 37 | 5-8-5 | 1067 |
| 621136 | 55073 | 55090 | AGGAGGATTAGGAAGAAA | 14 | 5-8-5 | 1068 |
| 621137 | 55261 | 55278 | CAAGGAAGGCGATCTGGG | 17 | 5-8-5 | 1069 |
| 621138 | 55623 | 55640 | GGTGGCACTTGAACAAGC | 61 | 5-8-5 | 1070 |

TABLE 24-continued

Inhibition of tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621139 | 55803 | 55820 | GGTGGAAAGGGAACCCGG | 43 | 5-8-5 | 1071 |
| 621140 | 55983 | 56000 | CCCCACGGGTACACAGAG | 20 | 5-8-5 | 1072 |
| 621141 | 56163 | 56180 | CGCTGCGAACGATGCACT | 63 | 5-8-5 | 1073 |
| 621142 | 56343 | 56360 | GAATGGTCCTTCTTACAG | 13 | 5-8-5 | 1074 |
| 621143 | 56526 | 56543 | CTGGGAAAACCAAGGCAA | 57 | 5-8-5 | 1075 |
| 621144 | 56706 | 56723 | CCCAGGCTGAGGAAGGAC | 40 | 5-8-5 | 1076 |
| 621145 | 56886 | 56903 | GATTGGCTTTTACATCTT | 48 | 5-8-5 | 1077 |
| 621146 | 57289 | 57306 | CGGTTTGAGTACAGTGGT | 50 | 5-8-5 | 1078 |
| 621147 | 57470 | 57487 | CTAACATCTTAGGGCACA | 73 | 5-8-5 | 1079 |
| 621148 | 57650 | 57667 | TTCCTCTGATGTCAGAAT | 51 | 5-8-5 | 1080 |
| 621149 | 58090 | 58107 | CCCCCTCGGTCGCCCAGG | 37 | 5-8-5 | 1081 |
| 621150 | 58271 | 58288 | TGTTTTAACTAAAAGCTT | 24 | 5-8-5 | 1082 |
| 621151 | 58451 | 58468 | GTATGAGGGCATAGATGA | 26 | 5-8-5 | 1083 |
| 621152 | 58631 | 58648 | ATCACACCACAGAATGTT | 29 | 5-8-5 | 1084 |
| 621153 | 58812 | 58829 | TACTCTTCTGTGGCAGCT | 66 | 5-8-5 | 1085 |
| 621154 | 59198 | 59215 | CAACAGCAAGGCCAGGCG | 44 | 5-8-5 | 1086 |
| 621155 | 59380 | 59397 | TAGATAATTTGAAATTTA | 0 | 5-8-5 | 1087 |
| 621156 | 59786 | 59803 | ACCTTAATCCCAGTATTT | 12 | 5-8-5 | 1088 |
| 621157 | 59966 | 59983 | TGCTTATGGTCCAGCTGT | 40 | 5-8-5 | 1089 |
| 621158 | 60146 | 60163 | GAGCCAGGCTTCAAAACC | 26 | 5-8-5 | 1090 |
| 621159 | 60326 | 60343 | TCCAGCACATTTAGGCGG | 32 | 5-8-5 | 1091 |
| 621160 | 60522 | 60539 | ATCTCAATAAAGCTATCG | 70 | 5-8-5 | 1092 |
| 621161 | 60702 | 60719 | CGCCCGCGGTGACTCAGC | 32 | 5-8-5 | 1093 |
| 621162 | 60906 | 60923 | GGAGTCAAGAGTCCAGGG | 44 | 5-8-5 | 1094 |
| 621163 | 61109 | 61126 | AGAAGGAATGATGAGGAA | 24 | 5-8-5 | 1095 |
| 621164 | 61290 | 61307 | GCAGTACAGTTTGGTAAT | 32 | 5-8-5 | 1096 |
| 621165 | 61476 | 61493 | TGGCTACTCTCTCAGGAG | 9 | 5-8-5 | 1097 |
| 621166 | 61656 | 61673 | GACCCTAGGTGGGTAAAG | 21 | 5-8-5 | 1098 |
| 621167 | 61836 | 61853 | GTCCCCTGAGGTGTTGTG | 0 | 5-8-5 | 1099 |
| 621168 | 62016 | 62033 | CCCAGACAACCTTCACCT | 34 | 5-8-5 | 1100 |
| 621169 | 62208 | 62225 | TGGGTTAAGACTCTGTCT | 11 | 5-8-5 | 1101 |
| 621170 | 62467 | 62484 | TGGAGCCGAGTGCGGTGG | 12 | 5-8-5 | 1102 |
| 621171 | 62657 | 62674 | TCTCTTCTGGATATTTCG | 49 | 5-8-5 | 1103 |
| 621172 | 62843 | 62860 | CGATTTAAAATGAATGAT | 20 | 5-8-5 | 1104 |
| 621173 | 63023 | 63040 | AGAACAAAGATAACAGTT | 0 | 5-8-5 | 1105 |
| 621174 | 63218 | 63235 | GCTAAATTGAGGCCCGGG | 42 | 5-8-5 | 1106 |

TABLE 24-continued

Inhibition of tau mRNA by 5-10-5 and 5-8-5 MOE gapmers targeting SEQ ID NO: 1

| ISIS NO | SEQ ID NO: 1 Start Site | SEQ ID NO: 1 Stop Site | Sequence | % inhibition | Motif | SEQ ID NO |
|---|---|---|---|---|---|---|
| 621175 | 63398 | 63415 | CTTTCTCCTTTCCTCAAT | 26 | 5-8-5 | 1107 |
| 621176 | 63578 | 63595 | TCTAAGCGAGACACACAG | 26 | 5-8-5 | 1108 |
| 621177 | 63758 | 63775 | TGATTTCTCTGGAAGAAC | 27 | 5-8-5 | 1109 |
| 621178 | 63938 | 63955 | GCCTGTGTCTTCTAACTC | 32 | 5-8-5 | 1110 |
| 621179 | 64184 | 64201 | GGCTGAGAAGCTGGGACC | 40 | 5-8-5 | 1111 |
| 621180 | 64365 | 64382 | TTTTTACTTGAGATGTCA | 38 | 5-8-5 | 1112 |
| 621181 | 64543 | 64560 | GTAGGTGTCATCATCATC | 83 | 5-8-5 | 1113 |
| 621182 | 64723 | 64740 | CAACACTGACTGAGCACA | 56 | 5-8-5 | 1114 |
| 621183 | 64903 | 64920 | GCATTGGCTGGGCTAGGT | 73 | 5-8-5 | 1115 |
| 621184 | 65092 | 65109 | TATTTACTATGCAAAATA | 18 | 5-8-5 | 1116 |
| 621185 | 65273 | 65290 | AGCACCACAGAGCAGATG | 19 | 5-8-5 | 1117 |
| 621186 | 65453 | 65470 | CTCAGTGTGGAGTTCTGC | 44 | 5-8-5 | 1118 |
| 621187 | 65634 | 65651 | CATTTTTCAACCACTTAA | 44 | 5-8-5 | 1119 |
| 621188 | 65815 | 65832 | GTAAGGCTTTGTGGGCCA | 32 | 5-8-5 | 1120 |
| 621189 | 66148 | 66165 | TACTTTGCATTATTTATT | 44 | 5-8-5 | 1121 |
| 621190 | 66535 | 66552 | TTGGCTTTCATTATAATT | 13 | 5-8-5 | 1122 |
| 621191 | 66736 | 66753 | GGACGGTTGGGAAATAGG | 18 | 5-8-5 | 1123 |
| 621192 | 66916 | 66933 | GAGCAACTGTTCATAGGG | 49 | 5-8-5 | 1124 |
| 621193 | 67096 | 67113 | TCTGCACATCGACACATC | 34 | 5-8-5 | 1125 |
| 621194 | 67538 | 67555 | AGGCTAGGCCCCATGGCT | 21 | 5-8-5 | 1126 |
| 621195 | 67718 | 67735 | GCACCCCATCCTTCAGC | 30 | 5-8-5 | 1127 |

TABLE 25

Inhibition of Tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 613412 | 73879 | 73898 | GTGATCTTCCATCACTTCGA | 87 | 5-10-5 | 25 |
| 620887 | 98891 98928 | 98908 98945 | GTTTTCAAACACACCTTC | 96 | 5-8-5 | 665 |
| 621350 | 99702 | 99719 | CCAGGAGATGAAGTAGCA | 75 | 5-8-5 | 1128 |
| 621351 | n/a | n/a | ACTCTTGGGAAACAAAGT | 31 | 5-8-5 | 1129 |
| 621352 | 100065 | 100082 | GGAAGCAGCCAGGGACGG | 38 | 5-8-5 | 1130 |
| 621353 | 100288 | 100305 | CTGCCTGGCCAATTAAAT | 28 | 5-8-5 | 1131 |
| 621354 | 100468 | 100485 | CAAACTAATATTAACACT | 0 | 5-8-5 | 1132 |

TABLE 25-continued

Inhibition of Tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621355 | 100648 | 100665 | TACTCAATTCCAGGCAAG | 71 | 5-8-5 | 1133 |
| 621356 | 100836 | 100853 | AATGGAAGTTCTAGTACG | 57 | 5-8-5 | 1134 |
| 621357 | 101188 | 101205 | CAATCACAGTTCTTTTTC | 45 | 5-8-5 | 1135 |
| 621358 | 101381 | 101398 | GTCTTAAACATAAACATA | 77 | 5-8-5 | 1136 |
| 621359 | 101759 | 101776 | TGAGAGGGATGGCCCCCA | 67 | 5-8-5 | 1137 |
| 621360 | n/a | n/a | CGCATAACACCACGCCCG | 90 | 5-8-5 | 1138 |
| 621361 | 102169 | 102186 | GCCAAAATCAGGAATGGG | 94 | 5-8-5 | 1139 |
| 621362 | 102349 | 102366 | GGCAGTCCCTGGGTTCCG | 77 | 5-8-5 | 1140 |
| 621363 | 102529 | 102546 | GTTGAACCTGACCAAGGA | 89 | 5-8-5 | 1141 |
| 621364 | 102709 | 102726 | AGCATGAGTTGTGCCAAG | 89 | 5-8-5 | 1142 |
| 621365 | 102889 | 102906 | CCCACTCCGCCACCTTGA | 67 | 5-8-5 | 1143 |
| 621366 | 103091 | 103108 | TACCAGAGCTGGGTGGTG | 13 | 5-8-5 | 1144 |
| 621367 | 103271 | 103288 | ACATTTGCCTCAGAAATC | 5 | 5-8-5 | 1145 |
| 621368 | 103593 | 103610 | GATTCAGGCTGGGAGTGG | 11 | 5-8-5 | 1146 |
| 621369 | 103773 | 103790 | CTCCGAGAGCTGCCACTT | 51 | 5-8-5 | 1147 |
| 621370 | 103966 | 103983 | TGCAGCAGACTCCTAACG | 33 | 5-8-5 | 1148 |
| 621371 | 104389 | 104406 | AGGAATCTCACTTTTGTC | 25 | 5-8-5 | 1149 |
| 621372 | 104569 | 104586 | AGGCTGCCCGTGCCACCA | 30 | 5-8-5 | 1150 |
| 621373 | 104749 | 104766 | TTAGTGAATGGCCATCCT | 33 | 5-8-5 | 1151 |
| 621374 | 105023 | 105040 | AAACTGCTTGAATTTGGG | 31 | 5-8-5 | 1152 |
| 621375 | 105203 | 105220 | TGTGAGTCCCCTGTAATC | 18 | 5-8-5 | 1153 |
| 621376 | 105383 | 105400 | TAAACAGGGCCTTAATGA | 0 | 5-8-5 | 1154 |
| 621377 | 105563 | 105580 | TCCTCCCGGCTCTAGAAA | 10 | 5-8-5 | 1155 |
| 621378 | 105745 | 105762 | GGAGACAGCCAGGCATGG | 18 | 5-8-5 | 1156 |
| 621379 | 106173 | 106190 | ATAATGTTTTTTATAGAG | 0 | 5-8-5 | 1157 |
| 621380 | 106365 | 106382 | GACTGGATTTTGTATTT | 30 | 5-8-5 | 1158 |
| 621381 | 106545 | 106562 | CGGAGTCTTATTCTGATG | 39 | 5-8-5 | 1159 |
| 621382 | 106725 | 106742 | CCGCAGCAATGCCCCTGC | 65 | 5-8-5 | 1160 |
| 621383 | 106905 | 106922 | TCTCGATCCCCTTCAAGA | 23 | 5-8-5 | 1161 |
| 621384 | 107085 | 107102 | CTGGGTGTCCTTTACCCT | 5 | 5-8-5 | 1162 |
| 621385 | 107265 | 107282 | CCTGCTCCACGCCTGCCT | 82 | 5-8-5 | 1163 |
| 621386 | 107445 | 107462 | TCAGGGCCTTTATCCTAA | 51 | 5-8-5 | 1164 |
| 621387 | 107625 | 107642 | TCGGCTCCACAGTCTTTG | 60 | 5-8-5 | 1165 |
| 621388 | 107805 | 107822 | CACCACTGGGTTAGGCAG | 38 | 5-8-5 | 1166 |
| 621389 | 108170 | 108187 | TCACCTTCCCGCCTCCCG | 16 | 5-8-5 | 1167 |

TABLE 25-continued

Inhibition of Tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621390 | 108359 | 108376 | TTGAAGAGGGTCCAGAGG | 3 | 5-8-5 | 1168 |
| 621391 | 108548 | 108565 | TGCCCAGAAGGCAGGTGG | 38 | 5-8-5 | 1169 |
| 621392 | 108728 | 108745 | GGCCCCCGAAGTCTGTGC | 62 | 5-8-5 | 1170 |
| 621393 | 108908 | 108925 | CGGTGCAGGACAGAGGTG | 57 | 5-8-5 | 1171 |
| 621394 | 109135 | 109152 | CGCGCACCACCACCACGC | 78 | 5-8-5 | 1172 |
| 621395 | 109315 | 109332 | TCAGGCTGGGCCCTAAGC | 50 | 5-8-5 | 1173 |
| 621396 | 109495 | 109512 | TCACCCTTCCCCAGCTCC | 45 | 5-8-5 | 1174 |
| 621397 | 109675 | 109692 | TCAGACCCAAGTGATAAG | 64 | 5-8-5 | 1175 |
| 621398 | 109855 | 109872 | GCAGGGTCTACACATGCG | 76 | 5-8-5 | 1176 |
| 621399 | 110045 | 110062 | CTGAGATGTTCTCTTCCT | 73 | 5-8-5 | 1177 |
| 621400 | 110225 | 110242 | AGCTGCGGTACAGGACAG | 68 | 5-8-5 | 1178 |
| 621401 | 110405 | 110422 | CCAGTGAGGGCCCCTCTG | 20 | 5-8-5 | 1179 |
| 621402 | 110585 | 110602 | GCCCCCAGAGGTGCATGG | 58 | 5-8-5 | 1180 |
| 621403 | 110769 | 110786 | GGAGCAGCAGACACATGC | 79 | 5-8-5 | 1181 |
| 621404 | 110949 | 110966 | GGAAGCTACTTCCCATGC | 43 | 5-8-5 | 1182 |
| 621406 | 111495 | 111512 | GGAGGAGGCCTGACACCC | 58 | 5-8-5 | 1183 |
| 621407 | 111675 | 111692 | TTTCCCTTTGGTGTTAGC | 91 | 5-8-5 | 1184 |
| 621408 | 111856 | 111873 | CCCCAAAGCAATCTATGT | 47 | 5-8-5 | 1185 |
| 621409 | 112036 | 112053 | TCTGGAGGGAACACTGCC | 60 | 5-8-5 | 1186 |
| 621410 | 112216 | 112233 | GGTTGAGGTTGAGGGTAG | 37 | 5-8-5 | 1187 |
| 621411 | 112396 | 112413 | ACTCCCGCAGGCCAAACA | 36 | 5-8-5 | 1188 |
| 621412 | 112603 | 112620 | GAGTGCCAACAGGCCCAG | 75 | 5-8-5 | 1189 |
| 621413 | 112784 | 112801 | TTCTAAGTACAATTTGGG | 67 | 5-8-5 | 1190 |
| 621414 | 112984 | 113001 | TTACTGGTTGTGTTTTCT | 94 | 5-8-5 | 1191 |
| 621415 | 113164 | 113181 | GAGTCTCAGTCTCACTGT | 76 | 5-8-5 | 1192 |
| 621416 | 113347 | 113364 | CATTCCTCCTGCTGCTGT | 83 | 5-8-5 | 1193 |
| 621417 | 113540 | 113557 | GCTCTGAAGAGCTCCACG | 83 | 5-8-5 | 1194 |
| 621418 | 113720 | 113737 | CTCTCTTCAGGGCCACCG | 82 | 5-8-5 | 1195 |
| 621419 | 113900 | 113917 | CTCTCTCGCCCTGCATGG | 48 | 5-8-5 | 1196 |
| 621420 | 114080 | 114097 | CTGGACATCCTCCGAGAA | 27 | 5-8-5 | 1197 |
| 621421 | 114260 | 114277 | CACCCAGGCTGCGGCCCA | 64 | 5-8-5 | 1198 |
| 621422 | 114440 | 114457 | CTGTGGTGCAAGCCTGTG | 42 | 5-8-5 | 1199 |
| 621423 | 114639 | 114656 | AGACGAGAGTGCGCCCAC | 78 | 5-8-5 | 1200 |
| 621424 | 115155 | 115172 | CCACATAAATGTTCTACA | 94 | 5-8-5 | 1201 |

TABLE 25-continued

Inhibition of Tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621425 | 115335 | 115352 | GGTACAGGAAAAGATGCC | 88 | 5-8-5 | 1202 |
| 621426 | 115515 | 115532 | ATCAGCTTAGGAACTGAC | 85 | 5-8-5 | 1203 |

TABLE 26

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 613412 | 73879 | 73898 | GTGATCTTCCATCACTTCGA | 86 | 5-10-5 | 25 |
| 620887 | 98891 98928 | 98908 98945 | GTTTTCAAACACACCTTC | 97 | 5-8-5 | 665 |
| 621427 | 115695 | 115712 | GTGCCTCACAGTTGGCTC | 39 | 5-8-5 | 1204 |
| 621428 | 115896 | 115913 | GAGAGGCTGTGGTGAGGT | 25 | 5-8-5 | 1205 |
| 621429 | 116077 | 116094 | GAAATCAGAATCCTGAAA | 66 | 5-8-5 | 1206 |
| 621430 | 116259 | 116276 | ATGTGGCTTTTTCTTGTT | 64 | 5-8-5 | 1207 |
| 621431 | 116595 | 116612 | GTTTTTTTCTGGCCGGGC | 90 | 5-8-5 | 1208 |
| 621432 | 116955 | 116972 | TTTTCAGTGGATAAGGCT | 78 | 5-8-5 | 1209 |
| 621433 | 117135 | 117152 | ACATAAACTCCTTCTTTG | 53 | 5-8-5 | 1210 |
| 621434 | 117315 | 117332 | TGGTGAATGTTGAAATTC | 78 | 5-8-5 | 1211 |
| 621435 | 117495 | 117512 | AGGACAAGGAGGCCATGT | 56 | 5-8-5 | 1212 |
| 621436 | 117787 | 117804 | TCAAATGACAGATTCTCA | 78 | 5-8-5 | 1213 |
| 621437 | 117967 | 117984 | CATCCCTACTTTCTCCCT | 24 | 5-8-5 | 1214 |
| 621438 | 118420 | 118437 | TAGAATCTTGCCTTGTCG | 34 | 5-8-5 | 1215 |
| 621439 | 118600 | 118617 | GATACAGACATACATTGT | 68 | 5-8-5 | 1216 |
| 621440 | 118831 | 118848 | AATTCTTTGTGATGATGG | 82 | 5-8-5 | 1217 |
| 621441 | 119044 | 119061 | GCACATATTTACATTTTA | 94 | 5-8-5 | 1218 |
| 621442 | 119224 | 119241 | GGTGAGAGAGCCAGCCTC | 59 | 5-8-5 | 1219 |
| 621443 | 119404 | 119421 | CAAACAGCCTCCCATGAA | 38 | 5-8-5 | 1220 |
| 621444 | 119584 | 119601 | ATATCCTAAGCATTGTCT | 71 | 5-8-5 | 1221 |
| 621445 | 119880 | 119897 | TACAGTGGCTCCTGTAAT | 18 | 5-8-5 | 1222 |
| 621446 | 120060 | 120077 | GCTCATCAAAGCAAAAAC | 84 | 5-8-5 | 1223 |
| 621447 | 120248 | 120265 | CTGGGCTGTCGGATCTGG | 69 | 5-8-5 | 1224 |
| 621448 | 120439 | 120456 | AAGCCACCATGCCTGTAA | 89 | 5-8-5 | 1225 |
| 621449 | 120660 | 120677 | ACACCATCACGGCTCAGT | 56 | 5-8-5 | 1226 |
| 621450 | 120840 | 120857 | AGGGAGTTGGAAAAACTG | 46 | 5-8-5 | 1227 |

TABLE 26-continued

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621451 | 121209 | 121226 | CAGGTTTGAGAAGCCCTG | 0 | 5-8-5 | 1228 |
| 621452 | 121389 | 121406 | AGACCCACCGGCACATTC | 56 | 5-8-5 | 1229 |
| 621453 | 121569 | 121586 | ATTTCCAGCGGGCTTTAC | 62 | 5-8-5 | 1230 |
| 621454 | 121761 | 121778 | GCTTGCTCGCAAGGACGC | 93 | 5-8-5 | 1231 |
| 621455 | 121941 | 121958 | CCACAGCACGGCGCATGG | 65 | 5-8-5 | 1232 |
| 621456 | 122121 | 122138 | ACACCCCTCCTAGAATA | 0 | 5-8-5 | 1233 |
| 621457 | 122301 | 122318 | ACCACCTTCAGCCCAACT | 22 | 5-8-5 | 1234 |
| 621458 | 122481 | 122498 | TAAGCTGGAGGCTTAGGA | 40 | 5-8-5 | 1235 |
| 621459 | 122678 | 122695 | GAACCTCCCGCCTTAGTC | 19 | 5-8-5 | 1236 |
| 621460 | 122913 | 122930 | TATATGATTGTTTTTGA | 0 | 5-8-5 | 1237 |
| 621461 | 123093 | 123110 | AGGAGCCTCGGGTGCCCA | 30 | 5-8-5 | 1238 |
| 621462 | 123273 | 123290 | TCAGGCCAGGCATTTTCT | 58 | 5-8-5 | 1239 |
| 621463 | 123453 | 123470 | CACTTAGCAGACACTGGT | 77 | 5-8-5 | 1240 |
| 621464 | 123633 | 123650 | TCCTCTGGCCGAGCTCAC | 58 | 5-8-5 | 1241 |
| 621465 | 123824 | 123841 | ACAGCGCGGGACACACGG | 77 | 5-8-5 | 1242 |
| 621466 | 124004 | 124021 | GCATCTCTTCTCACCAGG | 13 | 5-8-5 | 1243 |
| 621467 | 124184 | 124201 | GGATACCTGGAGGGCAGG | 13 | 5-8-5 | 1244 |
| 621468 | 124379 | 124396 | TGAGGCCAGCACTGAGGG | 29 | 5-8-5 | 1245 |
| 621469 | 124559 | 124576 | ACTGGAACCATCCCGAAT | 37 | 5-8-5 | 1246 |
| 621470 | 124752 | 124769 | GCAGTGGCCTTGTGTGGG | 19 | 5-8-5 | 1247 |
| 621471 | 124932 | 124949 | ACCCTGAGCTGCCAGCTG | 53 | 5-8-5 | 1248 |
| 621472 | 125112 | 125129 | CTGCACACTCAGTGTCCT | 78 | 5-8-5 | 1249 |
| 621473 | 125292 | 125309 | CTGGAAAGGCAGGAGTGG | 33 | 5-8-5 | 1250 |
| 621474 | 125472 | 125489 | AAGAGCCTCTGGGAAAAA | 50 | 5-8-5 | 1251 |
| 621475 | 125652 | 125669 | GGTGTAACTCAATGAGAA | 41 | 5-8-5 | 1252 |
| 621476 | 125832 | 125849 | GGCTACCTGGTTTATGAT | 32 | 5-8-5 | 1253 |
| 621477 | 126012 | 126029 | GGAGCGAGCTGGAGCCAC | 75 | 5-8-5 | 1254 |
| 621478 | 126332 | 126349 | GCTCACTCCGCTCACTGC | 74 | 5-8-5 | 1255 |
| 621479 | 126527 | 126544 | CTAGGTCTTATTCTATTT | 38 | 5-8-5 | 1256 |
| 621480 | 127208 | 127225 | AGGTTTTGTTGTGTGTT | 54 | 5-8-5 | 1257 |
| 621481 | 127396 | 127413 | CCTCTTCACCTTAAAAAA | 24 | 5-8-5 | 1258 |
| 621482 | 127591 | 127608 | AAACAAAGTCACAGAGGG | 67 | 5-8-5 | 1259 |
| 621483 | 127934 | 127951 | AGGATCACTTTCTTTTCT | 31 | 5-8-5 | 1260 |
| 621484 | 128271 | 128288 | TTGCTGAGTCTCACTCTG | 87 | 5-8-5 | 1261 |
| 621485 | 128451 | 128468 | CAGAATCTATAGCTGTGT | 51 | 5-8-5 | 1262 |

TABLE 26-continued

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621486 | 128631 | 128648 | ATACTTTCCACAGGGAGA | 45 | 5-8-5 | 1263 |
| 621487 | 128811 | 128828 | GAAGAAGGGTCCCTCTCT | 38 | 5-8-5 | 1264 |
| 621488 | 128993 | 129010 | ATGAGAGTACAACTCCAT | 44 | 5-8-5 | 1265 |
| 621489 | 129269 | 129286 | ACCCTTTCAGGCCGGGCG | 44 | 5-8-5 | 1266 |
| 621490 | 129678 | 129695 | TAAGTAAAGTCTGTTTTT | 47 | 5-8-5 | 1267 |
| 621491 | 129861 | 129878 | TAGAATGGTGTTTGGATA | 42 | 5-8-5 | 1268 |
| 621492 | 130040 | 130057 | GCAGTCTACAGGGCAAAG | 79 | 5-8-5 | 1269 |
| 621493 | 130234 | 130251 | ACCTTTTTATTTCCTCCG | 14 | 5-8-5 | 1270 |
| 621494 | 130414 | 130431 | AGCTCCAGGTGATTGAGA | 68 | 5-8-5 | 1271 |
| 621495 | 130691 | 130708 | GTCGCCATGTAAGAAATG | 46 | 5-8-5 | 1272 |
| 621496 | 130902 | 130919 | AGGGAGACTGATATGGTT | 31 | 5-8-5 | 1273 |
| 621497 | 131113 | 131130 | ATATTGCTTGACCTCAGG | 18 | 5-8-5 | 1274 |
| 621498 | 131543 | 131560 | AGTGGTTCTCGCTTTTTT | 75 | 5-8-5 | 1275 |
| 621499 | 131725 | 131742 | CAAGACAGGCAGGCAGAG | 19 | 5-8-5 | 1276 |
| 621500 | 131905 | 131922 | GTGCTTGGCTGCGCTTCT | 45 | 5-8-5 | 1277 |
| 621501 | 132085 | 132102 | CAGACCTCTATCTTTTAG | 24 | 5-8-5 | 1278 |
| 621502 | 132266 | 132283 | AGGAGGGTCTTTCCCGTG | 57 | 5-8-5 | 1279 |
| 621503 | 132446 | 132463 | AACTGGGCCACCATGAGA | 30 | 5-8-5 | 1280 |

TABLE 27

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621519 | 5901 | 5918 | CCTGCCGCTCGGCCGTCC | 19 | 5-8-5 | 1281 |
| 621520 | 5904 | 5921 | CGCCCTGCCGCTCGGCCG | 0 | 5-8-5 | 1282 |
| 621521 | 5919 | 5936 | GTGGGCGCGCGCGAGCGC | 7 | 5-8-5 | 1283 |
| 621522 | 5922 | 5939 | CTAGTGGGCGCGCGCGAG | 6 | 5-8-5 | 1284 |
| 621523 | 5925 | 5942 | CCACTAGTGGGCGCGCGC | 0 | 5-8-5 | 1285 |
| 621524 | 5928 | 5945 | CGGCCACTAGTGGGCGCG | 18 | 5-8-5 | 1286 |
| 621525 | 5931 | 5948 | CTCCGGCCACTAGTGGGC | 39 | 5-8-5 | 1287 |
| 621526 | 5934 | 5951 | CTCCTCCGGCCACTAGTG | 37 | 5-8-5 | 1288 |
| 621527 | 5937 | 5954 | CTTCTCCTCCGGCCACTA | 15 | 5-8-5 | 1289 |
| 621528 | 5940 | 5957 | AGCCTTCTCCTCCGGCCA | 0 | 5-8-5 | 1290 |
| 621529 | 5943 | 5960 | GGGAGCCTTCTCCTCCGG | 0 | 5-8-5 | 1291 |

TABLE 27-continued

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621530 | 5946 | 5963 | CGCGGGAGCCTTCTCCTC | 28 | 5-8-5 | 1292 |
| 621531 | 5949 | 5966 | CTCCGCGGGAGCCTTCTC | 0 | 5-8-5 | 1293 |
| 621532 | 5952 | 5969 | GGCCTCCGCGGGAGCCTT | 0 | 5-8-5 | 1294 |
| 621533 | 5955 | 5972 | CGCGGCCTCCGCGGGAGC | 0 | 5-8-5 | 1295 |
| 621534 | 5958 | 5975 | CAGCGCGGCCTCCGCGGG | 0 | 5-8-5 | 1296 |
| 621535 | 5961 | 5978 | GGGCAGCGCGGCCTCCGC | 31 | 5-8-5 | 1297 |
| 621536 | 5964 | 5981 | GGCGGGCAGCGCGGCCTC | 17 | 5-8-5 | 1298 |
| 621537 | 5987 | 6004 | ACGCGAGCCTCCCCAGGG | 10 | 5-8-5 | 1299 |
| 621538 | 5990 | 6007 | GGAACGCGAGCCTCCCCA | 33 | 5-8-5 | 1300 |
| 621539 | 5993 | 6010 | GCGGGAACGCGAGCCTCC | 0 | 5-8-5 | 1301 |
| 621540 | 5996 | 6013 | GCAGCGGGAACGCGAGCC | 0 | 5-8-5 | 1302 |
| 621541 | 5999 | 6016 | CGAGCAGCGGGAACGCGA | 0 | 5-8-5 | 1303 |
| 621542 | 6002 | 6019 | GCGCGAGCAGCGGGAACG | 9 | 5-8-5 | 1304 |
| 621543 | 6005 | 6022 | CAGGCGCGAGCAGCGGGA | 22 | 5-8-5 | 1305 |
| 621544 | 6008 | 6025 | GCGCAGGCGCGAGCAGCG | 1 | 5-8-5 | 1306 |
| 621545 | 6011 | 6028 | GCGGCGCAGGCGCGAGCA | 11 | 5-8-5 | 1307 |
| 621546 | 6014 | 6031 | CGGGCGGCGCAGGCGCGA | 47 | 5-8-5 | 1308 |
| 621547 | 6017 | 6034 | CGGCGGGCGGCGCAGGCG | 15 | 5-8-5 | 1309 |
| 621548 | 6020 | 6037 | GGCCGGCGGGCGGCGCAG | 0 | 5-8-5 | 1310 |
| 621549 | 6023 | 6040 | TGAGGCCGGCGGGCGGCG | 5 | 5-8-5 | 1311 |
| 621550 | 6026 | 6043 | TCCTGAGGCCGGCGGGCG | 20 | 5-8-5 | 1312 |
| 621551 | 6029 | 6046 | CGTTCCTGAGGCCGGCGG | 13 | 5-8-5 | 1313 |
| 621552 | 6045 | 6062 | GCCGGCGAAGAGGGCGCG | 0 | 5-8-5 | 1314 |
| 621553 | 6048 | 6065 | CGCGCCGGCGAAGAGGGC | 0 | 5-8-5 | 1315 |
| 621554 | 6051 | 6068 | GCGCGCGCCGGCGAAGAG | 0 | 5-8-5 | 1316 |
| 621555 | 6054 | 6071 | AGGGCGCGCGCCGGCGAA | 32 | 5-8-5 | 1317 |
| 621556 | 6057 | 6074 | GCGAGGGCGCGCGCCGGC | 15 | 5-8-5 | 1318 |
| 621557 | 6060 | 6077 | ACTGCGAGGGCGCGCGCC | 30 | 5-8-5 | 1319 |
| 621558 | 6063 | 6080 | GTGACTGCGAGGGCGCGC | 38 | 5-8-5 | 1320 |
| 621559 | 6066 | 6083 | GCGGTGACTGCGAGGGCG | 30 | 5-8-5 | 1321 |
| 621560 | 6069 | 6086 | GTGGCGGTGACTGCGAGG | 37 | 5-8-5 | 1322 |
| 621561 | 6072 | 6089 | TGGGTGGCGGTGACTGCG | 48 | 5-8-5 | 1323 |
| 621562 | 6075 | 6092 | TGGTGGGTGGCGGTGACT | 34 | 5-8-5 | 1324 |
| 621563 | 6078 | 6095 | AGCTGGTGGGTGGCGGTG | 54 | 5-8-5 | 1325 |
| 621564 | 6081 | 6098 | CGGAGCTGGTGGGTGGCG | 36 | 5-8-5 | 1326 |

TABLE 27-continued

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621565 | 6084 | 6101 | TGCCGGAGCTGGTGGGTG | 52 | 5-8-5 | 1327 |
| 621566 | 6087 | 6104 | TGGTGCCGGAGCTGGTGG | 64 | 5-8-5 | 1328 |
| 621567 | 6090 | 6107 | TGTTGGTGCCGGAGCTGG | 74 | 5-8-5 | 1329 |
| 621568 | 6093 | 6110 | TGCTGTTGGTGCCGGAGC | 50 | 5-8-5 | 1330 |
| 621569 | 6096 | 6113 | CGCTGCTGTTGGTGCCGG | 47 | 5-8-5 | 1331 |
| 621570 | 6111 | 6128 | GGGCGGTGGCAGCGGCGC | 86 | 5-8-5 | 1332 |
| 621571 | 6114 | 6131 | GGTGGGCGGTGGCAGCGG | 61 | 5-8-5 | 1333 |
| 621572 | 6117 | 6134 | GAAGGTGGGCGGTGGCAG | 19 | 5-8-5 | 1334 |
| 621573 | 6120 | 6137 | GCAGAAGGTGGGCGGTGG | 22 | 5-8-5 | 1335 |
| 621574 | 6123 | 6140 | GCGGCAGAAGGTGGGCGG | 18 | 5-8-5 | 1336 |
| 621575 | 6126 | 6143 | GCGGCGGCAGAAGGTGGG | 62 | 5-8-5 | 1337 |
| 621576 | 6129 | 6146 | GTGGCGGCGGCAGAAGGT | 79 | 5-8-5 | 1338 |
| 621577 | 6132 | 6149 | GTGGTGGCGGCGGCAGAA | 70 | 5-8-5 | 1339 |
| 621578 | 6135 | 6152 | GCTGTGGTGGCGGCGGCA | 78 | 5-8-5 | 1340 |
| 621579 | 6138 | 6155 | GTGGCTGTGGTGGCGGCG | 78 | 5-8-5 | 1341 |
| 621580 | 6141 | 6158 | AAGGTGGCTGTGGTGGCG | 72 | 5-8-5 | 1342 |
| 613412 | 73879 | 73898 | GTGATCTTCCATCACTTCGA | 78 | 5-8-5 | 25 |
| 620887 | 98891 98928 | 98908 98945 | GTTTTCAAACACACCTTC | 94 | 5-8-5 | 665 |
| 621504 | 132626 | 132643 | AAACCCTTCTCACAAAAC | 17 | 5-8-5 | 1343 |
| 621505 | 132812 | 132829 | CCTCCTGGTCCCTCCTCG | 12 | 5-8-5 | 1344 |
| 621506 | 132992 | 133009 | CCTATCCAGACCCACTCA | 10 | 5-8-5 | 1345 |
| 621507 | 133179 | 133196 | CACAACCACCCCGGGACG | 8 | 5-8-5 | 1346 |
| 621508 | 133359 | 133376 | GGACCAGGATGGTGTTTT | 44 | 5-8-5 | 1347 |
| 621509 | 133539 | 133556 | GGCTTTGATAAAAATATT | 8 | 5-8-5 | 1348 |
| 621510 | 133788 | 133805 | CGCCTCCGGGATCAAGCA | 47 | 5-8-5 | 1349 |
| 621511 | 133968 | 133985 | GGTTCGCATTTAAGCTAG | 28 | 5-8-5 | 1350 |
| 621512 | 134148 | 134165 | ACGGTCATTCTCAGCCCT | 59 | 5-8-5 | 1351 |
| 621513 | 134333 | 134350 | TAACCTCCAGAGCAACTG | 26 | 5-8-5 | 1352 |
| 621514 | 134513 | 134530 | GGCAGGTGGGCCACAAAA | 17 | 5-8-5 | 1353 |
| 621515 | 134696 | 134713 | TCAAAAGGCATGCACATT | 44 | 5-8-5 | 1354 |
| 621516 | 134876 | 134893 | TAGTATTCCGTCGCCACG | 40 | 5-8-5 | 1355 |
| 621517 | 135057 | 135074 | GAGCTGTTGTTTTATTG | 7 | 5-8-5 | 1356 |
| 621518 | 135369 | 135386 | GCCAGGGACTGTTTTTTG | 62 | 5-8-5 | 1357 |

TABLE 28

Inhibition of tau mRNA by 5-8-5 MOE gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621596 | n/a | n/a | TCACCTGATAGTCGACAG | 70 | 292 | 309 | 5-8-5 | 1358 |
| 621597 | n/a | n/a | AGTTCACCTGATAGTCGA | 61 | 295 | 312 | 5-8-5 | 1359 |
| 621598 | n/a | n/a | CAAAGTTCACCTGATAGT | 44 | 298 | 315 | 5-8-5 | 1360 |
| 621599 | n/a | n/a | GTTCAAAGTTCACCTGAT | 72 | 301 | 318 | 5-8-5 | 1361 |
| 621629 | n/a | n/a | GATTCTTTCAGGCCAGCG | 42 | 442 | 459 | 5-8-5 | 1362 |
| 621630 | n/a | n/a | GGAGATTCTTTCAGGCCA | 0 | 445 | 462 | 5-8-5 | 1363 |
| 621649 | n/a | n/a | ATCTTCCGCTGTTGGAGT | 43 | 527 | 544 | 5-8-5 | 1364 |
| 621650 | n/a | n/a | CACATCTTCCGCTGTTGG | 3 | 530 | 547 | 5-8-5 | 1365 |
| 621651 | n/a | n/a | TGTCACATCTTCCGCTGT | 0 | 533 | 550 | 5-8-5 | 1366 |
| 621652 | n/a | n/a | TGCTGTCACATCTTCCGC | 30 | 536 | 553 | 5-8-5 | 1367 |
| 621653 | n/a | n/a | AGGGTGCTGTCACATCTT | 61 | 540 | 557 | 5-8-5 | 1368 |
| 621581 | 6144 | 6161 | GAGAAGGTGGCTGTGGTG | 14 | 244 | 261 | 5-8-5 | 1369 |
| 621582 | 6147 | 6164 | GAGGAGAAGGTGGCTGTG | 53 | 247 | 264 | 5-8-5 | 1370 |
| 621583 | 6153 | 6170 | GCGGAGGAGGAGAAGGTG | 25 | 253 | 270 | 5-8-5 | 1371 |
| 621584 | 6156 | 6173 | ACAGCGGAGGAGGAGAAG | 2 | 256 | 273 | 5-8-5 | 1372 |
| 621585 | 6159 | 6176 | AGGACAGCGGAGGAGGAG | 38 | 259 | 276 | 5-8-5 | 1373 |
| 621586 | 6162 | 6179 | GAGAGGACAGCGGAGGAG | 53 | 262 | 279 | 5-8-5 | 1374 |
| 621587 | 6165 | 6182 | CGGGAGAGGACAGCGGAG | 43 | 265 | 282 | 5-8-5 | 1375 |
| 621588 | 6168 | 6185 | GGACGGGAGAGGACAGCG | 69 | 268 | 285 | 5-8-5 | 1376 |
| 621589 | 6171 | 6188 | CGAGGACGGGAGAGGACA | 0 | 271 | 288 | 5-8-5 | 1377 |
| 621590 | 6174 | 6191 | AGGCGAGGACGGGAGAGG | 13 | 274 | 291 | 5-8-5 | 1378 |
| 621591 | 6177 | 6194 | CAGAGGCGAGGACGGGAG | 10 | 277 | 294 | 5-8-5 | 1379 |
| 621592 | 6180 | 6197 | CGACAGAGGCGAGGACGG | 57 | 280 | 297 | 5-8-5 | 1380 |
| 621593 | 6183 | 6200 | AGTCGACAGAGGCGAGGA | 61 | 283 | 300 | 5-8-5 | 1381 |
| 621594 | 6186 | 6203 | GATAGTCGACAGAGGCGA | 65 | 286 | 303 | 5-8-5 | 1382 |
| 621595 | 6189 | 6206 | CCTGATAGTCGACAGAGG | 51 | 289 | 306 | 5-8-5 | 1383 |
| 621600 | 73838 | 73855 | CTGGTTCAAAGTTCACCT | 52 | 304 | 321 | 5-8-5 | 1384 |
| 621601 | 73841 | 73858 | ATCCTGGTTCAAAGTTCA | 62 | 307 | 324 | 5-8-5 | 1385 |
| 621602 | 73844 | 73861 | GCCATCCTGGTTCAAAGT | 42 | 310 | 327 | 5-8-5 | 1386 |
| 621603 | 73847 | 73864 | TCAGCCATCCTGGTTCAA | 38 | 313 | 330 | 5-8-5 | 1387 |
| 621604 | 73850 | 73867 | GGCTCAGCCATCCTGGTT | 65 | 316 | 333 | 5-8-5 | 1388 |
| 621605 | 73867 | 73884 | CTTCGAACTCCTGGCGGG | 20 | 333 | 350 | 5-8-5 | 1389 |
| 621606 | 73870 | 73887 | TCACTTCGAACTCCTGGC | 51 | 336 | 353 | 5-8-5 | 1390 |
| 621607 | 73873 | 73890 | CCATCACTTCGAACTCCT | 68 | 339 | 356 | 5-8-5 | 1391 |
| 621608 | 73876 | 73893 | CTTCCATCACTTCGAACT | 28 | 342 | 359 | 5-8-5 | 1392 |
| 613412 | 73879 | 73898 | GTGATCTTCCATCACTTCGA | 75 | 345 | 364 | 5-8-5 | 25 |

TABLE 28-continued

Inhibition of tau mRNA by 5-8-5 MOE
gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621609 | 73879 | 73896 | GATCTTCCATCACTTCGA | 68 | 345 | 362 | 5-8-5 | 1393 |
| 621610 | 73882 | 73899 | CGTGATCTTCCATCACTT | 13 | 348 | 365 | 5-8-5 | 1394 |
| 621611 | 73906 | 73923 | TGTCCCCCAACCCGTACG | 46 | 372 | 389 | 5-8-5 | 1395 |
| 621612 | 73909 | 73926 | TCCTGTCCCCCAACCCGT | 54 | 375 | 392 | 5-8-5 | 1396 |
| 621613 | 73912 | 73929 | CTTTCCTGTCCCCCAACC | 43 | 378 | 395 | 5-8-5 | 1397 |
| 621614 | 73915 | 73932 | GATCTTTCCTGTCCCCCA | 71 | 381 | 398 | 5-8-5 | 1398 |
| 621615 | 73918 | 73935 | CCTGATCTTTCCTGTCCC | 71 | 384 | 401 | 5-8-5 | 1399 |
| 621616 | 73921 | 73938 | CCCCCTGATCTTTCCTGT | 54 | 387 | 404 | 5-8-5 | 1400 |
| 621617 | 73924 | 73941 | AGCCCCCTGATCTTTCC | 40 | 390 | 407 | 5-8-5 | 1401 |
| 621618 | 73927 | 73944 | TGTAGCCCCCTGATCTT | 35 | 393 | 410 | 5-8-5 | 1402 |
| 621619 | 73930 | 73947 | TGGTGTAGCCCCCCTGAT | 31 | 396 | 413 | 5-8-5 | 1403 |
| 621620 | 73933 | 73950 | GCATGGTGTAGCCCCCCT | 71 | 399 | 416 | 5-8-5 | 1404 |
| 621621 | 73936 | 73953 | GGTGCATGGTGTAGCCCC | 62 | 402 | 419 | 5-8-5 | 1405 |
| 621622 | 73939 | 73956 | CTTGGTGCATGGTGTAGC | 54 | 405 | 422 | 5-8-5 | 1406 |
| 621623 | 73942 | 73959 | GGTCTTGGTGCATGGTGT | 65 | 408 | 425 | 5-8-5 | 1407 |
| 621624 | 73945 | 73962 | CTTGGTCTTGGTGCATGG | 63 | 411 | 428 | 5-8-5 | 1408 |
| 621625 | 73948 | 73965 | CCTCTTGGTCTTGGTGCA | 49 | 414 | 431 | 5-8-5 | 1409 |
| 621626 | 73951 | 73968 | CACCCTCTTGGTCTTGGT | 65 | 417 | 434 | 5-8-5 | 1410 |
| 621627 | 73956 | 73973 | CGTGTCACCCTCTTGGTC | 49 | 422 | 439 | 5-8-5 | 1411 |
| 621628 | 73959 | 73976 | GTCCGTGTCACCCTCTTG | 70 | 425 | 442 | 5-8-5 | 1412 |
| 621631 | 83395 | 83412 | AGATCCGTCCTCAGTGGG | 48 | 473 | 490 | 5-8-5 | 1413 |
| 621632 | 83398 | 83415 | CTCAGATCCGTCCTCAGT | 38 | 476 | 493 | 5-8-5 | 1414 |
| 621633 | 83401 | 83418 | TTCCTCAGATCCGTCCTC | 11 | 479 | 496 | 5-8-5 | 1415 |
| 621634 | 83404 | 83421 | CGGTTCCTCAGATCCGTC | 57 | 482 | 499 | 5-8-5 | 1416 |
| 621635 | 83407 | 83424 | GCCCGGTTCCTCAGATCC | 38 | 485 | 502 | 5-8-5 | 1417 |
| 621636 | 83410 | 83427 | AGAGCCCGGTTCCTCAGA | 63 | 488 | 505 | 5-8-5 | 1418 |
| 621637 | 83413 | 83430 | TTCAGAGCCCGGTTCCTC | 50 | 491 | 508 | 5-8-5 | 1419 |
| 621638 | 83416 | 83433 | GGTTTCAGAGCCCGGTTC | 48 | 494 | 511 | 5-8-5 | 1420 |
| 621639 | 83419 | 83436 | AGAGGTTTCAGAGCCCGG | 41 | 497 | 514 | 5-8-5 | 1421 |
| 621640 | 83422 | 83439 | ATCAGAGGTTTCAGAGCC | 40 | 500 | 517 | 5-8-5 | 1422 |
| 621641 | 83425 | 83442 | AGCATCAGAGGTTTCAGA | 23 | 503 | 520 | 5-8-5 | 1423 |
| 621642 | 83428 | 83445 | CTTAGCATCAGAGGTTTC | 50 | 506 | 523 | 5-8-5 | 1424 |
| 621643 | 83431 | 83448 | GCTCTTAGCATCAGAGGT | 69 | 509 | 526 | 5-8-5 | 1425 |
| 621644 | 83434 | 83451 | AGTGCTCTTAGCATCAGA | 80 | 512 | 529 | 5-8-5 | 1426 |
| 621645 | 83437 | 83454 | TGGAGTGCTCTTAGCATC | 50 | 515 | 532 | 5-8-5 | 1427 |
| 621646 | 83440 | 83457 | TGTTGGAGTGCTCTTAGC | 59 | 518 | 535 | 5-8-5 | 1428 |

TABLE 28-continued

Inhibition of tau mRNA by 5-8-5 MOE
gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621647 | 83443 | 83460 | CGCTGTTGGAGTGCTCTT | 70 | 521 | 538 | 5-8-5 | 1429 |
| 621648 | 83446 | 83463 | TTCCGCTGTTGGAGTGCT | 52 | 524 | 541 | 5-8-5 | 1430 |
| 621654 | 85904 | 85921 | CTAAGGGTGCTGTCACAT | 64 | 543 | 560 | 5-8-5 | 1431 |
| 621655 | 85907 | 85924 | CCACTAAGGGTGCTGTCA | 44 | 546 | 563 | 5-8-5 | 1432 |
| 621656 | 85910 | 85927 | CATCCACTAAGGGTGCTG | 55 | 549 | 566 | 5-8-5 | 1433 |
| 621657 | 85913 | 85930 | CCTCATCCACTAAGGGTG | 41 | 552 | 569 | 5-8-5 | 1434 |
| 620887 | 98891 98928 | 98908 98945 | GTTTTCAAACACACCTTC | 81 | n/a n/a | n/a n/a | 5-8-5 | 665 |

TABLE 29

Inhibition of Tau mRNA by 5-8-5 MOE
gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO |
|---|---|---|---|---|---|---|---|---|
| 621672 | n/a | n/a | GCTGTGGTTCCTTCTGGG | 51 | 613 | 630 | 5-8-5 | 1435 |
| 621676 | n/a | n/a | TCAGGCTCTTGGGTCACG | 0 | 685 | 702 | 5-8-5 | 1436 |
| 621677 | n/a | n/a | CTTTCAGGCTCTTGGGTC | 0 | 688 | 705 | 5-8-5 | 1437 |
| 621678 | n/a | n/a | CCACTTTCAGGCTCTTGG | 51 | 691 | 708 | 5-8-5 | 1438 |
| 613412 | 73879 | 73898 | GTGATCTTCCATCACTTCGA | 79 | 345 | 364 | 5-10-5 | 25 |
| 621658 | 85916 | 85933 | CTCCCTCATCCACTAAGG | 27 | 555 | 572 | 5-8-5 | 1439 |
| 621659 | 85919 | 85936 | GAGCTCCCTCATCCACTA | 35 | 558 | 575 | 5-8-5 | 1440 |
| 621660 | 85922 | 85939 | CGGGAGCTCCCTCATCCA | 25 | 561 | 578 | 5-8-5 | 1441 |
| 621661 | 85925 | 85942 | TGCCGGGAGCTCCCTCAT | 40 | 564 | 581 | 5-8-5 | 1442 |
| 621662 | 85928 | 85945 | GCTTGCCGGGAGCTCCCT | 47 | 567 | 584 | 5-8-5 | 1443 |
| 621663 | 85931 | 85948 | CCTGCTTGCCGGGAGCTC | 46 | 570 | 587 | 5-8-5 | 1444 |
| 621664 | 85934 | 85951 | CAGCCTGCTTGCCGGGAG | 45 | 573 | 590 | 5-8-5 | 1445 |
| 621665 | 85937 | 85954 | CGGCAGCCTGCTTGCCGG | 1 | 576 | 593 | 5-8-5 | 1446 |
| 621666 | 85940 | 85957 | GCGCGGCAGCCTGCTTGC | 31 | 579 | 596 | 5-8-5 | 1447 |
| 621667 | 85943 | 85960 | GCTGCGCGGCAGCCTGCT | 50 | 582 | 599 | 5-8-5 | 1448 |
| 621668 | 85962 | 85979 | TCTGGGATCTCCGTGTGG | 39 | 601 | 618 | 5-8-5 | 1449 |
| 621669 | 85965 | 85982 | CCTTCTGGGATCTCCGTG | 56 | 604 | 621 | 5-8-5 | 1450 |
| 621670 | 85968 | 85985 | GTTCCTTCTGGGATCTCC | 79 | 607 | 624 | 5-8-5 | 1451 |
| 621671 | 85971 | 85988 | GTGGTTCCTTCTGGGATC | 49 | 610 | 627 | 5-8-5 | 1452 |
| 621673 | 89894 | 89911 | CAATGCCTGCTTCTTCAG | 31 | 630 | 647 | 5-8-5 | 1453 |
| 621674 | 89899 | 89916 | GTCTCCAATGCCTGCTTC | 43 | 635 | 652 | 5-8-5 | 1454 |
| 621675 | 89902 | 89919 | GGTGTCTCCAATGCCTGC | 74 | 638 | 655 | 5-8-5 | 1455 |

TABLE 29-continued

Inhibition of Tau mRNA by 5-8-5 MOE gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO |
|---|---|---|---|---|---|---|---|---|
| 621679 | 94695 | 94712 | TTACCACTTTCAGGCTCT | 63 | 694 | 711 | 5-8-5 | 1456 |
| 621680 | 94700 | 94717 | CCACCTTACCACTTTCAG | 28 | 699 | 716 | 5-8-5 | 1457 |
| 621681 | 94703 | 94720 | GGACCACCTTACCACTTT | 62 | 702 | 719 | 5-8-5 | 1458 |
| 621682 | 94706 | 94723 | CCTGGACCACCTTACCAC | 33 | 705 | 722 | 5-8-5 | 1459 |
| 621683 | 94709 | 94726 | CTTCCTGGACCACCTTAC | 18 | 708 | 725 | 5-8-5 | 1460 |
| 621684 | 94712 | 94729 | AGCCTTCCTGGACCACCT | 61 | 711 | 728 | 5-8-5 | 1461 |
| 621685 | 94715 | 94732 | GGAAGCCTTCCTGGACCA | 54 | 714 | 731 | 5-8-5 | 1462 |
| 621686 | 94718 | 94735 | GGAGGAAGCCTTCCTGGA | 24 | 717 | 734 | 5-8-5 | 1463 |
| 621687 | 94721 | 94738 | CTCGGAGGAAGCCTTCCT | 48 | 720 | 737 | 5-8-5 | 1464 |
| 621688 | 94724 | 94741 | GCTCTCGGAGGAAGCCTT | 27 | 723 | 740 | 5-8-5 | 1465 |
| 621689 | 94727 | 94744 | CTGGCTCTCGGAGGAAGC | 19 | 726 | 743 | 5-8-5 | 1466 |
| 621690 | 94730 | 94747 | GGCCTGGCTCTCGGAGGA | 46 | 729 | 746 | 5-8-5 | 1467 |
| 621691 | 94749 | 94766 | TGGTGGCTCAGACCTGGG | 49 | 748 | 765 | 5-8-5 | 1468 |
| 621692 | 94752 | 94769 | AGCTGGTGGCTCAGACCT | 50 | 751 | 768 | 5-8-5 | 1469 |
| 621693 | 94755 | 94772 | ATGAGCTGGTGGCTCAGA | 17 | 754 | 771 | 5-8-5 | 1470 |
| 621694 | 94758 | 94775 | GACATGAGCTGGTGGCTC | 54 | 757 | 774 | 5-8-5 | 1471 |
| 621695 | 94761 | 94778 | CCGGACATGAGCTGGTGG | 26 | 760 | 777 | 5-8-5 | 1472 |
| 621696 | 94764 | 94781 | ATGCCGGACATGAGCTGG | 12 | 763 | 780 | 5-8-5 | 1473 |
| 621697 | 94767 | 94784 | GGCATGCCGGACATGAGC | 11 | 766 | 783 | 5-8-5 | 1474 |
| 621698 | 94770 | 94787 | CCAGGCATGCCGGACATG | 41 | 769 | 786 | 5-8-5 | 1475 |
| 621699 | 94773 | 94790 | GCCCCAGGCATGCCGGAC | 57 | 772 | 789 | 5-8-5 | 1476 |
| 621700 | 94776 | 94793 | GGAGCCCCAGGCATGCCG | 47 | 775 | 792 | 5-8-5 | 1477 |
| 621701 | 94793 | 94810 | GGCCCTCAGGCAGGAGGG | 0 | 792 | 809 | 5-8-5 | 1478 |
| 621702 | 94825 | 94842 | TGTCCCCGAAGGTTGGCG | 50 | 824 | 841 | 5-8-5 | 1479 |
| 621703 | 94828 | 94845 | TCCTGTCCCCGAAGGTTG | 38 | 827 | 844 | 5-8-5 | 1480 |
| 621704 | 94831 | 94848 | AGGTCCTGTCCCCGAAGG | 41 | 830 | 847 | 5-8-5 | 1481 |
| 621705 | 94834 | 94851 | CTCAGGTCCTGTCCCCGA | 60 | 833 | 850 | 5-8-5 | 1482 |
| 621706 | 94837 | 94854 | GTCCTCAGGTCCTGTCCC | 0 | 836 | 853 | 5-8-5 | 1483 |
| 621707 | 94840 | 94857 | TGTGTCCTCAGGTCCTGT | 23 | 839 | 856 | 5-8-5 | 1484 |
| 621708 | 94843 | 94860 | CTCTGTGTCCTCAGGTCC | 55 | 842 | 859 | 5-8-5 | 1485 |
| 621709 | 94846 | 94863 | GCCCTCTGTGTCCTCAGG | 35 | 845 | 862 | 5-8-5 | 1486 |
| 621710 | 94849 | 94866 | GCCGCCCTCTGTGTCCTC | 45 | 848 | 865 | 5-8-5 | 1487 |
| 621711 | 94852 | 94869 | GCGGCCGCCCTCTGTGTC | 0 | 851 | 868 | 5-8-5 | 1488 |
| 621712 | 94855 | 94872 | GTGGCGGCCGCCCTCTGT | 0 | 854 | 871 | 5-8-5 | 1489 |
| 621713 | 94875 | 94892 | TGCTTGAGCAGCTCAGGG | 67 | 874 | 891 | 5-8-5 | 1490 |
| 621714 | 94878 | 94895 | TGGTGCTTGAGCAGCTCA | 51 | 877 | 894 | 5-8-5 | 1491 |

TABLE 29-continued

Inhibition of Tau mRNA by 5-8-5 MOE
gapmers targeting SEQ ID NOs: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO |
|---|---|---|---|---|---|---|---|---|
| 621715 | 94882 | 94899 | AAGCTGGTGCTTGAGCAG | 27 | 881 | 898 | 5-8-5 | 1492 |
| 621716 | 94885 | 94902 | TAGAAGCTGGTGCTTGAG | 14 | 884 | 901 | 5-8-5 | 1493 |
| 621717 | 94888 | 94905 | TCCTAGAAGCTGGTGCTT | 0 | 887 | 904 | 5-8-5 | 1494 |
| 621718 | 94891 | 94908 | GTCTCCTAGAAGCTGGTG | 45 | 890 | 907 | 5-8-5 | 1495 |
| 621719 | 94894 | 94911 | CAGGTCTCCTAGAAGCTG | 47 | 893 | 910 | 5-8-5 | 1496 |
| 621720 | 94897 | 94914 | GTGCAGGTCTCCTAGAAG | 41 | 896 | 913 | 5-8-5 | 1497 |
| 621721 | 94900 | 94917 | CTGGTGCAGGTCTCCTAG | 36 | 899 | 916 | 5-8-5 | 1498 |
| 621722 | 94903 | 94920 | CTCCTGGTGCAGGTCTCC | 41 | 902 | 919 | 5-8-5 | 1499 |
| 621723 | 94906 | 94923 | CCCCTCCTGGTGCAGGTC | 39 | 905 | 922 | 5-8-5 | 1500 |
| 621724 | 94909 | 94926 | CGGCCCCTCCTGGTGCAG | 19 | 908 | 925 | 5-8-5 | 1501 |
| 621725 | 94912 | 94929 | CGGCGGCCCCTCCTGGTG | 22 | 911 | 928 | 5-8-5 | 1502 |
| 621726 | 94915 | 94932 | CAGCGGCGGCCCCTCCTG | 35 | 914 | 931 | 5-8-5 | 1503 |
| 621727 | 94918 | 94935 | CTTCAGCGGCGGCCCCTC | 46 | 917 | 934 | 5-8-5 | 1504 |
| 621728 | 94921 | 94938 | CCCCTTCAGCGGCGGCCC | 36 | 920 | 937 | 5-8-5 | 1505 |
| 621729 | 94924 | 94941 | TGCCCCCTTCAGCGGCGG | 17 | 923 | 940 | 5-8-5 | 1506 |
| 621730 | 94927 | 94944 | CCCTGCCCCCTTCAGCGG | 15 | 926 | 943 | 5-8-5 | 1507 |
| 621731 | 94930 | 94947 | GCCCCCTGCCCCCTTCAG | 27 | 929 | 946 | 5-8-5 | 1508 |
| 621732 | 94933 | 94950 | TTTGCCCCCTGCCCCCTT | 49 | 932 | 949 | 5-8-5 | 1509 |
| 621733 | 94936 | 94953 | CTCTTTGCCCCCTGCCCC | 22 | 935 | 952 | 5-8-5 | 1510 |
| 621734 | 94939 | 94956 | CCTCTCTTTGCCCCCTGC | 28 | 938 | 955 | 5-8-5 | 1511 |
| 620887 | 98891 98928 | 98908 98945 | GTTTTCAAACACACCTTC | 90 | n/a n/a | n/a n/a | 5-8-5 | 665 |

TABLE 30

Inhibition of tau mRNA by 5-10-5 MOE and 5-8-5 MOE
gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 613412 | 73879 | 73898 | GTGATCTTCCATCACTTCGA | 82 | 5-10-5 | 25 |
| 620887 | 98891 98928 | 98908 98945 | GTTTTCAAACACACCTTC | 92 | 5-8-5 | 665 |
| 621735 | 94942 | 94959 | CGGCCTCTCTTTGCCCCC | 34 | 5-8-5 | 1512 |
| 621736 | 94945 | 94962 | CCCCGGCCTCTCTTTGCC | 27 | 5-8-5 | 1513 |
| 621737 | 94948 | 94965 | GCTCCCCGGCCTCTCTTT | 44 | 5-8-5 | 1514 |
| 621738 | 94951 | 94968 | CTTGCTCCCCGGCCTCTC | 38 | 5-8-5 | 1515 |
| 621739 | 94954 | 94971 | CTCCTTGCTCCCCGGCCT | 37 | 5-8-5 | 1516 |

TABLE 30-continued

Inhibition of tau mRNA by 5-10-5 MOE and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621740 | 94957 | 94974 | CTCCTCCTTGCTCCCCGG | 33 | 5-8-5 | 1517 |
| 621741 | 94960 | 94977 | CACCTCCTCCTTGCTCCC | 37 | 5-8-5 | 1518 |
| 621742 | 94963 | 94980 | ATCCACCTCCTCCTTGCT | 32 | 5-8-5 | 1519 |
| 621743 | 94967 | 94984 | CTTCATCCACCTCCTCCT | 51 | 5-8-5 | 1520 |
| 621744 | 94970 | 94987 | GGTCTTCATCCACCTCCT | 61 | 5-8-5 | 1521 |
| 621745 | 94973 | 94990 | CGCGGTCTTCATCCACCT | 71 | 5-8-5 | 1522 |
| 621746 | 94976 | 94993 | CGTCGCGGTCTTCATCCA | 48 | 5-8-5 | 1523 |
| 621747 | 95038 | 95055 | CCGCCCATCTTGGGCTGG | 12 | 5-8-5 | 1524 |
| 621748 | 95041 | 95058 | AGGCCGCCCATCTTGGGC | 18 | 5-8-5 | 1525 |
| 621749 | 95044 | 95061 | GGGAGGCCGCCCATCTTG | 21 | 5-8-5 | 1526 |
| 621750 | 95060 | 95077 | CTCTGGCGGCTGTCTGGG | 47 | 5-8-5 | 1527 |
| 621751 | 95063 | 95080 | CTTCTCTGGCGGCTGTCT | 41 | 5-8-5 | 1528 |
| 621752 | 95066 | 95083 | TGGCTTCTCTGGCGGCTG | 53 | 5-8-5 | 1529 |
| 621753 | 95069 | 95086 | TGGTGGCTTCTCTGGCGG | 26 | 5-8-5 | 1530 |
| 621754 | 95072 | 95089 | TGCTGGTGGCTTCTCTGG | 57 | 5-8-5 | 1531 |
| 621755 | 95075 | 95092 | GGATGCTGGTGGCTTCTC | 65 | 5-8-5 | 1532 |
| 621756 | 95078 | 95095 | CTGGGATGCTGGTGGCTT | 66 | 5-8-5 | 1533 |
| 621757 | 95081 | 95098 | AGCCTGGGATGCTGGTGG | 51 | 5-8-5 | 1534 |
| 621758 | 95084 | 95101 | GGAAGCCTGGGATGCTGG | 57 | 5-8-5 | 1535 |
| 621759 | 95092 | 95109 | CTCCGCTGGGAAGCCTGG | 48 | 5-8-5 | 1536 |
| 621760 | 95095 | 95112 | ACCCTCCGCTGGGAAGCC | 38 | 5-8-5 | 1537 |
| 621761 | 95098 | 95115 | GGCACCCTCCGCTGGGAA | 54 | 5-8-5 | 1538 |
| 621762 | 95101 | 95118 | GATGGCACCCTCCGCTGG | 27 | 5-8-5 | 1539 |
| 621763 | 95121 | 95138 | AGGAAATCCACAGGGAGG | 15 | 5-8-5 | 1540 |
| 621764 | 95124 | 95141 | GAGAGGAAATCCACAGGG | 29 | 5-8-5 | 1541 |
| 621765 | 95127 | 95144 | TTGGAGAGGAAATCCACA | 45 | 5-8-5 | 1542 |
| 621766 | 95130 | 95147 | ACTTTGGAGAGGAAATCC | 38 | 5-8-5 | 1543 |
| 621767 | 95134 | 95151 | GGAAACTTTGGAGAGGAA | 56 | 5-8-5 | 1544 |
| 621768 | 95137 | 95154 | TGTGGAAACTTTGGAGAG | 26 | 5-8-5 | 1545 |
| 621769 | 95140 | 95157 | CTCTGTGGAAACTTTGGA | 69 | 5-8-5 | 1546 |
| 621770 | 95143 | 95160 | GATCTCTGTGGAAACTTT | 62 | 5-8-5 | 1547 |
| 621771 | 95146 | 95163 | TGGGATCTCTGTGGAAAC | 61 | 5-8-5 | 1548 |
| 621772 | 95149 | 95166 | GGCTGGGATCTCTGTGGA | 47 | 5-8-5 | 1549 |
| 621773 | 95152 | 95169 | TGAGGCTGGGATCTCTGT | 32 | 5-8-5 | 1550 |
| 621774 | 95155 | 95172 | CTCTGAGGCTGGGATCTC | 64 | 5-8-5 | 1551 |
| 621775 | 95161 | 95178 | GTCGGGCTCTGAGGCTGG | 42 | 5-8-5 | 1552 |

TABLE 30-continued

Inhibition of tau mRNA by 5-10-5 MOE and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621776 | 95164 | 95181 | CCCGTCGGGCTCTGAGGC | 34 | 5-8-5 | 1553 |
| 621777 | 95174 | 95191 | CTACACTGGGCCCGTCGG | 31 | 5-8-5 | 1554 |
| 621778 | 95177 | 95194 | GCCCTACACTGGGCCCGT | 48 | 5-8-5 | 1555 |
| 621779 | 95180 | 95197 | CCCGCCCTACACTGGGCC | 35 | 5-8-5 | 1556 |
| 621780 | 95183 | 95200 | TGGCCCGCCCTACACTGG | 51 | 5-8-5 | 1557 |
| 621781 | 95186 | 95203 | CTTTGGCCCGCCCTACAC | 4 | 5-8-5 | 1558 |
| 621782 | 95189 | 95206 | GCCCTTTGGCCCGCCCTA | 52 | 5-8-5 | 1559 |
| 621783 | 95192 | 95209 | CCTGCCCTTTGGCCCGCC | 42 | 5-8-5 | 1560 |
| 621784 | 95195 | 95212 | CATCCTGCCCTTTGGCCC | 49 | 5-8-5 | 1561 |
| 621785 | 95198 | 95215 | GGGCATCCTGCCCTTTGG | 15 | 5-8-5 | 1562 |
| 621786 | 95235 | 95252 | TTGGGTGTGATTTCCACG | 52 | 5-8-5 | 1563 |
| 621787 | 95253 | 95270 | GCCTGCTCCTTCTGCACG | 44 | 5-8-5 | 1564 |
| 621788 | 95256 | 95273 | TGCGCCTGCTCCTTCTGC | 64 | 5-8-5 | 1565 |
| 621789 | 95259 | 95276 | GAGTGCGCCTGCTCCTTC | 70 | 5-8-5 | 1566 |
| 621790 | 95262 | 95279 | TCCGAGTGCGCCTGCTCC | 53 | 5-8-5 | 1567 |
| 621791 | 95265 | 95282 | TCCTCCGAGTGCGCCTGC | 54 | 5-8-5 | 1568 |
| 621792 | 95268 | 95285 | TGCTCCTCCGAGTGCGCC | 52 | 5-8-5 | 1569 |
| 621793 | 95271 | 95288 | AAATGCTCCTCCGAGTGC | 72 | 5-8-5 | 1570 |
| 621794 | 95274 | 95291 | CCCAAATGCTCCTCCGAG | 75 | 5-8-5 | 1571 |
| 621795 | 95277 | 95294 | CTTCCCAAATGCTCCTCC | 47 | 5-8-5 | 1572 |
| 621796 | 95280 | 95297 | GCCCTTCCCAAATGCTCC | 58 | 5-8-5 | 1573 |
| 621797 | 95283 | 95300 | GCAGCCCTTCCCAAATGC | 39 | 5-8-5 | 1574 |
| 621798 | 95286 | 95303 | AATGCAGCCCTTCCCAAA | 61 | 5-8-5 | 1575 |
| 621799 | 95291 | 95308 | CTGGAAATGCAGCCCTTC | 64 | 5-8-5 | 1576 |
| 621800 | 95294 | 95311 | CCCCTGGAAATGCAGCCC | 49 | 5-8-5 | 1577 |
| 621801 | 95297 | 95314 | GGGCCCCTGGAAATGCAG | 29 | 5-8-5 | 1578 |
| 621802 | 95313 | 95330 | TCTGGCCCCTCTCCAGGG | 41 | 5-8-5 | 1579 |
| 621803 | 95316 | 95333 | GCCTCTGGCCCCTCTCCA | 42 | 5-8-5 | 1580 |
| 621804 | 95319 | 95336 | CGGGCCTCTGGCCCCTCT | 11 | 5-8-5 | 1581 |
| 621805 | 95322 | 95339 | CCCCGGGCCTCTGGCCCC | 13 | 5-8-5 | 1582 |
| 621806 | 95341 | 95358 | GTCCTCTCCCAAAGAGGG | 25 | 5-8-5 | 1583 |
| 621807 | 95344 | 95361 | TGTGTCCTCTCCCAAAGA | 20 | 5-8-5 | 1584 |
| 621808 | 95347 | 95364 | TTTTGTGTCCTCTCCCAA | 66 | 5-8-5 | 1585 |
| 621809 | 95365 | 95382 | CTCTGGAAGGTCAGCCTC | 53 | 5-8-5 | 1586 |

TABLE 30-continued

Inhibition of tau mRNA by 5-10-5 MOE and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 621810 | 95368 | 95385 | GGGCTCTGGAAGGTCAGC | 72 | 5-8-5 | 1587 |
| 621811 | 95371 | 95388 | AGAGGGCTCTGGAAGGTC | 57 | 5-8-5 | 1588 |

TABLE 31

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 613412 | 73879 | 73898 | GTGATCTTCCATCACTTCGA | 88 | 5-10-5 | 25 |
| 620887 | 98891 98928 | 98908 98945 | GTTTTCAAACACACCTTC | 96 | 5-8-5 | 665 |
| 623737 | 111219 | 111236 | CCTCCACCCAGCATGGTG | 56 | 5-8-5 | 1589 |
| 623738 | 111267 | 111284 | TCAAGTCACCCTTTCTCC | 78 | 5-8-5 | 1590 |
| 623739 | 111368 | 111385 | TTCAGACAATTTTTCTAG | 66 | 5-8-5 | 1591 |
| 623740 | 111629 | 111646 | TCAGACTCCGCCAGCTTT | 79 | 5-8-5 | 1592 |
| 623741 | 111678 | 111695 | TCTTTTCCCTTTGGTGTT | 34 | 5-8-5 | 1593 |
| 623742 | 111753 | 111770 | TTTCCCCCAATGATTTGC | 77 | 5-8-5 | 1594 |
| 623743 | 112016 | 112033 | CCACGACTCCCACAAGAT | 32 | 5-8-5 | 1595 |
| 623744 | 112213 | 112230 | TGAGGTTGAGGGTAGGTG | 50 | 5-8-5 | 1596 |
| 623745 | 112219 | 112236 | AGTGGTTGAGGTTGAGGG | 31 | 5-8-5 | 1597 |
| 623746 | 112304 | 112321 | CAGGCACTTGGAAACTGC | 90 | 5-8-5 | 1598 |
| 623747 | 112877 | 112894 | TTGTACTCTTTTTCCCCT | 65 | 5-8-5 | 1599 |
| 623748 | 112949 | 112966 | TTAGGAGTGCAAGGTTGT | 49 | 5-8-5 | 1600 |
| 623749 | 113352 | 113369 | TCCTACATTCCTCCTGCT | 67 | 5-8-5 | 1601 |
| 623750 | 113523 | 113540 | GTTGCAGTGTTCCACTAT | 90 | 5-8-5 | 1602 |
| 623751 | 113783 | 113800 | CCAGCAGATGCCGACAGC | 74 | 5-8-5 | 1603 |
| 623752 | 113809 | 113826 | GGGCCCTCACCCCTGCTT | 14 | 5-8-5 | 1604 |
| 623753 | 113830 | 113847 | CCAAGAAGGGCTGCTGAG | 8 | 5-8-5 | 1605 |
| 623754 | 114267 | 114284 | AAGCAGCCACCCAGGCTG | 17 | 5-8-5 | 1606 |
| 623755 | 114739 | 114756 | TATGAGGAGGGAGGAAAG | 13 | 5-8-5 | 1607 |
| 623756 | 115242 | 115259 | CTGACATCTCAGCCCAAG | 93 | 5-8-5 | 1608 |
| 621425 | 115335 | 115352 | GGTACAGGAAAAGATGCC | 77 | 5-8-5 | 1202 |
| 623757 | 115522 | 115539 | CAAGGTGATCAGCTTAGG | 82 | 5-8-5 | 1609 |
| 623758 | 115526 | 115543 | AGTCCAAGGTGATCAGCT | 89 | 5-8-5 | 1610 |
| 623759 | 115547 | 115564 | CCCACACAAGCCTCCTCT | 66 | 5-8-5 | 1611 |
| 623760 | 115791 | 115808 | TTTGTTTGGGTTCAGTTC | 59 | 5-8-5 | 1612 |

TABLE 31-continued

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623761 | 115803 | 115820 | CCTTGATCTGGTTTTGTT | 77 | 5-8-5 | 1613 |
| 623762 | 115993 | 116010 | ATCAAGGGAGAGAACGAT | 52 | 5-8-5 | 1614 |
| 623763 | 116229 | 116246 | AAAAGGCAACAAGCCTTT | 0 | 5-8-5 | 1615 |
| 623764 | 116769 | 116786 | CGAGGCAAAAGGGAAAT | 45 | 5-8-5 | 1616 |
| 623765 | 116791 | 116808 | TAACTTTGAGCTTCCTGG | 65 | 5-8-5 | 1617 |
| 623766 | 116944 | 116961 | TAAGGCTTAGAAGATTTG | 45 | 5-8-5 | 1618 |
| 623767 | 116978 | 116995 | GACGATCATTTTTTATTC | 72 | 5-8-5 | 1619 |
| 623768 | 116983 | 117000 | GGCTTGACGATCATTTTT | 77 | 5-8-5 | 1620 |
| 623769 | 117421 | 117438 | AGATCTCAGAGTTTGTAG | 68 | 5-8-5 | 1621 |
| 623770 | 117472 | 117489 | TCGCTGAGGTTCCGCAAC | 37 | 5-8-5 | 1622 |
| 623771 | 117489 | 117506 | AGGAGGCCATGTGAGGCT | 61 | 5-8-5 | 1623 |
| 623772 | 117547 | 117564 | TGGATAAATCTCTAGTGC | 54 | 5-8-5 | 1624 |
| 623773 | 117564 | 117581 | CACTCCTCCTTTAGAGAT | 38 | 5-8-5 | 1625 |
| 623774 | 117599 | 117616 | TTGTAATTCCTTCTCTGG | 65 | 5-8-5 | 1626 |
| 623775 | 117971 | 117988 | TAACCATCCCTACTTTCT | 42 | 5-8-5 | 1627 |
| 623776 | 119098 | 119115 | ACTGAAATCGCTCCTTTA | 58 | 5-8-5 | 1628 |
| 623777 | 119107 | 119124 | CCAATTATGACTGAAATC | 32 | 5-8-5 | 1629 |
| 623778 | 119313 | 119330 | GGTCAAAGTTATAAATAT | 57 | 5-8-5 | 1630 |
| 623779 | 119431 | 119448 | GGATTTGATGCAAAGAAA | 70 | 5-8-5 | 1631 |
| 623780 | 119740 | 119757 | GCGCAACCCAGCTACTCG | 7 | 5-8-5 | 1632 |
| 621445 | 119880 | 119897 | TACAGTGGCTCCTGTAAT | 28 | 5-8-5 | 1222 |
| 623781 | 119964 | 119981 | CTGTATACCTATACTTGG | 34 | 5-8-5 | 1633 |
| 623782 | 120043 | 120060 | CCGTTTTCTTACCACCCT | 92 | 5-8-5 | 1634 |
| 623783 | 120177 | 120194 | TTACTTGTCTGAATCTTC | 83 | 5-8-5 | 1635 |
| 623784 | 120204 | 120221 | TTCATCCCGTTTTTTTTC | 54 | 5-8-5 | 1636 |
| 623785 | 120309 | 120326 | GACCTCAGTGGCTCTTTT | 68 | 5-8-5 | 1637 |
| 623786 | 120513 | 120530 | TGTCCAGGATAGTTTGAA | 44 | 5-8-5 | 1638 |
| 623787 | 121033 | 121050 | GCTGAGCAAATGCTCCCG | 54 | 5-8-5 | 1639 |
| 623788 | 121194 | 121211 | CTGACCCCGTAGGCAGGA | 29 | 5-8-5 | 1640 |
| 623789 | 121478 | 121495 | ACCAGCCTGAGGTCAAGT | 73 | 5-8-5 | 1641 |
| 623790 | 121538 | 121555 | CAGGTCCTCACTTCACAA | 42 | 5-8-5 | 1642 |
| 623791 | 121767 | 121784 | CCGCCTGCTTGCTCGCAA | 92 | 5-8-5 | 1643 |
| 623792 | 121787 | 121804 | AGTGACACGCCACCCTGG | 80 | 5-8-5 | 1644 |
| 623793 | 121797 | 121814 | AAAAGGATGAGTGACAC | 28 | 5-8-5 | 1645 |
| 623794 | 121807 | 121824 | GGTAGCCAGAAAAAGGA | 49 | 5-8-5 | 1646 |
| 623795 | 121812 | 121829 | CCTTTGGTAGCCAGAAAA | 63 | 5-8-5 | 1647 |
| 623796 | 121817 | 121834 | CTGCACCTTTGGTAGCCA | 87 | 5-8-5 | 1648 |

TABLE 31-continued

Inhibition of tau mRNA by 5-10-5 and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623797 | 121822 | 121839 | ATTATCTGCACCTTTGGT | 67 | 5-8-5 | 1649 |
| 623798 | 121824 | 121841 | TAATTATCTGCACCTTTG | 49 | 5-8-5 | 1650 |
| 623799 | 121905 | 121922 | CACTGCCGCCTCCCGGGA | 65 | 5-8-5 | 1651 |
| 623800 | 121909 | 121926 | CTCACACTGCCGCCTCCC | 75 | 5-8-5 | 1652 |
| 623801 | 121911 | 121928 | TACTCACACTGCCGCCTC | 54 | 5-8-5 | 1653 |
| 623679 | 121913 | 121930 | GGTACTCACACTGCCGCC | 81 | 5-8-5 | 1654 |
| 623802 | 121915 | 121932 | AAGGTACTCACACTGCCG | 69 | 5-8-5 | 1655 |
| 623803 | 121920 | 121937 | GTGTGAAGGTACTCACAC | 18 | 5-8-5 | 1656 |
| 623804 | 121942 | 121959 | GCCACAGCACGGCGCATG | 80 | 5-8-5 | 1657 |
| 623805 | 121952 | 121969 | AATAATTCAAGCCACAGC | 88 | 5-8-5 | 1658 |
| 623806 | 121962 | 121979 | ACCACTTCCTAATAATTC | 39 | 5-8-5 | 1659 |
| 623807 | 121972 | 121989 | ACGCACTCACACCACTTC | 83 | 5-8-5 | 1660 |
| 623808 | 121982 | 121999 | TCGCAAGTGTACGCACTC | 94 | 5-8-5 | 1661 |
| 623809 | 121992 | 122009 | ATGCAGTGTCTCGCAAGT | 93 | 5-8-5 | 1662 |
| 623810 | 122227 | 122244 | TGATGGGTATTCTCAGCT | 77 | 5-8-5 | 1663 |

TABLE 32

Inhibition of tau mRNA by 5-10-5 MOE and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 613412 | 73879 | 73898 | GTGATCTTCCATCACTTCGA | 87 | 5-10-5 | 25 |
| 620887 | 9881 98928 | 98909 98945 | GTTTTCAAACACACCTTC | 83 | 5-8-5 | 665 |
| 622186 | 5897 | 5914 | CCGCTCGGCCGTCCGGCG | 6 | 5-8-5 | 1664 |
| 622187 | 5900 | 5917 | CTGCCGCTCGGCCGTCCG | 6 | 5-8-5 | 1665 |
| 622174 | 103089 | 103106 | CCAGAGCTGGGTGGTGTC | 12 | 5-8-5 | 1666 |
| 622182 | 125760 | 125777 | TGTAGACTATTTGCACCT | 74 | 5-8-5 | 1667 |
| 622120 | 135855 | 135872 | ATCACTGATTTTGAAGTC | 36 | 5-8-5 | 1668 |
| 622121 | 135858 | 135875 | CCCATCACTGATTTTGAA | 59 | 5-8-5 | 1669 |
| 622122 | 135861 | 135878 | ACTCCCATCACTGATTTT | 70 | 5-8-5 | 1670 |
| 622123 | 135864 | 135881 | CTTACTCCCATCACTGAT | 41 | 5-8-5 | 1671 |
| 622124 | 135867 | 135884 | GCTCTTACTCCCATCACT | 82 | 5-8-5 | 1672 |
| 622125 | 135870 | 135887 | TTTGCTCTTACTCCCATC | 87 | 5-8-5 | 1673 |
| 622126 | 135873 | 135890 | AAATTTGCTCTTACTCCC | 62 | 5-8-5 | 1674 |
| 622127 | 135876 | 135893 | ATGAAATTTGCTCTTACT | 70 | 5-8-5 | 1675 |
| 622128 | 135879 | 135896 | AAGATGAAATTTGCTCTT | 55 | 5-8-5 | 1676 |
| 622129 | 135882 | 135899 | GGAAAGATGAAATTTGCT | 84 | 5-8-5 | 1677 |

TABLE 32-continued

Inhibition of tau mRNA by 5-10-5 MOE and 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 622130 | 135885 | 135902 | TTTGGAAAGATGAAATTT | 12 | 5-8-5 | 1678 |
| 622131 | 135891 | 135908 | CATCAATTTGGAAAGATG | 43 | 5-8-5 | 1679 |
| 622132 | 135894 | 135911 | ACCCATCAATTTGGAAAG | 18 | 5-8-5 | 1680 |
| 622133 | 135897 | 135914 | CCCACCCATCAATTTGGA | 34 | 5-8-5 | 1681 |
| 622134 | 135900 | 135917 | TAGCCCACCCATCAATTT | 17 | 5-8-5 | 1682 |
| 622135 | 135903 | 135920 | TACTAGCCCACCCATCAA | 14 | 5-8-5 | 1683 |
| 622136 | 135906 | 135923 | TATTACTAGCCCACCCAT | 24 | 5-8-5 | 1684 |
| 622137 | 135909 | 135926 | TTTTATTACTAGCCCACC | 24 | 5-8-5 | 1685 |
| 622138 | 135912 | 135929 | ATATTTATTACTAGCCC | 33 | 5-8-5 | 1686 |
| 622139 | 135915 | 135932 | TAAATATTTATTACTAG | 0 | 5-8-5 | 1687 |
| 622140 | 135918 | 135935 | TTTTAAATATTTTATTAC | 0 | 5-8-5 | 1688 |
| 622141 | 135926 | 135943 | ATGTTTTTTTTAAATAT | 0 | 5-8-5 | 1689 |
| 622142 | 135939 | 135956 | GCCATGTTTTGAATGTT | 60 | 5-8-5 | 1690 |
| 622143 | 135942 | 135959 | GTGGCCATGTTTTTGAAT | 28 | 5-8-5 | 1691 |
| 622144 | 135945 | 135962 | GATGTGGCCATGTTTTTG | 63 | 5-8-5 | 1692 |
| 622145 | 135948 | 135965 | TTGGATGTGGCCATGTTT | 78 | 5-8-5 | 1693 |
| 622146 | 135951 | 135968 | ATGTTGGATGTGGCCATG | 71 | 5-8-5 | 1694 |
| 622147 | 135954 | 135971 | GAAATGTTGGATGTGGCC | 72 | 5-8-5 | 1695 |
| 622148 | 135957 | 135974 | GAGGAAATGTTGGATGTG | 55 | 5-8-5 | 1696 |
| 622149 | 135960 | 135977 | CCTGAGGAAATGTTGGAT | 77 | 5-8-5 | 1697 |
| 622150 | 135963 | 135980 | TTGCCTGAGGAAATGTTG | 55 | 5-8-5 | 1698 |
| 622151 | 139811 | 139828 | CCAAATTCACTTTTACAG | 54 | 5-8-5 | 1699 |
| 622152 | 139813 | 139830 | TTCCAAATTCACTTTTAC | 67 | 5-8-5 | 1700 |
| 622153 | 139815 | 139832 | ATTTCCAAATTCACTTTT | 52 | 5-8-5 | 1701 |
| 622154 | 139817 | 139834 | TTATTTCCAAATTCACTT | 52 | 5-8-5 | 1702 |
| 622155 | 139819 | 139836 | CTTTATTTCCAAATTCAC | 61 | 5-8-5 | 1703 |
| 622156 | 139821 | 139838 | AACTTTATTTCCAAATTC | 26 | 5-8-5 | 1704 |
| 622157 | 139823 | 139840 | ATAACTTTATTTCCAAAT | 23 | 5-8-5 | 1705 |
| 622158 | 139826 | 139843 | GTAATAACTTTATTTCCA | 65 | 5-8-5 | 1706 |
| 622159 | 139828 | 139845 | GAGTAATAACTTTATTTC | 25 | 5-8-5 | 1707 |
| 622160 | 139830 | 139847 | CAGAGTAATAACTTTATT | 9 | 5-8-5 | 1708 |
| 622161 | 139832 | 139849 | ATCAGAGTAATAACTTTA | 23 | 5-8-5 | 1709 |
| 622162 | 139834 | 139851 | TAATCAGAGTAATAACTT | 14 | 5-8-5 | 1710 |
| 622163 | 139836 | 139853 | TTTAATCAGAGTAATAAC | 4 | 5-8-5 | 1711 |

TABLE 33

Inhibition of Tau mRNA by 5-8-5 MOE gapmers targeting SEQ ID NO: 5 and 6

| ISIS NO | SEQ ID NO: 5 Start Site | SEQ ID NO: 5 Stop Site | Sequence | % inhibition | SEQ ID NO: 6 Start Site | SEQ ID NO: 6 Stop Site | Motif | SEQ ID NO |
|---|---|---|---|---|---|---|---|---|
| 622164 | n/a | n/a | GCTTCCGCTGTTGGAGTG | 22 | 526 | 543 | 5-8-5 | 1712 |
| 622165 | n/a | n/a | TCAGCTTCCGCTGTTGGA | 15 | 529 | 546 | 5-8-5 | 1713 |
| 622166 | n/a | n/a | TCTTCAGCTTCCGCTGTT | 0 | 532 | 549 | 5-8-5 | 1714 |
| 622167 | n/a | n/a | GCTTCTTCAGCTTCCGCT | 43 | 535 | 552 | 5-8-5 | 1715 |
| 622171 | n/a | n/a | GCCCCCTTGGCTTTTTG | 16 | 652 | 669 | 5-8-5 | 1716 |
| 622172 | n/a | n/a | TCAGCCCCCTTGGCTTTT | 15 | 655 | 672 | 5-8-5 | 1717 |
| 622173 | n/a | n/a | ACCATCAGCCCCCTTGGC | 49 | 659 | 676 | 5-8-5 | 1718 |
| 622175 | n/a | n/a | TCACCAGAGCTGGGTGGT | 15 | 778 | 795 | 5-8-5 | 1719 |
| 622176 | n/a | n/a | GGTTCACCAGAGCTGGGT | 80 | 781 | 798 | 5-8-5 | 1720 |
| 622177 | n/a | n/a | GGAGGTTCACCAGAGCTG | 79 | 784 | 801 | 5-8-5 | 1721 |
| 622178 | n/a | n/a | TTTGGAGGTTCACCAGAG | 45 | 787 | 804 | 5-8-5 | 1722 |
| 622179 | n/a | n/a | GATTTTGGAGGTTCACCA | 68 | 790 | 807 | 5-8-5 | 1723 |
| 622180 | n/a | n/a | TTGCACCTTCCCGCCTCC | 19 | 1046 | 1063 | 5-8-5 | 1724 |
| 622181 | n/a | n/a | AGACTATTTGCACCTTCC | 70 | 1053 | 1070 | 5-8-5 | 1725 |
| 622183 | 3 | 20 | CCCTTCGCGGTCCCTTCG | 0 | n/a | n/a | 5-8-5 | 1726 |
| 622184 | 6 | 23 | CTGCCCTTCGCGGTCCCT | 12 | n/a | n/a | 5-8-5 | 1727 |
| 622185 | 9 | 26 | GCGCTGCCCTTCGCGGTC | 0 | n/a | n/a | 5-8-5 | 1728 |
| 622188 | 424 | 441 | GTCCCCCAAACCCGTACG | 15 | n/a | n/a | 5-8-5 | 1729 |
| 622189 | 427 | 444 | CCTGTCCCCCAAACCCGT | 45 | n/a | n/a | 5-8-5 | 1730 |
| 622190 | 430 | 447 | TTTCCTGTCCCCCAAACC | 57 | n/a | n/a | 5-8-5 | 1731 |
| 622191 | 436 | 453 | TTGATCTTTCCTGTCCCC | 74 | n/a | n/a | 5-8-5 | 1732 |
| 622192 | 439 | 456 | CCCTTGATCTTTCCTGTC | 69 | n/a | n/a | 5-8-5 | 1733 |
| 622193 | 442 | 459 | GCCCCCTTGATCTTTCCT | 7 | n/a | n/a | 5-8-5 | 1734 |
| 622194 | 445 | 462 | GTAGCCCCCTTGATCTTT | 3 | n/a | n/a | 5-8-5 | 1735 |
| 622195 | 448 | 465 | GGTGTAGCCCCCTTGATC | 8 | n/a | n/a | 5-8-5 | 1736 |
| 622196 | 451 | 468 | CATGGTGTAGCCCCCTTG | 83 | n/a | n/a | 5-8-5 | 1737 |
| 622168 | 564 | 581 | ATGCGAGCTTGGGTCACG | 65 | 598 | 615 | 5-8-5 | 1738 |
| 622169 | 567 | 584 | ACCATGCGAGCTTGGGTC | 62 | 601 | 618 | 5-8-5 | 1739 |
| 622170 | 570 | 587 | CTGACCATGCGAGCTTGG | 91 | 604 | 621 | 5-8-5 | 1740 |

TABLE 34

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 613412 | 73879 | 73898 | GTGATCTTCCATCACTTCGA | 91 | 345 | 364 | 5-10-5 | 25 |
| 620887 | 98891 | 98908 | GTTTTCAAACACACCTTC | 97 | n/a | n/a | 5-8-5 | 665 |
|  | 98928 | 98945 |  |  | n/a | n/a |  |  |
| 621832 | n/a | n/a | GAGCTTTGAGTTGAGGGA | 14 | 1434 | 1451 | 5-8-5 | 1741 |
| 621833 | n/a | n/a | TGCGAGCTTTGAGTTGAG | 0 | 1437 | 1454 | 5-8-5 | 1742 |
| 621834 | n/a | n/a | CCATGCGAGCTTTGAGTT | 10 | 1440 | 1457 | 5-8-5 | 1743 |
| 621835 | n/a | n/a | TGACCATGCGAGCTTTGA | 83 | 1443 | 1460 | 5-8-5 | 1744 |
| 621836 | n/a | n/a | TACTGACCATGCGAGCTT | 91 | 1446 | 1463 | 5-8-5 | 1745 |
| 621848 | n/a | n/a | GATGTCTTGGCTTTTTG | 3 | 1492 | 1509 | 5-8-5 | 1746 |
| 621849 | n/a | n/a | GTGTGGATGTCTTGGCTT | 15 | 1497 | 1514 | 5-8-5 | 1747 |
| 621812 | 95374 | 95391 | TTCAGAGGGCTCTGGAAG | 0 | 1373 | 1390 | 5-8-5 | 1748 |
| 621813 | 95377 | 95394 | CTTTTCAGAGGGCTCTGG | 44 | 1376 | 1393 | 5-8-5 | 1749 |
| 621814 | 95380 | 95397 | CTGCTTTTCAGAGGGCTC | 56 | 1379 | 1396 | 5-8-5 | 1750 |
| 621815 | 95383 | 95400 | AGGCTGCTTTTCAGAGGG | 38 | 1382 | 1399 | 5-8-5 | 1751 |
| 621816 | 95386 | 95403 | AGCAGGCTGCTTTTCAGA | 40 | 1385 | 1402 | 5-8-5 | 1752 |
| 621817 | 95389 | 95406 | AGCAGCAGGCTGCTTTTC | 26 | 1388 | 1405 | 5-8-5 | 1753 |
| 621818 | 95392 | 95409 | AGCAGCAGCAGGCTGCTT | 12 | 1391 | 1408 | 5-8-5 | 1754 |
| 621819 | 95395 | 95412 | CGGAGCAGCAGCAGGCTG | 23 | 1394 | 1411 | 5-8-5 | 1755 |
| 621820 | 95398 | 95415 | CCGCGGAGCAGCAGCAGG | 34 | 1397 | 1414 | 5-8-5 | 1756 |
| 621821 | 95401 | 95418 | CCCCCGCGGAGCAGCAGC | 50 | 1400 | 1417 | 5-8-5 | 1757 |
| 621822 | 95404 | 95421 | CTTCCCCGCGGAGCAGC | 48 | 1403 | 1420 | 5-8-5 | 1758 |
| 621823 | 95407 | 95424 | GGGCTTCCCCCGCGGAGC | 0 | 1406 | 1423 | 5-8-5 | 1759 |
| 621824 | 95410 | 95427 | GACGGGCTTCCCCCGCGG | 7 | 1409 | 1426 | 5-8-5 | 1760 |
| 621825 | 95413 | 95430 | GCTGACGGGCTTCCCCCG | 36 | 1412 | 1429 | 5-8-5 | 1761 |
| 621826 | 95416 | 95433 | CCGGCTGACGGGCTTCCC | 54 | 1415 | 1432 | 5-8-5 | 1762 |
| 621827 | 95419 | 95436 | GACCCGGCTGACGGGCTT | 7 | 1418 | 1435 | 5-8-5 | 1763 |
| 621828 | 95423 | 95440 | GAGGGACCCGGCTGACGG | 6 | 1422 | 1439 | 5-8-5 | 1764 |
| 621829 | 95426 | 95443 | GTTGAGGGACCCGGCTGA | 27 | 1425 | 1442 | 5-8-5 | 1765 |
| 621830 | 95429 | 95446 | TGAGTTGAGGGACCCGGC | 50 | 1428 | 1445 | 5-8-5 | 1766 |
| 621831 | 95432 | 95449 | CTTTGAGTTGAGGGACCC | 50 | 1431 | 1448 | 5-8-5 | 1767 |
| 621837 | 98559 | 98576 | TTTTACTGACCATGCGAG | 77 | 1449 | 1466 | 5-8-5 | 1768 |
| 621838 | 98562 | 98579 | TGCTTTTACTGACCATGC | 95 | 1452 | 1469 | 5-8-5 | 1769 |
| 621839 | 98565 | 98582 | CTTTGCTTTTACTGACCA | 85 | 1455 | 1472 | 5-8-5 | 1770 |
| 621840 | 98568 | 98585 | CGTCTTTGCTTTTACTGA | 66 | 1458 | 1475 | 5-8-5 | 1771 |
| 621841 | 98571 | 98588 | TCCCGTCTTTGCTTTTAC | 79 | 1461 | 1478 | 5-8-5 | 1772 |
| 621842 | 98575 | 98592 | CCAGTCCCGTCTTTGCTT | 87 | 1465 | 1482 | 5-8-5 | 1773 |
| 621843 | 98578 | 98595 | CTTCCAGTCCCGTCTTTG | 64 | 1468 | 1485 | 5-8-5 | 1774 |

TABLE 34-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621844 | 98581 | 98598 | TCGCTTCCAGTCCCGTCT | 88 | 1471 | 1488 | 5-8-5 | 1775 |
| 621845 | 98584 | 98601 | TCATCGCTTCCAGTCCCG | 90 | 1474 | 1491 | 5-8-5 | 1776 |
| 621846 | 98587 | 98604 | TTGTCATCGCTTCCAGTC | 88 | 1477 | 1494 | 5-8-5 | 1777 |
| 621847 | 98590 | 98607 | TTTTTGTCATCGCTTCCA | 80 | 1480 | 1497 | 5-8-5 | 1778 |
| 621850 | 101406 | 101423 | GGTTTTAGCAGAGGAACG | 75 | 1514 | 1531 | 5-8-5 | 1779 |
| 621851 | 101409 | 101426 | CAAGGTTTTAGCAGAGGA | 83 | 1517 | 1534 | 5-8-5 | 1780 |
| 621852 | 101412 | 101429 | TTTCAAGGTTTTAGCAGA | 35 | 1520 | 1537 | 5-8-5 | 1781 |
| 621853 | 101415 | 101432 | ATTTTTCAAGGTTTTAGC | 79 | 1523 | 1540 | 5-8-5 | 1782 |
| 621854 | 101418 | 101435 | CCTATTTTTCAAGGTTTT | 71 | 1526 | 1543 | 5-8-5 | 1783 |
| 621855 | 101425 | 101442 | GGCAAGGCCTATTTTTCA | 83 | 1533 | 1550 | 5-8-5 | 1784 |
| 621856 | 101428 | 101445 | TAAGGCAAGGCCTATTTT | 23 | 1536 | 1553 | 5-8-5 | 1785 |
| 621857 | 101431 | 101448 | GGCTAAGGCAAGGCCTAT | 69 | 1539 | 1556 | 5-8-5 | 1786 |
| 621858 | 101457 | 101474 | TGAGCTACCAGGAGTGGG | 75 | 1565 | 1582 | 5-8-5 | 1787 |
| 621859 | 101460 | 101477 | GTCTGAGCTACCAGGAGT | 78 | 1568 | 1585 | 5-8-5 | 1788 |
| 621860 | 101463 | 101480 | AGGGTCTGAGCTACCAGG | 82 | 1571 | 1588 | 5-8-5 | 1789 |
| 621861 | 101466 | 101483 | CAGAGGGTCTGAGCTACC | 88 | 1574 | 1591 | 5-8-5 | 1790 |
| 621862 | 101469 | 101486 | GATCAGAGGGTCTGAGCT | 72 | 1577 | 1594 | 5-8-5 | 1791 |
| 621863 | 101472 | 101489 | TTGGATCAGAGGGTCTGA | 83 | 1580 | 1597 | 5-8-5 | 1792 |
| 621864 | 101478 | 101495 | GGAGGGTTGGATCAGAGG | 0 | 1586 | 1603 | 5-8-5 | 1793 |
| 621865 | 101481 | 101498 | GCTGGAGGGTTGGATCAG | 16 | 1589 | 1606 | 5-8-5 | 1794 |
| 621866 | 101491 | 101508 | ACACAGCAGGGCTGGAGG | 34 | 1599 | 1616 | 5-8-5 | 1795 |
| 621867 | 101494 | 101511 | GGCACACAGCAGGGCTGG | 67 | 1602 | 1619 | 5-8-5 | 1796 |
| 621868 | 101499 | 101516 | CTCTGGGCACACAGCAGG | 75 | 1607 | 1624 | 5-8-5 | 1797 |
| 621869 | 101502 | 101519 | TGGCTCTGGGCACACAGC | 90 | 1610 | 1627 | 5-8-5 | 1798 |
| 621870 | 101505 | 101522 | AGGTGGCTCTGGGCACAC | 92 | 1613 | 1630 | 5-8-5 | 1799 |
| 621871 | 101508 | 101525 | GGAAGGTGGCTCTGGGCA | 67 | 1616 | 1633 | 5-8-5 | 1800 |
| 621872 | 101511 | 101528 | AGAGGAAGGTGGCTCTGG | 43 | 1619 | 1636 | 5-8-5 | 1801 |
| 621873 | 101514 | 101531 | AGGAGAGGAAGGTGGCTC | 65 | 1622 | 1639 | 5-8-5 | 1802 |
| 621874 | 101517 | 101534 | TTTAGGAGAGGAAGGTGG | 26 | 1625 | 1642 | 5-8-5 | 1803 |
| 621875 | 101520 | 101537 | GTATTTAGGAGAGGAAGG | 0 | 1628 | 1645 | 5-8-5 | 1804 |
| 621876 | 101537 | 101554 | GAAGTGACAGAAGAGACG | 37 | 1645 | 1662 | 5-8-5 | 1805 |
| 621877 | 101540 | 101557 | CGGGAAGTGACAGAAGAG | 59 | 1648 | 1665 | 5-8-5 | 1806 |
| 621878 | 101543 | 101560 | GTTCGGGAAGTGACAGAA | 65 | 1651 | 1668 | 5-8-5 | 1807 |
| 621879 | 101546 | 101563 | CCAGTTCGGGAAGTGACA | 35 | 1654 | 1671 | 5-8-5 | 1808 |
| 621880 | 101549 | 101566 | CTGCCAGTTCGGGAAGTG | 69 | 1657 | 1674 | 5-8-5 | 1809 |
| 621881 | 101552 | 101569 | GAACTGCCAGTTCGGGAA | 48 | 1660 | 1677 | 5-8-5 | 1810 |

TABLE 34-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621882 | 101555 | 101572 | CCAGAACTGCCAGTTCGG | 66 | 1663 | 1680 | 5-8-5 | 1811 |
| 621883 | 101558 | 101575 | GCTCCAGAACTGCCAGTT | 69 | 1666 | 1683 | 5-8-5 | 1812 |
| 621884 | 101561 | 101578 | TTTGCTCCAGAACTGCCA | 74 | 1669 | 1686 | 5-8-5 | 1813 |
| 621885 | 101564 | 101581 | TCCTTTGCTCCAGAACTG | 61 | 1672 | 1689 | 5-8-5 | 1814 |
| 621886 | 101567 | 101584 | ATCTCCTTTGCTCCAGAA | 64 | 1675 | 1692 | 5-8-5 | 1815 |
| 621887 | 101570 | 101587 | TTCATCTCCTTTGCTCCA | 36 | 1678 | 1695 | 5-8-5 | 1816 |
| 621888 | 101573 | 101590 | AGTTTCATCTCCTTTGCT | 32 | 1681 | 1698 | 5-8-5 | 1817 |

TABLE 35

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 613412 | 73879 | 73898 | GTGATCTTCCATCACTTCGA | 87 | 345 | 364 | 5-10-5 | 25 |
| 620887 | 98891 98928 | 98908 98945 | GTTTTCAAACACACCTTC | 95 | n/a n/a | n/a n/a | 5-8-5 | 665 |
| 621890 | n/a | n/a | CCCTTGAGTTTCATCTCC | 30 | 1687 | 1704 | 5-8-5 | 1818 |
| 621891 | n/a | n/a | GCCCCCTTGAGTTTCATC | 8 | 1690 | 1707 | 5-8-5 | 1819 |
| 621892 | n/a | n/a | TCAGCCCCCTTGAGTTTC | 0 | 1693 | 1710 | 5-8-5 | 1820 |
| 621893 | n/a | n/a | CCATCAGCCCCCTTGAGT | 4 | 1696 | 1713 | 5-8-5 | 1821 |
| 621894 | n/a | n/a | TTACCATCAGCCCCCTTG | 75 | 1699 | 1716 | 5-8-5 | 1822 |
| 621912 | n/a | n/a | CGCAGAGCTGGGTGGTGT | 0 | 1814 | 1831 | 5-8-5 | 1823 |
| 621913 | n/a | n/a | AGTCGCAGAGCTGGGTGG | 0 | 1817 | 1834 | 5-8-5 | 1824 |
| 621914 | n/a | n/a | CTTAGTCGCAGAGCTGGG | 21 | 1820 | 1837 | 5-8-5 | 1825 |
| 621915 | n/a | n/a | TTGCTTAGTCGCAGAGCT | 12 | 1823 | 1840 | 5-8-5 | 1826 |
| 621916 | n/a | n/a | GACTTGCTTAGTCGCAGA | 29 | 1826 | 1843 | 5-8-5 | 1827 |
| 621925 | n/a | n/a | TTCACCTCTCTCAGATCT | 4 | 1871 | 1888 | 5-8-5 | 1828 |
| 621926 | n/a | n/a | AGGTTCACCTCTCTCAGA | 9 | 1874 | 1891 | 5-8-5 | 1829 |
| 621927 | n/a | n/a | TGGAGGTTCACCTCTCTC | 7 | 1877 | 1894 | 5-8-5 | 1830 |
| 621928 | n/a | n/a | TTTTGGAGGTTCACCTCT | 11 | 1880 | 1897 | 5-8-5 | 1831 |
| 621889 | 101576 | 101593 | TTGAGTTTCATCTCCTTT | 23 | 1684 | 1701 | 5-8-5 | 1832 |
| 621895 | 102978 | 102995 | GTTTTACCATCAGCCCCC | 88 | 1702 | 1719 | 5-8-5 | 1833 |
| 621896 | 102995 | 103012 | GCGGTGTGGCGATCTTCG | 42 | 1719 | 1736 | 5-8-5 | 1834 |
| 621897 | 102998 | 103015 | CCCGCGGTGTGGCGATCT | 33 | 1722 | 1739 | 5-8-5 | 1835 |
| 621898 | 103001 | 103018 | CTCCCCGCGGTGTGGCGA | 37 | 1725 | 1742 | 5-8-5 | 1836 |
| 621899 | 103004 | 103021 | CTGCTCCCCGCGGTGTGG | 50 | 1728 | 1745 | 5-8-5 | 1837 |

TABLE 35-continued

Inhibition of tau mRNA by 5-10-5 MOE and 5-8-5 MOE
gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621900 | 103007 | 103024 | GGGCTGCTCCCCGCGGTG | 43 | 1731 | 1748 | 5-8-5 | 1838 |
| 621901 | 103025 | 103042 | GGCCCTTCTGGCCTGGAG | 29 | 1749 | 1766 | 5-8-5 | 1839 |
| 621902 | 103029 | 103046 | GCCTGGCCCTTCTGGCCT | 34 | 1753 | 1770 | 5-8-5 | 1840 |
| 621903 | 103032 | 103049 | TTGGCCTGGCCCTTCTGG | 49 | 1756 | 1773 | 5-8-5 | 1841 |
| 621904 | 103050 | 103067 | GCTGGAATCCTGGTGGCG | 58 | 1774 | 1791 | 5-8-5 | 1842 |
| 621905 | 103053 | 103070 | TTTGCTGGAATCCTGGTG | 50 | 1777 | 1794 | 5-8-5 | 1843 |
| 621906 | 103056 | 103073 | GTTTTGCTGGAATCCTG | 62 | 1780 | 1797 | 5-8-5 | 1844 |
| 621907 | 103075 | 103092 | TGTCTTTGGAGCGGGCGG | 21 | 1799 | 1816 | 5-8-5 | 1845 |
| 621908 | 103078 | 103095 | TGGTGTCTTTGGAGCGGG | 57 | 1802 | 1819 | 5-8-5 | 1846 |
| 621909 | 103081 | 103098 | GGGTGGTGTCTTTGGAGC | 17 | 1805 | 1822 | 5-8-5 | 1847 |
| 621910 | 103084 | 103101 | GCTGGGTGGTGTCTTTGG | 44 | 1808 | 1825 | 5-8-5 | 1848 |
| 621911 | 103087 | 103104 | AGAGCTGGGTGGTGTCTT | 47 | 1811 | 1828 | 5-8-5 | 1849 |
| 621917 | 105442 | 105459 | CTGGACTTGCTTAGTCGC | 27 | 1829 | 1846 | 5-8-5 | 1850 |
| 621918 | 105445 | 105462 | TCTCTGGACTTGCTTAGT | 0 | 1832 | 1849 | 5-8-5 | 1851 |
| 621919 | 105448 | 105465 | TCTTCTCTGGACTTGCTT | 48 | 1835 | 1852 | 5-8-5 | 1852 |
| 621920 | 105451 | 105468 | TGGTCTTCTCTGGACTTG | 49 | 1838 | 1855 | 5-8-5 | 1853 |
| 621921 | 105454 | 105471 | GGGTGGTCTTCTCTGGAC | 33 | 1841 | 1858 | 5-8-5 | 1854 |
| 621922 | 105473 | 105490 | CAGATCTGGGCCCTGCAG | 36 | 1860 | 1877 | 5-8-5 | 1855 |
| 621923 | 105476 | 105493 | TCTCAGATCTGGGCCCTG | 70 | 1863 | 1880 | 5-8-5 | 1856 |
| 621924 | 105479 | 105496 | CTCTCTCAGATCTGGGCC | 32 | 1866 | 1883 | 5-8-5 | 1857 |
| 621929 | 107917 | 107934 | TGATTTTGGAGGTTCACC | 44 | 1883 | 1900 | 5-8-5 | 1858 |
| 621930 | 107920 | 107937 | CCCTGATTTTGGAGGTTC | 74 | 1886 | 1903 | 5-8-5 | 1859 |
| 621931 | 107923 | 107940 | ATCCCTGATTTTGGAGG | 26 | 1889 | 1906 | 5-8-5 | 1860 |
| 621932 | 107926 | 107943 | GCGATCCCTGATTTTGG | 45 | 1892 | 1909 | 5-8-5 | 1861 |
| 621933 | 107929 | 107946 | GCTGCGATCCCTGATTT | 38 | 1895 | 1912 | 5-8-5 | 1862 |
| 621934 | 107932 | 107949 | GCCGCTGCGATCCCTGA | 42 | 1898 | 1915 | 5-8-5 | 1863 |
| 621935 | 107935 | 107952 | GTAGCCGCTGCGATCCCC | 31 | 1901 | 1918 | 5-8-5 | 1864 |
| 621936 | 107938 | 107955 | GCTGTAGCCGCTGCGATC | 67 | 1904 | 1921 | 5-8-5 | 1865 |
| 621937 | 107941 | 107958 | GCTGCTGTAGCCGCTGCG | 23 | 1907 | 1924 | 5-8-5 | 1866 |
| 621938 | 107971 | 107988 | GCGGCTGCCGGGAGTGCC | 40 | 1937 | 1954 | 5-8-5 | 1867 |
| 621939 | 107974 | 107991 | GGAGCGGCTGCCGGGAGT | 1 | 1940 | 1957 | 5-8-5 | 1868 |
| 621940 | 107978 | 107995 | TGCGGGAGCGGCTGCCGG | 48 | 1944 | 1961 | 5-8-5 | 1869 |
| 621941 | 108021 | 108038 | ACCTTCTTGGGCTCCCGG | 24 | 1987 | 2004 | 5-8-5 | 1870 |
| 621942 | 108024 | 108041 | GCCACCTTCTTGGGCTCC | 28 | 1990 | 2007 | 5-8-5 | 1871 |
| 621943 | 108027 | 108044 | ACTGCCACCTTCTTGGGC | 19 | 1993 | 2010 | 5-8-5 | 1872 |
| 621944 | 108030 | 108047 | ACCACTGCCACCTTCTTG | 28 | 1996 | 2013 | 5-8-5 | 1873 |

TABLE 35-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621945 | 108033 | 108050 | CGGACCACTGCCACCTTC | 72 | 1999 | 2016 | 5-8-5 | 1874 |
| 621946 | 108036 | 108053 | GTACGGACCACTGCCACC | 57 | 2002 | 2019 | 5-8-5 | 1875 |
| 621947 | 108039 | 108056 | GGAGTACGGACCACTGCC | 25 | 2005 | 2022 | 5-8-5 | 1876 |
| 621948 | 108042 | 108059 | GGTGGAGTACGGACCACT | 30 | 2008 | 2025 | 5-8-5 | 1877 |
| 621949 | 108045 | 108062 | TTGGGTGGAGTACGGACC | 24 | 2011 | 2028 | 5-8-5 | 1878 |
| 621950 | 108052 | 108069 | CGGCGACTTGGGTGGAGT | 1 | 2018 | 2035 | 5-8-5 | 1879 |
| 621951 | 108055 | 108072 | AGACGGCGACTTGGGTGG | 4 | 2021 | 2038 | 5-8-5 | 1880 |
| 621952 | 108058 | 108075 | GGAAGACGGCGACTTGGG | 50 | 2024 | 2041 | 5-8-5 | 1881 |
| 621953 | 108061 | 108078 | GGCGGAAGACGGCGACTT | 66 | 2027 | 2044 | 5-8-5 | 1882 |
| 621954 | 108064 | 108081 | CTTGGCGGAAGACGGCGA | 38 | 2030 | 2047 | 5-8-5 | 1883 |
| 621955 | 108067 | 108084 | GCTCTTGGCGGAAGACGG | 24 | 2033 | 2050 | 5-8-5 | 1884 |
| 621956 | 108070 | 108087 | GCGGCTCTTGGCGGAAGA | 20 | 2036 | 2053 | 5-8-5 | 1885 |
| 621957 | 108073 | 108090 | CAGGCGGCTCTTGGCGGA | 46 | 2039 | 2056 | 5-8-5 | 1886 |
| 621958 | 108076 | 108093 | CTGCAGGCGGCTCTTGGC | 72 | 2042 | 2059 | 5-8-5 | 1887 |
| 621959 | 108079 | 108096 | TGTCTGCAGGCGGCTCTT | 52 | 2045 | 2062 | 5-8-5 | 1888 |
| 621960 | 108082 | 108099 | GGCTGTCTGCAGGCGGCT | 47 | 2048 | 2065 | 5-8-5 | 1889 |
| 621961 | 108101 | 108118 | GGTCTGGCATGGGCACGG | 73 | 2067 | 2084 | 5-8-5 | 1890 |
| 621962 | 108137 | 108154 | TCTCAGTGGAGCCGATCT | 39 | 2103 | 2120 | 5-8-5 | 1891 |
| 621963 | 108140 | 108157 | GGTTCTCAGTGGAGCCGA | 66 | 2106 | 2123 | 5-8-5 | 1892 |
| 621964 | 108143 | 108160 | TCAGGTTCTCAGTGGAGC | 65 | 2109 | 2126 | 5-8-5 | 1893 |
| 621965 | 108146 | 108163 | GCTTCAGGTTCTCAGTGG | 44 | 2112 | 2129 | 5-8-5 | 1894 |

TABLE 36

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 613412 | 73879 | 73898 | GTGATCTTCCATCACTTCGA | 88 | 345 | 364 | 5-10-5 | 25 |
| 620887 | 98891 98928 | 98908 98945 | GTTTTCAAACACACCTTC | 94 | n/a n/a | n/a n/a | 5-8-5 | 665 |
| 621973 | n/a | n/a | TGCACCTTCCCGCCTCCC | 66 | 2137 | 2154 | 5-8-5 | 1895 |
| 621974 | n/a | n/a | TATCTGCACCTTCCCGCC | 17 | 2141 | 2158 | 5-8-5 | 1896 |
| 621975 | n/a | n/a | AATTATCTGCACCTTCCC | 27 | 2144 | 2161 | 5-8-5 | 1897 |
| 621994 | n/a | n/a | TGCACACTGCCGCCTCCC | 74 | 2230 | 2247 | 5-8-5 | 1898 |
| 621995 | n/a | n/a | ACTATTTGCACACTGCCG | 28 | 2236 | 2253 | 5-8-5 | 1899 |
| 621996 | n/a | n/a | TAGACTATTTGCACACTG | 29 | 2239 | 2256 | 5-8-5 | 1900 |

TABLE 36-continued

Inhibition of tau mRNA by 5-10-5 MOE and 5-8-5 MOE
gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 621997 | n/a | n/a | TTGTAGACTATTTGCACA | 62 | 2242 | 2259 | 5-8-5 | 1901 |
| 622012 | n/a | n/a | CTCCTGGTTTATGATGGA | 24 | 2310 | 2327 | 5-8-5 | 1902 |
| 622013 | n/a | n/a | GGCCACCTCCTGGTTTAT | 21 | 2316 | 2333 | 5-8-5 | 1903 |
| 622014 | n/a | n/a | CACCTGGCCACCTCCTGG | 44 | 2321 | 2338 | 5-8-5 | 1904 |
| 622041 | n/a | n/a | ATCTTTTTATTTCCTCCG | 32 | 2422 | 2439 | 5-8-5 | 1905 |
| 622042 | n/a | n/a | TTTCAATCTTTTTATTTC | 16 | 2427 | 2444 | 5-8-5 | 1906 |
| 621966 | 108149 | 108166 | GGTGCTTCAGGTTCTCAG | 48 | 2115 | 2132 | 5-8-5 | 1907 |
| 621967 | 108153 | 108170 | GGCTGGTGCTTCAGGTTC | 46 | 2119 | 2136 | 5-8-5 | 1908 |
| 621968 | 108156 | 108173 | CCCGGCTGGTGCTTCAGG | 50 | 2122 | 2139 | 5-8-5 | 1909 |
| 621969 | 108159 | 108176 | CCTCCCGGCTGGTGCTTC | 22 | 2125 | 2142 | 5-8-5 | 1910 |
| 621970 | 108162 | 108179 | CCGCCTCCCGGCTGGTGC | 27 | 2128 | 2145 | 5-8-5 | 1911 |
| 621971 | 108165 | 108182 | TTCCCGCCTCCCGGCTGG | 5 | 2131 | 2148 | 5-8-5 | 1912 |
| 621972 | 108168 | 108185 | ACCTTCCCGCCTCCCGGC | 39 | 2134 | 2151 | 5-8-5 | 1913 |
| 621976 | 121826 | 121843 | ATTAATTATCTGCACCTT | 76 | 2147 | 2164 | 5-8-5 | 1914 |
| 621977 | 121829 | 121846 | CTTATTAATTATCTGCAC | 73 | 2150 | 2167 | 5-8-5 | 1915 |
| 621978 | 121833 | 121850 | GCTTCTTATTAATTATCT | 68 | 2154 | 2171 | 5-8-5 | 1916 |
| 621979 | 121836 | 121853 | CCAGCTTCTTATTAATTA | 44 | 2157 | 2174 | 5-8-5 | 1917 |
| 621980 | 121839 | 121856 | GATCCAGCTTCTTATTAA | 31 | 2160 | 2177 | 5-8-5 | 1918 |
| 621981 | 121842 | 121859 | TAAGATCCAGCTTCTTAT | 44 | 2163 | 2180 | 5-8-5 | 1919 |
| 621982 | 121845 | 121862 | TGCTAAGATCCAGCTTCT | 69 | 2166 | 2183 | 5-8-5 | 1920 |
| 621983 | 121848 | 121865 | CGTTGCTAAGATCCAGCT | 82 | 2169 | 2186 | 5-8-5 | 1921 |
| 621984 | 121864 | 121881 | CCACACTTGGACTGGACG | 73 | 2185 | 2202 | 5-8-5 | 1922 |
| 621985 | 121867 | 121884 | GAGCCACACTTGGACTGG | 80 | 2188 | 2205 | 5-8-5 | 1923 |
| 621986 | 121870 | 121887 | TTTGAGCCACACTTGGAC | 59 | 2191 | 2208 | 5-8-5 | 1924 |
| 621987 | 121873 | 121890 | TCCTTTGAGCCACACTTG | 66 | 2194 | 2211 | 5-8-5 | 1925 |
| 621988 | 121876 | 121893 | TTATCCTTTGAGCCACAC | 77 | 2197 | 2214 | 5-8-5 | 1926 |
| 621989 | 121879 | 121896 | ATATTATCCTTTGAGCCA | 54 | 2200 | 2217 | 5-8-5 | 1927 |
| 621990 | 121882 | 121899 | TTGATATTATCCTTTGAG | 69 | 2203 | 2220 | 5-8-5 | 1928 |
| 621991 | 121885 | 121902 | TGTTTGATATTATCCTTT | 92 | 2206 | 2223 | 5-8-5 | 1929 |
| 621992 | 121903 | 121920 | CTGCCGCCTCCCGGGACG | 51 | 2224 | 2241 | 5-8-5 | 1930 |
| 621993 | 121906 | 121923 | ACACTGCCGCCTCCCGGG | 70 | 2227 | 2244 | 5-8-5 | 1931 |
| 621998 | 125764 | 125781 | GGTTTGTAGACTATTTGC | 76 | 2245 | 2262 | 5-8-5 | 1932 |
| 621999 | 125767 | 125784 | ACTGGTTTGTAGACTATT | 62 | 2248 | 2265 | 5-8-5 | 1933 |
| 622000 | 125770 | 125787 | TCAACTGGTTTGTAGACT | 39 | 2251 | 2268 | 5-8-5 | 1934 |
| 622001 | 125777 | 125794 | GCTCAGGTCAACTGGTTT | 87 | 2258 | 2275 | 5-8-5 | 1935 |
| 622002 | 125780 | 125797 | CTTGCTCAGGTCAACTGG | 53 | 2261 | 2278 | 5-8-5 | 1936 |

TABLE 36-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 622003 | 125783 | 125800 | CACCTTGCTCAGGTCAAC | 68 | 2264 | 2281 | 5-8-5 | 1937 |
| 622004 | 125805 | 125822 | CTAATGAGCCACACTTGG | 51 | 2286 | 2303 | 5-8-5 | 1938 |
| 622005 | 125808 | 125825 | TGCCTAATGAGCCACACT | 65 | 2289 | 2306 | 5-8-5 | 1939 |
| 622006 | 125811 | 125828 | TGTTGCCTAATGAGCCAC | 69 | 2292 | 2309 | 5-8-5 | 1940 |
| 622007 | 125814 | 125831 | GGATGTTGCCTAATGAGC | 70 | 2295 | 2312 | 5-8-5 | 1941 |
| 622008 | 125817 | 125834 | GATGGATGTTGCCTAATG | 61 | 2298 | 2315 | 5-8-5 | 1942 |
| 622009 | 125820 | 125837 | TATGATGGATGTTGCCTA | 44 | 2301 | 2318 | 5-8-5 | 1943 |
| 622010 | 125823 | 125840 | GTTTATGATGGATGTTGC | 57 | 2304 | 2321 | 5-8-5 | 1944 |
| 622011 | 125826 | 125843 | CTGGTTTATGATGGATGT | 26 | 2307 | 2324 | 5-8-5 | 1945 |
| 622015 | 130141 | 130158 | TTTACTTCCACCTGGCCA | 36 | 2329 | 2346 | 5-8-5 | 1946 |
| 622016 | 130144 | 130161 | GATTTTACTTCCACCTGG | 49 | 2332 | 2349 | 5-8-5 | 1947 |
| 622017 | 130147 | 130164 | TCAGATTTTACTTCCACC | 76 | 2335 | 2352 | 5-8-5 | 1948 |
| 622018 | 130150 | 130167 | TTCTCAGATTTTACTTCC | 24 | 2338 | 2355 | 5-8-5 | 1949 |
| 622019 | 130153 | 130170 | AGCTTCTCAGATTTTACT | 30 | 2341 | 2358 | 5-8-5 | 1950 |
| 622020 | 130156 | 130173 | TCAAGCTTCTCAGATTTT | 39 | 2344 | 2361 | 5-8-5 | 1951 |
| 622021 | 130159 | 130176 | AAGTCAAGCTTCTCAGAT | 2 | 2347 | 2364 | 5-8-5 | 1952 |
| 622022 | 130162 | 130179 | TTGAAGTCAAGCTTCTCA | 53 | 2350 | 2367 | 5-8-5 | 1953 |
| 622023 | 130165 | 130182 | TCCTTGAAGTCAAGCTTC | 39 | 2353 | 2370 | 5-8-5 | 1954 |
| 622024 | 130168 | 130185 | CTGTCCTTGAAGTCAAGC | 19 | 2356 | 2373 | 5-8-5 | 1955 |
| 622025 | 130171 | 130188 | ACTCTGTCCTTGAAGTCA | 39 | 2359 | 2376 | 5-8-5 | 1956 |
| 622026 | 130174 | 130191 | TGGACTCTGTCCTTGAAG | 36 | 2362 | 2379 | 5-8-5 | 1957 |
| 622027 | 130177 | 130194 | GACTGGACTCTGTCCTTG | 75 | 2365 | 2382 | 5-8-5 | 1958 |
| 622028 | 130180 | 130197 | TTCGACTGGACTCTGTCC | 29 | 2368 | 2385 | 5-8-5 | 1959 |
| 622029 | 130183 | 130200 | ATCTTCGACTGGACTCTG | 33 | 2371 | 2388 | 5-8-5 | 1960 |
| 622030 | 130186 | 130203 | CCAATCTTCGACTGGACT | 49 | 2374 | 2391 | 5-8-5 | 1961 |
| 622031 | 130189 | 130206 | GACCCAATCTTCGACTGG | 74 | 2377 | 2394 | 5-8-5 | 1962 |
| 622032 | 130192 | 130209 | AGGGACCCAATCTTCGAC | 79 | 2380 | 2397 | 5-8-5 | 1963 |
| 622033 | 130195 | 130212 | TCCAGGGACCCAATCTTC | 77 | 2383 | 2400 | 5-8-5 | 1964 |
| 622034 | 130198 | 130215 | TTGTCCAGGGACCCAATC | 68 | 2386 | 2403 | 5-8-5 | 1965 |
| 622035 | 130201 | 130218 | ATATTGTCCAGGGACCCA | 6 | 2389 | 2406 | 5-8-5 | 1966 |
| 622036 | 130204 | 130221 | GTGATATTGTCCAGGGAC | 86 | 2392 | 2409 | 5-8-5 | 1967 |
| 622037 | 130207 | 130224 | TGGGTGATATTGTCCAGG | 68 | 2395 | 2412 | 5-8-5 | 1968 |
| 622038 | 130225 | 130242 | TTTCCTCCGCCAGGGACG | 77 | 2413 | 2430 | 5-8-5 | 1969 |
| 622039 | 130228 | 130245 | TTATTTCCTCCGCCAGGG | 52 | 2416 | 2433 | 5-8-5 | 1970 |
| 622040 | 130231 | 130248 | TTTTTATTTCCTCCGCCA | 61 | 2419 | 2436 | 5-8-5 | 1971 |

TABLE 37

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 613412 | 73879 | 73898 | GTGATCTTCCATCACTTCGA | 89 | 345 | 364 | 5-10-5 | 25 |
| 620887 | 98891 | 98908 | GTTTTCAAACACACCTTC | 98 | n/a | n/a | 5-8-5 | 665 |
|  | 98928 | 98945 |  |  | n/a | n/a |  |  |
| 622043 | n/a | n/a | GGGTTTCAATCTTTTTAT | 65 | 2430 | 2447 | 5-8-5 | 1972 |
| 622044 | 135477 | 135494 | GTCAGCTTGTGGGTTTCA | 86 | 2440 | 2457 | 5-8-5 | 1973 |
| 622045 | 135480 | 135497 | AAGGTCAGCTTGTGGGTT | 49 | 2443 | 2460 | 5-8-5 | 1974 |
| 622046 | 135484 | 135501 | GCGGAAGGTCAGCTTGTG | 26 | 2447 | 2464 | 5-8-5 | 1975 |
| 622047 | 135488 | 135505 | TCTCGCGGAAGGTCAGCT | 54 | 2451 | 2468 | 5-8-5 | 1976 |
| 622048 | 135491 | 135508 | CGTTCTCGCGGAAGGTCA | 63 | 2454 | 2471 | 5-8-5 | 1977 |
| 622049 | 135507 | 135524 | TCTGTCTTGGCTTTGGCG | 30 | 2470 | 2487 | 5-8-5 | 1978 |
| 622050 | 135510 | 135527 | TGGTCTGTCTTGGCTTTG | 72 | 2473 | 2490 | 5-8-5 | 1979 |
| 622051 | 135513 | 135530 | CCGTGGTCTGTCTTGGCT | 75 | 2476 | 2493 | 5-8-5 | 1980 |
| 622052 | 135516 | 135533 | GCCCCGTGGTCTGTCTTG | 39 | 2479 | 2496 | 5-8-5 | 1981 |
| 622053 | 135527 | 135544 | ACACGATCTCCGCCCCGT | 80 | 2490 | 2507 | 5-8-5 | 1982 |
| 622054 | 135530 | 135547 | TGTACACGATCTCCGCCC | 72 | 2493 | 2510 | 5-8-5 | 1983 |
| 622055 | 135533 | 135550 | ACTTGTACACGATCTCCG | 30 | 2496 | 2513 | 5-8-5 | 1984 |
| 622056 | 135536 | 135553 | GCGACTTGTACACGATCT | 72 | 2499 | 2516 | 5-8-5 | 1985 |
| 622057 | 135539 | 135556 | CTGGCGACTTGTACACGA | 65 | 2502 | 2519 | 5-8-5 | 1986 |
| 622058 | 135542 | 135559 | CCACTGGCGACTTGTACA | 35 | 2505 | 2522 | 5-8-5 | 1987 |
| 622059 | 135545 | 135562 | ACACCACTGGCGACTTGT | 46 | 2508 | 2525 | 5-8-5 | 1988 |
| 622060 | 135548 | 135565 | CAGACACCACTGGCGACT | 61 | 2511 | 2528 | 5-8-5 | 1989 |
| 622061 | 135551 | 135568 | CCCCAGACACCACTGGCG | 74 | 2514 | 2531 | 5-8-5 | 1990 |
| 622062 | 135554 | 135571 | TGTCCCCAGACACCACTG | 38 | 2517 | 2534 | 5-8-5 | 1991 |
| 622063 | 135572 | 135589 | TGAGATGCCGTGGAGACG | 36 | 2535 | 2552 | 5-8-5 | 1992 |
| 622064 | 135575 | 135592 | TGCTGAGATGCCGTGGAG | 34 | 2538 | 2555 | 5-8-5 | 1993 |
| 622065 | 135599 | 135616 | CGATGCTGCCGGTGGAGG | 43 | 2562 | 2579 | 5-8-5 | 1994 |
| 622066 | 135602 | 135619 | TGTCGATGCTGCCGGTGG | 51 | 2565 | 2582 | 5-8-5 | 1995 |
| 622067 | 135605 | 135622 | CCATGTCGATGCTGCCGG | 66 | 2568 | 2585 | 5-8-5 | 1996 |
| 622068 | 135608 | 135625 | CTACCATGTCGATGCTGC | 68 | 2571 | 2588 | 5-8-5 | 1997 |
| 622069 | 135611 | 135628 | AGTCTACCATGTCGATGC | 56 | 2574 | 2591 | 5-8-5 | 1998 |
| 622070 | 135614 | 135631 | GCGAGTCTACCATGTCGA | 68 | 2577 | 2594 | 5-8-5 | 1999 |
| 622071 | 135654 | 135671 | AGGGAGGCAGACACCTCG | 24 | 2617 | 2634 | 5-8-5 | 2000 |
| 622072 | 135657 | 135674 | GCCAGGGAGGCAGACACC | 73 | 2620 | 2637 | 5-8-5 | 2001 |
| 622073 | 135661 | 135678 | CTTGGCCAGGGAGGCAGA | 50 | 2624 | 2641 | 5-8-5 | 2002 |
| 622074 | 135664 | 135681 | CTGCTTGGCCAGGGAGGC | 44 | 2627 | 2644 | 5-8-5 | 2003 |
| 622075 | 135667 | 135684 | ACCCTGCTTGGCCAGGGA | 18 | 2630 | 2647 | 5-8-5 | 2004 |
| 622076 | 135678 | 135695 | CCTGATCACAAACCCTGC | 65 | 2641 | 2658 | 5-8-5 | 2005 |

TABLE 37-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 622077 | 135681 | 135698 | GGGCCTGATCACAAACCC | 82 | 2644 | 2661 | 5-8-5 | 2006 |
| 622078 | 135697 | 135714 | TTATTGACCGCCCCAGGG | 42 | 2660 | 2677 | 5-8-5 | 2007 |
| 622079 | 135700 | 135717 | CAATTATTGACCGCCCCA | 54 | 2663 | 2680 | 5-8-5 | 2008 |
| 622080 | 135703 | 135720 | CCACAATTATTGACCGCC | 95 | 2666 | 2683 | 5-8-5 | 2009 |
| 622081 | 135706 | 135723 | TCTCCACAATTATTGACC | 63 | 2669 | 2686 | 5-8-5 | 2010 |
| 622082 | 135709 | 135726 | TCCTCTCCACAATTATTG | 41 | 2672 | 2689 | 5-8-5 | 2011 |
| 622083 | 135712 | 135729 | CTCTCCTCTCCACAATTA | 76 | 2675 | 2692 | 5-8-5 | 2012 |
| 622084 | 135715 | 135732 | ATTCTCTCCTCTCCACAA | 57 | 2678 | 2695 | 5-8-5 | 2013 |
| 622085 | 135718 | 135735 | CTCATTCTCTCCTCTCCA | 72 | 2681 | 2698 | 5-8-5 | 2014 |
| 622086 | 135721 | 135738 | TCTCTCATTCTCTCCTCT | 69 | 2684 | 2701 | 5-8-5 | 2015 |
| 622087 | 135724 | 135741 | CACTCTCTCATTCTCTCC | 75 | 2687 | 2704 | 5-8-5 | 2016 |
| 622088 | 135727 | 135744 | CCACACTCTCTCATTCTC | 90 | 2690 | 2707 | 5-8-5 | 2017 |
| 622089 | 135730 | 135747 | TTTCCACACTCTCTCATT | 70 | 2693 | 2710 | 5-8-5 | 2018 |
| 622090 | 135733 | 135750 | TTTTTCCACACTCTCTC | 76 | 2696 | 2713 | 5-8-5 | 2019 |
| 622091 | 135737 | 135754 | CTTTTTTTTCCACACTC | 84 | 2700 | 2717 | 5-8-5 | 2020 |
| 622092 | 135740 | 135757 | ATTCTTTTTTTTCCACA | 67 | 2703 | 2720 | 5-8-5 | 2021 |
| 622093 | 135746 | 135763 | GTCATTATTCTTTTTTT | 54 | 2709 | 2726 | 5-8-5 | 2022 |
| 622094 | 135749 | 135766 | CGGGTCATTATTCTTTTT | 82 | 2712 | 2729 | 5-8-5 | 2023 |
| 622095 | 135752 | 135769 | GGCCGGGTCATTATTCTT | 72 | 2715 | 2732 | 5-8-5 | 2024 |
| 622096 | 135783 | 135800 | CTGCGAGGAGCAGCTGGG | 52 | 2746 | 2763 | 5-8-5 | 2025 |
| 622097 | 135786 | 135803 | GAACTGCGAGGAGCAGCT | 59 | 2749 | 2766 | 5-8-5 | 2026 |
| 622098 | 135789 | 135806 | ACCGAACTGCGAGGAGCA | 77 | 2752 | 2769 | 5-8-5 | 2027 |
| 622099 | 135792 | 135809 | TTAACCGAACTGCGAGGA | 62 | 2755 | 2772 | 5-8-5 | 2028 |
| 622100 | 135795 | 135812 | CAATTAACCGAACTGCGA | 55 | 2758 | 2775 | 5-8-5 | 2029 |
| 622101 | 135798 | 135815 | AACCAATTAACCGAACTG | 59 | 2761 | 2778 | 5-8-5 | 2030 |
| 622102 | 135801 | 135818 | ATTAACCAATTAACCGAA | 71 | 2764 | 2781 | 5-8-5 | 2031 |
| 622103 | 135804 | 135821 | GTGATTAACCAATTAACC | 70 | 2767 | 2784 | 5-8-5 | 2032 |
| 622104 | 135807 | 135824 | TAAGTGATTAACCAATTA | 42 | 2770 | 2787 | 5-8-5 | 2033 |
| 622105 | 135810 | 135827 | GGTTAAGTGATTAACCAA | 42 | 2773 | 2790 | 5-8-5 | 2034 |
| 622106 | 135813 | 135830 | GCAGGTTAAGTGATTAAC | 78 | 2776 | 2793 | 5-8-5 | 2035 |
| 622107 | 135816 | 135833 | AAAGCAGGTTAAGTGATT | 38 | 2779 | 2796 | 5-8-5 | 2036 |
| 622108 | 135819 | 135836 | ACAAAAGCAGGTTAAGTG | 55 | 2782 | 2799 | 5-8-5 | 2037 |
| 622109 | 135822 | 135839 | GTGACAAAAGCAGGTTAA | 82 | 2785 | 2802 | 5-8-5 | 2038 |
| 622110 | 135825 | 135842 | CGAGTGACAAAAGCAGGT | 86 | 2788 | 2805 | 5-8-5 | 2039 |
| 622111 | 135828 | 135845 | AGCCGAGTGACAAAAGCA | 93 | 2791 | 2808 | 5-8-5 | 2040 |
| 622112 | 135831 | 135848 | CAAAGCCGAGTGACAAAA | 73 | 2794 | 2811 | 5-8-5 | 2041 |

TABLE 37-continued

Inhibition of tau mRNA by 5-10-5 MOE and 5-8-5 MOE gapmers targeting SEQ ID NO: 1 and 2

| ISIS NO | SEQ ID NO: 1 start site | SEQ ID NO: 1 stop site | Sequence | % inhibition | SEQ ID NO: 2 start site | SEQ ID NO: 2 stop site | Motif | SEQ ID NO: |
|---|---|---|---|---|---|---|---|---|
| 622113 | 135834 | 135851 | AGCCAAAGCCGAGTGACA | 82 | 2797 | 2814 | 5-8-5 | 2042 |
| 622114 | 135837 | 135854 | CCGAGCCAAAGCCGAGTG | 82 | 2800 | 2817 | 5-8-5 | 2043 |
| 622115 | 135840 | 135857 | GTCCCGAGCCAAAGCCGA | 63 | 2803 | 2820 | 5-8-5 | 2044 |
| 622116 | 135843 | 135860 | GAAGTCCCGAGCCAAAGC | 59 | 2806 | 2823 | 5-8-5 | 2045 |
| 622117 | 135846 | 135863 | TTTGAAGTCCCGAGCCAA | 76 | 2809 | 2826 | 5-8-5 | 2046 |
| 622118 | 135849 | 135866 | GATTTTGAAGTCCCGAGC | 72 | 2812 | 2829 | 5-8-5 | 2047 |
| 622119 | 135852 | 135869 | ACTGATTTTGAAGTCCCG | 73 | 2815 | 2832 | 5-8-5 | 2048 |

TABLE 38

Inhibition of tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 620887 | 98891 98928 | 98908 98945 | GTTTTCAAACACACCTTC | 96 | 5-8-5 | 665 |
| 623853 | 12069 | 12086 | TGTTTGGATTTCTATCGG | 82 | 5-8-5 | 2049 |
| 623854 | 12077 | 12094 | TGACATGGTGTTTGGATT | 47 | 5-8-5 | 2050 |
| 623855 | 12079 | 12096 | GCTGACATGGTGTTTGGA | 77 | 5-8-5 | 2051 |
| 623856 | 12080 | 12097 | CGCTGACATGGTGTTTGG | 78 | 5-8-5 | 2052 |
| 623857 | 12081 | 12098 | TCGCTGACATGGTGTTTG | 83 | 5-8-5 | 2053 |
| 623858 | 12082 | 12099 | CTCGCTGACATGGTGTTT | 84 | 5-8-5 | 2054 |
| 623859 | 12083 | 12100 | ACTCGCTGACATGGTGTT | 74 | 5-8-5 | 2055 |
| 623860 | 12084 | 12101 | GACTCGCTGACATGGTGT | 89 | 5-8-5 | 2056 |
| 623861 | 12085 | 12102 | GGACTCGCTGACATGGTG | 77 | 5-8-5 | 2057 |
| 623862 | 16753 | 16770 | TTATCCAGGAAAAATATT | 21 | 5-8-5 | 2058 |
| 623863 | 16756 | 16773 | GGATTATCCAGGAAAAAT | 86 | 5-8-5 | 2059 |
| 623864 | 16758 | 16775 | TAGGATTATCCAGGAAAA | 76 | 5-8-5 | 2060 |
| 623865 | 16759 | 16776 | ATAGGATTATCCAGGAAA | 84 | 5-8-5 | 2061 |
| 623866 | 16760 | 16777 | TATAGGATTATCCAGGAA | 62 | 5-8-5 | 2062 |
| 623867 | 16761 | 16778 | CTATAGGATTATCCAGGA | 87 | 5-8-5 | 2063 |
| 623868 | 16763 | 16780 | CCCTATAGGATTATCCAG | 76 | 5-8-5 | 2064 |
| 623869 | 16764 | 16781 | TCCCTATAGGATTATCCA | 34 | 5-8-5 | 2065 |
| 623870 | 16766 | 16783 | TATCCCTATAGGATTATC | 56 | 5-8-5 | 2066 |
| 623871 | 16769 | 16786 | AGTTATCCCTATAGGATT | 16 | 5-8-5 | 2067 |
| 623872 | 16774 | 16791 | AGGCAAGTTATCCCTATA | 86 | 5-8-5 | 2068 |
| 623873 | 17416 | 17433 | ATCAGCACCTGACTGCGG | 78 | 5-8-5 | 2069 |
| 623874 | 17421 | 17438 | TTCAGATCAGCACCTGAC | 91 | 5-8-5 | 2070 |

TABLE 38-continued

Inhibition of tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623875 | 17424 | 17441 | GACTTCAGATCAGCACCT | 92 | 5-8-5 | 2071 |
| 623876 | 17426 | 17443 | AAGACTTCAGATCAGCAC | 92 | 5-8-5 | 2072 |
| 623877 | 17427 | 17444 | AAAGACTTCAGATCAGCA | 95 | 5-8-5 | 2073 |
| 623878 | 17428 | 17445 | CAAAGACTTCAGATCAGC | 96 | 5-8-5 | 2074 |
| 623879 | 17429 | 17446 | CCAAAGACTTCAGATCAG | 86 | 5-8-5 | 2075 |
| 623880 | 17430 | 17447 | ACCAAAGACTTCAGATCA | 65 | 5-8-5 | 2076 |
| 623881 | 17431 | 17448 | CACCAAAGACTTCAGATC | 51 | 5-8-5 | 2077 |
| 623882 | 17432 | 17449 | CCACCAAAGACTTCAGAT | 55 | 5-8-5 | 2078 |
| 623883 | 17434 | 17451 | GCCCACCAAAGACTTCAG | 77 | 5-8-5 | 2079 |
| 623884 | 17437 | 17454 | TCAGCCCACCAAAGACTT | 56 | 5-8-5 | 2080 |
| 623885 | 17442 | 17459 | TAAAGTCAGCCCACCAAA | 2 | 5-8-5 | 2081 |
| 623886 | 20943 | 20960 | GTTATTGGGACTGACCTT | 69 | 5-8-5 | 2082 |
| 623887 | 20948 | 20965 | GATTTGTTATTGGGACTG | 78 | 5-8-5 | 2083 |
| 613412 | 73879 | 73898 | GTGATCTTCCATCACTTCGA | 89 | 5-8-5 | 25 |
| 623811 | 122370 | 122387 | CAGTGGAGCCACTCAACG | 41 | 5-8-5 | 2084 |
| 623812 | 122380 | 122397 | CACCTGTCCACAGTGGAG | 58 | 5-8-5 | 2085 |
| 623813 | 122391 | 122408 | AACAAACGGGTCACCTGT | 63 | 5-8-5 | 2086 |
| 623814 | 122445 | 122462 | CGTGTAGGAGCAGCAGCT | 81 | 5-8-5 | 2087 |
| 623815 | 122538 | 122555 | CTTTGGTTTGGCTCTTTG | 64 | 5-8-5 | 2088 |
| 623816 | 123104 | 123121 | GCTGGTGGGAGAGGAGCC | 9 | 5-8-5 | 2089 |
| 623817 | 123288 | 123305 | ATGCGGGTGGCTGCCTCA | 65 | 5-8-5 | 2090 |
| 623818 | 123293 | 123310 | GCTGGATGCGGGTGGCTG | 24 | 5-8-5 | 2091 |
| 623819 | 123341 | 123358 | GTGCTCAGGGCAGGAAGC | 45 | 5-8-5 | 2092 |
| 623820 | 123590 | 123607 | CAAAGCTCAAACAGCTGA | 56 | 5-8-5 | 2093 |
| 623821 | 123601 | 123618 | AGAACCAGGATCAAAGCT | 41 | 5-8-5 | 2094 |
| 623822 | 123704 | 123721 | GCTCCGCCTCAGCAGCAC | 71 | 5-8-5 | 2095 |
| 623823 | 123722 | 123739 | GTGTGCACTCTCTCCCCA | 45 | 5-8-5 | 2096 |
| 623824 | 123877 | 123894 | GGCTAGCCCGCAGACGAG | 31 | 5-8-5 | 2097 |
| 623825 | 123976 | 123993 | CCTGTGAAGGTGCTCAGA | 58 | 5-8-5 | 2098 |
| 623826 | 124033 | 124050 | GATCCAGTGCCCCCAGAT | 54 | 5-8-5 | 2099 |
| 623827 | 124057 | 124074 | GGAGAGGCTAGGGCTCAG | 68 | 5-8-5 | 2100 |
| 623828 | 124223 | 124240 | AGAGGAGTGGATGGCAGT | 37 | 5-8-5 | 2101 |
| 623829 | 124293 | 124310 | TGGCCTGGGTGAGGTAAC | 23 | 5-8-5 | 2102 |
| 623830 | 124296 | 124313 | CTCTGGCCTGGGTGAGGT | 28 | 5-8-5 | 2103 |
| 623831 | 124596 | 124613 | AGGGCAGGTGGTGGTTTC | 8 | 5-8-5 | 2104 |
| 623832 | 124780 | 124797 | GACATTCCTGGAGTCCCC | 83 | 5-8-5 | 2105 |
| 623833 | 124859 | 124876 | TGGCAGACAGACAGGTCC | 87 | 5-8-5 | 2106 |
| 623834 | 124909 | 124926 | AGTCAAAGAACCAGCTCC | 68 | 5-8-5 | 2107 |

TABLE 38-continued

Inhibition of tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623835 | 124949 | 124966 | TCCCTCTGGGAATGATGA | 41 | 5-8-5 | 2108 |
| 623836 | 124965 | 124982 | GCCTCCAGGGCACCGCTC | 76 | 5-8-5 | 2109 |
| 623837 | 124972 | 124989 | GCCTGTGGCCTCCAGGGC | 43 | 5-8-5 | 2110 |
| 623838 | 124977 | 124994 | AGGAGGCCTGTGGCCTCC | 11 | 5-8-5 | 2111 |
| 623839 | 125075 | 125092 | AATAGGAACAAAGCAACA | 25 | 5-8-5 | 2112 |
| 623840 | 125086 | 125103 | CTGTCTTTAGCAATAGGA | 84 | 5-8-5 | 2113 |
| 623841 | 125100 | 125117 | TGTCCTGGACATTCCTGT | 66 | 5-8-5 | 2114 |
| 623842 | 125291 | 125308 | TGGAAAGGCAGGAGTGGG | 0 | 5-8-5 | 2115 |
| 623843 | 125306 | 125323 | TCTGAAAAATCTTGCTGG | 51 | 5-8-5 | 2116 |
| 623844 | 125310 | 125327 | AGCATCTGAAAAATCTTG | 82 | 5-8-5 | 2117 |
| 623845 | 125322 | 125339 | ATGAGTATGCACAGCATC | 68 | 5-8-5 | 2118 |
| 623846 | 125337 | 125354 | AAAGTGATCAATATGATG | 33 | 5-8-5 | 2119 |
| 623847 | 125390 | 125407 | GTCACTCCCTTTCCTGAC | 68 | 5-8-5 | 2120 |
| 623848 | 125408 | 125425 | ACGCTTAAGTGTAAAAAT | 38 | 5-8-5 | 2121 |
| 623849 | 125557 | 125574 | AAATGTGTTGTCGAAATT | 19 | 5-8-5 | 2122 |
| 623850 | 125567 | 125584 | CAGGGTGGAAAAATGTGT | 33 | 5-8-5 | 2123 |
| 623851 | 125598 | 125615 | TTCCCAGCTGCCATGAGG | 33 | 5-8-5 | 2124 |
| 623852 | 125743 | 125760 | TGGAGATGAGAGAGGAGG | 0 | 5-8-5 | 2125 |

TABLE 39

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623661 | 6196 | 6213 | GCGCTTACCTGATAGTCG | 36 | 5-8-5 | 2126 |
| 613412 | 73879 | 73898 | GTGATCTTCCATCACTTCGA | 87 | 5-8-5 | 25 |
| 623662 | 73981 | 73998 | TCCACTAACCTTTCAGGC | 30 | 5-8-5 | 2127 |
| 623663 | 83368 | 83385 | GGGAGATTCTGGAACACA | 72 | 5-8-5 | 2128 |
| 623664 | 83455 | 83472 | GGGCCCACCTTCCGCTGT | 22 | 5-8-5 | 2129 |
| 623665 | 85895 | 85912 | CTGTCACATCTAGAAACC | 21 | 5-8-5 | 2130 |
| 623666 | 85982 | 85999 | TACCCTCACCTGTGGTTC | 0 | 5-8-5 | 2131 |
| 623667 | 89885 | 89902 | CTTCTTCAGCTGGTGTAT | 22 | 5-8-5 | 2132 |
| 623668 | 89951 | 89968 | TTCACTGACCTTGGGTCA | 0 | 5-8-5 | 2133 |
| 623669 | 94688 | 94705 | TTTCAGGCTCTGTGTGGA | 61 | 5-8-5 | 2134 |
| 623670 | 95441 | 95458 | GACACAGACCTTTGAGTT | 53 | 5-8-5 | 2135 |
| 623671 | 98550 | 98567 | CCATGCGAGCTGATAAAA | 39 | 5-8-5 | 2136 |
| 621344 | 98607 | 98624 | GTCAGCTTACCTTGGCTT | 34 | 5-8-5 | 814 |
| 620887 | 98891 98928 | 98908 98945 | GTTTTCAAACACACCTTC | 94 | 5-8-5 | 665 |

TABLE 39-continued

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623672 | 101387 | 101404 | GTGGATGTCTTAAACATA | 89 | 5-8-5 | 2137 |
| 623673 | 101586 | 101603 | TTTCCTTACCTTGAGTTT | 0 | 5-8-5 | 2138 |
| 623674 | 102970 | 102987 | ATCAGCCCCTGTAAATG | 7 | 5-8-5 | 2139 |
| 623675 | 103097 | 103114 | TCTTCTTACCAGAGCTGG | 0 | 5-8-5 | 2140 |
| 623676 | 107909 | 107926 | GAGGTTCACCTGGGAAGG | 0 | 5-8-5 | 2141 |
| 623677 | 108175 | 108192 | CACTCTCACCTTCCCGCC | 6 | 5-8-5 | 2142 |
| 623712 | 108255 | 108272 | CCTCCAGGCGCAGCCCTA | 92 | 5-8-5 | 2143 |
| 623713 | 108413 | 108430 | CCTGAGGAGGGCACTCAC | 28 | 5-8-5 | 2144 |
| 623714 | 108530 | 108547 | GGAACCGCTGTGGGTGCC | 60 | 5-8-5 | 2145 |
| 623715 | 108565 | 108582 | TGGGTGGCAGTGTATTCT | 63 | 5-8-5 | 2146 |
| 623716 | 108690 | 108707 | GGAGAGCTCGCGAGCACC | 69 | 5-8-5 | 2147 |
| 623717 | 108896 | 108913 | GAGGTGGCTACCCACGGC | 59 | 5-8-5 | 2148 |
| 623718 | 109561 | 109578 | CCAGAAGGCCCAGCACAT | 51 | 5-8-5 | 2149 |
| 623719 | 109574 | 109591 | CGAGGCCCAGTGCCCAGA | 59 | 5-8-5 | 2150 |
| 623720 | 109607 | 109624 | AGGCCCAGGGTTCCAGAA | 55 | 5-8-5 | 2151 |
| 623721 | 109623 | 109640 | AGGCAAGCTGACACGCAG | 73 | 5-8-5 | 2152 |
| 623722 | 110101 | 110118 | CAGGAAAAGGCCGGACCT | 37 | 5-8-5 | 2153 |
| 623723 | 110103 | 110120 | AGCAGGAAAAGGCCGGAC | 78 | 5-8-5 | 2154 |
| 623724 | 110182 | 110199 | TTCCCCAAGGTCTCTAAC | 14 | 5-8-5 | 2155 |
| 623725 | 110413 | 110430 | AGGAAAGGCCAGTGAGGG | 8 | 5-8-5 | 2156 |
| 623726 | 110500 | 110517 | TTGTTATGTGACTTGAGG | 74 | 5-8-5 | 2157 |
| 623727 | 110630 | 110647 | ATTCCCCACCATGGGACA | 17 | 5-8-5 | 2158 |
| 623728 | 110635 | 110652 | AGGACATTCCCCACCATG | 9 | 5-8-5 | 2159 |
| 623729 | 110648 | 110665 | AGATAAGGAGAGAAGGAC | 15 | 5-8-5 | 2160 |
| 623730 | 110755 | 110772 | ATGCTCAGTGTGGTCAGA | 73 | 5-8-5 | 2161 |
| 623731 | 110852 | 110869 | AGGGCCGGCCACCTGCAC | 56 | 5-8-5 | 2162 |
| 623732 | 110919 | 110936 | TCTGTCTCTGGCAACCTG | 85 | 5-8-5 | 2163 |
| 623733 | 110954 | 110971 | AACAGGGAAGCTACTTCC | 6 | 5-8-5 | 2164 |
| 623734 | 111077 | 111094 | GGGCCTTCAATGGAAAGT | 21 | 5-8-5 | 2165 |
| 623735 | 111153 | 111170 | GGTCGCCTGACTCTCACC | 66 | 5-8-5 | 2166 |
| 623736 | 111174 | 111191 | CCCTTTCTACACTTGGCA | 81 | 5-8-5 | 2167 |
| 623678 | 121820 | 121837 | TATCTGCACCTTTGGTAG | 30 | 5-8-5 | 2168 |
| 623685 | 121830 | 121847 | TCTTATTAATTATCTGCA | 81 | 5-8-5 | 2169 |
| 623686 | 121831 | 121848 | TTCTTATTAATTATCTGC | 74 | 5-8-5 | 2170 |
| 623687 | 121834 | 121851 | AGCTTCTTATTAATTATC | 46 | 5-8-5 | 2171 |
| 623688 | 121835 | 121852 | CAGCTTCTTATTAATTAT | 6 | 5-8-5 | 2172 |
| 623689 | 121837 | 121854 | TCCAGCTTCTTATTAATT | 4 | 5-8-5 | 2173 |

TABLE 39-continued

Inhibition of Tau mRNA by 5-8-5 MOE gapmers targeting SEQ ID NO: 1

| ISIS NO | SEQ ID NO: 1 start site | SEQ ID NO: 1 stop site | Sequence | % inhibition | Motif | SEQ ID NO: |
|---|---|---|---|---|---|---|
| 623690 | 121838 | 121855 | ATCCAGCTTCTTATTAAT | 2 | 5-8-5 | 2174 |
| 623691 | 121840 | 121857 | AGATCCAGCTTCTTATTA | 2 | 5-8-5 | 2175 |
| 623692 | 121841 | 121858 | AAGATCCAGCTTCTTATT | 17 | 5-8-5 | 2176 |
| 623693 | 121843 | 121860 | CTAAGATCCAGCTTCTTA | 41 | 5-8-5 | 2177 |
| 623694 | 121844 | 121861 | GCTAAGATCCAGCTTCTT | 75 | 5-8-5 | 2178 |
| 623695 | 121846 | 121863 | TTGCTAAGATCCAGCTTC | 50 | 5-8-5 | 2179 |
| 623696 | 121847 | 121864 | GTTGCTAAGATCCAGCTT | 52 | 5-8-5 | 2180 |
| 623697 | 121865 | 121882 | GCCACACTTGGACTGGAC | 88 | 5-8-5 | 2181 |
| 623698 | 121866 | 121883 | AGCCACACTTGGACTGGA | 89 | 5-8-5 | 2182 |
| 623699 | 121868 | 121885 | TGAGCCACACTTGGACTG | 59 | 5-8-5 | 2183 |
| 623700 | 121869 | 121886 | TTGAGCCACACTTGGACT | 62 | 5-8-5 | 2184 |
| 623701 | 121872 | 121889 | CCTTTGAGCCACACTTGG | 69 | 5-8-5 | 2185 |
| 623702 | 121874 | 121891 | ATCCTTTGAGCCACACTT | 64 | 5-8-5 | 2186 |
| 623703 | 121875 | 121892 | TATCCTTTGAGCCACACT | 69 | 5-8-5 | 2187 |
| 623704 | 121877 | 121894 | ATTATCCTTTGAGCCACA | 76 | 5-8-5 | 2188 |
| 623705 | 121878 | 121895 | TATTATCCTTTGAGCCAC | 76 | 5-8-5 | 2189 |
| 623706 | 121880 | 121897 | GATATTATCCTTTGAGCC | 54 | 5-8-5 | 2190 |
| 623707 | 121881 | 121898 | TGATATTATCCTTTGAGC | 65 | 5-8-5 | 2191 |
| 623708 | 121884 | 121901 | GTTTGATATTATCCTTTG | 94 | 5-8-5 | 2192 |
| 623709 | 121886 | 121903 | GTGTTTGATATTATCCTT | 85 | 5-8-5 | 2193 |
| 623710 | 121887 | 121904 | CGTGTTTGATATTATCCT | 78 | 5-8-5 | 2194 |
| 623711 | 121904 | 121921 | ACTGCCGCCTCCCGGGAC | 50 | 5-8-5 | 2195 |
| 623679 | 121913 | 121930 | GGTACTCACACTGCCGCC | 72 | 5-8-5 | 1654 |
| 623680 | 125753 | 125770 | TATTTGCACCTGGAGATG | 0 | 5-8-5 | 2196 |
| 623681 | 125835 | 125852 | CAGGGCTACCTGGTTTAT | 26 | 5-8-5 | 2197 |
| 623682 | 130128 | 130145 | GGCCACCTCCTAGAACAC | 8 | 5-8-5 | 2198 |
| 623683 | 130241 | 130258 | CCCCTTTACCTTTTTATT | 0 | 5-8-5 | 2199 |
| 623684 | 135466 | 135483 | GGTTTCAATCTGCAAGAA | 39 | 5-8-5 | 2200 |

Example 11: Dose-Dependent Antisense Inhibition of Human Tau in SH-SY5Y Cells

Gapmers from studies described above exhibiting significant in vitro inhibition of tau mRNA were selected and tested at various doses in SH-SY5Y cells. The antisense oligonucleotides were tested in a series of experiments that had similar culture conditions. The results for each experiment are presented in separate tables shown below. Cells were plated at a density of 20,000 cells per well and transfected using electroporation with 0.938 µM, 0.1.875 µM, 3.750 µM, 7.500 µM, and 15.00 µM concentrations of antisense oligonucleotide, as specified in the Tables below. After a treatment period of approximately 16 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells. Tau mRNA levels were significantly reduced in a dose-dependent manner in antisense oligonucleotide treated cells.

TABLE 40

| ISIS No | 0.938 µM | 1.875 µM | 3.750 µM | 7.500 µM | 15.00 µM |
|---|---|---|---|---|---|
| 613369 | 57 | 67 | 81 | 91 | 96 |
| 613370 | 83 | 91 | 96 | 98 | 97 |

TABLE 40-continued

| ISIS No | 0.938 μM | 1.875 μM | 3.750 μM | 7.500 μM | 15.00 μM |
|---|---|---|---|---|---|
| 613371 | 68 | 78 | 95 | 95 | 97 |
| 613412 | 41 | 55 | 73 | 86 | 96 |
| 620887 | 53 | 76 | 90 | 93 | 95 |
| 621238 | 58 | 80 | 76 | 93 | 96 |
| 621251 | 68 | 77 | 87 | 89 | 90 |
| 621263 | 57 | 69 | 81 | 92 | 95 |
| 621302 | 46 | 66 | 80 | 78 | 87 |
| 621309 | 56 | 64 | 84 | 86 | 90 |
| 621311 | 38 | 54 | 69 | 77 | 86 |
| 621312 | 42 | 36 | 57 | 83 | 90 |
| 621318 | 40 | 54 | 71 | 87 | 87 |
| 621346 | 42 | 46 | 60 | 64 | 78 |
| 621870 | 42 | 62 | 76 | 85 | 92 |

TABLE 41

| ISIS No | 0.938 μM | 1.875 μM | 3.750 μM | 7.500 μM | 15.00 μM |
|---|---|---|---|---|---|
| 613412 | 14 | 45 | 68 | 84 | 92 |
| 620887 | 57 | 74 | 87 | 93 | 95 |
| 620888 | 63 | 78 | 76 | 94 | 96 |
| 620890 | 76 | 86 | 92 | 96 | 97 |
| 620891 | 67 | 79 | 91 | 96 | 96 |
| 620918 | 38 | 55 | 65 | 81 | 88 |
| 620940 | 38 | 52 | 73 | 89 | 96 |
| 620947 | 26 | 47 | 58 | 78 | 87 |
| 620958 | 32 | 38 | 61 | 79 | 93 |
| 621013 | 49 | 75 | 86 | 92 | 94 |
| 621049 | 38 | 45 | 68 | 78 | 80 |
| 621056 | 40 | 45 | 70 | 81 | 90 |
| 621078 | 23 | 28 | 48 | 67 | 84 |
| 621082 | 22 | 32 | 53 | 62 | 90 |
| 621088 | 26 | 43 | 59 | 80 | 92 |

TABLE 42

| ISIS No | 0.938 μM | 1.875 μM | 3.750 μM | 7.500 μM | 15.00 μM |
|---|---|---|---|---|---|
| 613412 | 17 | 45 | 62 | 84 | 89 |
| 620887 | 52 | 71 | 91 | 96 | 95 |
| 621147 | 28 | 37 | 59 | 69 | 84 |
| 621181 | 39 | 61 | 78 | 85 | 83 |
| 621183 | 31 | 43 | 64 | 72 | 87 |
| 621836 | 24 | 39 | 64 | 81 | 93 |
| 621838 | 33 | 59 | 70 | 91 | 97 |
| 621844 | 20 | 38 | 64 | 80 | 91 |
| 621845 | 30 | 37 | 62 | 72 | 90 |
| 621861 | 19 | 35 | 59 | 80 | 92 |
| 621869 | 30 | 56 | 64 | 83 | 91 |
| 622125 | 14 | 28 | 52 | 73 | 85 |
| 622129 | 26 | 36 | 60 | 71 | 84 |
| 622170 | 18 | 42 | 72 | 77 | 91 |
| 622196 | 11 | 39 | 59 | 74 | 89 |

TABLE 43

| ISIS No | 0.938 μM | 1.875 μM | 3.750 μM | 7.500 μM | 15.00 μM |
|---|---|---|---|---|---|
| 613412 | 21 | 42 | 64 | 82 | 95 |
| 620887 | 60 | 79 | 92 | 95 | 95 |
| 623746 | 19 | 43 | 54 | 81 | 91 |
| 623750 | 50 | 63 | 75 | 83 | 90 |
| 623758 | 37 | 54 | 72 | 80 | 82 |
| 623805 | 25 | 33 | 48 | 74 | 86 |
| 623807 | 15 | 29 | 44 | 75 | 88 |
| 623833 | 16 | 60 | 65 | 86 | 89 |
| 623860 | 51 | 71 | 80 | 85 | 85 |

TABLE 43-continued

| ISIS No | 0.938 μM | 1.875 μM | 3.750 μM | 7.500 μM | 15.00 μM |
|---|---|---|---|---|---|
| 623867 | 9 | 51 | 48 | 74 | 86 |
| 623874 | 24 | 28 | 72 | 84 | 94 |
| 623875 | 38 | 62 | 80 | 93 | 95 |
| 623876 | 40 | 63 | 83 | 93 | 95 |
| 623877 | 59 | 76 | 92 | 97 | 96 |
| 623878 | 50 | 73 | 90 | 94 | 95 |

TABLE 44

| ISIS No | 0.938 μM | 1.875 μM | 3.750 μM | 7.500 μM | 15.00 μM |
|---|---|---|---|---|---|
| 613412 | 8 | 25 | 58 | 77 | 87 |
| 620887 | 49 | 77 | 87 | 95 | 86 |
| 621360 | 27 | 46 | 68 | 83 | 90 |
| 621361 | 52 | 73 | 89 | 92 | 94 |
| 621363 | 28 | 45 | 71 | 76 | 77 |
| 621364 | 39 | 58 | 77 | 90 | 95 |
| 621407 | 38 | 60 | 75 | 82 | 78 |
| 621414 | 41 | 66 | 80 | 90 | 83 |
| 621424 | 54 | 72 | 87 | 94 | 90 |
| 621425 | 8 | 22 | 52 | 74 | 84 |
| 621426 | 33 | 46 | 63 | 84 | 91 |
| 621740 | 0 | 1 | 6 | 33 | 65 |
| 621793 | 4 | 15 | 30 | 41 | 52 |
| 621794 | 29 | 38 | 57 | 78 | 85 |
| 621810 | 15 | 39 | 45 | 73 | 79 |

TABLE 45

| ISIS No | 0.938 μM | 1.875 μM | 3.750 μM | 7.500 μM | 15.00 μM |
|---|---|---|---|---|---|
| 613412 | 40 | 72 | 78 | 92 | 94 |
| 620887 | 58 | 79 | 92 | 96 | 97 |
| 621431 | 62 | 63 | 79 | 85 | 87 |
| 621441 | 71 | 80 | 84 | 95 | 95 |
| 621446 | 53 | 70 | 82 | 89 | 94 |
| 621448 | 46 | 60 | 85 | 89 | 93 |
| 621454 | 63 | 70 | 81 | 89 | 94 |
| 621484 | 60 | 65 | 75 | 88 | 93 |
| 621570 | 26 | 55 | 81 | 79 | 90 |
| 621576 | 23 | 34 | 71 | 75 | 80 |
| 621578 | 30 | 45 | 67 | 81 | 90 |
| 621579 | 14 | 28 | 49 | 69 | 88 |
| 621598 | 38 | 55 | 73 | 88 | 94 |
| 621670 | 37 | 57 | 79 | 82 | 92 |
| 621675 | 31 | 35 | 51 | 79 | 87 |

TABLE 46

| ISIS No | 0.938 μM | 1.875 μM | 3.750 μM | 7.500 μM | 15.00 μM |
|---|---|---|---|---|---|
| 613412 | 21 | 38 | 70 | 84 | 92 |
| 620887 | 50 | 63 | 83 | 91 | 96 |
| 621894 | 35 | 16 | 32 | 54 | 70 |
| 621895 | 23 | 48 | 61 | 82 | 89 |
| 621961 | 8 | 14 | 47 | 57 | 75 |
| 621983 | 33 | 52 | 63 | 72 | 83 |
| 621991 | 36 | 56 | 68 | 86 | 92 |
| 622001 | 8 | 33 | 60 | 77 | 90 |
| 622080 | 29 | 53 | 69 | 67 | 93 |
| 622088 | 20 | 45 | 66 | 84 | 91 |
| 622091 | 14 | 33 | 47 | 70 | 82 |
| 622110 | 25 | 24 | 64 | 80 | 90 |
| 622111 | 17 | 41 | 74 | 86 | 92 |
| 623747 | 12 | 47 | 53 | 82 | 87 |

TABLE 47

| ISIS No | 0.938 μM | 1.875 μM | 3.750 μM | 7.500 μM | 15.00 μM |
|---|---|---|---|---|---|
| 613412 | 22 | 34 | 49 | 77 | 77 |
| 620887 | 51 | 68 | 83 | 94 | 95 |
| 623672 | 33 | 43 | 64 | 82 | 88 |
| 623697 | 37 | 53 | 59 | 80 | 90 |
| 623698 | 32 | 57 | 63 | 84 | 92 |
| 623708 | 47 | 68 | 82 | 88 | 95 |
| 623709 | 14 | 37 | 62 | 76 | 89 |
| 623712 | 22 | 45 | 70 | 86 | 92 |
| 623732 | 18 | 37 | 54 | 76 | 87 |
| 623756 | 23 | 38 | 68 | 86 | 94 |
| 623782 | 50 | 72 | 83 | 90 | 93 |
| 623791 | 58 | 71 | 87 | 93 | 95 |
| 623796 | 44 | 57 | 74 | 79 | 85 |
| 623808 | 30 | 55 | 73 | 84 | 91 |
| 623809 | 31 | 42 | 66 | 82 | 93 |

Example 12: Antisense Inhibition of Human Tau in HepG2 Cells by 5-10-5 MOE, 5-8-5 MOE, 4-8-6 MOE, or 6-8-4 MOE Gapmers Antisense oligonucleotides were designed targeting a tau nucleic acid and were tested for their effects on tau mRNA in vitro. The antisense oligonucleotides were tested in a series of experiments that had similar culture conditions. ISIS 613412 was also included in the assays. The results for each experiment are presented in separate tables shown below. Cultured HepG2 cells at a density of 20,000 cells per well were transfected using electroporation with 8,000 nM antisense oligonucleotide. After a treatment period of approximately 24 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-8-5 MOE, 4-8-6 MOE, or 6-8-4 MOE gapmers. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 4-8-6 MOE gapmers are 18 nucleosides in length, wherein the central gap segment comprises of eight 2'-deoxynucleosides and is flanked by wing segments on the 5' direction and the 3' direction comprising four and six nucleosides respectively. The 6-8-4 MOE gapmers are 18 nucleosides in length, wherein the central gap segment comprises of eight 2'-deoxynucleosides and is flanked by wing segments on the 5' direction and the 3' direction comprising six and four nucleosides respectively. Each nucleoside in the 5' wing segment and each nucleoside in the 3' wing segment has a 2'-MOE modification. The internucleoside linkage motif throughout for each gapmer in the tables below, except for ISIS 613412, is 5'-sooossssssssssooss-3', wherein each "s" represents a phosphorothioate internucleoside linkage and wherein each "o" represents a phosphodiester internucleoside linkage. The internucleoside linkage motif for ISIS 613412 is 5'-soooosssssssssssooss-3', wherein each "s" represents a phosphorothioate internucleoside linkage and wherein each "o" represents a phosphodiester internucleoside linkage. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in the Tables below is targeted to human tau genomic sequence, designated herein as SEQ ID NO: 1 (GENBANK Accession No. NT_010783.15 truncated from nucleotides 9240000 to 9381000).

TABLE 48

Inhibition of tau mRNA by 5-10-5 MOE gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 613412 | 73879 | 73898 | GTGATCTTCCATCACTTCGA | 5-10-5 | 90 | 25 |
| 620887 | 98891 98928 | 98908 98945 | GTTTTCAAACACACCTTC | 5-10-5 | 93 | 665 |
| 623888 | 20951 | 20968 | TTCGATTTGTTATTGGGA | 5-10-5 | 79 | 2201 |
| 623889 | 20953 | 20970 | ACTTCGATTTGTTATTGG | 5-10-5 | 61 | 2202 |
| 623890 | 20954 | 20971 | GACTTCGATTTGTTATTG | 5-10-5 | 30 | 2203 |
| 623891 | 20955 | 20972 | TGACTTCGATTTGTTATT | 5-10-5 | 62 | 2204 |
| 623892 | 20956 | 20973 | CTGACTTCGATTTGTTAT | 5-10-5 | 60 | 2205 |
| 623893 | 20957 | 20974 | GCTGACTTCGATTTGTTA | 5-10-5 | 43 | 2206 |
| 623894 | 20958 | 20975 | AGCTGACTTCGATTTGTT | 5-10-5 | 83 | 2207 |
| 623895 | 20959 | 20976 | CAGCTGACTTCGATTTGT | 5-10-5 | 68 | 2208 |
| 623896 | 20961 | 20978 | CCCAGCTGACTTCGATTT | 5-10-5 | 11 | 2209 |
| 623897 | 20964 | 20981 | ACGCCCAGCTGACTTCGA | 5-10-5 | 65 | 2210 |
| 623898 | 27148 | 27165 | TGCCTTATATATGCTGAA | 5-10-5 | 82 | 2211 |
| 623899 | 27153 | 27170 | TTACATGCCTTATATATG | 5-10-5 | 31 | 2212 |

TABLE 48-continued

Inhibition of tau mRNA by 5-10-5 MOE gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 623900 | 27156 | 27173 | CAGTTACATGCCTTATAT | 5-10-5 | 33 | 2213 |
| 623901 | 27158 | 27175 | TTCAGTTACATGCCTTAT | 5-10-5 | 72 | 2214 |
| 623902 | 27159 | 27176 | GTTCAGTTACATGCCTTA | 5-10-5 | 92 | 2215 |
| 623903 | 27169 | 27186 | AAAGTGCTGTGTTCAGTT | 5-10-5 | 71 | 2216 |
| 623904 | 27174 | 27191 | CCTCTAAAGTGCTGTGTT | 5-10-5 | 35 | 2217 |
| 623905 | 28215 | 28232 | GACTTTTCTCAATGTAAC | 5-10-5 | 43 | 2218 |
| 623906 | 28220 | 28237 | CTGCAGACTTTTCTCAAT | 5-10-5 | 61 | 2219 |
| 623907 | 28226 | 28243 | ACCTCTCTGCAGACTTTT | 5-10-5 | 79 | 2220 |
| 623908 | 28227 | 28244 | CACCTCTCTGCAGACTTT | 5-10-5 | 81 | 2221 |
| 623909 | 28228 | 28245 | GCACCTCTCTGCAGACTT | 5-10-5 | 82 | 2222 |
| 623910 | 28229 | 28246 | GGCACCTCTCTGCAGACT | 5-10-5 | 81 | 2223 |
| 623911 | 28230 | 28247 | TGGCACCTCTCTGCAGAC | 5-10-5 | 36 | 2224 |
| 623912 | 28231 | 28248 | CTGGCACCTCTCTGCAGA | 5-10-5 | 11 | 2225 |
| 623913 | 28233 | 28250 | TGCTGGCACCTCTCTGCA | 5-10-5 | 51 | 2226 |
| 623914 | 28236 | 28253 | TGATGCTGGCACCTCTCT | 5-10-5 | 63 | 2227 |
| 623915 | 28241 | 28258 | CCTTGTGATGCTGGCACC | 5-10-5 | 79 | 2228 |
| 623916 | 75133 | 75150 | TTTTTAGCATTAAAAGAG | 5-10-5 | 0 | 2229 |
| 623917 | 75144 | 75161 | GTGTTTTCTTATTTTTAG | 5-10-5 | 80 | 2230 |
| 623918 | 75149 | 75166 | GCAAGGTGTTTTCTTATT | 5-10-5 | 55 | 2231 |
| 623919 | 86762 | 86779 | TAGGCCTCTTCTGCATTT | 5-10-5 | 27 | 2232 |
| 623920 | 86767 | 86784 | CTGGCTAGGCCTCTTCTG | 5-10-5 | 54 | 2233 |
| 623921 | 86770 | 86787 | ATCCTGGCTAGGCCTCTT | 5-10-5 | 69 | 2234 |
| 623922 | 86772 | 86789 | AAATCCTGGCTAGGCCTC | 5-10-5 | 67 | 2235 |
| 623923 | 86773 | 86790 | GAAATCCTGGCTAGGCCT | 5-10-5 | 55 | 2236 |
| 623924 | 86774 | 86791 | TGAAATCCTGGCTAGGCC | 5-10-5 | 64 | 2237 |
| 623925 | 86775 | 86792 | GTGAAATCCTGGCTAGGC | 5-10-5 | 77 | 2238 |
| 623926 | 86776 | 86793 | GGTGAAATCCTGGCTAGG | 5-10-5 | 57 | 2239 |
| 623927 | 86777 | 86794 | TGGTGAAATCCTGGCTAG | 5-10-5 | 8 | 2240 |
| 623928 | 86778 | 86795 | CTGGTGAAATCCTGGCTA | 5-10-5 | 45 | 2241 |
| 623929 | 86780 | 86797 | TGCTGGTGAAATCCTGGC | 5-10-5 | 63 | 2242 |
| 623930 | 86783 | 86800 | CACTGCTGGTGAAATCCT | 5-10-5 | 70 | 2243 |
| 623931 | 121716 | 121733 | ACCCTGGACCCGCCTACT | 5-10-5 | 49 | 2244 |
| 623932 | 121721 | 121738 | GCGCCACCCTGGACCCGC | 5-10-5 | 84 | 2245 |
| 623933 | 121724 | 121741 | CATGCGCCACCCTGGACC | 5-10-5 | 52 | 2246 |
| 623934 | 121726 | 121743 | GACATGCGCCACCCTGGA | 5-10-5 | 80 | 2247 |
| 623935 | 121727 | 121744 | TGACATGCGCCACCCTGG | 5-10-5 | 74 | 2248 |
| 623936 | 121728 | 121745 | GTGACATGCGCCACCCTG | 5-10-5 | 90 | 2249 |

TABLE 48-continued

Inhibition of tau mRNA by 5-10-5 MOE gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 623937 | 121729 | 121746 | AGTGACATGCGCCACCCT | 5-10-5 | 84 | 2250 |
| 623938 | 121730 | 121747 | GAGTGACATGCGCCACCC | 5-10-5 | 92 | 2251 |
| 623939 | 121731 | 121748 | TGAGTGACATGCGCCACC | 5-10-5 | 86 | 2252 |
| 623940 | 121732 | 121749 | ATGAGTGACATGCGCCAC | 5-10-5 | 64 | 2253 |
| 623941 | 121734 | 121751 | CGATGAGTGACATGCGCC | 5-10-5 | 76 | 2254 |
| 623942 | 121737 | 121754 | TTTCGATGAGTGACATGC | 5-10-5 | 60 | 2255 |
| 623943 | 121742 | 121759 | TCCACTTTCGATGAGTGA | 5-10-5 | 34 | 2256 |
| 623944 | 121938 | 121955 | CAGCACGGCGCATGGGAC | 5-10-5 | 26 | 2257 |
| 623945 | 121939 | 121956 | ACAGCACGGCGCATGGGA | 5-10-5 | 62 | 2258 |
| 623946 | 121940 | 121957 | CACAGCACGGCGCATGGG | 5-10-5 | 57 | 2259 |
| 621455 | 121941 | 121958 | CCACAGCACGGCGCATGG | 5-10-5 | 44 | 1232 |
| 623804 | 121942 | 121959 | GCCACAGCACGGCGCATG | 5-10-5 | 85 | 1657 |
| 623947 | 121943 | 121960 | AGCCACAGCACGGCGCAT | 5-10-5 | 83 | 2260 |
| 623948 | 121944 | 121961 | AAGCCACAGCACGGCGCA | 5-10-5 | 56 | 2261 |
| 623949 | 121946 | 121963 | TCAAGCCACAGCACGGCG | 5-10-5 | 58 | 2262 |
| 623950 | 121949 | 121966 | AATTCAAGCCACAGCACG | 5-10-5 | 52 | 2263 |
| 623951 | 121954 | 121971 | CTAATAATTCAAGCCACA | 5-10-5 | 56 | 2264 |
| 623952 | 125424 | 125441 | GACATTTGCTCAGCAAAC | 5-10-5 | 74 | 2265 |
| 623953 | 125426 | 125443 | CAGACATTTGCTCAGCAA | 5-10-5 | 62 | 2266 |
| 623954 | 125427 | 125444 | CCAGACATTTGCTCAGCA | 5-10-5 | 75 | 2267 |
| 623955 | 125428 | 125445 | CCCAGACATTTGCTCAGC | 5-10-5 | 65 | 2268 |
| 623956 | 125429 | 125446 | ACCCAGACATTTGCTCAG | 5-10-5 | 30 | 2269 |
| 623957 | 125430 | 125447 | GACCCAGACATTTGCTCA | 5-10-5 | 30 | 2270 |
| 623958 | 125431 | 125448 | AGACCCAGACATTTGCTC | 5-10-5 | 41 | 2271 |
| 623959 | 125432 | 125449 | AAGACCCAGACATTTGCT | 5-10-5 | 69 | 2272 |
| 623960 | 125434 | 125451 | GCAAGACCCAGACATTTG | 5-10-5 | 73 | 2273 |
| 623961 | 125437 | 125454 | TGTGCAAGACCCAGACAT | 5-10-5 | 62 | 2274 |
| 623962 | 125442 | 125459 | GTCATTGTGCAAGACCCA | 5-10-5 | 87 | 2275 |

TABLE 49

Inhibition of tau mRNA by 5-10-5 MOE, 5-8-5 MOE, 4-8-6 MOE, and 6-8-4 gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 613412 | 73879 | 73898 | GTGATCTTCCATCACTTCGA | 5-10-5 | 87 | 25 |
| 620887 | 98891 98928 | 98908 98945 | GTTTTCAAACACACCTTC | 5-8-5 | 96 | 665 |
| 620888 | 98881 98918 | 98898 98935 | ACACCTTCATTTACTGTC | 5-8-5 | 96 | 897 |

TABLE 49-continued

Inhibition of tau mRNA by 5-10-5 MOE, 5-8-5 MOE, 4-8-6 MOE, and 6-8-4 gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 620889 | 98890 98927 | 98907 98944 | TTTTCAAACACACCTTCA | 5-8-5 | 85 | 898 |
| 620890 | 98892 98929 | 98909 98946 | GGTTTTCAAACACACCTT | 5-8-5 | 95 | 899 |
| 620891 | 98893 98930 | 98910 98947 | TGGTTTTCAAACACACCT | 5-8-5 | 96 | 900 |
| 623963 | 73877 | 73894 | TCTTCCATCACTTCGAAC | 5-8-5 | 58 | 2276 |
| 623964 | 73878 | 73895 | ATCTTCCATCACTTCGAA | 5-8-5 | 44 | 2277 |
| 623965 | 73880 | 73897 | TGATCTTCCATCACTTCG | 5-8-5 | 51 | 2278 |
| 623966 | 73881 | 73898 | GTGATCTTCCATCACTTC | 5-8-5 | 45 | 2279 |
| 623967 | 73931 | 73948 | ATGGTGTAGCCCCCCTGA | 5-8-5 | 66 | 2280 |
| 623968 | 73932 | 73949 | CATGGTGTAGCCCCCCTG | 5-8-5 | 87 | 2281 |
| 623969 | 73934 | 73951 | TGCATGGTGTAGCCCCCC | 5-8-5 | 94 | 2282 |
| 623970 | 73935 | 73952 | GTGCATGGTGTAGCCCCC | 5-8-5 | 90 | 2283 |
| 623971 | 73957 | 73974 | CCGTGTCACCCTCTTGGT | 5-8-5 | 83 | 2284 |
| 623972 | 73958 | 73975 | TCCGTGTCACCCTCTTGG | 5-8-5 | 79 | 2285 |
| 623973 | 73960 | 73977 | CGTCCGTGTCACCCTCTT | 5-8-5 | 92 | 2286 |
| 623974 | 83429 | 83446 | TCTTAGCATCAGAGGTTT | 5-8-5 | 70 | 2287 |
| 623975 | 83430 | 83447 | CTCTTAGCATCAGAGGTT | 5-8-5 | 76 | 2288 |
| 623976 | 83432 | 83449 | TGCTCTTAGCATCAGAGG | 5-8-5 | 72 | 2289 |
| 623977 | 83433 | 83450 | GTGCTCTTAGCATCAGAG | 5-8-5 | 86 | 2290 |
| 623978 | 95266 | 95283 | CTCCTCCGAGTGCGCCTG | 5-8-5 | 24 | 2291 |
| 623979 | 95267 | 95284 | GCTCCTCCGAGTGCGCCT | 5-8-5 | 77 | 2292 |
| 623980 | 95269 | 95286 | ATGCTCCTCCGAGTGCGC | 5-8-5 | 58 | 2293 |
| 623981 | 95270 | 95287 | AATGCTCCTCCGAGTGCG | 5-8-5 | 79 | 2294 |
| 623982 | 95272 | 95289 | CAAATGCTCCTCCGAGTG | 5-8-5 | 34 | 2295 |
| 623983 | 98557 | 98574 | TTACTGACCATGCGAGCT | 5-8-5 | 79 | 2296 |
| 623984 | 98558 | 98575 | TTTACTGACCATGCGAGC | 5-8-5 | 73 | 2297 |
| 623985 | 98560 | 98577 | CTTTTACTGACCATGCGA | 5-8-5 | 85 | 2298 |
| 623986 | 98561 | 98578 | GCTTTTACTGACCATGCG | 5-8-5 | 91 | 2299 |
| 623987 | 98563 | 98580 | TTGCTTTTACTGACCATG | 5-8-5 | 96 | 2300 |
| 623988 | 135784 | 135801 | ACTGCGAGGAGCAGCTGG | 5-8-5 | 43 | 2301 |
| 623989 | 135785 | 135802 | AACTGCGAGGAGCAGCTG | 5-8-5 | 31 | 2302 |
| 623990 | 135787 | 135804 | CGAACTGCGAGGAGCAGC | 5-8-5 | 62 | 2303 |
| 623991 | 135788 | 135805 | CCGAACTGCGAGGAGCAG | 5-8-5 | 73 | 2304 |
| 623992 | 135790 | 135807 | AACCGAACTGCGAGGAGC | 5-8-5 | 73 | 2305 |
| 623993 | 135868 | 135885 | TGCTCTTACTCCCATCAC | 5-8-5 | 59 | 2306 |
| 623994 | 135869 | 135886 | TTGCTCTTACTCCCATCA | 5-8-5 | 85 | 2307 |
| 623995 | 135871 | 135888 | ATTTGCTCTTACTCCCAT | 5-8-5 | 77 | 2308 |

TABLE 49-continued

Inhibition of tau mRNA by 5-10-5 MOE, 5-8-5 MOE, 4-8-6 MOE, and 6-8-4 gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 623996 | 135872 | 135889 | AATTTGCTCTTACTCCCA | 5-8-5 | 80 | 2309 |
| 625423 | 98879 | 98896 | ACCTTCATTTACTGTCAG | 5-8-5 | 90 | 2310 |
| 625424 | 98880 | 98897 | CACCTTCATTTACTGTCA | 5-8-5 | 94 | 2311 |
| 625425 | 98882<br>98919 | 98899<br>98936 | CACACCTTCATTTACTGT | 5-8-5<br>5-8-5 | 89 | 2312 |
| 625426 | 98883<br>98920 | 98900<br>98937 | ACACACCTTCATTTACTG | 5-8-5 | 87 | 2313 |
| 625427 | 98884<br>98921 | 98901<br>98938 | AACACACCTTCATTTACT | 5-8-5 | 86 | 2314 |
| 625428 | 98885<br>98922 | 98902<br>98939 | AAACACACCTTCATTTAC | 5-8-5 | 49 | 2315 |
| 625429 | 98886<br>98923 | 98903<br>98940 | CAAACACACCTTCATTTA | 5-8-5 | 66 | 2316 |
| 625430 | 98887<br>98924 | 98904<br>98941 | TCAAACACACCTTCATTT | 5-8-5 | 70 | 2317 |
| 625431 | 98888<br>98925 | 98905<br>98942 | TTCAAACACACCTTCATT | 5-8-5 | 74 | 2318 |
| 625432 | 98889<br>98926 | 98906<br>98943 | TTTCAAACACACCTTCAT | 5-8-5 | 81 | 2319 |
| 625433 | 98894 | 98911 | TTGGTTTTCAAACACACC | 5-8-5 | 92 | 2320 |
| 625434 | 75128 | 75145 | AGCATTAAAAGAGAAAAG | 5-8-5 | 13 | 2321 |
| 625435 | 75136 | 75153 | TTATTTTTAGCATTAAAA | 5-8-5 | 0 | 2322 |
| 625436 | 75138 | 75155 | TCTTATTTTTAGCATTAA | 5-8-5 | 52 | 2323 |
| 625437 | 75139 | 75156 | TTCTTATTTTTAGCATTA | 5-8-5 | 86 | 2324 |
| 625438 | 75140 | 75157 | TTTCTTATTTTTAGCATT | 5-8-5 | 40 | 2325 |
| 625439 | 75141 | 75158 | TTTTCTTATTTTTAGCAT | 5-8-5 | 0 | 2326 |
| 625440 | 75142 | 75159 | GTTTTCTTATTTTTAGCA | 5-8-5 | 82 | 2327 |
| 625441 | 75143 | 75160 | TGTTTTCTTATTTTTAGC | 5-8-5 | 68 | 2328 |
| 625442 | 75146 | 75163 | AGGTGTTTTCTTATTTTT | 5-8-5 | 83 | 2329 |
| 625443 | 75454 | 75171 | GGGCTGCAAGGTGTTTTC | 5-8-5 | 69 | 2330 |
| 625444 | 98881<br>98918 | 98898<br>98935 | ACACCTTCATTTACTGTC | 4-8-6 | 90 | 897 |
| 625445 | 98882<br>98919 | 98899<br>98936 | CACACCTTCATTTACTGT | 4-8-6 | 82 | 2312 |
| 625446 | 98883<br>98920 | 98900<br>98937 | ACACACCTTCATTTACTG | 4-8-6 | 84 | 2313 |
| 625447 | 98884<br>98921 | 98901<br>98938 | AACACACCTTCATTTACT | 4-8-6 | 40 | 2314 |
| 625448 | 98889<br>98926 | 98906<br>98943 | TTTCAAACACACCTTCAT | 4-8-6 | 83 | 2319 |
| 625449 | 98890<br>98927 | 98907<br>98944 | TTTTCAAACACACCTTCA | 4-8-6 | 0 | 898 |
| 625450 | 98891<br>98928 | 98908<br>98945 | GTTTTCAAACACACCTTC | 4-8-6 | 94 | 665 |

TABLE 49-continued

Inhibition of tau mRNA by 5-10-5 MOE, 5-8-5 MOE, 4-8-6 MOE, and 6-8-4 gapmers targeting SEQ ID NO: 1

| ISIS NO | SEQ ID NO: 1 Start Site | SEQ ID NO: 1 Stop Site | Sequence | Motif | % inhibition | SEQ ID NO |
|---|---|---|---|---|---|---|
| 625451 | 98892 98929 | 98909 98946 | GGTTTTCAAACACACCTT | 4-8-6 | 94 | 899 |
| 625452 | 98893 98930 | 98910 98947 | TGGTTTTCAAACACACCT | 4-8-6 | 94 | 900 |
| 625453 | 98881 98918 | 98898 98935 | ACACCTTCATTTACTGTC | 6-8-4 | 96 | 897 |
| 625454 | 98882 98919 | 98899 98936 | CACACCTTCATTTACTGT | 6-8-4 | 96 | 2312 |
| 625455 | 98883 98920 | 98900 98937 | ACACACCTTCATTTACTG | 6-8-4 | 93 | 2313 |
| 625456 | 98884 98921 | 98901 98938 | AACACACCTTCATTTACT | 6-8-4 | 88 | 2314 |
| 625457 | 98889 98926 | 98906 98943 | TTTCAAACACACCTTCAT | 6-8-4 | 85 | 2319 |
| 625458 | 98890 98927 | 98907 98944 | TTTTCAAACACACCTTCA | 6-8-4 | 90 | 898 |
| 625459 | 98891 98928 | 98908 98945 | GTTTTCAAACACACCTTC | 6-8-4 | 97 | 665 |
| 625460 | 98892 98929 | 98909 98946 | GGTTTTCAAACACACCTT | 6-8-4 | 97 | 899 |
| 625461 | 98893 98930 | 98910 98946 | TGGTTTTCAAACACACCT | 6-8-4 | 96 | 900 |

Example 13: Dose-Dependent Antisense Inhibition of Human Tau in SH-SY5Y Cells by MOE Gapmers Gapmers from studies described above exhibiting significant in vitro inhibition of tau mRNA were selected and tested at various doses in SH-SY5Y cells. The antisense oligonucleotides were tested in a series of experiments that had similar culture conditions. The results for each experiment are presented in separate tables shown below. Cells were plated at a density of 20,000 cells per well and transfected using electroporation with 0.938 µM, 0.1875 µM, 3.750 µM, 7.500 µM, and 15.00 µM concentrations of antisense oligonucleotide, as specified in the Tables below. After a treatment period of approximately 16 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells. Tau mRNA levels were significantly reduced in a dose-dependent manner in antisense oligonucleotide treated cells.

TABLE 50

| ISIS No | 0.938 µM | 1.875 µM | 3.750 µM | 7.500 µM | 15.00 µM |
|---|---|---|---|---|---|
| 613412 | 57 | 53 | 49 | 83 | 91 |
| 620887 | 68 | 84 | 95 | 95 | 97 |
| 620919 | 35 | 54 | 76 | 95 | 96 |
| 620930 | 32 | 49 | 76 | 86 | 92 |

TABLE 50-continued

| ISIS No | 0.938 µM | 1.875 µM | 3.750 µM | 7.500 µM | 15.00 µM |
|---|---|---|---|---|---|
| 620946 | 41 | 61 | 73 | 90 | 92 |
| 620971 | 61 | 63 | 75 | 88 | 96 |
| 620976 | 40 | 68 | 80 | 91 | 96 |
| 620978 | 49 | 49 | 78 | 93 | 94 |
| 620988 | 64 | 58 | 76 | 92 | 95 |
| 621031 | 51 | 72 | 90 | 89 | 92 |
| 621032 | 35 | 55 | 81 | 89 | 96 |
| 621041 | 48 | 73 | 80 | 88 | 95 |
| 621236 | 62 | 59 | 78 | 86 | 88 |
| 621239 | 46 | 62 | 63 | 94 | 94 |
| 621254 | 63 | 67 | 88 | 84 | 87 |

TABLE 51

| ISIS No | 0.938 µM | 1.875 µM | 3.750 µM | 7.500 µM | 15.00 µM |
|---|---|---|---|---|---|
| 613412 | 33 | 54 | 63 | 89 | 95 |
| 620887 | 72 | 90 | 95 | 96 | 96 |
| 620889 | 20 | 45 | 72 | 87 | 95 |
| 621417 | 52 | 68 | 81 | 88 | 92 |
| 621434 | 45 | 64 | 69 | 84 | 76 |
| 621440 | 58 | 72 | 77 | 88 | 87 |
| 621492 | 40 | 60 | 80 | 78 | 83 |
| 621599 | 43 | 73 | 83 | 91 | 95 |
| 621615 | 36 | 67 | 74 | 81 | 87 |
| 621620 | 48 | 74 | 88 | 95 | 98 |
| 621644 | 4 | 28 | 33 | 55 | 65 |

TABLE 51-continued

| ISIS No | 0.938 μM | 1.875 μM | 3.750 μM | 7.500 μM | 15.00 μM |
|---|---|---|---|---|---|
| 623685 | 30 | 48 | 73 | 87 | 93 |
| 623872 | 31 | 61 | 80 | 90 | 94 |
| 623879 | 22 | 50 | 74 | 88 | 95 |
| 623932 | 39 | 62 | 80 | 91 | 95 |

TABLE 52

| ISIS No | 0.938 μM | 1.875 μM | 3.750 μM | 7.500 μM | 15.00 μM |
|---|---|---|---|---|---|
| 613412 | 23 | 51 | 50 | 87 | 94 |
| 620887 | 64 | 82 | 92 | 95 | 96 |
| 620891 | 79 | 89 | 93 | 96 | 96 |
| 623757 | 38 | 58 | 73 | 85 | 95 |
| 623783 | 30 | 40 | 67 | 78 | 91 |
| 623804 | 51 | 70 | 81 | 87 | 92 |
| 623902 | 62 | 77 | 90 | 87 | 95 |
| 623936 | 46 | 70 | 84 | 91 | 94 |
| 623937 | 48 | 58 | 79 | 91 | 93 |
| 623938 | 39 | 63 | 76 | 90 | 93 |
| 623939 | 29 | 57 | 77 | 91 | 93 |
| 623962 | 44 | 68 | 78 | 87 | 91 |
| 625442 | 32 | 57 | 66 | 82 | 88 |
| 625459 | 74 | 87 | 95 | 96 | 98 |
| 625460 | 88 | 94 | 97 | 97 | 98 |

TABLE 53

| ISIS No | 0.938 μM | 1.875 μM | 3.750 μM | 7.500 μM | 15.00 μM |
|---|---|---|---|---|---|
| 613412 | 6 | 11 | 20 | 0 | 35 |
| 620887 | 71 | 86 | 92 | 95 | 96 |
| 620888 | 73 | 89 | 93 | 95 | 96 |
| 620890 | 82 | 90 | 94 | 95 | 96 |
| 623969 | 41 | 62 | 84 | 94 | n.d. |
| 623987 | 46 | 71 | 89 | 96 | 97 |
| 625424 | 50 | 73 | 88 | 94 | 96 |
| 625433 | 64 | 83 | 90 | 95 | 95 |
| 625450 | 69 | 84 | 91 | 96 | 97 |
| 625451 | 85 | 91 | 95 | 93 | 95 |
| 625452 | 67 | 83 | 91 | 93 | 95 |
| 625453 | 72 | 85 | 91 | 94 | 96 |
| 625454 | 73 | 86 | 93 | 95 | 96 |
| 625455 | 44 | 68 | 86 | 92 | 94 |
| 625461 | 75 | 84 | 94 | 95 | 97 |

TABLE 54

| ISIS No | 0.938 μM | 1.875 μM | 3.750 μM | 7.500 μM | 15.00 μM |
|---|---|---|---|---|---|
| 613412 | 11 | 30 | 65 | 82 | 83 |
| 620887 | 59 | 77 | 66 | 95 | 79 |
| 623968 | 43 | 57 | 72 | 86 | 93 |
| 623970 | 29 | 54 | 77 | 88 | 94 |
| 623973 | 48 | 65 | 80 | 93 | 94 |
| 623977 | 38 | 60 | 72 | 82 | 89 |
| 623986 | 45 | 53 | 80 | 91 | 96 |
| 625423 | 43 | 57 | 75 | 77 | 95 |
| 625425 | 39 | 49 | 78 | 88 | 93 |
| 625426 | 15 | 43 | 61 | 82 | 92 |
| 625427 | 16 | 35 | 64 | 81 | 93 |
| 625437 | 30 | 45 | 64 | 84 | 91 |
| 625444 | 28 | 45 | 67 | 84 | 92 |
| 625446 | 16 | 33 | 58 | 76 | 92 |
| 625456 | 27 | 43 | 57 | 86 | 91 |
| 625458 | 19 | 45 | 61 | 85 | 93 |

TABLE 55

| ISIS No | 0.938 μM | 1.875 μM | 3.750 μM | 7.500 μM | 15.00 μM |
|---|---|---|---|---|---|
| 613412 | 0 | 10 | 31 | 71 | 77 |
| 620887 | 33 | 58 | 74 | 82 | 92 |
| 621842 | 7 | 31 | 45 | 72 | 87 |
| 621846 | 0 | 0 | 28 | 62 | 90 |
| 623903 | 0 | 0 | 25 | 71 | 83 |
| 623985 | 0 | 17 | 41 | 74 | 84 |
| 623994 | 19 | 42 | 67 | 81 | 83 |
| 625457 | 0 | 5 | 57 | 69 | 80 |

Example 14: Design of 5-7-6 MOE, 5-8-5 MOE, 5-9-5 MOE, and 5-10-5 MOE Gapmers with Phosphorothioate and Phosphodiester Internucleoside Linkages at a Hot Spot Region of Human Tau Antisense oligonucleotides were designed targeting a tau nucleic acid at a region identified as a 'hotspot' in the studies above.

The newly designed chimeric antisense oligonucleotides in the Table below were designed as 5-7-6 MOE, 5-8-5 MOE, 5-9-5 MOE, or 5-10-5 MOE gapmers. The 5-7-6 MOE gapmers are 18 nucleosides in length, wherein the central gap segment comprises of seven 2'-deoxynucleosides and is flanked by wing segments on the 5' direction and the 3' direction comprising five and six nucleosides respectively. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are either phosphorothioate linkages or phosphodiester linkages. The 'Chemistry' column describes the internucleoside linkages of each oligonucleotide. 's' indicates phosphorothioate linkage and 'o' indicates phosphodiester linkage. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted in the human gene sequence. Each gapmer listed in the Table below is targeted to either the human tau genomic sequence, designated herein as SEQ ID NO: 1 (GENBANK Accession No. NT_010783.15 truncated from nucleotides 9240000 to 9381000) or to the human tau mRNA sequence, designated herein as SEQ ID NO: 2 (GENBANK Accession No. NM_001123066.3). 'n/a' indicates that the antisense oligonucleotide does not target that particular gene sequence with 100% complementarity.

TABLE 56

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664511 | 135820 | 135837 | GACAAAAGCAGGTTAAGT | 2783 | 2800 | sooosssssssssooss | 5-8-5 | 2331 |
| 664714 | 135820 | 135838 | TGACAAAAGCAGGTTAAGT | 2783 | 2801 | sooosssssssssssooss | 5-9-5 | 2332 |
| 664661 | 135820 | 135839 | GTGACAAAAGCAGGTTAAGT | 2783 | 2802 | sooossssssssssssooss | 5-10-5 | 2333 |
| 664767 | 135820 | 135837 | GACAAAAGCAGGTTAAGT | 2783 | 2800 | sooosssssssssooss | 5-7-6 | 2331 |
| 664512 | 135821 | 135838 | TGACAAAAGCAGGTTAAG | 2784 | 2801 | sooosssssssssooss | 5-8-5 | 2334 |
| 664715 | 135821 | 135839 | GTGACAAAAGCAGGTTAAG | 2784 | 2802 | sooosssssssssssooss | 5-9-5 | 2335 |
| 664662 | 135821 | 135840 | AGTGACAAAAGCAGGTTAAG | 2784 | 2803 | sooossssssssssssooss | 5-10-5 | 2336 |
| 664768 | 135821 | 135838 | TGACAAAAGCAGGTTAAG | 2784 | 2801 | sooosssssssssooss | 5-7-6 | 2334 |
| 622109 | 135822 | 135839 | GTGACAAAAGCAGGTTAA | 2785 | 2802 | sooosssssssssooss | 5-8-5 | 2038 |
| 664716 | 135822 | 135840 | AGTGACAAAAGCAGGTTAA | 2785 | 2803 | sooosssssssssssooss | 5-9-5 | 2337 |
| 664663 | 135822 | 135841 | GAGTGACAAAAGCAGGTTAA | 2785 | 2804 | sooossssssssssssooss | 5-10-5 | 2338 |
| 664769 | 135822 | 135839 | GTGACAAAAGCAGGTTAA | 2785 | 2802 | sooosssssssssooss | 5-7-6 | 2038 |
| 664513 | 135823 | 135840 | AGTGACAAAAGCAGGTTA | 2786 | 2803 | sooosssssssssooss | 5-8-5 | 2339 |
| 664717 | 135823 | 135841 | GAGTGACAAAAGCAGGTTA | 2786 | 2804 | sooosssssssssssooss | 5-9-5 | 2340 |
| 664664 | 135823 | 135842 | CGAGTGACAAAAGCAGGTTA | 2786 | 2805 | sooossssssssssssooss | 5-10-5 | 2341 |
| 664770 | 135823 | 135840 | AGTGACAAAAGCAGGTTA | 2786 | 2803 | sooosssssssssooss | 5-7-6 | 2339 |
| 664514 | 135824 | 135841 | GAGTGACAAAAGCAGGTT | 2787 | 2804 | sooosssssssssooss | 5-8-5 | 2342 |
| 664718 | 135824 | 135842 | CGAGTGACAAAAGCAGGTT | 2787 | 2805 | sooosssssssssssooss | 5-9-5 | 2343 |
| 664665 | 135824 | 135843 | CCGAGTGACAAAAGCAGGTT | 2787 | 2806 | sooossssssssssssooss | 5-10-5 | 2344 |
| 664771 | 135824 | 135841 | GAGTGACAAAAGCAGGTT | 2787 | 2804 | sooosssssssssooss | 5-7-6 | 2342 |
| 622110 | 135825 | 135842 | CGAGTGACAAAAGCAGGT | 2788 | 2805 | sooosssssssssooss | 5-8-5 | 2039 |
| 664719 | 135825 | 135843 | CCGAGTGACAAAAGCAGGT | 2788 | 2806 | sooosssssssssssooss | 5-9-5 | 2345 |
| 664666 | 135825 | 135844 | GCCGAGTGACAAAAGCAGGT | 2788 | 2807 | sooossssssssssssooss | 5-10-5 | 2346 |
| 664772 | 135825 | 135842 | CGAGTGACAAAAGCAGGT | 2788 | 2805 | sooosssssssssooss | 5-7-6 | 2039 |
| 664515 | 135826 | 135843 | CCGAGTGACAAAAGCAGG | 2789 | 2806 | sooosssssssssooss | 5-8-5 | 2347 |
| 664720 | 135826 | 135844 | GCCGAGTGACAAAAGCAGG | 2789 | 2807 | sooosssssssssssooss | 5-9-5 | 2348 |
| 664667 | 135826 | 135845 | AGCCGAGTGACAAAAGCAGG | 2789 | 2808 | sooossssssssssssooss | 5-10-5 | 2349 |
| 664773 | 135826 | 135843 | CCGAGTGACAAAAGCAGG | 2789 | 2806 | sooosssssssssooss | 5-7-6 | 2347 |
| 664516 | 135827 | 135844 | GCCGAGTGACAAAAGCAG | 2790 | 2807 | sooosssssssssooss | 5-8-5 | 2350 |
| 664721 | 135827 | 135845 | AGCCGAGTGACAAAAGCAG | 2790 | 2808 | sooosssssssssssooss | 5-9-5 | 2351 |
| 664668 | 135827 | 135846 | AAGCCGAGTGACAAAAGCAG | 2790 | 2809 | sooossssssssssssooss | 5-10-5 | 2352 |
| 664774 | 135827 | 135844 | GCCGAGTGACAAAAGCAG | 2790 | 2807 | sooosssssssssooss | 5-7-6 | 2350 |
| 622111 | 135828 | 135845 | AGCCGAGTGACAAAAGCA | 2791 | 2808 | sooosssssssssooss | 5-8-5 | 2040 |
| 664722 | 135828 | 135846 | AAGCCGAGTGACAAAAGCA | 2791 | 2809 | sooosssssssssssooss | 5-9-5 | 2353 |
| 664669 | 135828 | 135847 | AAAGCCGAGTGACAAAAGCA | 2791 | 2810 | sooossssssssssssooss | 5-10-5 | 2354 |
| 664775 | 135828 | 135845 | AGCCGAGTGACAAAAGCA | 2791 | 2808 | sooosssssssssooss | 5-7-6 | 2040 |
| 664517 | 135829 | 135846 | AAGCCGAGTGACAAAAGC | 2792 | 2809 | sooosssssssssooss | 5-8-5 | 2355 |

TABLE 56-continued

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664723 | 135829 | 135847 | AAAGCCGAGTGACAAAAGC | 2792 | 2810 | sooossssssssssooss | 5-9-5 | 2356 |
| 664670 | 135829 | 135848 | CAAAGCCGAGTGACAAAAGC | 2792 | 2811 | sooossssssssssssooss | 5-10-5 | 2357 |
| 664776 | 135829 | 135846 | AAGCCGAGTGACAAAAGC | 2792 | 2809 | sooossssssssooss | 5-7-6 | 2355 |
| 664518 | 135830 | 135847 | AAAGCCGAGTGACAAAAG | 2793 | 2810 | sooossssssssooss | 5-8-5 | 2358 |
| 664724 | 135830 | 135848 | CAAAGCCGAGTGACAAAAG | 2793 | 2811 | sooossssssssssooss | 5-9-5 | 2359 |
| 664671 | 135830 | 135849 | CCAAAGCCGAGTGACAAAAG | 2793 | 2812 | sooossssssssssssooss | 5-10-5 | 2360 |
| 664777 | 135830 | 135847 | AAAGCCGAGTGACAAAAG | 2793 | 2810 | sooossssssssooss | 5-7-6 | 2358 |
| 622112 | 135831 | 135848 | CAAAGCCGAGTGACAAAA | 2794 | 2811 | sooossssssssooss | 5-8-5 | 2041 |
| 664725 | 135831 | 135849 | CCAAAGCCGAGTGACAAAA | 2794 | 2812 | sooossssssssssooss | 5-9-5 | 2361 |
| 664672 | 135831 | 135850 | GCCAAAGCCGAGTGACAAAA | 2794 | 2813 | sooossssssssssssooss | 5-10-5 | 2362 |
| 664778 | 135831 | 135848 | CAAAGCCGAGTGACAAAA | 2794 | 2811 | sooossssssssooss | 5-7-6 | 2041 |
| 664519 | 135832 | 135849 | CCAAAGCCGAGTGACAAA | 2795 | 2812 | sooossssssssooss | 5-8-5 | 2363 |
| 664726 | 135832 | 135850 | GCCAAAGCCGAGTGACAAA | 2795 | 2813 | sooossssssssssooss | 5-9-5 | 2364 |
| 664673 | 135832 | 135851 | AGCCAAAGCCGAGTGACAAA | 2795 | 2814 | sooossssssssssssooss | 5-10-5 | 2365 |
| 664779 | 135832 | 135849 | CCAAAGCCGAGTGACAAA | 2795 | 2812 | sooossssssssooss | 5-7-6 | 2363 |
| 664520 | 135833 | 135850 | GCCAAAGCCGAGTGACAA | 2796 | 2813 | sooossssssssooss | 5-8-5 | 2366 |
| 664727 | 135833 | 135851 | AGCCAAAGCCGAGTGACAA | 2796 | 2814 | sooossssssssssooss | 5-9-5 | 2367 |
| 664674 | 135833 | 135852 | GAGCCAAAGCCGAGTGACAA | 2796 | 2815 | sooossssssssssssooss | 5-10-5 | 2368 |
| 664780 | 135833 | 135850 | GCCAAAGCCGAGTGACAA | 2796 | 2813 | sooossssssssooss | 5-7-6 | 2366 |
| 622113 | 135834 | 135851 | AGCCAAAGCCGAGTGACA | 2797 | 2814 | sooossssssssooss | 5-8-5 | 2042 |
| 664728 | 135834 | 135852 | GAGCCAAAGCCGAGTGACA | 2797 | 2815 | sooossssssssssooss | 5-9-5 | 2369 |
| 664675 | 135834 | 135853 | CGAGCCAAAGCCGAGTGACA | 2797 | 2816 | sooossssssssssssooss | 5-10-5 | 2419 |
| 664781 | 135834 | 135851 | AGCCAAAGCCGAGTGACA | 2797 | 2814 | sooossssssssooss | 5-7-6 | 2042 |
| 664521 | 135835 | 135852 | GAGCCAAAGCCGAGTGAC | 2798 | 2815 | sooossssssssooss | 5-8-5 | 2420 |
| 664729 | 135835 | 135853 | CGAGCCAAAGCCGAGTGAC | 2798 | 2816 | sooossssssssssooss | 5-9-5 | 2421 |
| 664676 | 135835 | 135854 | CCGAGCCAAAGCCGAGTGAC | 2798 | 2817 | sooossssssssssssooss | 5-10-5 | 2422 |
| 664782 | 135835 | 135852 | GAGCCAAAGCCGAGTGAC | 2798 | 2815 | sooossssssssooss | 5-7-6 | 2420 |
| 664522 | 135836 | 135853 | CGAGCCAAAGCCGAGTGA | 2799 | 2816 | sooossssssssooss | 5-8-5 | 2423 |
| 664730 | 135836 | 135854 | CCGAGCCAAAGCCGAGTGA | 2799 | 2817 | sooossssssssssooss | 5-9-5 | 2424 |
| 664677 | 135836 | 135855 | CCCGAGCCAAAGCCGAGTGA | 2799 | 2818 | sooossssssssssssooss | 5-10-5 | 2425 |
| 664783 | 135836 | 135853 | CGAGCCAAAGCCGAGTGA | 2799 | 2816 | sooossssssssooss | 5-7-6 | 2423 |
| 622114 | 135837 | 135854 | CCGAGCCAAAGCCGAGTG | 2800 | 2817 | sooossssssssooss | 5-8-5 | 2043 |
| 664731 | 135837 | 135855 | CCCGAGCCAAAGCCGAGTG | 2800 | 2818 | sooossssssssssooss | 5-9-5 | 2426 |
| 664678 | 135837 | 135856 | TCCCGAGCCAAAGCCGAGTG | 2800 | 2819 | sooossssssssssssooss | 5-10-5 | 2427 |
| 664784 | 135837 | 135854 | CCGAGCCAAAGCCGAGTG | 2800 | 2817 | sooossssssssooss | 5-7-6 | 2043 |
| 664523 | 135838 | 135855 | CCCGAGCCAAAGCCGAGT | 2801 | 2818 | sooossssssssooss | 5-8-5 | 2428 |

TABLE 56-continued

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664732 | 135838 | 135856 | TCCCGAGCCAAAGCCGAGT | 2801 | 2819 | sooossssssssssooss | 5-9-5 | 2429 |
| 664679 | 135838 | 135857 | GTCCCGAGCCAAAGCCGAGT | 2801 | 2820 | sooossssssssssssooss | 5-10-5 | 2430 |
| 664785 | 135838 | 135855 | CCCGAGCCAAAGCCGAGT | 2801 | 2818 | sooossssssssssooss | 5-7-6 | 2428 |
| 664524 | 135839 | 135856 | TCCCGAGCCAAAGCCGAG | 2802 | 2819 | sooossssssssssooss | 5-8-5 | 2431 |
| 664733 | 135839 | 135857 | GTCCCGAGCCAAAGCCGAG | 2802 | 2820 | sooossssssssssooss | 5-9-5 | 2432 |
| 664680 | 135839 | 135858 | AGTCCCGAGCCAAAGCCGAG | 2802 | 2821 | sooossssssssssssooss | 5-10-5 | 2433 |
| 664786 | 135839 | 135856 | TCCCGAGCCAAAGCCGAG | 2802 | 2819 | sooossssssssssooss | 5-7-6 | 2431 |
| 622115 | 135840 | 135857 | GTCCCGAGCCAAAGCCGA | 2803 | 2820 | sooossssssssssooss | 5-8-5 | 2044 |
| 664734 | 135840 | 135858 | AGTCCCGAGCCAAAGCCGA | 2803 | 2821 | sooossssssssssooss | 5-9-5 | 2434 |
| 664681 | 135840 | 135859 | AAGTCCCGAGCCAAAGCCGA | 2803 | 2822 | sooossssssssssssooss | 5-10-5 | 2435 |
| 664787 | 135840 | 135857 | GTCCCGAGCCAAAGCCGA | 2803 | 2820 | sooossssssssssooss | 5-7-6 | 2044 |
| 664525 | 135841 | 135858 | AGTCCCGAGCCAAAGCCG | 2804 | 2821 | sooossssssssssooss | 5-8-5 | 2436 |
| 664735 | 135841 | 135859 | AAGTCCCGAGCCAAAGCCG | 2804 | 2822 | sooossssssssssooss | 5-9-5 | 2437 |
| 664682 | 135841 | 135860 | GAAGTCCCGAGCCAAAGCCG | 2804 | 2823 | sooossssssssssssooss | 5-10-5 | 2438 |
| 664788 | 135841 | 135858 | AGTCCCGAGCCAAAGCCG | 2804 | 2821 | sooossssssssssooss | 5-7-6 | 2436 |
| 664526 | 135842 | 135859 | AAGTCCCGAGCCAAAGCC | 2805 | 2822 | sooossssssssssooss | 5-8-5 | 2439 |
| 664736 | 135842 | 135860 | GAAGTCCCGAGCCAAAGCC | 2805 | 2823 | sooossssssssssooss | 5-9-5 | 2440 |
| 664683 | 135842 | 135861 | TGAAGTCCCGAGCCAAAGCC | 2805 | 2824 | sooossssssssssssooss | 5-10-5 | 2441 |
| 664789 | 135842 | 135859 | AAGTCCCGAGCCAAAGCC | 2805 | 2822 | sooossssssssssooss | 5-7-6 | 2439 |
| 622116 | 135843 | 135860 | GAAGTCCCGAGCCAAAGC | 2806 | 2823 | sooossssssssssooss | 5-8-5 | 2045 |
| 664737 | 135843 | 135861 | TGAAGTCCCGAGCCAAAGC | 2806 | 2824 | sooossssssssssooss | 5-9-5 | 2442 |
| 664684 | 135843 | 135862 | TTGAAGTCCCGAGCCAAAGC | 2806 | 2825 | sooossssssssssssooss | 5-10-5 | 2443 |
| 664790 | 135843 | 135860 | GAAGTCCCGAGCCAAAGC | 2806 | 2823 | sooossssssssssooss | 5-7-6 | 2045 |
| 664527 | 135844 | 135861 | TGAAGTCCCGAGCCAAAG | 2807 | 2824 | sooossssssssssooss | 5-8-5 | 2478 |
| 664738 | 135844 | 135862 | TTGAAGTCCCGAGCCAAAG | 2807 | 2825 | sooossssssssssooss | 5-9-5 | 2532 |
| 664685 | 135844 | 135863 | TTTGAAGTCCCGAGCCAAAG | 2807 | 2826 | sooossssssssssssooss | 5-10-5 | 2533 |
| 664791 | 135844 | 135861 | TGAAGTCCCGAGCCAAAG | 2807 | 2824 | sooossssssssssooss | 5-7-6 | 2478 |
| 664528 | 135845 | 135862 | TTGAAGTCCCGAGCCAAA | 2808 | 2825 | sooossssssssssooss | 5-8-5 | 2479 |
| 664739 | 135845 | 135863 | TTTGAAGTCCCGAGCCAAA | 2808 | 2826 | sooossssssssssooss | 5-9-5 | 2534 |
| 664686 | 135845 | 135864 | TTTTGAAGTCCCGAGCCAAA | 2808 | 2827 | sooossssssssssssooss | 5-10-5 | 2535 |
| 664792 | 135845 | 135862 | TTGAAGTCCCGAGCCAAA | 2808 | 2825 | sooossssssssssooss | 5-7-6 | 2479 |
| 622117 | 135846 | 135863 | TTTGAAGTCCCGAGCCAA | 2809 | 2826 | sooossssssssssooss | 5-8-5 | 2046 |
| 664740 | 135846 | 135864 | TTTTGAAGTCCCGAGCCAA | 2809 | 2827 | sooossssssssssooss | 5-9-5 | 2536 |
| 664687 | 135846 | 135865 | ATTTTGAAGTCCCGAGCCAA | 2809 | 2828 | sooossssssssssssooss | 5-10-5 | 2537 |
| 664793 | 135846 | 135863 | TTTGAAGTCCCGAGCCAA | 2809 | 2826 | sooossssssssssooss | 5-7-6 | 2538 |
| 664529 | 135847 | 135864 | TTTTGAAGTCCCGAGCCA | 2810 | 2827 | sooossssssssssooss | 5-8-5 | 2480 |
| 664741 | 135847 | 135865 | ATTTTGAAGTCCCGAGCCA | 2810 | 2828 | sooossssssssssooss | 5-9-5 | 2539 |

TABLE 56-continued

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664688 | 135847 | 135866 | GATTTTGAAGTCCCGAGCCA | 2810 | 2829 | sooosssssssssssooss | 5-10-5 | 2540 |
| 664794 | 135847 | 135864 | TTTTGAAGTCCCGAGCCA | 2810 | 2827 | sooossssssssoooss | 5-7-6 | 2480 |
| 664530 | 135848 | 135865 | ATTTTGAAGTCCCGAGCC | 2811 | 2828 | sooossssssssssooss | 5-8-5 | 2481 |
| 664742 | 135848 | 135866 | GATTTTGAAGTCCCGAGCC | 2811 | 2829 | sooosssssssssssooss | 5-9-5 | 2541 |
| 664689 | 135848 | 135867 | TGATTTTGAAGTCCCGAGCC | 1644 | 1663 | sooosssssssssssooss | 5-10-5 | 56 |
| 664795 | 135848 | 135865 | ATTTTGAAGTCCCGAGCC | 2811 | 2828 | sooossssssssoooss | 5-7-6 | 2481 |
| 622118 | 135849 | 135866 | GATTTTGAAGTCCCGAGC | 2812 | 2829 | sooossssssssssooss | 5-8-5 | 2047 |
| 664743 | 135849 | 135867 | TGATTTTGAAGTCCCGAGC | 2812 | 2830 | sooosssssssssssooss | 5-9-5 | 2542 |
| 664690 | 135849 | 135868 | CTGATTTTGAAGTCCCGAGC | 2812 | 2831 | sooosssssssssssooss | 5-10-5 | 464 |
| 664796 | 135849 | 135866 | GATTTTGAAGTCCCGAGC | 2812 | 2829 | sooossssssssoooss | 5-7-6 | 2047 |
| 664531 | 135850 | 135867 | TGATTTTGAAGTCCCGAG | 2813 | 2830 | sooossssssssssooss | 5-8-5 | 2482 |
| 664744 | 135850 | 135868 | CTGATTTTGAAGTCCCGAG | 2813 | 2831 | sooosssssssssssooss | 5-9-5 | 2543 |
| 664691 | 135850 | 135869 | ACTGATTTTGAAGTCCCGAG | 2813 | 2832 | sooosssssssssssooss | 5-10-5 | 2544 |
| 664797 | 135850 | 135867 | TGATTTTGAAGTCCCGAG | 2813 | 2830 | sooossssssssoooss | 5-7-6 | 2482 |
| 664532 | 135851 | 135868 | CTGATTTTGAAGTCCCGA | 2814 | 2831 | sooossssssssssooss | 5-8-5 | 2483 |
| 664745 | 135851 | 135869 | ACTGATTTTGAAGTCCCGA | 2814 | 2832 | sooosssssssssssooss | 5-9-5 | 2545 |
| 664692 | 135851 | 135870 | CACTGATTTTGAAGTCCCGA | 2814 | 2833 | sooosssssssssssooss | 5-10-5 | 2546 |
| 664798 | 135851 | 135868 | CTGATTTTGAAGTCCCGA | 2814 | 2831 | sooossssssssoooss | 5-7-6 | 2483 |
| 622119 | 135852 | 135869 | ACTGATTTTGAAGTCCCG | 2815 | 2832 | sooossssssssssooss | 5-8-5 | 2048 |
| 664746 | 135852 | 135870 | CACTGATTTTGAAGTCCCG | 2815 | 2833 | sooosssssssssssooss | 5-9-5 | 2547 |
| 664693 | 135852 | 135871 | TCACTGATTTTGAAGTCCCG | 2815 | 2834 | sooosssssssssssooss | 5-10-5 | 2548 |
| 664799 | 135852 | 135869 | ACTGATTTTGAAGTCCCG | 2815 | 2832 | sooossssssssoooss | 5-7-6 | 2549 |
| 664533 | 135853 | 135870 | CACTGATTTTGAAGTCCC | 2816 | 2833 | sooossssssssssooss | 5-8-5 | 2370 |
| 664747 | 135853 | 135871 | TCACTGATTTTGAAGTCCC | 2816 | 2834 | sooosssssssssssooss | 5-9-5 | 2371 |
| 664694 | 135853 | 135872 | ATCACTGATTTTGAAGTCCC | 1649 | 1668 | sooosssssssssssooss | 5-10-5 | 57 |
| 664800 | 135853 | 135870 | CACTGATTTTGAAGTCCC | 2816 | 2833 | sooossssssssoooss | 5-7-6 | 2370 |
| 664534 | 135854 | 135871 | TCACTGATTTTGAAGTCC | 2817 | 2834 | sooossssssssssooss | 5-8-5 | 2372 |
| 664748 | 135854 | 135872 | ATCACTGATTTTGAAGTCC | 2817 | 2835 | sooosssssssssssooss | 5-9-5 | 2373 |
| 664695 | 135854 | 135873 | CATCACTGATTTTGAAGTCC | 2817 | 2836 | sooosssssssssssooss | 5-10-5 | 2374 |
| 664801 | 135854 | 135871 | TCACTGATTTTGAAGTCC | 2817 | 2834 | sooossssssssoooss | 5-7-6 | 2372 |
| 622120 | 135855 | 135872 | ATCACTGATTTTGAAGTC | 2818 | 2835 | sooossssssssssooss | 5-8-5 | 1668 |
| 664749 | 135855 | 135873 | CATCACTGATTTTGAAGTC | 2818 | 2836 | sooosssssssssssooss | 5-9-5 | 2375 |
| 664696 | 135855 | 135874 | CCATCACTGATTTTGAAGTC | 2818 | 2837 | sooosssssssssssooss | 5-10-5 | 2376 |
| 664802 | 135855 | 135872 | ATCACTGATTTTGAAGTC | 2818 | 2835 | sooossssssssoooss | 5-7-6 | 1668 |
| 664535 | 135856 | 135873 | CATCACTGATTTTGAAGT | 2819 | 2836 | sooossssssssssooss | 5-8-5 | 2377 |
| 664750 | 135856 | 135874 | CCATCACTGATTTTGAAGT | 2819 | 2837 | sooosssssssssssooss | 5-9-5 | 2378 |

TABLE 56-continued

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664697 | 135856 | 135875 | CCCATCACTGATTTTGAAGT | 2819 | 2838 | sooosssssssssssooss | 5-10-5 | 2379 |
| 664803 | 135856 | 135873 | CATCACTGATTTTGAAGT | 2819 | 2836 | sooosssssssssooss | 5-7-6 | 2377 |
| 664536 | 135857 | 135874 | CCATCACTGATTTTGAAG | 2820 | 2837 | soosssssssssooss | 5-8-5 | 2380 |
| 664751 | 135857 | 135875 | CCCATCACTGATTTTGAAG | 2820 | 2838 | sooossssssssssooss | 5-9-5 | 2381 |
| 664698 | 135857 | 135876 | TCCCATCACTGATTTTGAAG | 2820 | 2839 | sooosssssssssssooss | 5-10-5 | 2382 |
| 664804 | 135857 | 135874 | CCATCACTGATTTTGAAG | 2820 | 2837 | sooosssssssssooss | 5-7-6 | 2380 |
| 622121 | 135858 | 135875 | CCCATCACTGATTTTGAA | 2821 | 2838 | soosssssssssooss | 5-8-5 | 1669 |
| 664752 | 135858 | 135876 | TCCCATCACTGATTTTGAA | 2821 | 2839 | sooossssssssssooss | 5-9-5 | 2383 |
| 664699 | 135858 | 135877 | CTCCCATCACTGATTTTGAA | 2821 | 2840 | sooosssssssssssooss | 5-10-5 | 2384 |
| 664805 | 135858 | 135875 | CCCATCACTGATTTTGAA | 2821 | 2838 | sooosssssssssooss | 5-7-6 | 1669 |
| 664537 | 135859 | 135876 | TCCCATCACTGATTTTGA | 2822 | 2839 | soosssssssssooss | 5-8-5 | 2385 |
| 664753 | 135859 | 135877 | CTCCCATCACTGATTTTGA | 2822 | 2840 | sooossssssssssooss | 5-9-5 | 2386 |
| 664700 | 135859 | 135878 | ACTCCCATCACTGATTTTGA | 2822 | 2841 | sooosssssssssssooss | 5-10-5 | 2387 |
| 664806 | 135859 | 135876 | TCCCATCACTGATTTTGA | 2822 | 2839 | sooosssssssssooss | 5-7-6 | 2385 |
| 664538 | 135860 | 135877 | CTCCCATCACTGATTTTG | 2823 | 2840 | soosssssssssooss | 5-8-5 | 2388 |
| 664754 | 135860 | 135878 | ACTCCCATCACTGATTTTG | 2823 | 2841 | sooossssssssssooss | 5-9-5 | 2389 |
| 664701 | 135860 | 135879 | TACTCCCATCACTGATTTTG | 2823 | 2842 | sooosssssssssssooss | 5-10-5 | 2390 |
| 664807 | 135860 | 135877 | CTCCCATCACTGATTTTG | 2823 | 2840 | sooosssssssssooss | 5-7-6 | 2388 |
| 622122 | 135861 | 135878 | ACTCCCATCACTGATTTT | 2824 | 2841 | soosssssssssooss | 5-8-5 | 1670 |
| 664755 | 135861 | 135879 | TACTCCCATCACTGATTTT | 2824 | 2842 | sooossssssssssooss | 5-9-5 | 2391 |
| 664702 | 135861 | 135880 | TTACTCCCATCACTGATTTT | 2824 | 2843 | sooosssssssssssooss | 5-10-5 | 2392 |
| 664808 | 135861 | 135878 | ACTCCCATCACTGATTTT | 2824 | 2841 | sooosssssssssooss | 5-7-6 | 1670 |
| 664539 | 135862 | 135879 | TACTCCCATCACTGATTT | 2825 | 2842 | soosssssssssooss | 5-8-5 | 2393 |
| 664756 | 135862 | 135880 | TTACTCCCATCACTGATTT | 2825 | 2843 | sooossssssssssooss | 5-9-5 | 2394 |
| 664703 | 135862 | 135881 | CTTACTCCCATCACTGATTT | 2825 | 2844 | sooosssssssssssooss | 5-10-5 | 2395 |
| 664809 | 135862 | 135879 | TACTCCCATCACTGATTT | 2825 | 2842 | sooosssssssssooss | 5-7-6 | 2393 |
| 664540 | 135863 | 135880 | TTACTCCCATCACTGATT | 2826 | 2843 | soosssssssssooss | 5-8-5 | 2396 |
| 664757 | 135863 | 135881 | CTTACTCCCATCACTGATT | 2826 | 2844 | sooossssssssssooss | 5-9-5 | 2397 |
| 664704 | 135863 | 135882 | TCTTACTCCCATCACTGATT | 2826 | 2845 | sooosssssssssssooss | 5-10-5 | 2398 |
| 664810 | 135863 | 135880 | TTACTCCCATCACTGATT | 2826 | 2843 | sooosssssssssooss | 5-7-6 | 2396 |
| 622123 | 135864 | 135881 | CTTACTCCCATCACTGAT | 2827 | 2844 | soosssssssssooss | 5-8-5 | 1671 |
| 664758 | 135864 | 135882 | TCTTACTCCCATCACTGAT | 2827 | 2845 | sooossssssssssooss | 5-9-5 | 2399 |
| 664705 | 135864 | 135883 | CTCTTACTCCCATCACTGAT | 2827 | 2846 | sooosssssssssssooss | 5-10-5 | 2400 |
| 664811 | 135864 | 135881 | CTTACTCCCATCACTGAT | 2827 | 2844 | sooosssssssssooss | 5-7-6 | 1671 |
| 664541 | 135865 | 135882 | TCTTACTCCCATCACTGA | 2828 | 2845 | soosssssssssooss | 5-8-5 | 2401 |
| 664759 | 135865 | 135883 | CTCTTACTCCCATCACTGA | 2828 | 2846 | sooossssssssssooss | 5-9-5 | 2402 |
| 664706 | 135865 | 135884 | GCTCTTACTCCCATCACTGA | 2828 | 2847 | sooosssssssssssooss | 5-10-5 | 2403 |

TABLE 56-continued

MOE gapmers targeting SEQ ID NOs: 1 and 2

| ISIS NO | SEQ ID NO: 1 Start Site | SEQ ID NO: 1 Stop Site | Sequence | SEQ ID NO: 2 Start Site | SEQ ID NO: 2 Stop Site | Linkage chemistry | Motif | SEQ ID NO |
|---|---|---|---|---|---|---|---|---|
| 664812 | 135865 | 135882 | TCTTACTCCCATCACTGA | 2828 | 2845 | sooossssssssssooss | 5-7-6 | 2401 |
| 664542 | 135866 | 135883 | CTCTTACTCCCATCACTG | 2829 | 2846 | sooossssssssssooss | 5-8-5 | 2404 |
| 664760 | 135866 | 135884 | GCTCTTACTCCCATCACTG | 2829 | 2847 | sooossssssssssooss | 5-9-5 | 2405 |
| 664707 | 135866 | 135885 | TGCTCTTACTCCCATCACTG | 2829 | 2848 | sooosssssssssssooss | 5-10-5 | 2406 |
| 664813 | 135866 | 135883 | CTCTTACTCCCATCACTG | 2829 | 2846 | sooossssssssssooss | 5-7-6 | 2404 |
| 622124 | 135867 | 135884 | GCTCTTACTCCCATCACT | 2830 | 2847 | sooossssssssssooss | 5-8-5 | 1672 |
| 664761 | 135867 | 135885 | TGCTCTTACTCCCATCACT | 2830 | 2848 | sooossssssssssooss | 5-9-5 | 2407 |
| 664708 | 135867 | 135886 | TTGCTCTTACTCCCATCACT | 2830 | 2849 | sooosssssssssssooss | 5-10-5 | 2408 |
| 664814 | 135867 | 135884 | GCTCTTACTCCCATCACT | 2830 | 2847 | sooossssssssssooss | 5-7-6 | 1672 |
| 623993 | 135868 | 135885 | TGCTCTTACTCCCATCAC | 2831 | 2848 | sooossssssssssooss | 5-8-5 | 2306 |
| 664762 | 135868 | 135886 | TTGCTCTTACTCCCATCAC | 2831 | 2849 | sooossssssssssooss | 5-9-5 | 2409 |
| 664709 | 135868 | 135887 | TTTGCTCTTACTCCCATCAC | 2831 | 2850 | sooosssssssssssooss | 5-10-5 | 2410 |
| 664815 | 135868 | 135885 | TGCTCTTACTCCCATCAC | 2831 | 2848 | sooossssssssssooss | 5-7-6 | 2306 |
| 623994 | 135869 | 135886 | TTGCTCTTACTCCCATCA | 2832 | 2849 | sooossssssssssooss | 5-8-5 | 2307 |
| 664763 | 135869 | 135887 | TTTGCTCTTACTCCCATCA | 2832 | 2850 | sooossssssssssooss | 5-9-5 | 2411 |
| 664710 | 135869 | 135888 | ATTTGCTCTTACTCCCATCA | 2832 | 2851 | sooosssssssssssooss | 5-10-5 | 2412 |
| 664816 | 135869 | 135886 | TTGCTCTTACTCCCATCA | 2832 | 2849 | sooossssssssssooss | 5-7-6 | 2307 |
| 622125 | 135870 | 135887 | TTTGCTCTTACTCCCATC | 2833 | 2850 | sooossssssssssooss | 5-8-5 | 1673 |
| 664764 | 135870 | 135888 | ATTTGCTCTTACTCCCATC | 2833 | 2851 | sooossssssssssooss | 5-9-5 | 2413 |
| 664711 | 135870 | 135889 | AATTTGCTCTTACTCCCATC | 2833 | 2852 | sooosssssssssssooss | 5-10-5 | 2414 |
| 664817 | 135870 | 135887 | TTTGCTCTTACTCCCATC | 2833 | 2850 | sooossssssssssooss | 5-7-6 | 1673 |
| 623995 | 135871 | 135888 | ATTTGCTCTTACTCCCAT | 2834 | 2851 | sooossssssssssooss | 5-8-5 | 2308 |
| 664765 | 135871 | 135889 | AATTTGCTCTTACTCCCAT | 2834 | 2852 | sooossssssssssooss | 5-9-5 | 2415 |
| 664712 | 135871 | 135890 | AAATTTGCTCTTACTCCCAT | 2834 | 2853 | sooosssssssssssooss | 5-10-5 | 2416 |
| 664818 | 135871 | 135888 | ATTTGCTCTTACTCCCAT | 2834 | 2851 | sooossssssssssooss | 5-7-6 | 2308 |
| 623996 | 135872 | 135889 | AATTTGCTCTTACTCCCA | 2835 | 2852 | sooossssssssssooss | 5-8-5 | 2309 |
| 664766 | 135872 | 135890 | AAATTTGCTCTTACTCCCA | 2835 | 2853 | sooossssssssssooss | 5-9-5 | 2417 |
| 664713 | 135872 | 135891 | GAAATTTGCTCTTACTCCCA | 2835 | 2854 | sooosssssssssssooss | 5-10-5 | 2418 |
| 664819 | 135872 | 135889 | AATTTGCTCTTACTCCCA | 2835 | 2852 | sooossssssssssooss | 5-7-6 | 2309 |

Example 15: Intracerebroventricular Administration of Antisense Oligonucleotides Against Human Tau mRNA in Htau Mice Selected compounds were tested for efficacy by ICV administration in human tau transgenic mice (Duff et al., Neurobiology of Disease 7:87-98, 2000).

Treatment and Surgery

Groups of 4 mice each were administered ISIS 613255, ISIS 613329, ISIS 613344, ISIS 613361, ISIS 613369, ISIS 613370, ISIS 613397, ISIS 613045, ISIS 613099, ISIS 613118, ISIS 613136 with a 200 µg dose delivered by ICV bolus injection. A control group of 2 mice was similarly treated with ISIS 424880 and a control group of 4 mice was similarly treated with PBS. All procedures were performed under isofluorane anesthesia and in accordance with IACUC regulations. For mouse ICV bolus injections, the antisense oligonucleotide was injected into the right lateral ventricle of human tau transgenic mice. Ten microliters of solution containing 300 µg of oligonucleotide in PBS was injected over approximately 10 seconds. Tissue was collected 14 days after oligonucleotide administration.

RNA Analysis

On day 14 after the oligonucleotide administration, RNA was extracted from the hippocampus, spinal cord and cortex for real-time PCR analysis of tau mRNA levels. Human tau mRNA levels were measured using the human primer probe set RTS3104. Results were calculated as percent inhibition of human tau mRNA expression compared to the control. All the antisense oligonucleotides effect significant inhibition of human tau mRNA levels.

TABLE 57

Percent reduction of human tau mRNA levels in hTau mice

| ISIS No | Cortex | Hippocampus | Spinal Cord |
|---|---|---|---|
| 613255 | 30 | 46 | 36 |
| 613329 | 20 | 69 | 67 |
| 613344 | 41 | 42 | 34 |
| 613361 | 69 | 57 | 72 |
| 613369 | 17 | 48 | 46 |
| 613370 | 42 | 61 | 63 |
| 613397 | 33 | 41 | 57 |
| 613045 | 12 | 38 | 47 |
| 613099 | 42 | 55 | 54 |
| 613118 | 64 | 73 | 58 |
| 613136 | 26 | 39 | 27 |
| 424880 | 50 | 53 | 55 |

Example 16: Antisense Inhibition of Human Tau in SH-SY5Y Cells 5-7-6 MOE, 5-8-5 MOE, 5-9-5 MOE, and 5-10-5 MOE Gapmers The antisense oligonucleotides described in the Examples above, as well as newly designed antisense oligonucleotides targeting a human tau nucleic acid, were tested in a series of experiments that had similar culture conditions. The results for each experiment are presented in separate tables shown below. Cultured SH-SY5Y cells were transfected using electroporation with 8,000 nM antisense oligonucleotide. After a treatment period of approximately 24 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells.

The newly designed chimeric antisense oligonucleotides in the Tables below were designed as 5-7-6 MOE, 5-8-5 MOE, 5-9-5 MOE, or 5-10-5 MOE gapmers. The 5-7-6 MOE gapmers are 18 nucleosides in length, wherein the central gap segment comprises of seven 2'-deoxynucleosides and is flanked by wing segments on the 5' direction and the 3' direction comprising five and six nucleosides respectively. The 5-8-5 MOE gapmers are 18 nucleosides in length, wherein the central gap segment comprises of eight 2'-deoxynucleosides and is flanked by wing segments on the 5' direction and the 3' direction comprising five nucleosides each. The 5-9-5 MOE gapmers are 19 nucleosides in length, wherein the central gap segment comprises of nine 2'-deoxynucleosides and is flanked by wing segments on the 5' direction and the 3' direction comprising five nucleosides each. The 5-10-5 MOE gapmers are 20 nucleosides in length, wherein the central gap segment comprises of ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. The internucleoside linkages throughout each gapmer are either phosphorothioate linkages or phosphodiester linkages. The 'Linkage Chemistry' column describes the internucleoside linkages of each oligonucleotide. 's' indicates phosphorothioate linkage and 'o' indicates phosphodiester linkage. All cytosine residues throughout each gapmer are 5-methylcytosines.

"Start site" indicates the 5'-most nucleoside to which the gapmer is targeted in the human gene sequence. "Stop site" indicates the 3'-most nucleoside to which the gapmer is targeted in the human gene sequence. Each gapmer listed in the Table below is targeted to either the human tau genomic sequence, designated herein as SEQ ID NO: 1 (GENBANK Accession No. NT_010783.15 truncated from nucleotides 9240000 to 9381000) or to the human tau mRNA sequence, designated herein as SEQ ID NO: 2 (GENBANK Accession No. NM_001123066.3). 'n/a' indicates that the antisense oligonucleotide does not target that particular gene sequence with 100% complementarity.

TABLE 58

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 623965 | 73880 | 73897 | TGATCTTCCATCACTTCG | n/a | n/a | sooosssssssssooss | 5-8-5 | 52 | 2278 |
| 620887 | 98891 98928 | 98908 98945 | GTTTTCAAACACACCTTC | n/a | n/a | sooosssssssssooss | 5-8-5 | 91 | 665 |
| 664511 | 135820 | 135837 | GACAAAAGCAGGTTAAGT | 2783 | 2800 | sooosssssssssooss | 5-8-5 | 65 | 2331 |
| 664767 | 135820 | 135837 | GACAAAAGCAGGTTAAGT | 2783 | 2800 | sooossssssssoooss | 5-7-6 | 21 | 2331 |
| 664512 | 135821 | 135838 | TGACAAAAGCAGGTTAAG | 2784 | 2801 | sooosssssssssooss | 5-8-5 | 60 | 2334 |
| 664768 | 135821 | 135838 | TGACAAAAGCAGGTTAAG | 2784 | 2801 | sooossssssssoooss | 5-7-6 | 30 | 2334 |
| 622109 | 135822 | 135839 | GTGACAAAAGCAGGTTAA | 2785 | 2802 | sooosssssssssooss | 5-8-5 | 72 | 2038 |
| 664769 | 135822 | 135839 | GTGACAAAAGCAGGTTAA | 2785 | 2802 | sooossssssssoooss | 5-7-6 | 49 | 2038 |
| 664513 | 135823 | 135840 | AGTGACAAAAGCAGGTTA | 2786 | 2803 | sooosssssssssooss | 5-8-5 | 56 | 2339 |
| 664770 | 135823 | 135840 | AGTGACAAAAGCAGGTTA | 2786 | 2803 | sooossssssssoooss | 5-7-6 | 45 | 2339 |

TABLE 58-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 664514 | 135824 | 135841 | GAGTGACAAAAGCAGGTT | 2787 | 2804 | sooossssssssssooss | 5-8-5 | 84 | 2342 |
| 664771 | 135824 | 135841 | GAGTGACAAAAGCAGGTT | 2787 | 2804 | sooossssssssssooss | 5-7-6 | 63 | 2342 |
| 622110 | 135825 | 135842 | CGAGTGACAAAAGCAGGT | 2788 | 2805 | sooossssssssssooss | 5-8-5 | 77 | 2039 |
| 664772 | 135825 | 135842 | CGAGTGACAAAAGCAGGT | 2788 | 2805 | sooossssssssssooss | 5-7-6 | 37 | 2039 |
| 664515 | 135826 | 135843 | CCGAGTGACAAAAGCAGG | 2789 | 2806 | sooossssssssssooss | 5-8-5 | 70 | 2347 |
| 664773 | 135826 | 135843 | CCGAGTGACAAAAGCAGG | 2789 | 2806 | sooossssssssssooss | 5-7-6 | 62 | 2347 |
| 664516 | 135827 | 135844 | GCCGAGTGACAAAAGCAG | 2790 | 2807 | sooossssssssssooss | 5-8-5 | 79 | 2350 |
| 664774 | 135827 | 135844 | GCCGAGTGACAAAAGCAG | 2790 | 2807 | sooossssssssssooss | 5-7-6 | 70 | 2350 |
| 622111 | 135828 | 135845 | AGCCGAGTGACAAAAGCA | 2791 | 2808 | sooossssssssssooss | 5-8-5 | 75 | 2040 |
| 664775 | 135828 | 135845 | AGCCGAGTGACAAAAGCA | 2791 | 2808 | sooossssssssssooss | 5-7-6 | 78 | 2040 |
| 664517 | 135829 | 135846 | AAGCCGAGTGACAAAAGC | 2792 | 2809 | sooossssssssssooss | 5-8-5 | 67 | 2355 |
| 664776 | 135829 | 135846 | AAGCCGAGTGACAAAAGC | 2792 | 2809 | sooossssssssssooss | 5-7-6 | 50 | 2355 |
| 664518 | 135830 | 135847 | AAAGCCGAGTGACAAAAG | 2793 | 2810 | sooossssssssssooss | 5-8-5 | 47 | 2358 |
| 664777 | 135830 | 135847 | AAAGCCGAGTGACAAAAG | 2793 | 2810 | sooossssssssssooss | 5-7-6 | 42 | 2358 |
| 622112 | 135831 | 135848 | CAAAGCCGAGTGACAAAA | 2794 | 2811 | sooossssssssssooss | 5-8-5 | 46 | 2041 |
| 664778 | 135831 | 135848 | CAAAGCCGAGTGACAAAA | 2794 | 2811 | sooossssssssssooss | 5-7-6 | 34 | 2041 |
| 664519 | 135832 | 135849 | CCAAAGCCGAGTGACAAA | 2795 | 2812 | sooossssssssssooss | 5-8-5 | 57 | 2363 |
| 664779 | 135832 | 135849 | CCAAAGCCGAGTGACAAA | 2795 | 2812 | sooossssssssssooss | 5-7-6 | 34 | 2363 |
| 664520 | 135833 | 135850 | GCCAAAGCCGAGTGACAA | 2796 | 2813 | sooossssssssssooss | 5-8-5 | 63 | 2366 |
| 664780 | 135833 | 135850 | GCCAAAGCCGAGTGACAA | 2796 | 2813 | sooossssssssssooss | 5-7-6 | 66 | 2366 |
| 622113 | 135834 | 135851 | AGCCAAAGCCGAGTGACA | 2797 | 2814 | sooossssssssssooss | 5-8-5 | 70 | 2042 |
| 664781 | 135834 | 135851 | AGCCAAAGCCGAGTGACA | 2797 | 2814 | sooossssssssssooss | 5-7-6 | 74 | 2042 |
| 664521 | 135835 | 135852 | GAGCCAAAGCCGAGTGAC | 2798 | 2815 | sooossssssssssooss | 5-8-5 | 71 | 2420 |
| 664782 | 135835 | 135852 | GAGCCAAAGCCGAGTGAC | 2798 | 2815 | sooossssssssssooss | 5-7-6 | 31 | 2420 |
| 664522 | 135836 | 135853 | CGAGCCAAAGCCGAGTGA | 2799 | 2816 | sooossssssssssooss | 5-8-5 | 50 | 2423 |
| 664783 | 135836 | 135853 | CGAGCCAAAGCCGAGTGA | 2799 | 2816 | sooossssssssssooss | 5-7-6 | 30 | 2423 |
| 622114 | 135837 | 135854 | CCGAGCCAAAGCCGAGTG | 2800 | 2817 | sooossssssssssooss | 5-8-5 | 72 | 2043 |
| 664784 | 135837 | 135854 | CCGAGCCAAAGCCGAGTG | 2800 | 2817 | sooossssssssssooss | 5-7-6 | 76 | 2043 |
| 664523 | 135838 | 135855 | CCCGAGCCAAAGCCGAGT | 2801 | 2818 | sooossssssssssooss | 5-8-5 | 70 | 2428 |
| 664785 | 135838 | 135855 | CCCGAGCCAAAGCCGAGT | 2801 | 2818 | sooossssssssssooss | 5-7-6 | 56 | 2428 |
| 664524 | 135839 | 135856 | TCCCGAGCCAAAGCCGAG | 2802 | 2819 | sooossssssssssooss | 5-8-5 | 55 | 2431 |
| 664786 | 135839 | 135856 | TCCCGAGCCAAAGCCGAG | 2802 | 2819 | sooossssssssssooss | 5-7-6 | 36 | 2431 |
| 622115 | 135840 | 135857 | GTCCCGAGCCAAAGCCGA | 2803 | 2820 | sooossssssssssooss | 5-8-5 | 59 | 2044 |
| 664787 | 135840 | 135857 | GTCCCGAGCCAAAGCCGA | 2803 | 2820 | sooossssssssssooss | 5-7-6 | 54 | 2044 |
| 664525 | 135841 | 135858 | AGTCCCGAGCCAAAGCCG | 2804 | 2821 | sooossssssssssooss | 5-8-5 | 74 | 2436 |
| 664788 | 135841 | 135858 | AGTCCCGAGCCAAAGCCG | 2804 | 2821 | sooossssssssssooss | 5-7-6 | 77 | 2436 |
| 664789 | 135842 | 135859 | AAGTCCCGAGCCAAAGCC | 2805 | 2822 | sooossssssssssooss | 5-7-6 | 42 | 2439 |

TABLE 58-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 664790 | 135843 | 135860 | GAAGTCCCGAGCCAAAGC | 2806 | 2823 | sooosssssssssooss | 5-7-6 | 38 | 2045 |
| 664791 | 135844 | 135861 | TGAAGTCCCGAGCCAAAG | 2807 | 2824 | sooosssssssssooss | 5-7-6 | 44 | 2478 |
| 664792 | 135845 | 135862 | TTGAAGTCCCGAGCCAAA | 2808 | 2825 | sooosssssssssooss | 5-7-6 | 44 | 2479 |
| 664793 | 135846 | 135863 | TTTGAAGTCCCGAGCCAA | 2809 | 2826 | sooosssssssssooss | 5-7-6 | 29 | 2046 |
| 664794 | 135847 | 135864 | TTTTGAAGTCCCGAGCCA | 2810 | 2827 | sooosssssssssooss | 5-7-6 | 32 | 2480 |
| 664795 | 135848 | 135865 | ATTTTGAAGTCCCGAGCC | 2811 | 2828 | sooosssssssssooss | 5-7-6 | 15 | 2481 |
| 664796 | 135849 | 135866 | GATTTTGAAGTCCCGAGC | 2812 | 2829 | sooosssssssssooss | 5-7-6 | 76 | 2047 |
| 664797 | 135850 | 135867 | TGATTTTGAAGTCCCGAG | 2813 | 2830 | sooosssssssssooss | 5-7-6 | 70 | 2482 |
| 664798 | 135851 | 135868 | CTGATTTTGAAGTCCCGA | 2814 | 2831 | sooosssssssssooss | 5-7-6 | 75 | 2483 |
| 664799 | 135852 | 135869 | ACTGATTTTGAAGTCCCG | 2815 | 2832 | sooosssssssssooss | 5-7-6 | 79 | 2048 |
| 664800 | 135853 | 135870 | CACTGATTTTGAAGTCCC | 2816 | 2833 | sooosssssssssooss | 5-7-6 | 82 | 2370 |
| 664534 | 135854 | 135871 | TCACTGATTTTGAAGTCC | 2817 | 2834 | sooosssssssssooss | 5-8-5 | 78 | 2372 |
| 664801 | 135854 | 135871 | TCACTGATTTTGAAGTCC | 2817 | 2834 | sooosssssssssooss | 5-7-6 | 29 | 2372 |
| 664802 | 135855 | 135872 | ATCACTGATTTTGAAGTC | 2818 | 2835 | sooosssssssssooss | 5-7-6 | 52 | 1668 |
| 664803 | 135856 | 135873 | CATCACTGATTTTGAAGT | 2819 | 2836 | sooosssssssssooss | 5-7-6 | 55 | 2377 |
| 664804 | 135857 | 135874 | CCATCACTGATTTTGAAG | 2820 | 2837 | sooosssssssssooss | 5-7-6 | 38 | 2380 |
| 664805 | 135858 | 135875 | CCCATCACTGATTTTGAA | 2821 | 2838 | sooosssssssssooss | 5-7-6 | 62 | 1669 |
| 664806 | 135859 | 135876 | TCCCATCACTGATTTTGA | 2822 | 2839 | sooosssssssssooss | 5-7-6 | 72 | 2385 |
| 664807 | 135860 | 135877 | CTCCCATCACTGATTTTG | 2823 | 2840 | sooosssssssssooss | 5-7-6 | 55 | 2388 |
| 664808 | 135861 | 135878 | ACTCCCATCACTGATTTT | 2824 | 2841 | sooosssssssssooss | 5-7-6 | 38 | 1670 |
| 664809 | 135862 | 135879 | TACTCCCATCACTGATTT | 2825 | 2842 | sooosssssssssooss | 5-7-6 | 54 | 2393 |
| 664810 | 135863 | 135880 | TTACTCCCATCACTGATT | 2826 | 2843 | sooosssssssssooss | 5-7-6 | 39 | 2396 |
| 664811 | 135864 | 135881 | CTTACTCCCATCACTGAT | 2827 | 2844 | sooosssssssssooss | 5-7-6 | 39 | 1671 |
| 664812 | 135865 | 135882 | TCTTACTCCCATCACTGA | 2828 | 2845 | sooosssssssssooss | 5-7-6 | 45 | 2401 |
| 664813 | 135866 | 135883 | CTCTTACTCCCATCACTG | 2829 | 2846 | sooosssssssssooss | 5-7-6 | 61 | 2404 |
| 664814 | 135867 | 135884 | GCTCTTACTCCCATCACT | 2830 | 2847 | sooosssssssssooss | 5-7-6 | 14 | 1672 |
| 664815 | 135868 | 135885 | TGCTCTTACTCCCATCAC | 2831 | 2848 | sooosssssssssooss | 5-7-6 | 70 | 2306 |
| 664816 | 135869 | 135886 | TTGCTCTTACTCCCATCA | 2832 | 2849 | sooosssssssssooss | 5-7-6 | 72 | 2307 |
| 664817 | 135870 | 135887 | TTTGCTCTTACTCCCATC | 2833 | 2850 | sooosssssssssooss | 5-7-6 | 62 | 1673 |
| 664818 | 135871 | 135888 | ATTTGCTCTTACTCCCAT | 2834 | 2851 | sooosssssssssooss | 5-7-6 | 69 | 2308 |
| 664819 | 135872 | 135889 | AATTTGCTCTTACTCCCA | 2835 | 2852 | sooosssssssssooss | 5-7-6 | 67 | 2309 |

TABLE 59

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665045 | 21592 | 21609 | ACATCCAAATAACAATAT | n/a | n/a | sooosssssssssooss | 5-8-5 | 1 | 2444 |
| 665046 | 21617 | 21634 | TCCTGTCTCAAACACCTA | n/a | n/a | sooosssssssssooss | 5-8-5 | 44 | 2445 |

TABLE 59-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665047 | 30083 | 30100 | AGCTTATCACAGTAGGTG | n/a | n/a | sooosssssssssooss | 5-8-5 | 94 | 2446 |
| 665048 | 30108 | 30125 | CCTTTGCTTCACACACCA | n/a | n/a | sooosssssssssooss | 5-8-5 | 67 | 2447 |
| 621013 | 30133 | 30150 | AGCTCACTACAGCAGGCA | n/a | n/a | sooosssssssssooss | 5-8-5 | 90 | 868 |
| 665049 | 30158 | 30175 | TGGTTCTACAACCTGCCC | n/a | n/a | sooosssssssssooss | 5-8-5 | 57 | 2448 |
| 665050 | 30183 | 30200 | CCTTTGTAACCTTGGAAC | n/a | n/a | sooosssssssssooss | 5-8-5 | 25 | 2449 |
| 665051 | 33838 | 33855 | AGTTAAAAGATGGCAACC | n/a | n/a | sooosssssssssooss | 5-8-5 | 32 | 2450 |
| 665052 | 33863 | 33880 | CTGGGCATTTTGATAAAA | n/a | n/a | sooosssssssssooss | 5-8-5 | 28 | 2451 |
| 621031 | 33888 | 33905 | GGTATAATTTGTTTGGAC | n/a | n/a | sooosssssssssooss | 5-8-5 | 85 | 886 |
| 665053 | 33913 | 33930 | AGTGCCAGACATTTTCAA | n/a | n/a | sooosssssssssooss | 5-8-5 | 20 | 2452 |
| 665054 | 33938 | 33955 | CTGGCACAACAGGCATTG | n/a | n/a | sooosssssssssooss | 5-8-5 | 25 | 2453 |
| 621041 | 35721 | 35738 | TTGCCATCTTGGACAGGG | n/a | n/a | sooosssssssssooss | 5-8-5 | 70 | 896 |
| 665055 | 35746 | 35763 | GTGGTACAGAGGCTGTGT | n/a | n/a | sooosssssssssooss | 5-8-5 | 47 | 2454 |
| 665056 | 35771 | 35788 | TTGCAGATTCTGAATACC | n/a | n/a | sooosssssssssooss | 5-8-5 | 78 | 2455 |
| 665057 | 64499 | 64516 | TATGATTCCCAGGAGTCT | n/a | n/a | sooosssssssssooss | 5-8-5 | 0 | 2456 |
| 621181 | 64543 | 64560 | GTAGGTGTCATCATCATC | n/a | n/a | sooosssssssssooss | 5-8-5 | 77 | 1113 |
| 665058 | 64568 | 64585 | GTGACCCTTCAGGGCAAT | n/a | n/a | sooosssssssssooss | 5-8-5 | 35 | 2457 |
| 665059 | 64593 | 64610 | ATGCAGGTGCCTTGCAGG | n/a | n/a | sooosssssssssooss | 5-8-5 | 36 | 2458 |
| 623965 | 73880 | 73897 | TGATCTTCCATCACTTCG | n/a | n/a | sooosssssssssooss | 5-8-5 | 48 | 2278 |
| 665060 | 77364 | 77381 | CCTGCTGCCAACAGTAGA | n/a | n/a | sooosssssssssooss | 5-8-5 | 51 | 2459 |
| 665061 | 77389 | 77406 | CCCTCACGGGCTGTTGTG | n/a | n/a | sooosssssssssooss | 5-8-5 | 20 | 2460 |
| 621236 | 77414 | 77431 | TCATCTGTGAAGCGGACG | 73377 | 73394 | sooosssssssssooss | 5-8-5 | 79 | 706 |
| 665062 | 77439 | 77456 | ACGGTCTGAGCATGAGGC | n/a | n/a | sooosssssssssooss | 5-8-5 | 77 | 2461 |
| 665063 | 77464 | 77481 | AGCCATGGACCTGCTCTG | n/a | n/a | sooosssssssssooss | 5-8-5 | 48 | 2462 |
| 665064 | 77731 | 77748 | GACAGTATACCCCACATC | n/a | n/a | sooosssssssssooss | 5-8-5 | 48 | 2463 |
| 621238 | 77781 | 77798 | GTTATTTTGGAACAGTTT | 73744 | 73761 | sooosssssssssooss | 5-8-5 | 89 | 708 |
| 665065 | 78142 | 78159 | AAGAGTGGTAAAACCTAC | n/a | n/a | sooosssssssssooss | 5-8-5 | 51 | 2464 |
| 665066 | 80259 | 80276 | GCTCACCAGCAGGAACTT | n/a | n/a | sooosssssssssooss | 5-8-5 | 56 | 2465 |
| 665067 | 80284 | 80301 | AAGGGCCCAGTGTAGCAC | n/a | n/a | sooosssssssssooss | 5-8-5 | 66 | 2466 |
| 621251 | 80309 | 80326 | AGTCATTATCATGTCACC | 76272 | 76289 | sooosssssssssooss | 5-8-5 | 73 | 721 |
| 665068 | 80334 | 80351 | CCAATAAGTGGCAGTGAT | n/a | n/a | sooosssssssssooss | 5-8-5 | 49 | 2467 |
| 665069 | 80359 | 80376 | ACCATGCCTGGCAGATGA | n/a | n/a | sooosssssssssooss | 5-8-5 | 66 | 2468 |
| 665070 | 80799 | 80816 | CTTAGTCATCTTCCCTCA | n/a | n/a | sooosssssssssooss | 5-8-5 | 64 | 2469 |
| 665071 | 80824 | 80841 | ATTTCTGAATTCTTTGCC | n/a | n/a | sooosssssssssooss | 5-8-5 | 69 | 2470 |
| 621254 | 80849 | 80866 | GGTAACATGTAAAGCTTC | 76812 | 76829 | sooosssssssssooss | 5-8-5 | 76 | 724 |
| 665072 | 82508 | 82525 | CTTACACTCTGGAAGGTT | n/a | n/a | sooosssssssssooss | 5-8-5 | 74 | 2471 |
| 665073 | 82533 | 82550 | TATCCAGGGCTGAGCAGG | n/a | n/a | sooosssssssssooss | 5-8-5 | 38 | 2472 |
| 621263 | 82558 | 82575 | ATGGGCTTATCAATGCAT | 78521 | 78538 | sooosssssssssooss | 5-8-5 | 80 | 733 |

TABLE 59-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665074 | 82583 | 82600 | GGAGTCAATCTGCCCTGG | n/a | n/a | sooossssssssssooss | 5-8-5 | 54 | 2473 |
| 665075 | 82608 | 82625 | CTTCCCTGTGGCACTTTG | n/a | n/a | sooossssssssssooss | 5-8-5 | 29 | 2474 |
| 665076 | 89600 | 89617 | ATGCCTCACTCAACAAGG | n/a | n/a | sooossssssssssooss | 5-8-5 | 26 | 2475 |
| 665077 | 89625 | 89642 | CTCCACTTTGGGACCAGG | n/a | n/a | sooossssssssssooss | 5-8-5 | 87 | 2476 |
| 621302 | 89650 | 89667 | GCTATGACCTAGTAGGAA | n/a | n/a | sooossssssssssooss | 5-8-5 | 68 | 772 |
| 665078 | 89675 | 89692 | GGCACAGCACCCACATGC | n/a | n/a | sooossssssssssooss | 5-8-5 | 66 | 2477 |
| 665079 | 89700 | 89717 | GGTGATAAAAGTTCACTA | n/a | n/a | sooossssssssssooss | 5-8-5 | 63 | 2531 |
| 620887 | 98891 98928 | 98908 98945 | GTTTTCAAACACACCTTC | n/a | n/a | sooossssssssssooss | 5-8-5 | 91 | 665 |
| 664526 | 135842 | 135859 | AAGTCCCGAGCCAAAGCC | 2805 | 2822 | sooossssssssssooss | 5-8-5 | 55 | 2439 |
| 622116 | 135843 | 135860 | GAAGTCCCGAGCCAAAGC | 2806 | 2823 | sooossssssssssooss | 5-8-5 | 63 | 2045 |
| 664527 | 135844 | 135861 | TGAAGTCCCGAGCCAAAG | 2807 | 2824 | sooossssssssssooss | 5-8-5 | 40 | 2478 |
| 664528 | 135845 | 135862 | TTGAAGTCCCGAGCCAAA | 2808 | 2825 | sooossssssssssooss | 5-8-5 | 61 | 2479 |
| 622117 | 135846 | 135863 | TTTGAAGTCCCGAGCCAA | 2809 | 2826 | sooossssssssssooss | 5-8-5 | 55 | 2046 |
| 664529 | 135847 | 135864 | TTTTGAAGTCCCGAGCCA | 2810 | 2827 | sooossssssssssooss | 5-8-5 | 25 | 2480 |
| 664530 | 135848 | 135865 | ATTTTGAAGTCCCGAGCC | 2811 | 2828 | sooossssssssssooss | 5-8-5 | 38 | 2481 |
| 622118 | 135849 | 135866 | GATTTTGAAGTCCCGAGC | 2812 | 2829 | sooossssssssssooss | 5-8-5 | 63 | 2047 |
| 664531 | 135850 | 135867 | TGATTTTGAAGTCCCGAG | 2813 | 2830 | sooossssssssssooss | 5-8-5 | 66 | 2482 |
| 664532 | 135851 | 135868 | CTGATTTTGAAGTCCCGA | 2814 | 2831 | sooossssssssssooss | 5-8-5 | 73 | 2483 |
| 622119 | 135852 | 135869 | ACTGATTTTGAAGTCCCG | 2815 | 2832 | sooossssssssssooss | 5-8-5 | 66 | 2048 |
| 664533 | 135853 | 135870 | CACTGATTTTGAAGTCCC | 2816 | 2833 | sooossssssssssooss | 5-8-5 | 72 | 2370 |
| 664534 | 135854 | 135871 | TCACTGATTTTGAAGTCC | 2817 | 2834 | sooossssssssssooss | 5-8-5 | 61 | 2372 |
| 622120 | 135855 | 135872 | ATCACTGATTTTGAAGTC | 2818 | 2835 | sooossssssssssooss | 5-8-5 | 47 | 1668 |
| 664535 | 135856 | 135873 | CATCACTGATTTTGAAGT | 2819 | 2836 | sooossssssssssooss | 5-8-5 | 59 | 2377 |
| 664536 | 135857 | 135874 | CCATCACTGATTTTGAAG | 2820 | 2837 | sooossssssssssooss | 5-8-5 | 34 | 2380 |
| 622121 | 135858 | 135875 | CCCATCACTGATTTTGAA | 2821 | 2838 | sooossssssssssooss | 5-8-5 | 49 | 1669 |
| 664537 | 135859 | 135876 | TCCCATCACTGATTTTGA | 2822 | 2839 | sooossssssssssooss | 5-8-5 | 61 | 2385 |
| 664538 | 135860 | 135877 | CTCCCATCACTGATTTTG | 2823 | 2840 | sooossssssssssooss | 5-8-5 | 76 | 2388 |
| 622122 | 135861 | 135878 | ACTCCCATCACTGATTTT | 2824 | 2841 | sooossssssssssooss | 5-8-5 | 38 | 1670 |
| 664539 | 135862 | 135879 | TACTCCCATCACTGATTT | 2825 | 2842 | sooossssssssssooss | 5-8-5 | 57 | 2393 |
| 664540 | 135863 | 135880 | TTACTCCCATCACTGATT | 2826 | 2843 | sooossssssssssooss | 5-8-5 | 32 | 2396 |
| 622123 | 135864 | 135881 | CTTACTCCCATCACTGAT | 2827 | 2844 | sooossssssssssooss | 5-8-5 | 33 | 1671 |
| 664541 | 135865 | 135882 | TCTTACTCCCATCACTGA | 2828 | 2845 | sooossssssssssooss | 5-8-5 | 50 | 2401 |
| 664542 | 135866 | 135883 | CTCTTACTCCCATCACTG | 2829 | 2846 | sooossssssssssooss | 5-8-5 | 58 | 2404 |
| 622124 | 135867 | 135884 | GCTCTTACTCCCATCACT | 2830 | 2847 | sooossssssssssooss | 5-8-5 | 64 | 1672 |
| 623993 | 135868 | 135885 | TGCTCTTACTCCCATCAC | n/a | n/a | sooossssssssssooss | 5-8-5 | 65 | 2306 |
| 623994 | 135869 | 135886 | TTGCTCTTACTCCCATCA | n/a | n/a | sooossssssssssooss | 5-8-5 | 63 | 2307 |
| 622125 | 135870 | 135887 | TTTGCTCTTACTCCCATC | 2833 | 2850 | sooossssssssssooss | 5-8-5 | 75 | 1673 |

TABLE 59-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 623995 | 135871 | 135888 | ATTTGCTCTTACTCCCAT | n/a | n/a | sooossssssssssooss | 5-8-5 | 60 | 2308 |
| 623996 | 135872 | 135889 | AATTTGCTCTTACTCCCA | n/a | n/a | sooossssssssssooss | 5-8-5 | 72 | 2309 |

TABLE 60

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665043 | 73879 | 73897 | TGATCTTCCATCACTTCGA | 345 | 364 | sooossssssssssssooss | 5-9-5 | 67 | 2484 |
| 665044 | 98890 98927 | 98908 98945 | GTTTTCAAACACACCTTCA | n/a | n/a | sooossssssssssssooss | 5-9-5 | 90 | 2485 |
| 665081 | 120039 | 120057 | TTTTCTTACCACCCTAACA | n/a | n/a | sooossssssssssssooss | 5-9-5 | 28 | 2486 |
| 665082 | 120041 | 120059 | CGTTTTCTTACCACCCTAA | n/a | n/a | sooossssssssssssooss | 5-9-5 | 86 | 2487 |
| 665083 | 120045 | 120063 | AAACCGTTTTCTTACCACC | n/a | n/a | sooossssssssssssooss | 5-9-5 | 86 | 2488 |
| 665084 | 120047 | 120065 | AAAAACCGTTTTCTTACCA | n/a | n/a | sooossssssssssssooss | 5-9-5 | 65 | 2489 |
| 665085 | 120060 | 120078 | AGCTCATCAAAGCAAAAAC | n/a | n/a | sooossssssssssssooss | 5-9-5 | 65 | 2490 |
| 665086 | 120110 | 120128 | TCAAAGACTATGTATTTT | n/a | n/a | sooossssssssssssooss | 5-9-5 | 54 | 2491 |
| 665087 | 120389 | 120407 | TGTAAATAATTGCCAAGTG | n/a | n/a | sooossssssssssssooss | 5-9-5 | 61 | 2492 |
| 665088 | 120439 | 120457 | TAAGCCACCATGCCTGTAA | n/a | n/a | sooossssssssssssooss | 5-9-5 | 61 | 2493 |
| 665089 | 121711 | 121729 | TGGACCCGCCTACTTGCTC | n/a | n/a | sooossssssssssssooss | 5-9-5 | 85 | 2494 |
| 665090 | 121736 | 121754 | TTTCGATGAGTGACATGCG | n/a | n/a | sooossssssssssssooss | 5-9-5 | 50 | 2495 |
| 665091 | 121761 | 121779 | TGCTTGCTCGCAAGGACGC | n/a | n/a | sooossssssssssssooss | 5-9-5 | 80 | 2496 |
| 665092 | 121765 | 121783 | CGCCTGCTTGCTCGCAAGG | n/a | n/a | sooossssssssssssooss | 5-9-5 | 82 | 2497 |
| 665093 | 121767 | 121785 | CCCGCCTGCTTGCTCGCAA | n/a | n/a | sooossssssssssssooss | 5-9-5 | 92 | 2498 |
| 665094 | 121769 | 121787 | GACCCGCCTGCTTGCTCGC | n/a | n/a | sooossssssssssssooss | 5-9-5 | 91 | 2499 |
| 665095 | 121771 | 121789 | TGGACCCGCCTGCTTGCTC | n/a | n/a | sooossssssssssssooss | 5-9-5 | 83 | 2500 |
| 665096 | 121773 | 121791 | CCTGGACCCGCCTGCTTGC | n/a | n/a | sooossssssssssssooss | 5-9-5 | 88 | 2501 |
| 665097 | 121775 | 121793 | ACCCTGGACCCGCCTGCTT | n/a | n/a | sooossssssssssssooss | 5-9-5 | 60 | 2502 |
| 665098 | 121786 | 121804 | AGTGACACGCCACCCTGGA | n/a | n/a | sooossssssssssssooss | 5-9-5 | 62 | 2503 |
| 665099 | 121811 | 121829 | CCTTTGGTAGCCAGAAAAA | n/a | n/a | sooossssssssssssooss | 5-9-5 | 53 | 2504 |
| 665100 | 121817 | 121835 | TCTGCACCTTTGGTAGCCA | n/a | n/a | sooossssssssssssooss | 5-9-5 | 84 | 2505 |
| 665101 | 121938 | 121956 | ACAGCACGGCGCATGGAC | n/a | n/a | sooossssssssssssooss | 5-9-5 | 54 | 2506 |
| 665102 | 121940 | 121958 | CCACAGCACGGCGCATGGG | n/a | n/a | sooossssssssssssooss | 5-9-5 | 84 | 2507 |
| 665103 | 121942 | 121960 | AGCCACAGCACGGCGCATG | n/a | n/a | sooossssssssssssooss | 5-9-5 | 85 | 2508 |
| 664714 | 135820 | 135838 | TGACAAAAGCAGGTTAAGT | 2783 | 2801 | sooossssssssssssooss | 5-9-5 | 54 | 2332 |
| 664715 | 135821 | 135839 | GTGACAAAAGCAGGTTAAG | 2784 | 2802 | sooossssssssssssooss | 5-9-5 | 65 | 2335 |
| 664716 | 135822 | 135840 | AGTGACAAAAGCAGGTTAA | 2785 | 2803 | sooossssssssssssooss | 5-9-5 | 79 | 2337 |
| 664717 | 135823 | 135841 | GAGTGACAAAAGCAGGTTA | 2786 | 2804 | sooossssssssssssooss | 5-9-5 | 70 | 2340 |
| 664718 | 135824 | 135842 | CGAGTGACAAAAGCAGGTT | 2787 | 2805 | sooossssssssssssooss | 5-9-5 | 89 | 2343 |

TABLE 60-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 664719 | 135825 | 135843 | CCGAGTGACAAAAGCAGGT | 2788 | 2806 | sooosssssssssssooss | 5-9-5 | 84 | 2345 |
| 664720 | 135826 | 135844 | GCCGAGTGACAAAAGCAGG | 2789 | 2807 | sooosssssssssssooss | 5-9-5 | 71 | 2348 |
| 664721 | 135827 | 135845 | AGCCGAGTGACAAAAGCAG | 2790 | 2808 | sooosssssssssssooss | 5-9-5 | 81 | 2351 |
| 664722 | 135828 | 135846 | AAGCCGAGTGACAAAAGCA | 2791 | 2809 | sooosssssssssssooss | 5-9-5 | 68 | 2353 |
| 664723 | 135829 | 135847 | AAAGCCGAGTGACAAAAGC | 2792 | 2810 | sooosssssssssssooss | 5-9-5 | 51 | 2356 |
| 664724 | 135830 | 135848 | CAAAGCCGAGTGACAAAAG | 2793 | 2811 | sooosssssssssssooss | 5-9-5 | 47 | 2359 |
| 664725 | 135831 | 135849 | CCAAAGCCGAGTGACAAAA | 2794 | 2812 | sooosssssssssssooss | 5-9-5 | 69 | 2361 |
| 664726 | 135832 | 135850 | GCCAAAGCCGAGTGACAAA | 2795 | 2813 | sooosssssssssssooss | 5-9-5 | 76 | 2364 |
| 664727 | 135833 | 135851 | AGCCAAAGCCGAGTGACAA | 2796 | 2814 | sooosssssssssssooss | 5-9-5 | 64 | 2367 |
| 664728 | 135834 | 135852 | GAGCCAAAGCCGAGTGACA | 2797 | 2815 | sooosssssssssssooss | 5-9-5 | 78 | 2369 |
| 664729 | 135835 | 135853 | CGAGCCAAAGCCGAGTGAC | 2798 | 2816 | sooosssssssssssooss | 5-9-5 | 74 | 2421 |
| 664730 | 135836 | 135854 | CCGAGCCAAAGCCGAGTGA | 2799 | 2817 | sooosssssssssssooss | 5-9-5 | 76 | 2424 |
| 664731 | 135837 | 135855 | CCCGAGCCAAAGCCGAGTG | 2800 | 2818 | sooosssssssssssooss | 5-9-5 | 75 | 2426 |
| 664732 | 135838 | 135856 | TCCCGAGCCAAAGCCGAGT | 2801 | 2819 | sooosssssssssssooss | 5-9-5 | 80 | 2429 |
| 664733 | 135839 | 135857 | GTCCCGAGCCAAAGCCGAG | 2802 | 2820 | sooosssssssssssooss | 5-9-5 | 70 | 2432 |
| 664734 | 135840 | 135858 | AGTCCCGAGCCAAAGCCGA | 2803 | 2821 | sooosssssssssssooss | 5-9-5 | 59 | 2434 |
| 664735 | 135841 | 135859 | AAGTCCCGAGCCAAAGCCG | 2804 | 2822 | sooosssssssssssooss | 5-9-5 | 58 | 2437 |
| 664736 | 135842 | 135860 | GAAGTCCCGAGCCAAAGCC | 2805 | 2823 | sooosssssssssssooss | 5-9-5 | 76 | 2440 |
| 664737 | 135843 | 135861 | TGAAGTCCCGAGCCAAAGC | 2806 | 2824 | sooosssssssssssooss | 5-9-5 | 46 | 2442 |
| 664738 | 135844 | 135862 | TTGAAGTCCCGAGCCAAAG | 2807 | 2825 | sooosssssssssssooss | 5-9-5 | 46 | 2550 |
| 664739 | 135845 | 135863 | TTTGAAGTCCCGAGCCAAA | 2808 | 2826 | sooosssssssssssooss | 5-9-5 | 56 | 2551 |
| 664740 | 135846 | 135864 | TTTTGAAGTCCCGAGCCAA | 2809 | 2827 | sooosssssssssssooss | 5-9-5 | 44 | 2552 |
| 664741 | 135847 | 135865 | ATTTTGAAGTCCCGAGCCA | 2810 | 2828 | sooosssssssssssooss | 5-9-5 | 61 | 2553 |
| 664742 | 135848 | 135866 | GATTTTGAAGTCCCGAGCC | 2811 | 2829 | sooosssssssssssooss | 5-9-5 | 59 | 2554 |
| 664743 | 135849 | 135867 | TGATTTTGAAGTCCCGAGC | 2812 | 2830 | sooosssssssssssooss | 5-9-5 | 64 | 2555 |
| 664744 | 135850 | 135868 | CTGATTTTGAAGTCCCGAG | 2813 | 2831 | sooosssssssssssooss | 5-9-5 | 67 | 2556 |
| 664745 | 135851 | 135869 | ACTGATTTTGAAGTCCCGA | 2814 | 2832 | sooosssssssssssooss | 5-9-5 | 73 | 2557 |
| 664746 | 135852 | 135870 | CACTGATTTTGAAGTCCCG | 2815 | 2833 | sooosssssssssssooss | 5-9-5 | 86 | 2558 |
| 664747 | 135853 | 135871 | TCACTGATTTTGAAGTCCC | 2816 | 2834 | sooosssssssssssooss | 5-9-5 | 76 | 2371 |
| 664748 | 135854 | 135872 | ATCACTGATTTTGAAGTCC | 2817 | 2835 | sooosssssssssssooss | 5-9-5 | 74 | 2373 |
| 664749 | 135855 | 135873 | CATCACTGATTTTGAAGTC | 2818 | 2836 | sooosssssssssssooss | 5-9-5 | 50 | 2375 |
| 664750 | 135856 | 135874 | CCATCACTGATTTTGAAGT | 2819 | 2837 | sooosssssssssssooss | 5-9-5 | 57 | 2378 |
| 664751 | 135857 | 135875 | CCCATCACTGATTTTGAAG | 2820 | 2838 | sooosssssssssssooss | 5-9-5 | 64 | 2381 |
| 664752 | 135858 | 135876 | TCCCATCACTGATTTTGAA | 2821 | 2839 | sooosssssssssssooss | 5-9-5 | 59 | 2383 |
| 664753 | 135859 | 135877 | CTCCCATCACTGATTTTGA | 2822 | 2840 | sooosssssssssssooss | 5-9-5 | 73 | 2386 |
| 664754 | 135860 | 135878 | ACTCCCATCACTGATTTTG | 2823 | 2841 | sooosssssssssssooss | 5-9-5 | 75 | 2389 |
| 664755 | 135861 | 135879 | TACTCCCATCACTGATTTT | 2824 | 2842 | sooosssssssssssooss | 5-9-5 | 40 | 2391 |
| 664756 | 135862 | 135880 | TTACTCCCATCACTGATTT | 2825 | 2843 | sooosssssssssssooss | 5-9-5 | 43 | 2394 |

TABLE 60-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 664757 | 135863 | 135881 | CTTACTCCCATCACTGATT | 2826 | 2844 | sooossssssssssooss | 5-9-5 | 70 | 2397 |
| 664758 | 135864 | 135882 | TCTTACTCCCATCACTGAT | 2827 | 2845 | sooossssssssssooss | 5-9-5 | 61 | 2399 |
| 664759 | 135865 | 135883 | CTCTTACTCCCATCACTGA | 2828 | 2846 | sooossssssssssooss | 5-9-5 | 68 | 2402 |
| 664760 | 135866 | 135884 | GCTCTTACTCCCATCACTG | 2829 | 2847 | sooossssssssssooss | 5-9-5 | 82 | 2405 |
| 664761 | 135867 | 135885 | TGCTCTTACTCCCATCACT | 2830 | 2848 | sooossssssssssooss | 5-9-5 | 76 | 2407 |
| 664762 | 135868 | 135886 | TTGCTCTTACTCCCATCAC | 2831 | 2849 | sooossssssssssooss | 5-9-5 | 77 | 2409 |
| 664763 | 135869 | 135887 | TTTGCTCTTACTCCCATCA | 2832 | 2850 | sooossssssssssooss | 5-9-5 | 83 | 2411 |
| 664764 | 135870 | 135888 | ATTTGCTCTTACTCCCATC | 2833 | 2851 | sooossssssssssooss | 5-9-5 | 82 | 2413 |
| 664765 | 135871 | 135889 | AATTTGCTCTTACTCCCAT | 2834 | 2852 | sooossssssssssooss | 5-9-5 | 77 | 2415 |
| 664766 | 135872 | 135890 | AAATTTGCTCTTACTCCCA | 2835 | 2853 | sooossssssssssooss | 5-9-5 | 69 | 2417 |

TABLE 61

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665041 | 73879 | 73898 | GTGATCTTCCATCACTTCGA | 345 | 364 | sooossssssssssssooss | 5-10-5 | 86 | 25 |
| 665044 | 98890 98927 | 98908 98945 | GTTTTCAAACACACCTTCA | n/a | n/a | sooossssssssssooss | 5-9-5 | 90 | 2485 |
| 665201 | 102119 | 102138 | GGTTTGTTTTTAAACAATT | n/a | n/a | sooossssssssssssooss | 5-10-5 | 57 | 2509 |
| 665202 | 102144 | 102163 | GAACCCAATGAGAGTAGCAA | n/a | n/a | sooossssssssssssooss | 5-10-5 | 86 | 2510 |
| 665203 | 102169 | 102188 | TTGCCAAAATCAGGAATGGG | n/a | n/a | sooossssssssssssooss | 5-10-5 | 87 | 2511 |
| 665204 | 102194 | 102213 | TCAGGGCAATCTGGAAGCAT | n/a | n/a | sooossssssssssssooss | 5-10-5 | 79 | 2512 |
| 665205 | 102659 | 102678 | ACTCTCCACTCCATGTCAAT | n/a | n/a | sooossssssssssssooss | 5-10-5 | 26 | 2513 |
| 665206 | 102684 | 102703 | CAGAGCTCACAGCAATGATC | n/a | n/a | sooossssssssssssooss | 5-10-5 | 78 | 2514 |
| 665207 | 102709 | 102728 | TCAGCATGAGTTGTGCCAAG | n/a | n/a | sooossssssssssssooss | 5-10-5 | 91 | 2515 |
| 665208 | 102734 | 102753 | CCAGAGGAACTGTGTGCATT | n/a | n/a | sooossssssssssssooss | 5-10-5 | 79 | 2516 |
| 665209 | 102759 | 102778 | CCAAGTTCCCTGAGGACATT | n/a | n/a | sooossssssssssssooss | 5-10-5 | 13 | 2517 |
| 665210 | 112934 | 112953 | GTTGTGTTTCTGGTTTATT | n/a | n/a | sooossssssssssssooss | 5-10-5 | 96 | 2518 |
| 665211 | 112959 | 112978 | TTTTTTTTTAAGTTAGGAGT | n/a | n/a | sooossssssssssssooss | 5-10-5 | 20 | 2519 |
| 665212 | 112984 | 113003 | TTTTACTGGTTGTGTTTTCT | n/a | n/a | sooossssssssssssooss | 5-10-5 | 90 | 2520 |
| 665213 | 113009 | 113028 | CAGCTCTTAATGCTGTTATA | n/a | n/a | sooossssssssssssooss | 5-10-5 | 90 | 2521 |
| 665214 | 113498 | 113517 | TTCAGCTCCTGCACCCAGCA | n/a | n/a | sooossssssssssssooss | 5-10-5 | 54 | 2522 |
| 665215 | 113548 | 113567 | TTTTGCTTTTGCTCTGAAGA | n/a | n/a | sooossssssssssssooss | 5-10-5 | 57 | 2523 |
| 665216 | 115105 | 115124 | TTGCTATTAAATATAATGTA | n/a | n/a | sooossssssssssssooss | 5-10-5 | 35 | 2524 |
| 665217 | 115130 | 115149 | GCTTTTTAAAGTGACAACTG | n/a | n/a | sooossssssssssssooss | 5-10-5 | 78 | 2525 |
| 665218 | 115155 | 115174 | TTCCACATAAATGTTCTACA | n/a | n/a | sooossssssssssssooss | 5-10-5 | 93 | 2526 |
| 665219 | 115205 | 115224 | CCCTGATTGAGGAGAGGCAA | n/a | n/a | sooossssssssssssooss | 5-10-5 | 77 | 2527 |
| 665220 | 116595 | 116614 | ATGTTTTTTTCTGGCCGGGC | n/a | n/a | sooossssssssssssooss | 5-10-5 | 85 | 2528 |

TABLE 61-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 665221 | 116620 | 116639 | TTCAGTATCTGCCACATACT | n/a | n/a | sooossssssssssssooss | 5-10-5 | 64 | 2529 |
| 665222 | 116645 | 116664 | TGAATCAAAGGACATTAAGC | n/a | n/a | sooossssssssssssooss | 5-10-5 | 69 | 2530 |
| 664661 | 135820 | 135839 | GTGACAAAAGCAGGTTAAGT | 2783 | 2802 | sooossssssssssssooss | 5-10-5 | 78 | 2333 |
| 664662 | 135821 | 135840 | AGTGACAAAAGCAGGTTAAG | 2784 | 2803 | sooossssssssssssooss | 5-10-5 | 18 | 2336 |
| 664663 | 135822 | 135841 | GAGTGACAAAAGCAGGTTAA | 2785 | 2804 | sooossssssssssssooss | 5-10-5 | 79 | 2338 |
| 664664 | 135823 | 135842 | CGAGTGACAAAAGCAGGTTA | 2786 | 2805 | sooossssssssssssooss | 5-10-5 | 66 | 2341 |
| 664665 | 135824 | 135843 | CCGAGTGACAAAAGCAGGTT | 2787 | 2806 | sooossssssssssssooss | 5-10-5 | 94 | 2344 |
| 664666 | 135825 | 135844 | GCCGAGTGACAAAAGCAGGT | 2788 | 2807 | sooossssssssssssooss | 5-10-5 | 89 | 2346 |
| 664667 | 135826 | 135845 | AGCCGAGTGACAAAAGCAGG | 2789 | 2808 | sooossssssssssssooss | 5-10-5 | 29 | 2349 |
| 664668 | 135827 | 135846 | AAGCCGAGTGACAAAAGCAG | 2790 | 2809 | sooossssssssssssooss | 5-10-5 | 72 | 2352 |
| 664669 | 135828 | 135847 | AAAGCCGAGTGACAAAAGCA | 2791 | 2810 | sooossssssssssssooss | 5-10-5 | 53 | 2354 |
| 664670 | 135829 | 135848 | CAAAGCCGAGTGACAAAAGC | 2792 | 2811 | sooossssssssssssooss | 5-10-5 | 55 | 2357 |
| 664671 | 135830 | 135849 | CCAAAGCCGAGTGACAAAAG | 2793 | 2812 | sooossssssssssssooss | 5-10-5 | 58 | 2360 |
| 664672 | 135831 | 135850 | GCCAAAGCCGAGTGACAAAA | 2794 | 2813 | sooossssssssssssooss | 5-10-5 | 80 | 2362 |
| 664673 | 135832 | 135851 | AGCCAAAGCCGAGTGACAAA | 2795 | 2814 | sooossssssssssssooss | 5-10-5 | 52 | 2365 |
| 664674 | 135833 | 135852 | GAGCCAAAGCCGAGTGACAA | 2796 | 2815 | sooossssssssssssooss | 5-10-5 | 71 | 2368 |
| 664675 | 135834 | 135853 | CGAGCCAAAGCCGAGTGACA | 2797 | 2816 | sooossssssssssssooss | 5-10-5 | 76 | 2419 |
| 664676 | 135835 | 135854 | CCGAGCCAAAGCCGAGTGAC | 2798 | 2817 | sooossssssssssssooss | 5-10-5 | 78 | 2422 |
| 664677 | 135836 | 135855 | CCCGAGCCAAAGCCGAGTGA | 2799 | 2818 | sooossssssssssssooss | 5-10-5 | 77 | 2425 |
| 664678 | 135837 | 135856 | TCCCGAGCCAAAGCCGAGTG | 2800 | 2819 | sooossssssssssssooss | 5-10-5 | 73 | 2427 |
| 664679 | 135838 | 135857 | GTCCCGAGCCAAAGCCGAGT | 2801 | 2820 | sooossssssssssssooss | 5-10-5 | 73 | 2430 |
| 664680 | 135839 | 135858 | AGTCCCGAGCCAAAGCCGAG | 2802 | 2821 | sooossssssssssssooss | 5-10-5 | 20 | 2433 |
| 664681 | 135840 | 135859 | AAGTCCCGAGCCAAAGCCGA | 2803 | 2822 | sooossssssssssssooss | 5-10-5 | 64 | 2435 |
| 664682 | 135841 | 135860 | GAAGTCCCGAGCCAAAGCCG | 2804 | 2823 | sooossssssssssssooss | 5-10-5 | 60 | 2438 |
| 664683 | 135842 | 135861 | TGAAGTCCCGAGCCAAAGCC | 2805 | 2824 | sooossssssssssssooss | 5-10-5 | 64 | 2441 |
| 664684 | 135843 | 135862 | TTGAAGTCCCGAGCCAAAGC | 2806 | 2825 | sooossssssssssssooss | 5-10-5 | 52 | 2443 |
| 664685 | 135844 | 135863 | TTTGAAGTCCCGAGCCAAAG | 2807 | 2826 | sooossssssssssssooss | 5-10-5 | 45 | 2559 |
| 664686 | 135845 | 135864 | TTTTGAAGTCCCGAGCCAAA | 2808 | 2827 | sooossssssssssssooss | 5-10-5 | 56 | 2560 |
| 664687 | 135846 | 135865 | ATTTTGAAGTCCCGAGCCAA | 2809 | 2828 | sooossssssssssssooss | 5-10-5 | 67 | 2561 |
| 664688 | 135847 | 135866 | GATTTTGAAGTCCCGAGCCA | 2810 | 2829 | sooossssssssssssooss | 5-10-5 | 73 | 2562 |
| 664689 | 135848 | 135867 | TGATTTTGAAGTCCCGAGCC | 1644 | 1663 | sooossssssssssssooss | 5-10-5 | 67 | 56 |
| 664690 | 135849 | 135868 | CTGATTTTGAAGTCCCGAGC | 2812 | 2831 | sooossssssssssssooss | 5-10-5 | 73 | 464 |
| 664691 | 135850 | 135869 | ACTGATTTTGAAGTCCCGAG | 2813 | 2832 | sooossssssssssssooss | 5-10-5 | 85 | 2563 |
| 664692 | 135851 | 135870 | CACTGATTTTGAAGTCCCGA | 2814 | 2833 | sooossssssssssssooss | 5-10-5 | 89 | 2564 |
| 664693 | 135852 | 135871 | TCACTGATTTTGAAGTCCCG | 2815 | 2834 | sooossssssssssssooss | 5-10-5 | 75 | 2565 |
| 424880 | 135853 | 135872 | ATCACTGATTTTGAAGTCCC | 2816 | 2835 | ssssssssssssssssssss | 5-10-5 | 62 | 57 |
| 664694 | 135853 | 135872 | ATCACTGATTTTGAAGTCCC | 1649 | 1668 | sooossssssssssssooss | 5-10-5 | 85 | 57 |

TABLE 61-continued

| ISIS NO | SEQ ID NO: 1 start site | SEQ ID NO: 1 stop site | Sequence | SEQ ID NO: 2 start site | SEQ ID NO: 2 stop site | Linkage Chemistry | Motif | % inhibition | SEQ ID NO |
|---|---|---|---|---|---|---|---|---|---|
| 664695 | 135854 | 135873 | CATCACTGATTTTGAAGTCC | 2817 | 2836 | sooossssssssssssooss | 5-10-5 | 83 | 2374 |
| 664696 | 135855 | 135874 | CCATCACTGATTTTGAAGTC | 2818 | 2837 | sooossssssssssssooss | 5-10-5 | 66 | 2376 |
| 664697 | 135856 | 135875 | CCCATCACTGATTTTGAAGT | 2819 | 2838 | sooossssssssssssooss | 5-10-5 | 58 | 2379 |
| 664698 | 135857 | 135876 | TCCCATCACTGATTTTGAAG | 2820 | 2839 | sooossssssssssssooss | 5-10-5 | 71 | 2382 |
| 664699 | 135858 | 135877 | CTCCCATCACTGATTTTGAA | 2821 | 2840 | sooossssssssssssooss | 5-10-5 | 32 | 2384 |
| 664700 | 135859 | 135878 | ACTCCCATCACTGATTTTGA | 2822 | 2841 | sooossssssssssssooss | 5-10-5 | 71 | 2387 |
| 664701 | 135860 | 135879 | TACTCCCATCACTGATTTTG | 2823 | 2842 | sooossssssssssssooss | 5-10-5 | 75 | 2390 |
| 664702 | 135861 | 135880 | TTACTCCCATCACTGATTTT | 2824 | 2843 | sooossssssssssssooss | 5-10-5 | 46 | 2392 |
| 664703 | 135862 | 135881 | CTTACTCCCATCACTGATTT | 2825 | 2844 | sooossssssssssssooss | 5-10-5 | 22 | 2395 |
| 664704 | 135863 | 135882 | TCTTACTCCCATCACTGATT | 2826 | 2845 | sooossssssssssssooss | 5-10-5 | 72 | 2398 |
| 664705 | 135864 | 135883 | CTCTTACTCCCATCACTGAT | 2827 | 2846 | sooossssssssssssooss | 5-10-5 | 70 | 2400 |
| 664706 | 135865 | 135884 | GCTCTTACTCCCATCACTGA | 2828 | 2847 | sooossssssssssssooss | 5-10-5 | 77 | 2403 |
| 664707 | 135866 | 135885 | TGCTCTTACTCCCATCACTG | 2829 | 2848 | sooossssssssssssooss | 5-10-5 | 88 | 2406 |
| 664708 | 135867 | 135886 | TTGCTCTTACTCCCATCACT | 2830 | 2849 | sooossssssssssssooss | 5-10-5 | 86 | 2408 |
| 664709 | 135868 | 135887 | TTTGCTCTTACTCCCATCAC | 2831 | 2850 | sooossssssssssssooss | 5-10-5 | 16 | 2410 |
| 664710 | 135869 | 135888 | ATTTGCTCTTACTCCCATCA | 2832 | 2851 | sooossssssssssssooss | 5-10-5 | 80 | 2412 |
| 664711 | 135870 | 135889 | AATTTGCTCTTACTCCCATC | 2833 | 2852 | sooossssssssssssooss | 5-10-5 | 65 | 2414 |
| 664712 | 135871 | 135890 | AAATTTGCTCTTACTCCCAT | 2834 | 2853 | sooossssssssssssooss | 5-10-5 | 60 | 2416 |
| 664713 | 135872 | 135891 | GAAATTTGCTCTTACTCCCA | 2835 | 2854 | sooossssssssssssooss | 5-10-5 | 85 | 2418 |

Example 17: Dose-Dependent Antisense Inhibition of Human Tau in SH-SY5Y Cells

Gapmers from studies described above exhibiting significant in vitro inhibition of tau mRNA were selected and tested at various doses in SH-SY5Y cells. The antisense oligonucleotides were tested in a series of experiments that had similar culture conditions. The results for each experiment are presented in separate tables shown below. Cells were plated at a density of 20,000 cells per well and transfected using electroporation with 0.247 µM, 0.741 µM, 2.22 µM, 6.67 µM, and 20.00 µM concentrations of antisense oligonucleotide, as specified in the Tables below. After a treatment period of approximately 16 hours, RNA was isolated from the cells and tau mRNA levels were measured by quantitative real-time PCR. Human primer probe set RTS3104 was used to measure mRNA levels. Tau mRNA levels were adjusted according to total RNA content, as measured by RIBOGREEN®. Results are presented as percent inhibition of tau, relative to untreated control cells. Tau mRNA levels were significantly reduced in a dose-dependent manner in antisense oligonucleotide treated cells.

TABLE 62

| ISIS No | 0.247 µM | 0.741 µM | 2.22 µM | 6.67 µM | 20.00 µM | $IC_{50}$ (µM) |
|---|---|---|---|---|---|---|
| 620887 | 18 | 39 | 71 | 88 | 95 | 1.2 |
| 664662 | 5 | 16 | 34 | 59 | 68 | 6.4 |

TABLE 62-continued

| ISIS No | 0.247 µM | 0.741 µM | 2.22 µM | 6.67 µM | 20.00 µM | $IC_{50}$ (µM) |
|---|---|---|---|---|---|---|
| 664665 | 16 | 41 | 69 | 89 | 96 | 1.2 |
| 664667 | 5 | 20 | 39 | 78 | 90 | 2.9 |
| 664680 | 7 | 11 | 21 | 56 | 81 | 5.9 |
| 664699 | 0 | 1 | 28 | 59 | 85 | 5.7 |
| 664709 | 8 | 16 | 48 | 66 | 89 | 3.1 |
| 665044 | 15 | 33 | 59 | 84 | 94 | 1.6 |
| 665205 | 0 | 7 | 35 | 51 | 86 | 5.3 |
| 665207 | 22 | 36 | 57 | 82 | 93 | 1.4 |
| 665210 | 15 | 47 | 74 | 94 | 97 | 1.0 |
| 665212 | 6 | 22 | 56 | 82 | 95 | 2.1 |
| 665213 | 0 | 18 | 57 | 78 | 93 | 2.5 |
| 665217 | 10 | 28 | 63 | 86 | 95 | 1.7 |
| 665218 | 10 | 31 | 64 | 85 | 93 | 1.7 |

TABLE 63

| ISIS No | 0.247 µM | 0.741 µM | 2.22 µM | 6.67 µM | 20.00 µM | $IC_{50}$ (µM) |
|---|---|---|---|---|---|---|
| 664718 | 26 | 34 | 60 | 88 | 86 | 1.3 |
| 664745 | 34 | 39 | 67 | 87 | 95 | 0.9 |
| 664746 | 15 | 37 | 60 | 87 | 92 | 1.5 |
| 664760 | 32 | 50 | 75 | 89 | 97 | 0.7 |
| 665044 | 21 | 44 | 75 | 92 | 97 | 0.9 |
| 665082 | 5 | 27 | 67 | 87 | 96 | 1.7 |
| 665083 | 17 | 34 | 67 | 85 | 97 | 1.4 |
| 665089 | 9 | 26 | 53 | 84 | 94 | 2.0 |

TABLE 63-continued

| ISIS No | 0.247 µM | 0.741 µM | 2.22 µM | 6.67 µM | 20.00 µM | IC$_{50}$ (µM) |
|---|---|---|---|---|---|---|
| 665093 | 11 | 57 | 81 | 93 | 95 | 0.9 |
| 665094 | 25 | 53 | 76 | 91 | 93 | 0.7 |
| 665095 | 20 | 33 | 63 | 89 | 95 | 1.4 |
| 665096 | 5 | 37 | 57 | 86 | 95 | 1.8 |
| 665102 | 8 | 36 | 61 | 90 | 96 | 1.6 |
| 665103 | 6 | 24 | 59 | 83 | 92 | 2.1 |

TABLE 64

| ISIS No | 0.247 µM | 0.741 µM | 2.22 µM | 6.67 µM | 20.00 µM | IC$_{50}$ (µM) |
|---|---|---|---|---|---|---|
| 620887 | 26 | 45 | 72 | 89 | 96 | 1.2 |
| 621013 | 26 | 49 | 82 | 93 | 97 | 0.7 |
| 621031 | 25 | 41 | 66 | 84 | 92 | 1.1 |
| 621041 | 26 | 55 | 70 | 89 | 92 | 0.7 |
| 621238 | 23 | 41 | 59 | 85 | 95 | 1.2 |
| 621251 | 33 | 56 | 74 | 88 | 92 | 0.5 |
| 664514 | 11 | 36 | 68 | 79 | 91 | 1.6 |
| 664516 | 16 | 36 | 64 | 82 | 94 | 1.5 |
| 664534 | 18 | 35 | 48 | 76 | 91 | 1.9 |
| 664775 | 24 | 30 | 59 | 79 | 92 | 1.6 |
| 664788 | 11 | 21 | 26 | 55 | 73 | 6.2 |
| 664799 | 26 | 37 | 63 | 79 | 90 | 1.3 |
| 664800 | 15 | 0 | 61 | 75 | 90 | 2.7 |
| 665047 | 43 | 65 | 82 | 95 | 98 | 0.2 |
| 665077 | 19 | 44 | 63 | 85 | 96 | 1.2 |

Example 18: Intracerebroventricular Administration of Antisense Oligonucleotides Against Human Tau mRNA in Htau Mice Selected compounds were tested for efficacy by ICV administration in human tau transgenic mice (Duff et al., Neurobiology of Disease 7:87-98, 2000).

Treatment and Surgery

Groups of 4 mice each were administered ISIS 613099, ISIS 613361, ISIS 613370, ISIS 623782, or ISIS 623996 with a 200 µg dose delivered by ICV bolus injection. A control group of 2 mice was similarly treated with ISIS 424880 and a control group of 4 mice was similarly treated with PBS. All procedures were performed under isofluorane anesthesia and in accordance with IACUC regulations. For mouse ICV bolus injections, the antisense oligonucleotide was injected into the right lateral ventricle of human tau transgenic mice. Ten microliters of solution containing 200 µg of oligonucleotide in PBS was injected over approximately 10 seconds. Tissue was collected 14 days after oligonucleotide administration.

RNA Analysis

On day 14 after the oligonucleotide administration, RNA was extracted from the hippocampus, spinal cord and cortex for real-time PCR analysis of tau mRNA levels. Human tau mRNA levels were measured using the human primer probe set RTS3104. Results were calculated as percent inhibition of human tau mRNA expression compared to the control. All the antisense oligonucleotides effect significant inhibition of human tau mRNA levels in several tissues.

TABLE 65

Percent reduction of human tau mRNA levels in hTau mice

| ISIS No | Cortex | Hippocampus | Spinal Cord |
|---|---|---|---|
| 613099 | 41.8 | 55.2 | 54.1 |
| 613361 | 69.4 | 57.3 | 72.5 |
| 613370 | 42.2 | 61.0 | 63.0 |
| 623782 | 62.2 | 79.1 | 70.8 |
| 623996 | 74.1 | 69.2 | 76.4 |
| 424880 | 50.3 | 53.1 | 55.2 |

Example 19: Design of Oligonucleotides Targeting Human Tau

ISIS No. 603054 was designed to target human Tau. The nucleobase sequence and linkage chemistry of of ISIS No. 603054 is given in table 66 below. ISIS No. 603054 is a 5-10-5 MOE gapmer. ISIS No. 603054 is 20 nucleosides in length, wherein the central gap segment comprises ten 2'-deoxynucleosides and is flanked by wing segments on the 5' direction and the 3' direction comprising five nucleosides each. Each nucleoside in the 5' wing segment and each nucleoside in the 3' wing segment has a 2'-MOE modification. All cytosine residues throughout each gapmer are 5-methylcytosines. "Start site" indicates the 5'-most nucleoside to which the gapmer is targeted in the human gene sequence. "Stop site" indicates the 3'-most nucleoside to which the gapmer is targeted human gene sequence. Each gapmer listed in Table 1 below is targeted to either the human tau genomic sequence, designated herein as SEQ ID NO: 1 (GENBANK Accession No. NT_010783.15 truncated from nucleotides 9240000 to 9381000) or to the human tau mRNA sequence, designated herein as SEQ ID NO: 2 (GENBANK Accession No. NM_001123066.3).

TABLE 66

ICV in vivo study in hTau mice and WT C57Bl6 mice

| ISIS NO | SEQ ID NO: 1 start site | SEQ ID NO: 1 stop site | Sequence | SEQ ID NO: 2 start site | SEQ ID NO: 2 stop site | Linkage Chemistry | SEQ ID NO. |
|---|---|---|---|---|---|---|---|
| 603054 | 135853 | 135872 | ATCACTGATTTTGAAGTCCC | 2816 | 2835 | sooosssssssssssooos | 57 |

Example 20: In Vivo Analysis in Mice of Oligonucleotides Targeting Human Tau Oligonucleotides, shown in the table below, were designed to target Tau. Mice, either human tau transgenic mice "hTau" (Duff et al., Neurobiology of Disease 7:87-98, 2000; Davies et al. J. Neurochem. (2003) 86, 582-590) or wild-type WT C57Bl6 mice were separated into groups of 3 or 4 mice. Each mouse in each group of mice was administered a single ICV dose of either 300 ug or 200 ug each of the oligonucleotides in the table below. At 3 hours post injection, each mouse was evaluated according to 7 different criteria. The 7 criteria are (1) the mouse was bright, alert, and responsive; (2) the mouse was standing or hunched without stimuli; (3) the mouse shows any movement without stimuli (4) the mouse demonstrates forward movement after its lifted; (5) the mouse demonstrates any movement after its lifted; (6) the mouse responds to a tail pinch; (7) regular breathing. For each of the 7 different criteria, each mouse was given a sub-score of 0 if it met the criteria or 1 if it did not. After all of the 7 criteria were evaluated, the sub-scores were summed for each mouse and then averaged for each group. For example, if a mouse was bright, alert, and responsive 3 hours after the 300 μg ICV dose, and met all other other criteria, it would get a summed score of 0. If another mouse was not bright, alert, and responsive 3 hours after the 300 μg ICV dose but met all other criteria, it would receive a score of 1. Saline treated mice generally receive a score of 0. Results are presented as the average score for each treatment group in Table 67 below. "ND" means no data. These results demonstrate that ISIS 613099, ISIS 613361, ISIS 613370, ISIS 623782, ISIS 623996, ISIS 424880, and ISIS 603054 were well tolerated.

TABLE 67

ICV in vivo study in hTau mice and WT C57Bl6 mice

| | Line: | | |
|---|---|---|---|
| | hTau | | WT C57Bl6 |
| | Dose: | | |
| | 300 ug | 200 ug | 300 ug |
| 613099 | 0 | ND | ND |
| 613361 | 0 | ND | ND |
| 613370 | 0 | ND | ND |
| 623782 | 0 | ND | ND |
| 623996 | 0 | ND | ND |
| 424880 | ND | 3 | ND |
| 603054 | ND | ND | 0.25 |

Example 20: In Vivo Analysis in Rats of Oligonucleotides Targeting Human Tau

Sprague Dawley rats were separated into groups of 4 rats each. Each rat in each group of rats was administered a single 1 mg intrathecal (IT) dose or a single 3 mg intrathecal (IT) dose of ISIS 613099, ISIS 613361, ISIS 613370, ISIS 623782, ISIS 623996, ISIS 424880, or ISIS 603054. At 3 hours after injection, the movement of 7 different parts of the body was evaluated for each rat. The 7 body parts are (1) the rat's tail; (2) the rat's posterior posture; (3) the rat's hind limbs; (4) the rat's hind paws; (5) the rat's forepaws; (6) the rat's anterior posture; and (7) the rat's head. For each of the 7 different body parts, each rat was given a sub-score of 0 if the body part was moving or 1 if the body part was paralyzed. After each of the 7 body parts were evaluated, the sub-scores were summed for each rat and then averaged for each group. For example, if a rat's tail, head, and all other evaluated body parts were moving 3 hours after the 3 mg IT dose, it would get a summed score of 0. If another rat was not moving its tail 3 hours after the 3 mg IT dose but all other evaluated body parts were moving, it would receive a score of 1. Saline treated rats generally receive a score of 0. A score of at the top end of the range would be suggestive of toxicity. Results are presented as the average score for each treatment group in Table 68 below.

TABLE 68

1 mg and 3 mg IT bolus in vivo study

| | Score 3 hours after injection | |
|---|---|---|
| ISIS | Dose | |
| No. | 1 mg | 3 mg |
| 613099 | 0.25 | 3 |
| 613361 | 0 | 0.33 |
| 613370 | 0 | 0 |
| 623782 | 0.25 | 0.75 |
| 623996 | 0 | 2 |
| 424880 | 2.3 | 6 |
| 603054 | 1.25 | 2.75 |

SEQUENCE LISTING

The patent contains a lengthy sequence listing. A copy of the sequence listing is available in electronic form from the USPTO web site (https://seqdata.uspto.gov/?pageRequest=docDetail&DocID=US12091662B2). An electronic copy of the sequence listing will also be available from the USPTO upon request and payment of the fee set forth in 37 CFR 1.19(b)(3).

What is claimed is:

1. A compound comprising:
(i) a modified oligonucleotide according to the following formula:

Ges Teo Teo Geo Ces Ads Gds Tds Gds Tds Tds mCds mCds Aeo mCeo Tes Aes Te(nucleobase sequence of SEQ ID NO:1602); wherein A=an adenine,
mC=a 5-methylcytosine
G=a guanine,
T=a thymine,
e=a 2'-O-methoxyethyl modified nucleoside,
d=a 2'-deoxynucleoside,
o=a phosphodiester internucleoside linkage, and
s=a phosphorothioate internucleoside linkage, or
(ii) a salt thereof.

2. A composition comprising the compound of claim 1, and at least one of a pharmaceutically acceptable carrier or diluent.

3. A method of treating a tau associated disease in a human subject in need thereof, the method comprising administering to the human subject the compound of claim 1.

4. The method of claim 3, wherein the tau associated disease is a neurodegenerative disorder.

5. The method of claim 4, wherein the neurodegenerative disorder is a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

6. The compound of claim 1, wherein the compound comprises the modified oligonucleotide.

7. The compound of claim 1, wherein the compound comprises a salt of the modified oligonucleotide.

8. The composition of claim 2, wherein the compound comprises the modified oligonucleotide.

9. The composition of claim 2, wherein the compound comprises a salt of the modified oligonucleotide.

10. The method of claim 3, wherein the compound comprises the modified oligonucleotide.

11. The method of claim 10, wherein the tau associated disease is a neurodegenerative disorder.

12. The method of claim 11, wherein the neurodegenerative disorder is a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

13. The method of claim 3, wherein the compound comprises a salt of the modified oligonucleotide.

14. The method of claim 13, wherein the tau associated disease is a neurodegenerative disorder.

15. The method of claim 14, wherein the neurodegenerative disorder is a Tauopathy, Alzheimer's Disease, Fronto-temporal Dementia (FTD), FTDP-17, Progressive Supranuclear Palsy (PSP), Chronic Traumatic Encephalopathy (CTE), Corticobasal Ganglionic Degeneration (CBD), Epilepsy, or Dravet's Syndrome.

* * * * *